United States Patent
Shlomchik et al.

(10) Patent No.: US 10,876,111 B2
(45) Date of Patent: Dec. 29, 2020

(54) METHODS AND MATERIALS FOR CLONING FUNCTIONAL T CELL RECEPTORS FROM SINGLE T CELLS

(71) Applicant: University of Pittsburgh—Of the Commonwealth System of Higher Education, Pittsburgh, PA (US)

(72) Inventors: Mark Shlomchik, Pittsburgh, PA (US); Adriana Turqueti Neves, Olching (DE); Eduardo Schittler Neves, Olching (DE); Constantinos George Panousis, Pittsburgh, PA (US); Alexander McIntyre Rowe, Pittsburgh, PA (US)

(73) Assignee: University of Pittsburgh—Of the Commonwealth System of Higher Education, Pittsburgh, PA (US)

(*) Notice: Subject to any disclaimer, the term of this patent is extended or adjusted under 35 U.S.C. 154(b) by 0 days.

(21) Appl. No.: 15/826,671

(22) Filed: Nov. 29, 2017

(65) Prior Publication Data
US 2018/0223275 A1   Aug. 9, 2018

Related U.S. Application Data

(60) Provisional application No. 62/427,335, filed on Nov. 29, 2016.

(51) Int. Cl.
| | | |
|---|---|---|
| C12P 19/34 | (2006.01) | |
| C12Q 1/686 | (2018.01) | |
| C12N 15/10 | (2006.01) | |
| C07K 14/725 | (2006.01) | |
| C12N 5/0783 | (2010.01) | |

(52) U.S. Cl.
CPC ...... *C12N 15/1096* (2013.01); *C07K 14/7051* (2013.01); *C12N 5/0636* (2013.01); *C12P 19/34* (2013.01); *C12Q 1/686* (2013.01)

(58) Field of Classification Search
None
See application file for complete search history.

(56) References Cited

U.S. PATENT DOCUMENTS

| | | |
|---|---|---|
| 6,416,971 B1 | 7/2002 | Reinherz et al. |
| 7,749,697 B2 | 6/2010 | Oleksiewicz et al. |
| 2013/0289261 A1 | 10/2013 | Finn et al. |
| 2015/0203886 A1 | 7/2015 | Kishi et al. |
| 2015/0337369 A1 | 11/2015 | Davis et al. |
| 2019/0040381 A1* | 2/2019 | Thomas ............. C12N 15/1003 |

OTHER PUBLICATIONS

International Search Report and Written Opinion in International Application No. PCT/US2017/63813, dated Jun. 1, 2018, 17 pages.
Invitation to Pay Additional Fees in International Application No. PCT/US2017/63813, dated Apr. 3, 2018, 2 pages.
Gibson et al., "Enzymatic assembly of DNA molecules up to several hundred kilobases," *Nat Methods.*, 6(5):343-345, May 2009.
Guo et al., "Rapid cloning, expression, and functional characterization of paired αβ and γδ T-cell receptor chains from single-cell analysis," *Mol Ther Meth Clin Dev.*, 3:15054, Jan. 27, 2016.
Hamana et al., "A novel, rapid and efficient method of cloning functional antigen-specific T-cell receptors from single human and mouse T-cells," *Biochem Biophys Res Comm.*, 474(4):709-714, Jun. 10, 2016.
Han et al., "Linking T-cell receptor sequence to functional phenotype at the single-cell level," *Nat Biotechnol.*, 32(7):684-692, Jul. 2014.
Holst et al., "Generation of T-cell receptor retrogenic mice," *Nat Protoc.*, 1(1):406-417, 2006.
Howie et al., "High-throughput pairing of T cell receptor α and β sequences," *Sci Transl Med.*, 7(301):301ra131, Oct. 14, 2015.
Kobayashi et al., "A new cloning and expression system yields and validates TCRs from blood lymphocytes of patients with cancer within 10 days," *Nat Med.*, 19(11):1542-1546, Nov. 2013.
Moysey et al., "Amplification and one-step expression cloning of human T cell receptor genes," *Anal Biochem.*, 326(2):284-286, Mar. 15, 2004.
SantaLucia., "A unified view of polymer, dumbbell, and oligonucleotide DNA nearest-neighbor thermodynamics," *PNAS USA.*, 95:1460-1465, Feb. 17, 1998.
Sprouse et al., "Rapid identification and expression of human TCRs in retrogenic mice," *J Immunol Methods.*, 439:29-36, Dec. 2016.
Wälchli et al., "A practical approach to T-cell receptor cloning and expression," *PLoS One.*, 6(11):e27930, Nov. 2011.
International Preliminary Report on Patentability in International Application No. PCT/US2017/063813 dated Jun. 13, 2019, 13 pages.
Extended European Search Report in European Application No. 17875651.6 dated Oct. 16, 2019, 8 pages.
Ferradini et al., "The use of anchored polymerase chain reaction for the study of large numbers of human T-cell receptor transcripts," Molecular immunology, 30(13):1143-50, Sep. 1993.

(Continued)

*Primary Examiner* — Channing S Mahatan
(74) *Attorney, Agent, or Firm* — Fish & Richardson P.C.

(57) ABSTRACT

This document provides methods and materials involved in cloning functional TCRs from single T cells. For example, methods and materials for obtaining nucleic acid encoding a TCR from a single T cell and arranging that nucleic acid to form nucleic acid vectors successfully designed to express a TCR, kits for obtaining nucleic acid encoding a TCR from a single T cell and arranging that nucleic acid to form nucleic acid vectors successfully designed to express a TCR, methods for making such kits, collections of nucleic acid primers designed to amplify the entire coding sequence of both variable regions for each expressed V segment for functional αβ or γδ TCRs of a particular mammalian species, methods for using such collections of nucleic acid primers to clone functional TCRs from single T cells, and kits containing such collections of nucleic acid primers to clone functional TCRs from single T cells are provided.

23 Claims, 25 Drawing Sheets

Specification includes a Sequence Listing.

(56) References Cited

OTHER PUBLICATIONS

Kobayashi et al., "A novel system for cloning human TCRs: Cutting short the way to TCR-based anticancer therapy," Oncoimmunology, 3(1):e27258, Jan. 2014.

Moonka and Elwyn, "A consensus primer to amplify both α and β chains of the human T cell receptor," Journal of immunological methods, 169(1):41-51, Feb. 1994.

Abad et al., "T-Cell Receptor Gene Therapy of Established Tumors in a Murine Melanoma Model," J. Immunother., 31(1):1-6, Jan. 2008.

Battye et al., "Single Cell Sorting and Cloning," J. Immunol. Methods, 243(1-2):25-32, Sep. 2000.

Bunse et al., "Rnai-Mediated Tcr Knockdown Prevents Autoimmunity in Mice Caused by Mixed Tcr Dimers Following Tcr Gene Transfer," Mol. Ther., 22(11):1983-91, Nov. 2014.

Dossa et al., "Development of T-Cell Immunotherapy for Hematopoietic Stem Cell Transplantation Recipients at Risk of Leukemia Relapse," Blood, 131(1):108-20, Jan. 2018.

Frey et al., "Optimizing Chimeric Antigen Receptor T-Cell Therapy for Adults with Acute Lymphoblastic Leukemia," J. Clin. Oncol., 38(5):415-22, Feb. 2020.

Jones et al., "Lentiviral Vector Design for Optimal T Cell Receptor Gene Expression in the Transduction of Peripheral Blood Lymphocytes and Tumor-Infiltrating Lymphocytes," Hum. Gene Ther., 20(6):630-40, Jun. 2009.

Klinger et al., "Multiplex Identification of Antigen-Specific T Cell Receptors Using a Combination of Immune Assays and Immune Receptor Sequencing," PLoS One, 10(10):e0141561, 2015.

Morton et al., "Simultaneous Deletion of Endogenous Tcralphabeta for Tcr Gene Therapy Creates an Improved and Safe Cellular Therapeutic," Mol. Ther., 28(1):64-74, Jan. 2020.

Reuss et al., "Tcr-Engineered T Cells: A Model of Inducible Tcr Expression to Dissect the Interrelationship between Two Tcrs," Eur. J. Immunol., 44(1):265-74, Jan. 2014.

Spear et al., "Tcr Gene-Modified T Cells Can Efficiently Treat Established Hepatitis C-Associated Hepatocellular Carcinoma Tumors," Cancer Immunol., Immunother., 65(3):293-304, Mar. 2016.

Sprouse et al., "Streamlined Single Cell Tcr Isolation and Generation of Retroviral Vectors for in Vitro and in Vivo Expression of Human Tcrs," J. Vis. Exp., 10(127):e55379, Sep. 2017.

Stadtmauer et al., "Crispr-Engineered T Cells in Patients with Refractory Cancer," Science, Feb. 2020.

Starck et al., "Immunotherapy with Tcr-Redirected T Cells: Comparison of Tcr-Transduced and Tcr-Engineered Hematopoietic Stem Cell-Derived T Cells," J. Immunol., 192(1):206-13, Jan. 2014.

Zhang et al., "Transduction of Human T Cells with a Novel T-Cell Receptor Confers Anti-Hcv Reactivity," PLoS Pathog., 6(7), Jul. 2010.

Magarian-Blander et al., "Intercellular and intracellular events following the MHC-unrestricted TCR recognition of a tumor-specific peptide epitope on the epithelial antigen MUC1," The Journal of Immunology, Apr. 1998, 160(7):3111-20.

* cited by examiner

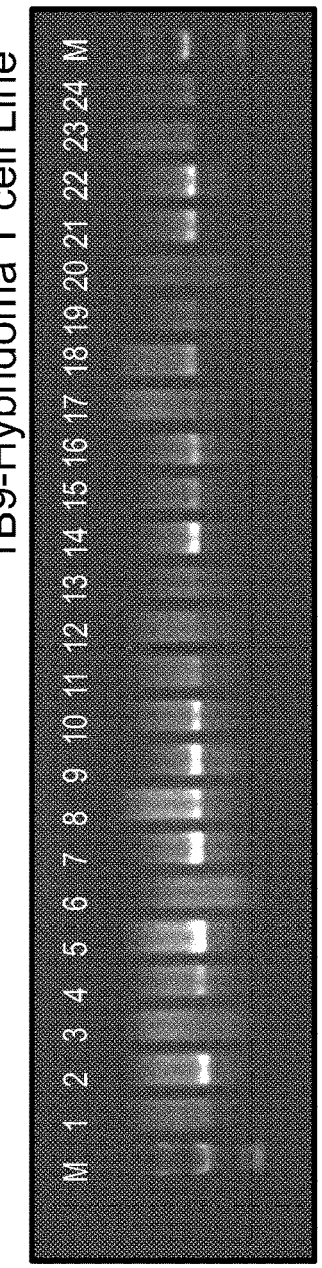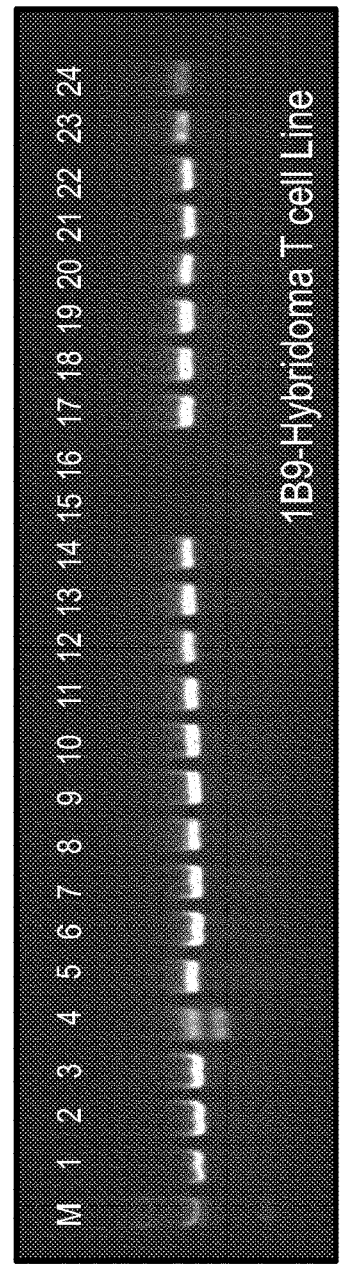
FIG. 6C
FIG. 6D

CD8+T cells from a C57BL/6 mouse

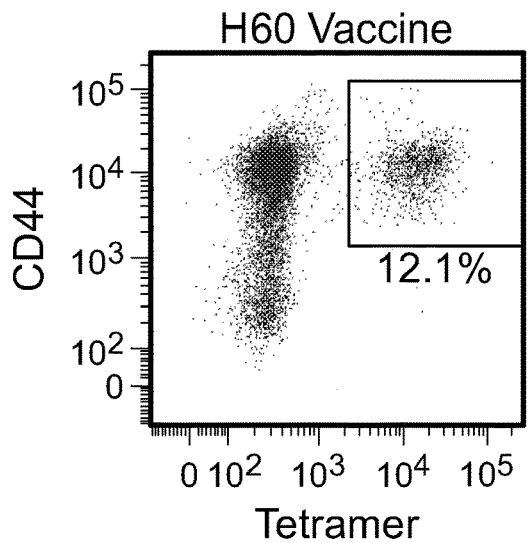
FIG. 11A
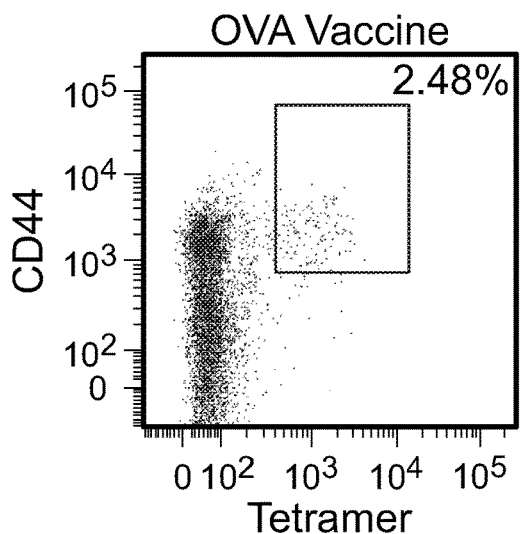
FIG. 11B
| Vβ Usage | | |
|---|---|---|
| TCRβ Gene | % of H60 | % of OVA |
| TRBV1 | 23.2 | 0.0 |
| TRBV2 | 15.2 | 0.0 |
| TRBV3 | 4.5 | 5.6 |
| TRBV4 | 1.0 | 0.0 |
| TRBV12-1 | 12.6 | 48.1 |
| TRBV12-2 | 12.6 | 0.0 |
| TRBV13-1 | 2.5 | 0.0 |
| TRBV13-2 | 0.5 | 0.0 |
| TRBV14 | 1.0 | 25.9 |
| TRBV15 | 2.0 | 0.0 |
| TRBV16 | 15.7 | 7.4 |
| TRBV17 | 2.0 | 13.0 |
| TRBV19 | 1.0 | 0.0 |
| TRBV20 | 2.5 | 0.0 |
| TRBV24 | 0.5 | 0.0 |
| TRBV26 | 2.5 | 0.0 |
| TRBV30 | 0.5 | 0.0 |
FIG. 11C

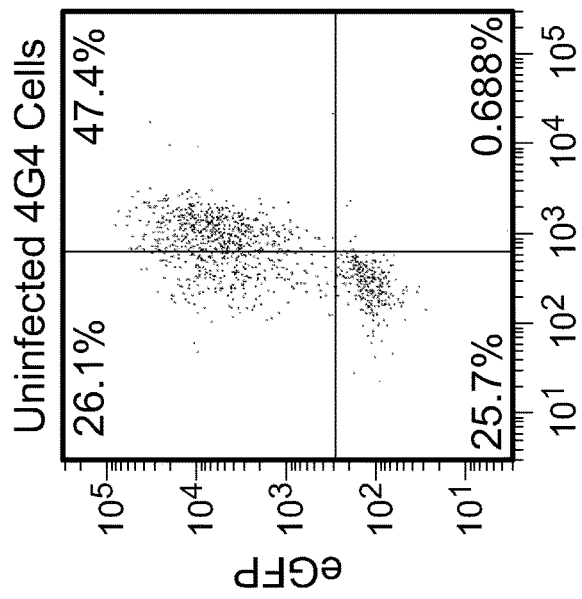
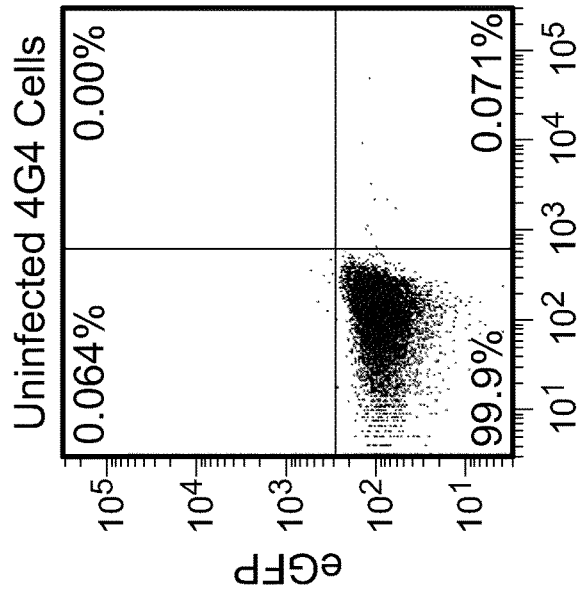
FIG. 12A
FIG. 12B

PCR STRATEGY

SCREENING FOR POSITIVE CLONES

Digestion with ClaI

Clones tested in functional assay

About 50% correct clones
Arrows show clones tested

GIBSON ASSEMBLY OPTIMIZATION FROM SINGLE CELL PCR-TEST WITH DO11.10

Test 1
50ng linearized vector = 2μl
100ng alpha single cell do11 from3/20
100ng beta single cell do11 from3/20
100ng fragment B=0,6μl Test 2
50ng linearized vector = 2μl
100ng alpha single cell do11 from3/20
100ng beta single cell do11 from3/20
100ng fragment B=0,6μl 80% efficiency Arrows indicate clones with expected ClaI digestion pattern Fragment b:

```
5' acatccagaacctgctgtgtaccagttcaggtctcaggacgacagcaccctgcctgttcaccgactttgactccaaatcaatgtgccgaaaacatggaactgttcat 130
3' tgtaggtcctgggtcttggacgacacatggtcaattttctaggagcacaggtcgtcagtccagagtcctgctgggagacgacaagtggctgaaactgaggttgtacctctgacacttgacttgcaagta
                                                                                                    ↑
                                                                    Cα
```
Overlap with 3' end of VJ amplicons I Q N P E P A V Y Q L K D P R S Q D S T L C L F T D F D S Q I N V P K T M E S G T F F I

```
cactgacacaaactgctgctggacatgaaagctatggattccaagagcaatggggccattgcctgagcaaccagacaagcttcacctgccaagatatcttcaaagaatgccacctaccccagttca 260
gtgactgtttttgacgacgacctgtacttcgatacctaaggttctctgttaccgacctgttgtctgttcgaagtgacgttctataaaagttcttacgtggtgatggggtcaagt
                                                                                            ↑
                                                                    Cα
```

T D K T V L D M K A M D S K S N G A I A W S N Q T S F T C Q D I F K E T N A T Y P S S

```
gacgttccctgtgatgccacgttgaccgagaaaagcttttgaaacagatatgaacctaaacttttcaaaaactaaccttgtctatacttgattgtgaaagttttgaaagttaactgctcatga 390
ctgcaagggacactacggtcaactgctgcttttcgaagttgctctggacactacggtgcaacggacttgaaacttttgaaacttttgaacagtcaatacccctgaggcttagaggacgacttcatcgcctaattgacgagtact
                                                                                            ↑
                                                                    Cα
```

D V P C D A T L T E K S F E T D M N L N F Q N L S V M G L R I L L L K V A G F N L L M

```
cgctgaggctgtgtggttccagtgggctccggaggccacgagttctctctgttaaagcaaggaggagacgtgaagaaaaaccccgtccc 3' (SEQ ID NO: 337)
gcgactccgacaccaggtcacccgaccagggtcacccgaggcctcctggtgctgaagagacaattttcgttcgcctctctgcacctcttcttgggcccaggg ⓟ 5'  476
```
                Linker after Cα           P2A down of Cα                Overlap with 5' end of VDJ amplicons

Cα

T L R L W S S G S G A T N F S L L K Q A G D V E E N P G P          (SEQ ID NO: 456)

FIG. 22

Cb in acceptor vector:

```
                    Pmel        RsrII
5' (P)ccttctctaggcgccggaattcatatcgatgcatgcGGCGGTGTTTAAACGGGTCGACCGGAGATCTGAGAAATGTGACTCCACCCAAGGTCTCCTTGTTTGAGCATCAAAAGCAGAGATTGCAAA
     ||||||||||||||||||||||||||||||||||||||||||||||||||||||||||||||||||||||||||||||||||||||||||||||||||||||||||||||||||||||||||||||    130
3' ggaagagatccgcgccttaagtatagctacgtacgCCGCCACAAATTTGCCGCCACAAATTTGCCGCCACAAATTTGCCGCCACAAATTTGCCGCCACAAATTTGCCGCCACAAATTTGCCGCCACAAATTTGCCGCCACAAATTTGCCGCCACAAATTTGCCGCCACAAATTTGCCGCCACAAATTTGCCGCCACAAATTTGCCGCCACAAATTTGCCGCCACAAATTTGCCGCCACAAATTTGCCGCCACAAATTTGCCGCCACAAATTTGCCGCCACAAATTTGCCGCCACAAATTT
   |pMIGII|   |Linker|                                                                          |beta-Constant
```

(SEQ ID NO: 457)
606

METHODS AND MATERIALS FOR CLONING FUNCTIONAL T CELL RECEPTORS FROM SINGLE T CELLS

CROSS-REFERENCE TO RELATED APPLICATIONS

This application claims priority to U.S. Application Ser. No. 62/427,335, filed on Nov. 29, 2016. The disclosure of the prior application is considered part of the disclosure of this application, and is incorporated in its entirety into this application.

STATEMENT REGARDING FEDERALLY SPONSORED RESEARCH OR DEVELOPMENT

This invention was made with government support under grant AR044077 awarded by the National Institutes of Health. The government has certain rights in this invention.

SEQUENCE LISTING

The instant application contains a Sequence Listing which has been submitted electronically in ASCII format and is hereby incorporated by reference in its entirety. Said ASCII copy, created on Feb. 26, 2018, is named 45049_0006001_SL.txt and is 11,064 bytes in size.

BACKGROUND

1. Technical Field

This document relates to methods and materials involved in cloning functional T cell receptors (TCRs) from single T cells. For example, this document relates to methods and materials involved in using effective and streamlined combinations of amplification steps, cloning steps, and reagents to obtain nucleic acid encoding a TCR from a single T cell and to arrange that nucleic acid to form a nucleic acid vector successfully designed to express a TCR (e.g. a fully intact TCR) having the variable chain combinations (e.g., the α/β variable chain combination or the γ/δ variable chain combination) as present in that single T cell.

2. Background

TCRs are found on the surface of T cells and include two different polypeptide chains. In humans, about 95 percent of T cells have TCRs that include an alpha (α) chain and a beta (β) chain, and about 5 percent of T cells have TCRs that include a gamma (γ) chain and a delta (δ) chain. Such T cells can be referred to as αβ or γδ T cells, respectively.

Each chain (e.g., the α, β, γ, and δ chain) includes a variable (V) region and a constant (C) region. The V region of the α chains is formed from the recombination of V and J segments of the α gene. Likewise, the V region of the γ chains is formed from the recombination of V and J segments of the γ gene. The V region of the β chains, however, is formed from the recombination of V, D, and J segments of the β gene, and the V region of the δ chains is formed from the recombination of V, D, and J segments of the δ gene. Thus, there are several factors that contribute to the tremendous variability observed in a mammal's (e.g., a human's) T cell repertoire. For example, the specificity of one particular αβ TCR is determined by, inter alia, (a) the specific combination of VJ segments of the α chain, (b) the specific combination of VDJ segments of the β chain, and (c) the specific pairing of those two chains (that α chain and that β chain) that come together to form that particular αβ TCR. In addition, the joining of the VJ exons and VDJ exons into coding sequences is a notably imprecise process; nucleotides are lost from the edges of the gene segments and additional bases are added (Matsuzaki et al., Eur. J. Immunol., 23(12): 3345-9 (1993); Cabaniols et al., J. Exp. Med., 194(9):1385-1390 (1991)).

SUMMARY

This document provides methods and materials involved in cloning functional TCRs from single T cells. For example, this document provides methods and materials for obtaining nucleic acid encoding a TCR from a single T cell and arranging that nucleic acid to form nucleic acid vectors successfully designed to express a TCR (e.g., a fully intact TCR such as a fully intact TCR having the variable chain combination as present in that single T cell), kits for obtaining nucleic acid encoding a TCR from a single T cell and arranging that nucleic acid to form nucleic acid vectors successfully designed to express a TCR (e.g., a fully intact TCR such as a fully intact TCR having the variable chain combination as present in that single T cell), and methods for making such kits. A cloned αβ TCR having the variable chain combination as present in a single T cell used to clone that TCR can include the VJ α segment combination as present in that single T cell, the VDJ β segment combination as present in that single T cell, the nucleotide sequence of the entire α variable region as present in that single T cell, and the nucleotide sequence of the entire β variable region as present in that single T cell. Likewise, a cloned γδ TCR having the variable chain combination as present in a single T cell used to clone that TCR can include the VJ γ segment combination as present in that single T cell, the VDJ δ segment combination as present in that single T cell, the nucleotide sequence of the entire γ variable region as present in that single T cell, and the nucleotide sequence of the entire δ variable region as present in that single T cell.

This document also provides collections of nucleic acid primers designed to amplify the entire coding sequence of both variable regions (e.g., the α variable region and β variable region, or the γ variable region and δ variable region) for each expressed V segment (e.g., each expressed α V segment and β V segment, or each expressed γ V segment and δ V segment) for functional αβ or γδ TCRs of a particular mammalian species (e.g., a mouse or a human), methods for using such collections of nucleic acid primers to clone functional TCRs from single T cells, and kits containing such collections of nucleic acid primers to clone functional TCRs from single T cells.

In general, the methods and materials provided herein can allow one to perform highly multiplexed reactions to clone many different TCRs (e.g., hundreds to thousands or more different TCRs) directly from single T cells quickly (e.g., simultaneously in some cases) and in a manner that misses few, if any, α/β variable chain combinations (or γ/δ variable chain combinations). For example, the methods and materials provided herein can be performed to clone many different αβ TCRs (e.g., hundreds to thousands or more different αβ TCRs) directly from single αβ T cells in a manner that misses less than 10 percent (e.g., less than 9 percent, less than 8 percent, less than 7 percent, less than 6 percent, less than 5 percent, less than 4 percent, less than 3 percent, less than 2 percent, or less than 1 percent) of the α variable chains and less than 10 percent (e.g., less than 9 percent, less than 8 percent, less than 7 percent, less than 6 percent, less than 5 percent, less than 4 percent, less than 3 percent, less than 2 percent, or less than 1 percent) of the β variable chains possible for α/β variable chain combinations of a species (e.g., mice or human species). Likewise, the methods and materials provided herein can be performed to clone many different γδ TCRs (e.g., hundreds to thousands or more different γδ TCRs) directly from single γδ T cells in a manner that misses less than 10 percent (e.g., less than 9 percent, less than 8 percent, less than 7 percent, less than 6 percent, less than 5 percent, less than 4 percent, less than 3 percent, less than 2 percent, or less than 1 percent) of the γ variable chains and less than 10 percent (e.g., less than 9 percent, less than 8 percent, less than 7 percent, less than 6 percent, less than 5 percent, less than 4 percent, less than 3 percent, less than 2 percent, or less than 1 percent) of the δ variable chains possible for γ/δ variable chain combinations of a species (e.g., mice or human species). In some cases, the methods and materials provided herein can include (a) obtaining a sample of T cells, (b) sorting those T cells into isolated locations (e.g., wells) such that most, if not all, isolated locations (e.g., each well) contain a single T cell, (c) lysing (e.g., simultaneously lysing) the single T cells located in separate isolated locations (e.g., separate wells) to release the RNA of each single T cell, (d) performing (e.g., simultaneously performing) reverse transcription using the released RNA as template, appropriate primers for cDNA synthesis from RNA, and a reverse transcriptase enzyme to produce cDNA within each isolated location (e.g., each well); that cDNA representing the RNA expressed by the single T cell that was located in that isolated location (e.g., well), (e) performing (e.g., simultaneously performing), for each isolated location, a first round amplification reaction (e.g., a first round polymerase chain reaction (PCR)) of a nested amplification procedure (e.g., a nested PCR procedure) using the produced cDNA as template, a first round primer collection (e.g., a first round PCR primer collection), and a polymerase (e.g., Taq polymerase) to produce at least an amplification product containing a nucleic acid sequence of the α variable chain (or γ variable chain) of the TCR of the single T cell of that isolated location and an amplification product containing a nucleic acid sequence of the β variable chain (or δ variable chain) of the TCR of that same single T cell of that same isolated location, (f) performing (e.g., simultaneously performing), for each isolated location, a second round amplification reaction (e.g., a second round PCR) of a nested amplification procedure (e.g., a nested PCR procedure) using the amplification products of the first round amplification reaction as template, a second round primer collection (e.g., a second round PCR primer collection), and a polymerase (e.g., Taq polymerase) to produce at least a first amplification product containing a nucleic acid sequence of the α variable chain (or γ variable chain) of the TCR of the single T cell of that isolated location and a second amplification product containing a nucleic acid sequence of the β variable chain (or δ variable chain) of the TCR of that same single T cell of that same isolated location, and (g) cloning, for each isolated location, the first and second amplification products into an expression vector designed to express a functional TCR having the α/β or γ/δ variable chain combination (or a portion thereof such as the V segments of the α/β or γ/δ variable chain combination) as was present in the single T cell used to generate the amplification products.

The resulting expression vectors can be introduced into cells such that those cells express the cloned TCRs. Such cells and/or the TCRs they express from the introduced expression vectors can be screened to identify TCRs with desired capabilities. For example, cells expressing cloned TCRs that recognize particular antigens (e.g., peptides derived from tumor polypeptides) can be identified, and those cells, the TCR expression vectors they contain, or the cloned TCR constructs can be used for further analysis or for therapeutic applications.

In some cases, expression of cloned TCRs on the surface and expression of functional TCRs can be assessed by introducing the expression vectors provided herein into TCR-negative reporter cells designed to express a measurable marker signal or marker polypeptide once the signaling apparatus of a functional TCR is engaged. In these cases, an antibody designed to non-specifically activate TCRs (e.g., an anti-CD3 antibody) can be used to screen for functional TCRs. In some cases, the cloned TCRs provided herein can be screened for antigen specificity. For example, reporter cells expressing cloned TCRs can be screened for the recognition of particular antigens (e.g., peptides derived from tumor polypeptides). In some cases, primary T cells (e.g., human primary T cells) can be transfected with expression vectors provided herein and screened for antigen specificity via T cell proliferation assays.

The methods and materials provided herein can allow clinicians, medical professionals, laboratory personnel, and researchers to use a collection of T cells having different TCRs to generate collections of expression vectors that express functional versions of those different TCRs that have the same variable chain combinations or portions thereof (e.g., the same α/β variable chain combination or the same γ/δ variable chain combination) as present in original T cells used to generate the collection. Such collections of expression vectors can be obtained quickly, efficiently, inexpensively, and effectively. For example, in some cases, using the methods and materials provided herein, a collection of expression vectors that express functional versions of many different TCRs with authentic variable chain combinations as found in T cells obtained from a mammal (e.g., a human) can be generated within less than 12 days (e.g., from 4 to 11 days, from 5 to 11 days, from 6 to 11 days, from 7 to 11 days, from 8 to 11 days, from 4 to 10 days, from 5 to 10 days, from 6 to 10 days, from 7 to 10 days, from 8 to 10 days, from 4 to 9 days, from 5 to 9 days, from 6 to 9 days, from 7 to 9 days, from 4 to 8 days, from 5 to 8 days, from 6 to 8 days, or from 7 to 8 days), using less than 12 steps (e.g., from 5 to 11 steps, from 6 to 11 steps, from 7 to 11 steps, from 8 to 11 steps, from 5 to 10 steps, from 6 to 10 steps, from 7 to 10 steps, from 8 to 10 steps, from 5 to 9 steps, from 6 to 9 steps, from 7 to 9 steps, or from 8 to 9 steps), for less than about 10 dollars per TCR, and with greater than about 80 percent (e.g., greater than about 85, 90, or 95 percent) effectiveness (based on sorting a single T cell into each of 384 wells of 384-well plate). In some cases, the methods and materials provided herein can be performed without performing nucleic acid sequencing, without performing restriction endonuclease cleavage steps, without performing other steps or techniques as described herein, and/or without using particular reagents or materials as described herein.

The methods and materials provided herein also can allow users to capture successfully most, if not all, functional TCRs from a sorted T cell population. For example, in some cases, the methods and materials provided herein can include a nested amplification procedure (e.g., a nested PCR procedure) that includes primer collections designed to amplify every known functional V segment of the two variable chains of a particular TCR (e.g., any of the known functional V segments of the α variable and β variable chains of a particular αβ TCR or any of the known functional V segments of the γ variable and δ variable chains of a particular γδ TCR) of a mammal (e.g., a human). Having the ability to clone most, if not all, functional TCRs from a sorted T cell population can allow users to identify particular TCRs, including rare TCRs, that might otherwise be missed. It is these rare TCRs that might be missed that could provide a rich source of new cloned TCRs for effective therapies such as cancer therapies involving the delivery of effective T cells.

In some cases, the methods and materials provided herein can allow users to obtain additional information about the single T cells from which functional TCR clones are generated. In some cases, the flow cytometry techniques used for single cell sorting described herein can be used to distinguish activated and experienced cells from naïve T cells by staining those cells for activation markers. When applying the methods and materials provided herein in methods for treating a particular disease (e.g., cancer), T cells can be isolated from a patient that have already been activated and expanded within that patient. Once these T cells are isolated, and cDNA is generated from single cell RNA, an additional level of selection can be applied. For example, in addition to using cDNA produced from the RNA of a single T cell to amplify and clone the variable chains (or portions thereof) of that T cell's TCR, that cDNA also can be used to assess RNA expression and/or RNA expression levels within that T cell.

In the case of $CD8^+$ T cells, TCRs associated with polyfunctional (e.g., multi-cytokine producers) effector cells or TCRs associated with quiescent or exhausted long-lived memory cells can be identified by examining the relative mRNA levels for expression of transcription factors such as Eomesodermin and T-bet (McLane et al., *J. Immunol.*, 190(7):3207-3215 (2013); and Buggert et al., *PLoS Pathog.*, 10(7):e1004251 (2014)).

In some cases, T cells can be stimulated (e.g., in vitro stimulated) prior to sorting, and then RNA expression can be assessed (via, e.g., qPCR) to determine which T cells responded to the stimulation. Any appropriate type of stimulation can be used including, without limitation, non-specific stimulation such as stimulation with concanavalin A, phytohemagglutinin-P, phorbol esters plus ionomycin, phorbol myristate acetate plus calcium ionophores, or antibodies having the ability to cross link TCRs (e.g., anti-CD3 antibodies plus anti-CD28 antibodies, or anti-TCR β antibodies) or antigen-specific stimulation such as stimulation with one or more particular antigens as described elsewhere (Downward et al., *Nature*, 346:719-23 (1990); and Dasgupta et al., *Proc. Natl. Acad. Sci. USA*, 84:1094-8 (1987)). In some cases, cytokine expression levels such as TNF-α, IFN-γ, IL-2, IL-4, IL-5, IL-10, IL-13, or IL-17 expression levels can be determined and compared to non-stimulated populations. Once single T cells are sorted, the methods provided herein can be used to determine which T cells were making particular cytokines in response to the stimulation (e.g., in response to a peptide antigen used to stimulate the T cells). In these cases, antigen specific T cells can be determined without laborious methods of expanding reactive T cells or the destructive methods of paraformaldehyde fixation and intracellular cytokine staining, which can reduce the ability to clone TCRs effectively. In such cases, particular TCRs generated from active and antigen specific T cells, as opposed to inactive bystander, T cells can be quickly identified.

In some cases, cytokine expression levels such as TNF-α, IFN-γ, IL-2, IL-4, IL-5, IL-10, IL-13, or IL-17 expression levels can be determined for the single T cells used to clone functional TCRs, thereby allowing a particular TCR to be identified based on the particular phenotype (e.g., elevated IFN-γ expression) of the T cell that provided the variable chains (or portions thereof) of that particular TCR. In such cases, particular TCRs generated from active, as opposed to inactive, T cells can be quickly identified. In some cases, particular TCRs generated from inactive, as opposed to active, T cells can be quickly identified.

In some cases, the absence of cytokine production by a T cell does not necessarily reflect an absence of TCR specificity. TCR initiated signals to a cell can be subverted and/or repressed by numerous inhibitory co-receptors (Sheppard et al., *FEBS Lett.*, 574(1-3):37-41 (2004); and Yokosuka et al., *J. Exp. Med.*, 209(6):1201-1217 (2012)). In some cases, TCRs can be obtained using T cells refractory to stimulation, and the specificity of the cloned TCR can be tested or screened in cells where canonical TCR signaling is not repressed.

In some cases, a MHC-peptide complex (or HLA-peptide complex) can be used to identify cloned TCRs that recognize such a complex. In these cases, it is possible that clonal exclusion during an immune response and/or a lack of antigen priming may result in TCRs with this specificity not being present in the activated and/or expanded TCR pool. In such cases, the methods and materials provided herein, which in some cases only requires a single T cell to be present, can be used to clone a naïve or inactivated TCR that recognizes such a complex. In some cases, pools of naïve T cells can be stained with MHC-peptide tetramers (or HLA-peptide tetramers), and any MHC-peptide (or HLA-peptide) responsive TCRs among the naïve T cells can be used to clone those TCRs using the methods and materials provided herein.

In general, one aspect of this document features a A method for obtaining a plurality of nucleic acid vectors containing nucleic acid encoding functional T cell receptors. The method comprises, or consists essentially of, (a) obtaining a device comprising a plurality of separate locations, wherein each of the separate locations contains cDNA generated from RNA obtained from a single T cell that was sorted into the separate locations, (b) performing a nested amplification procedure using the cDNA of each of the plurality of separate locations as template to obtain a first amplification product and a second amplification product for the cDNA of each of the plurality of separate locations, wherein the first amplification product comprises nucleic acid encoding a Vα or Vγ segment, and wherein the second amplification product comprises nucleic acid encoding a Vβ or Vδ segment, and (c) assembling the first amplification product and the second amplification product for the cDNA of each of the plurality of separate locations into a nucleic acid vector to obtain an assembled nucleic acid vector for the cDNA of each of the plurality of separate locations, wherein the assembled nucleic acid vectors for the cDNA of each of the plurality of separate locations comprises nucleic acid encoding a functional T cell receptor. The plurality can be greater than 50. The plurality can be greater than 500. The plurality can be greater than 5000. The plurality of nucleic acid vectors can be a plurality of nucleic acid expression vectors. The device can comprise a multi-well plate. The multi-well plate can be a 96-well plate, a 384-well plate, or a 1536-well plate. The cDNA generated from RNA obtained from a single T cell single can comprise cDNA generated from RNA obtained from a single human T cell. The first amplification product can comprise nucleic acid encoding an L sequence of a Vα or Vγ segment. The first amplification product can comprise nucleic acid encoding a Jα or Jγ segment. The first amplification product can comprise nucleic acid encoding a 5' portion of a Cα or Cγ region. The first amplification product can comprise nucleic acid encoding an L sequence of a Vα or Vγ segment, a Jα or Jγ segment, and a 5' portion of a Cα or Cγ region. The second amplification product can comprise nucleic acid encoding an L sequence of a Vβ or Vδ segment. The second amplification product can comprise nucleic acid encoding a Dβ or Dδ segment. The second amplification product can comprise nucleic acid encoding a Jβ or Jδ segment. The second amplification product can comprise nucleic acid encoding a 5' portion of a Cβ or Cδ region. The second amplification product can comprise nucleic acid encoding an L sequence of a Vβ or Vδ segment, a Dβ or Dδ segment, a Jβ or Jδ segment, and a 5' portion of a Cβ or Cδ region. The first amplification product can comprise an adapter sequence added to an amplified template sequence of the cDNA via a second round amplification of the nested amplification procedure. The second amplification product can comprise an adapter sequence added to an amplified template sequence of the cDNA via a second round amplification of the nested amplification procedure. The first amplification product can comprise a first adapter sequence added to an amplified template sequence of the cDNA via a second round amplification of the nested amplification procedure, and the second amplification product can comprise a second adapter sequence added to an amplified template sequence of the cDNA via a second round amplification of the nested amplification procedure, wherein the first and second adapter sequence are different. The functional T cell receptor of each of the assembled nucleic acid vectors can comprise a Vα/Vβ combination or Vγ/Vδ combination as present in the single T cell originating the RNA. The functional T cell receptor of each of the assembled nucleic acid vectors can comprise (a) a full-length α variable region and a full-length β variable region or (b) a full-length γ variable region and a full-length δ variable region. The functional T cell receptor of each of the assembled nucleic acid vectors can comprise (a) a full-length α variable region and a full-length β variable region as present in the single T cell originating the RNA or (b) a full-length γ variable region and a full-length δ variable region as present in the single T cell originating the RNA. The functional T cell receptor of each of the assembled nucleic acid vectors can comprise (a) a full-length α constant region and a full-length β constant region or (b) a full-length γ constant region and a full-length δ constant region. Each of the assembled nucleic acid vectors can comprise a nucleic acid sequence encoding a self-cleaving peptide or an internal ribosome entry site (IRES). The method can comprise sorting single T cells into the separate locations. The method can comprise performing a reverse transcription reaction to obtain the cDNA. The assembling step can comprise seamless cloning. Each of the assembled nucleic acid vectors can be obtained without performing nucleic acid sequencing. Each of the assembled nucleic acid vectors can be obtained without performing a restriction endonuclease cleavage reaction.

Unless otherwise defined, all technical and scientific terms used herein have the same meaning as commonly understood by one of ordinary skill in the art to which this invention pertains. Although methods and materials similar or equivalent to those described herein can be used to practice the invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

The details of one or more embodiments of the invention are set forth in the accompanying drawings and the description below. Other features, objects, and advantages of the invention will be apparent from the description and drawings, and from the claims.

DESCRIPTION OF THE DRAWINGS

FIG. 2B is a schematic of a nested PCR procedure involving the use of two separate pools of forward Vβ primers to produce an amplification product containing a 5' added adapter sequence (AS) followed by the leader (L) sequence of a Vβ segment, a Vβ segment, a Dβ segment, a Jβ segment, and a portion of the 5' end of Cβ, according to one embodiment. In this embodiment, the primers from the pool of forward Vβ primers for the second round of PCR adds the adapter sequence, which can be used to clone the produced amplification product into an expression vector.

FIG. 3B is a schematic of a nested PCR procedure involving the use of one pool of forward Vβ primers and a primer to an adapter sequence to produce an amplification product containing a 5' added adapter sequence (AS) followed by the leader (L) sequence of a Vβ segment, a Vβ segment, a Dβ segment, a Jβ segment, and a portion of the 5' end of Cβ, according to one embodiment. In this embodiment, the primers from the pool of forward Vβ primers used in the first round of PCR adds the adapter sequence, which can be used both as a primer target sequence for the second round and to clone the produced amplification product into an expression vector.

FIGS. 6A-6D show results for RNA extraction, cDNA conversion, and detection of TCR chains down to a single cell level using the hybridoma T cell line 1B9, and also the results for sorting single cells into 384-well PCR plates. FIG. 6A provides the amplification efficiency of GAPDH from serial cell dilutions (10-0.08 cells/well) using SYBR green real time PCR. FIG. 6B shows that the conditions for RNA extraction and cDNA conversion are able to detect the mouse TCR beta chain TRBV17 expressed in the 1B9 hybridoma cell line down to the single cell level using a two-fold serial dilution (10-0.08 cells/well), the forward primer mTRBV17 (SEQ ID NO:251), and reverse primer mTRBCn (SEQ ID NO:273). FIG. 6C shows further confirmation for detection at the single cell level with the use of a glass pipette and a micromanipulator controlled under a microscope. Single cells were plated in a 384-well PCR plate with detection of mTRBV17 in 22 out of 24 wells. FIG. 6D shows the results of the conditions using the BD FACSaria sorter to plate single cells into 384-well PCR plates. Again 22 out of 24 wells tested positive for the detection of the mTRBV17 mouse TCR β chain.

FIG. 9A shows the FACS staining and gating used to isolate of LIVE/CD8 positive T cells isolated from the spleen of a C57/BL6 mouse. The gates were arranged sequential such that the far left panel was the first gate empty and very subsequent panel to the right the population defined by the previous gate. The CD8$^+$CD4$^-$ events as defined in the far right panel were sorted as single cells into two 384-well PCR plates using the FACSaria sorter. RNA was extracted and converted to cDNA in each individual well that contained a single cell for both 384-well PCR plates. First round amplification for the mouse mTRAV and mTRBV sequences was performed in one mixed PCR reaction combining all the primers listed in Table 3 and Table 4 plus reverse primers mTRAC (SEQ ID NO:266) and mTRBC (SEQ ID NO:269). Following the first round amplification, two separate nested PCR reactions were performed: one for the amplification of the mTRAVs using all the primers listed in Table 7 plus reverse primer mTRACn (SEQ ID NO:271), and a second amplification reaction for the amplification of the mTRBVs using all the primers listed in Table 8 plus reverse primer mTRBCn (SEQ ID NO:273). The first 24 wells from each of the two plates were analyzed by ethidium bromide gel electrophoresis (FIG. 9B). For each individual single cell in wells A1-A8, B1-B8, and C1-C8 for both plates, the mTRAV amplification is shown in the top, and the mTRBV amplification is shown in the bottom. mTRAV and mTRBV DNA amplified products exhibited different sizes as they were from a polyclonal T cell population and represent variants from the whole T cell repertoire.

FIGS. 11A-F. Wild-type female C57Bl/6 mice were vaccinated with H60 peptide (LTFNYRNL; SEQ ID NO:278) or OVA peptide (SINFEKL; SEQ ID NO:279) conjugated to an anti-DEC205 antibody as described elsewhere (Li et al., *Blood*, 118:5965-76 (2011)). (A) Splenocytes from a single H60 vaccinated mouse stained with H60-MHC 1 tetramer. The plot was gated on Live, CD8$^+$, TCR$^+$, and CD4$^-$ cells. Single CD44$^{hi}$ tetramer$^+$ cells (as defined by the gate drawn on the plot) were sorted into the individual wells of a 384-well plate, and the α and β TCR chains were amplified via nested PCR. The first round of amplification was carried out using all the primers in Table 3 and Table 4 combined with TCRα and TCRβ directed reverse primers (SEQ ID NO:266 and SEQ ID NO:269, respectively). For the second round, a portion of the first round PCR product was used to amplify TCRα or TCRβ chains in two separate reactions using a multiplex of all the primers included in Table 7 plus a reverse primer (SEQ ID NO:271) in one reaction and all the primer listed in Table 8 plus a reverse primer (SEQ ID NO:273) in the other reaction. (B) Splenocytes from a single OVA vaccinated mouse stained with OVA-MHC 1 tetramer. The plot was gated on Live, CD8$^+$, and TCR$^+$ cells. Single CD44$^{hi}$ tetramer$^+$ cells (as defined by the gate drawn on the plot) were sorted into the individual wells of a 384-well plate, and the α and β TCR chains were amplified via nested PCR. The first round of amplification was carried out using all the primers in Table 3 and Table 4 combined with TCRα and TCRβ directed reverse primers (SEQ ID NO:266 and SEQ ID NO:269, respectively). For the second round, a portion of the first round PCR product was used to amplify TCRα or TCRβ chains in two separate reactions using a multiplex of all the primers included in Table 7 plus a reverse primer (SEQ ID NO:271) in one reaction and all the primer listed in Table 8 plus a reverse primer (SEQ ID NO:273) in the other reaction. (C) To confirm that the methods can identify clonally distinct populations, the α (data not shown) and β chains from individual wells were sequenced using sanger sequencing. For the H60 vaccinated mice, 198 TCR$^+$ wells were sequenced, representing cells from two mice. For the OVA vaccinated mice, 54 TCR$^+$ wells were sequenced, representing cloned TCRs from four mice. The TRBV usage alone indicates that these methods can be used to isolate clonally distinct populations. Based on the sequencing results, five unique TCR pairs were selected from the amplification of H60-specific TCR pairs. These TCR pairs were cloned into retroviral vectors using seamless cloning techniques, and the ability of these vectors to express TCR on the surface of a cell was assessed using 58$^{-/-}$ TCR$^{-/-}$ hybridomas. The TCR viral vector used was constructed using a TRBV2 sequence and TRAV13D-2 sequence cloned from a single T cell. Following infection with the TCR-expressing virus, the cells were stained with anti-Vβ4 (the gene product of TRBV2) and assessed by flow cytometry. (D) Uninfected 58$^{-/-}$ TCR$^{-/-}$ hybridomas stained with anti-Vβ4 and assessed for the expression of the Tdtomato gene. (E) Cells infected with TRBV15-expressing virus and stained with anti-Vβ4 and assessed for expression of the Tdtomato gene. (F) Cells infected with TRBV2-expressing virus and stained with anti-Vβ4 and assessed for expression of the Tdtomato gene.

FIGS. 12A–B. The TCR$^{-/-}$ 4G4 hybridoma cells line is a cell line transfected with the NFAT-RE Luciferase plasmid (Clipstone et al., Nature, 357:695-7 (1992)). (A) TCR αβ- and eGFP-expressing viral constructs were assembled using seamless cloning techniques, and the retroviruses were generated using PLAT-E cells. 4G4 cells were infected with the TCR retrovirus, and 24 hours later TCR β expression and eGFP expression were assessed by flow cytometry. Uninfected cells (left panel) expressed no GFP and did not stain for TCRβ. Infected cultures contained cells that expressed both TCRβ and eGFP (upper right quadrant of right panel). (B) Infected or uninfected cell cultures were placed into culture with plate bound anti-CD3 antibodies for a period of 3.5 hours. The relative light units (RLUs) produced by the TCR expressing culture (Infected) was compared the to the RLU of cells that were not infected (Unifected).

FIG. 22 is a schematic illustrating a fragment b nucleotide sequence (SEQ ID NO: 337). Approximate regions of homology (overlap) to the amplicons are shown. FIG. 22 also discloses SEQ ID NO: 456.

FIG. 23 is a schematic illustrating the Cβ nucleotide sequence (SEQ ID NO: 457) in the acceptor vector pMIGII.

DETAILED DESCRIPTION

Figure 1:
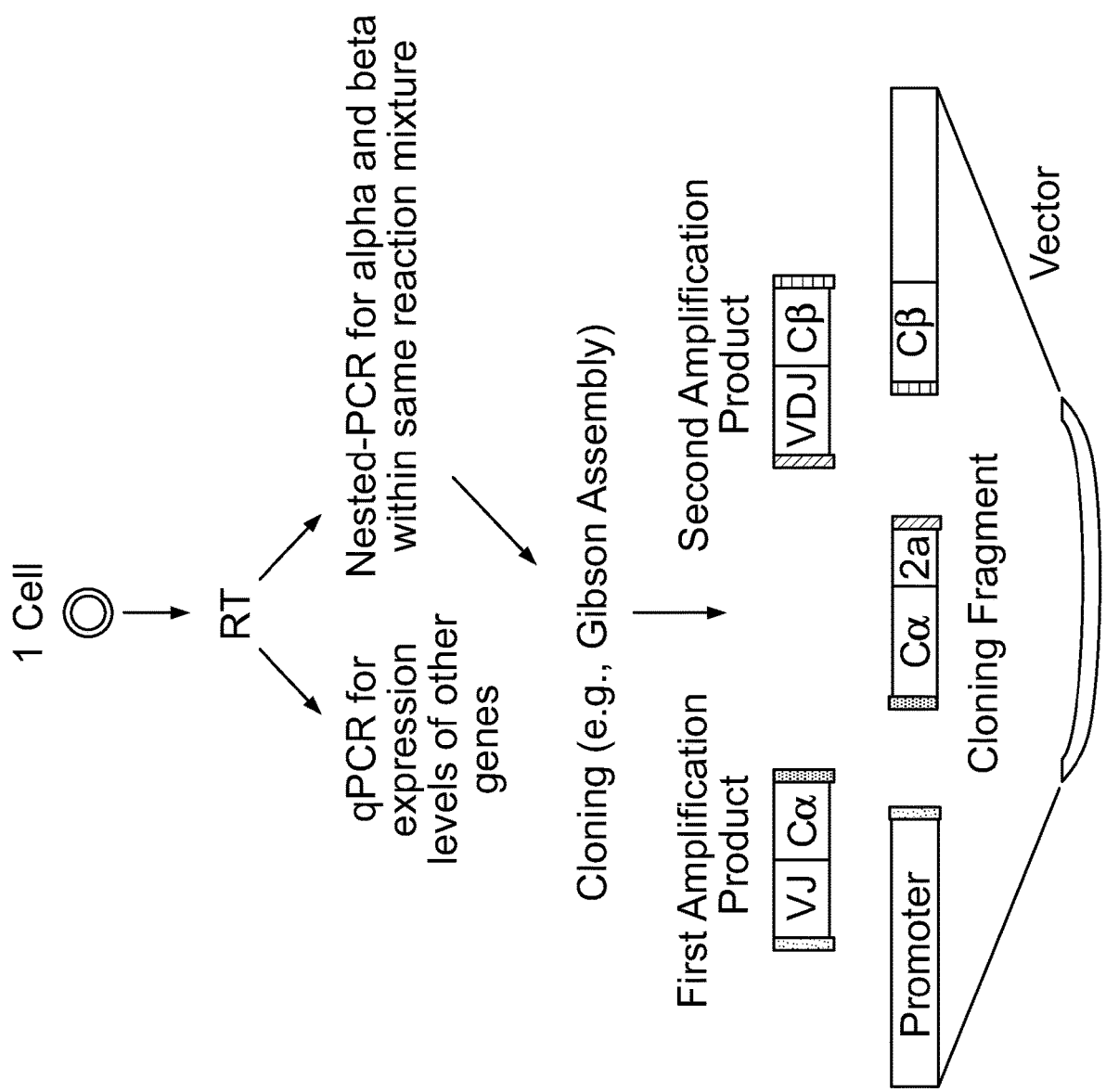
FIG. 1 is a general overview schematic of a TCR cloning method going from a single T cell to an expression vector, according to one embodiment.

This document provides methods and materials involved in cloning functional TCRs from single T cells. For example, this document provides methods and materials for obtaining nucleic acid encoding a TCR from a single T cell and arranging that nucleic acid to form nucleic acid vectors successfully designed to express a TCR (e.g., a fully intact TCR such as a fully intact TCR having the variable chain combination as present in that single T cell). In general, a method for cloning a functional TCR from a single T cell can include the steps of sorting T cells into separate locations, lysing the single T cells to release RNA, performing reverse transcription to produce cDNA from the released RNA, performing a nested amplification reaction to generate a first amplification product for the Vα (or Vγ) of each single T cell and a second amplification product for the Vβ (or Vδ) of each single T cell within the same nested amplification reaction mixture for each single cell, and cloning the first and second amplification products into an expression vector (FIG. 1). In some cases, a portion of the cDNA from the reverse transcription step can be used to perform amplification reactions (e.g., PCR or quantitative PCR (qPCR)) to detect the presence, absence, or amount of expression of other genes (e.g., IFNγ) by the single T cells (FIG. 1).

Any type of T cell can be obtained and used as described herein to generate an expression vector designed to express a functional TCR. For example, cytotoxic T lymphocytes (CTLs), regulatory T cells ($T_{regs}$), helper T cells, tumor-infiltrating T lymphocytes (TILs), naïve T cells, activated T cells, memory T cells, T cells with known antigen specificity, T cells with unknown antigen specificity, expanded populations of MHC class I-restricted T cells, expanded populations of MEW class II-restricted T cells, or combinations thereof can be obtained and used as described herein to generate expression vectors designed to express functional TCRs. In some cases, a sample containing a mixture of different types of T cells (e.g., a mixture of MEW class I-restricted T cells and MHC class II-restricted T cells) can be obtained and used as described herein to obtain expression vectors designed to express functional TCRs.

In addition, any appropriate sample containing live T cells can be used to obtain T cells that can be used as described herein. Examples of samples containing T cells that can be used as described herein to generate expression vectors designed to express functional TCRs include, without limitation, blood samples, peripheral blood mononuclear cell (PBMC) samples, isolated lymphocyte samples, tissue samples (e.g., skin, lymph node samples, mucosal tissue, viral lesions within skin or mucosal tissue, or tumor samples), cell culture samples (e.g., cell culture samples of T cell lines such as Jurkat cells, 1301 cells, or T cell leukemia lines), samples of T cells expand ex vivo to specific antigens or vaccines, and samples from tissue of recently deceased mouse or human cadavers. Examples of tissue samples that can be used as a source of T cells for the methods described herein include, without limitation, lymph node samples, tumor samples, thymus samples, bone marrow samples, gut biopsy samples, lung biopsy samples, renal biopsy samples, and organ transplant biopsy samples. Any appropriate type of tumor sample can be used as a source of T cells for the methods described herein including, without limitation, breast tumor samples, prostate tumor samples, colon cancer samples, lung cancer samples, melanoma samples, and pancreatic cancer samples. In some cases, a sample containing T cells can be obtained from a site of inflammation, a site of tissue rejection, a site of infection, a site of disease, a site of an immune response, a site of autoimmune infiltration, a site of an allergic reaction, a site of a tumor, or a site of transplant reaction. When using a tissue sample such as a tumor sample, the tissue sample (e.g., tumor sample) can be obtained from a mammal (e.g., a human) and disrupted or digested to form a cell suspension that includes T cells. In some cases, a tissue sample (e.g., a tumor sample) can be obtained from a mammal (e.g., a human) that was treated with a therapeutic vaccine with or without being subjected to an immune-modulatory therapy to obtain a population of antigen specific T cells from that tissue sample (e.g., from that tumor sample).

In some cases, to obtain TILs, tissue obtained from a resected solid tumor and/or tumor biopsy can be digested to form a single cell suspension. The single cell suspension can be stained for T cell specific markers and/or tumor associated cell characteristics to distinguish T cells from tumor cells. Tumor specific surface markers can be selected based on the tumor subtype (e.g., the surface protein Met-72 can be used for certain melanomas). In some cases, the Vybrant® DyeCycle™ reagents to determine cell cycle and/or stains such as 7AAD staining for cellular DNA content, propidium iodide staining, and/or Hoechst staining for DNA content can be used (Loken, *Cytometry*, 1(2):136-142 (1980); and Schmid and Sakamoto, *Curr. Protoc. Cytom.*, Chapter 7: Unit 7 16 (2001)). In some cases, tumor cells can be identified by the absence of immune cell associated surface proteins such as an absence of CD45, CD4, CD8, TCR (3, CD11b, CD19, or combinations thereof. The distinguished T cells and tumor cells can be sorted, and the TCRs cloned from the T cells as described herein. In some cases, the sorted tumor cells can be isolated and further analyzed (e.g., sequenced). This dual sorting system can allow one to obtain genetic information from both tumor cells and the associated TILs, concurrently.

In some cases, microdissection techniques such as laser microbeam microdissection (LMM), laser pressure catapulting (LPC), micro dissection of membrane mounted tissue (MOMeNT), or laser capture microdissection (LCM) can be used to separate T cells from other cells (e.g., tumor cells or diseased tissue) as described elsewhere (Pinzani et al., *Mol. Aspects Med.*, 27:140-59 (2006); and Tjernlund et al., *PloS One*, 11:e0149907 (2016)).

In some cases, a sample containing T cells for use in the methods provided herein can be a sample of freshly isolated T cells that were not expanded to generate clones of T cells.

The T cells used as described herein to generate expression vectors designed to express functional TCRs can be from any appropriate mammal. For example, T cells from humans, monkeys, horses, bovine species, pigs, dogs, cats, rats, or mice can be used as described herein to generate expression vectors designed to express functional TCRs.

Once T cells are obtained, they can be sorted into separate locations of, for example, a container such as a multi-well plate in a manner that places a single T cell into a single location (e.g., one T cell/well). Any appropriate cell sorting method can be used to sort single T cells into separate locations. For example, a T cell population can be stained with particular fluorescent agents that bind to specific markers and single-cell-sorted into separate wells of a multi-well plate using a cell sorter. In some cases, fluorescent agents such as carboxyfluorescein succinimidyl ester (CFSE), fluorescently-labeled antibodies (e.g., fluorescently-labeled anti-CD3 antibodies, fluorescently-labeled anti-CD4 antibodies, fluorescently-labeled anti-CD8 antibodies, fluorescently-labeled anti-CD69 antibodies, fluorescently-labeled anti-CD40L antibodies, fluorescently-labeled anti-CD44 antibodies, or fluorescently-labeled anti-CD62L antibodies), fluorescently-labeled peptide-tetramer complexes (e.g., fluorescently-labeled tumor antigen-tetramer complexes), or combinations thereof can be used to stain T cells for cell sorting. For example, fluorescently-labeled anti-CD3 antibodies (e.g., fluorescein-labeled anti-CD3 antibodies such as FITC-OKT3) and fluorescently-labeled anti-CD8 antibodies (e.g., phycoerythrin-labeled anti-CD8 antibodies such as PE-SK1) can be used to stain $CD8^+$ T cells such that single $CD8^+$ T cells can be sorted into separate locations. Examples of fluorescent labels that can be used during cell sorting include, without limitation, fluorescein, phycoerythrin, Cy3, Cy5, Rhodamine, Alexa 488, and Brilliant Violet.

In some cases, one or more fluorescent agents (e.g., fluorescently-labeled antibodies) other than those designed and used to help identify and sort T cells (e.g., $CD3^+$ T cells) or particular types of T cells (e.g., $CD4^+$ or $CD8^+$ T cells) can be included during the sorting process to provide additional information about the phenotype of the sorted T cells even though the fluorescent signals from those fluorescent agents may or may not be used to sort the T cells. For example, fluorescent agents that bind to surface proteins or markers such as PD-1, TIM3, LAG3, CD28, CD152, CD44, CD69, CD107a, CD11b, CD62L, CD127, CD30, CD27, or CD45RA/CDR45O can be used to capture expression information about those surface proteins or markers by each sorted T cell. Since the specific location of each single sorted T cell is known, then the levels of each fluorescent signal for each of those particular sorted T cells are also known and can be associated with the T cell that produced them. For example, during a cell sorting process using fluorescently-labeled anti-CD3 antibodies, fluorescently-labeled anti-CD8 antibodies, fluorescently-labeled anti-CD28 antibodies, and fluorescently-labeled anti-CD152 antibodies, florescent signals from all four antibodies can be captured and assigned to the cell generating those signals with the signals from the anti-CD3 and anti-CD8 antibodies being used to identify the cell as being a $CD3^+/CD8^+$ T cell so that that T cell can be sorted into a particular separate location of a container. In this case, the fluorescent level of all four markers, even though two (i.e., the CD28 and CD152 markers) were not used for the actual sorting, can be assigned to the T cell that generated those signals.

This expression information obtained at the time of sorting T cells into separate locations (e.g., wells) can provide important information about the single-cell-sorted T cells. For example, with this information, expression vectors expressing TCRs that are generated as described herein from, for example, $CD28^+$ T cells can be selected after being constructed based on the fluorescent signals from fluorescently-labeled anti-CD28 antibodies during the earlier sorting process even though $CD28^+$ expression was not used as a criterion for sorting (e.g., $CD28^+$ and $CD28^-$ T cells were both single-cell-sorted during the sorting process). In some cases, CD45RO can be used as a marker to identify naïve T cells, and CD45RA can be used as a marker to identify primed T cells (e.g., primed human T cells).

In some cases, the presence (or absence) of staining from any particular fluorescent agent can be used as a criterion for sorting, in which case each of the expression vectors expressing a TCR generated from those sorted single T cells will be from a T cell positive (or negative) for the marker of that fluorescent agent. For example, when using the presence of $CD28^+$ staining as a criterion for sorting, each of the expression vectors expressing a TCR is expressing a TCR that was generated from a single $CD28^+$ T cell. In such cases, information about the particular degree of staining (e.g., degree of $CD28^+$ staining) can be associated with each single T cell sorted and used, even though that marker was used as a sorting criterion. This information is useful when assessing the functional attributes of the cloned TCRs.

Any appropriate container can be used when sorting T cells during the methods described herein. For example, multi-well plates such as 96-well plates, 384-well plates, 1536-well plates, or microtubes can be used. In some cases, a container can be designed to hold individual drops that are spatially separated from each other, thereby forming the separate locations where each drop contains a single T cell (e.g., 1 T cell/drop). For example, single T cells can be sorted into individual drops on a surface (e.g., a flat surface) as described elsewhere (Kanz et al., *Cytometry*, 7:491-4 (1986)).

In some cases, an individual TCR cloning procedure can be performed as described herein using one or more than one multi-well plate. For example, two or more (e.g., 5, 10, 15, 20, 25, 30, 35, 40, 45, 50, or more) 384-well plates or 1536-well plates can be used to clone TCRs from single T cells obtained from a single source (e.g., from one human) using the methods described herein. Though not as desirable, in some cases, sorting single T cells into separate locations may result in some separate locations (e.g., some separate wells) having two or more T cells. The locations with potentially more than a single T cell can remain within the cloning process as about 25 percent of the products derived from two cells can reconstruct the authentic TCR of at least one starting cell and can be identified in a subsequent screening process.

Any appropriate cell sorter can be used to sort T cells during the methods described herein. Examples of cell sorters that can be used include, without limitation, a BD FACSAria II sorter, a BD FACSAria III sorter, a MOFLO XDβ sorter, a MOFLO Astrios EQ sorter, a Sony iCyt SY3200 Cell Sorter, and a Sony SH800S Cell Sorter. When sorting T cells, the volume of an aerosolized droplet containing the sorted T cell can be from about 1 nL to about 4 nL, and the droplet containing the sorted T cell can be collected in a volume of fluid ranging from about 0.1 μL to about 5 (e.g., from about 0.5 μL to about 5 μL, from about 1 μL to about 5 μL, from about 2 μL to about 5 μL, from about 0.5 μL to about 4 μL, from about 0.5 μL to about 3 μL, from about 0.5 μL to about 2 μL, or from about 0.5 μL to about 1 μL).

Once the T cells are sorted (e.g., 1 T cell/well), the single T cells can be lysed to release the RNA of each T cell. Any appropriate method can be used to lyse single T cells that were sorted into separate locations. For example, sonication, one or more freeze/thaw cycles, treatment with one or more cell lysis agents, heating, osmotic stress, enzymatic digestion, or combinations thereof can be used to lyse single T cells to release RNA.

After releasing the RNA for the single T cells, reverse transcription can be performed to generate cDNA from the released RNA. Any appropriate set of primers can be used with the RNA as template to generate cDNA from the released RNA. In some cases, random oligomers can be used to generate cDNA from RNA released from the single T cells. Examples of random oligomers that can be used as primers to generate cDNA from the released RNA include, without limitation, random hexamer primers, random nonamer primers, random decamer primers, or random pentadecamer primers. In some cases, poly-T primers (e.g., oligo (dT)$_{18}$ (SEQ ID NO: 442) primers) can be used to generate cDNA from the released RNA. In some cases, primers specific for RNA encoding TCRs can be used alone or together with primers specific for RNA encoding other polypeptides to generate cDNA from the released RNA. For example, primers specific for RNA encoding TCRs can be used together with primers specific for RNA encoding any of the other polypeptides whose expression or expression level is being assessed (e.g., TNF-α, IFN-γ, IL-2, IL-4, IL-5, IL-10, IL-13, or IL-17).

Any appropriate reverse transcriptase enzyme can be used to perform reverse transcription to generate cDNA from the released RNA. Examples of reverse transcriptase enzymes that can be used as described herein included, without limitation, avian myeloblastosis virus (AMV) reverse transcriptases (available commercially from Promega) and Moloney murine leukemia virus (MMLV) reverse transcriptases such as Superscript III, Superscript IV (available commercially both from ThermoFisher Scientific), iScript (available commercially from Biorad), and Accuscript HiFi (available commercially from Agilent). Other ingredients for performing reverse transcription can include, without limitation, dNTPs, non-denaturing detergents (e.g., IGEPAL CA-630), RNase inhibitors such as RNasin (commercially available from Promega), and RNase OUT (commercially available from ThermoScientific).

A reverse transcription reaction provided herein can include an optional step of heating the RNA to a temperature from about 55° C. to about 75° C. (e.g., from about 60° C. to about 70° C., from about 62° C. to about 68° C., or from about 64° C. to about 66° C.) for a period of time from about 2 minutes to about 10 minutes (e.g., from about 2 minutes to about 8 minutes, from about 3 minutes to about 7 minutes, or from about 4 minutes to about 6 minutes). In some cases, a reverse transcription reaction can include a step of heating the RNA to about 65° C. for about 5 minutes. This heating step can be performed using the RNA in the presence of one or more ingredients involved in a reverse transcription reaction (e.g., primers, dNTPs, a non-denaturing detergent, or a combination thereof). In some cases, a heating step can be performed with all the needed ingredients involved in a reverse transcription reaction except the reverse transcriptase enzyme. After performing an optional heating step, the samples can be placed on ice for primer binding.

A reverse transcription reaction provided herein can be performed by contacting the RNA with a reverse transcriptase enzyme in the presence of primers, dNTPs, and optionally a detergent (e.g., a non-denaturing detergent) at a temperature from about 30° C. to about 55° C. (e.g., from about 35° C. to about 50° C., from about 37° C. to about 47° C., or from about 40° C. to about 45° C.) for a period of time from about 20 minutes to about 90 minutes (e.g., from about 25 minutes to about 80 minutes, from about 30 minutes to about 60 minutes, or from about 35 minutes to about 45 minutes). In some cases, a reverse transcription reaction can be performed at about 42° C. for about 40 minutes.

In some cases, high quality cDNA can be generated in a high throughput and effective manner from RNA obtained from single T cells using the methods and materials described herein. For example, in one embodiment, high quality cDNA can be generated in a high throughput and effective manner from RNA obtained from single T cells by quickly lysing each single T cell and performing a reverse transcription reaction as described herein. In some cases, the resulting cDNA generated from a single T cell can be of such high quality that a portion (e.g., about 75 percent or less, about 50 percent or less, about 25 percent or less, about 10 percent or less, from about 75 percent to about 10 percent, from about 75 percent to about 25 percent, from about 75 percent to about 50 percent, from about 60 percent to about 40 percent, from about 50 percent to about 10 percent, or about 50 percent of the final total cDNA reaction mixture) can be used to continue with the nested amplification and cloning steps to obtain expression vectors expressing a functional TCR having the variable chain combination (or at least the Vα segment and Vβ segment combination or at least the Vγ segment and Vδ segment combination) as present in that single T cell successfully.

In some cases, one or more of the ingredients used to perform a nested amplification reaction described herein can be added the reaction mixtures for the reverse transcription reactions before, during, or after performance of the reverse transcription reactions. For example, a reverse transcription reaction can be performed as described herein in the presence of a primer collection for a first round of a nested amplification reaction described herein, in the presence of a primer collection for a second round of a nested amplification reaction described herein, in the presence of a polymerase enzyme designed for thermal cycling (e.g., Taq polymerase), or in the presence of a combination thereof.

In some cases, a reverse transcription reaction can be performed as described herein to completion in the absence of one or more ingredients used to perform a nested amplification reaction described herein. For example, a reverse transcription reaction can be performed as described herein to completion in the absence of a primer collection for a first round of a nested amplification reaction described herein, in the absence of a primer collection for a second round of a nested amplification reaction described herein, in the absence of a polymerase enzyme designed for thermal cycling (e.g., Taq polymerase), or in the absence of a combination thereof.

When only using a portion of the generated cDNA to continue with the nested amplification and cloning steps to obtain expression vectors expressing functional TCRs having the variable chain combinations (or at least the Vα segment and Vβ segment combinations or at least the Vγ segment and Vδ segment combinations) as present in the single T cells as described herein, the remaining cDNA (or a portion of the remaining cDNA) generated from RNA obtained from single T cells can be used to obtain other important information about the phenotype of the single T cells via techniques such as PCR to detect the presence or absence of gene expression or techniques such as qPCR to detect the levels of gene expression. For example, a portion of cDNA generated from a single T cell (e.g., about 75 percent or less, about 50 percent or less, about 25 percent or less, about 10 percent or less, from about 75 percent to about 10 percent, from about 75 percent to about 25 percent, from about 75 percent to about 50 percent, from about 60 percent to about 40 percent, from about 50 percent to about 10 percent, or about 50 percent of the final total cDNA reaction mixture) can be used to detect the presence, absence, or amount of RNA expression exhibited by single-cell-sorted T cells. The expression (or lack thereof) for any particular RNA can be assessed as described herein for single-cell-sorted T cells. For example, the presence, absence, or amount of RNA encoding a polypeptide such as a cytokine (e.g., TGF-β, TNF-α, IFN-γ, EBI3, p40, p35, IL-2, IL-4, IL-5, IL-6, IL-10, IL-13, or IL-17), a receptor (e.g., CD3, CD25, CD27, CD28, CD30, CD40L, CD122, CXCR3, CXCR6, CCR5, CCR6, CCR7, FASL, LFA-1, ICOS, CTLA-4, PD-1, LAG3, Tim-3, or VLA-4), a transcription factor (e.g., RORyT, FOXP3, FOXO1, RUNX1, T-bet, Eomesdermin, Gata-3, Bcl-2, Bcl-6, BIM, Blimp-1, or p53), an enzyme (e.g., granzyme A, granzyme B, a DNA methyltransferase, or histone/protein deacetylase (HDAC) such as HDAC1 or HDAC9), a suppresser of cytokine signaling (e.g., SOCS1 or SOCS9), an inhibitor of kappa B kinase, or a chemokine (e.g., CCL2/MCβ-1, CCL3/MIP-1α, CCL4, CCL5/RANTES, CCL6, CXCL12, or CXCL16) can be determined for a single T cell. In some cases, the presence, absence, or amount of a microRNA (e.g., miRNA-17, miRNA-31, miRNA-139, or miRNA-150 can be determined for a single T cell as described herein. In some cases, the presence, absence, or amount of RNA expression assessed for single T cells as described herein can be used to identify particular single T cells as having a desirable phenotype. For example, single T cells can be identified as being activated by detecting the presence or amount of IL-2 or IFN-γ RNA expression.

Any appropriate technique can be used to detect the presence or absence of RNA expression for particular RNAs using cDNA generated from single T cells as described herein. For example, PCR, real-time PCR, or PCR including the use of fluorescent probes (e.g., SYBR green) or Taqman probes can be used to detect the presence or absence of RNA expression of particular RNAs. Likewise, any appropriate technique can be used to detect the amount of RNA expression for particular RNAs using cDNA generated from single T cells as described herein. For example, qPCR can be used to detect the amount of RNA expression of particular RNAs.

Several targets can be pre-amplified or amplified directly from the cDNA and analyzed simultaneously using specific primer pairs and/or Taqman probes labeled with a fluorescent dye such as FAM, TET, HEX, JOE, Cy3, TAMRA, Rox, LCRed, Texas Red, LC640, or Cy5 and a quencher such as BHQ1, BHQ2, BHQ3, TAMARA, DABCYL, or Iowa Black FQ. In some cases, quantification of the expression levels of target mRNAs can be normalized against one or more reference nucleic acids. Examples of reference nucleic acids that can be used for normalization include, without limitation, ACTB, ALAS1, B2M, GAPDH, HBB, HMBS, HPRT1, IPO8, PGK1, PPIA, RPLP0, RPL13A, SDHA, TBP, TFRC, YWHAZ, and 18S. Software such as Norm-Finder can be used for the identification of stable nucleic acids that can be used for normalization.

All or a portion (e.g., about a quarter, about a third, about a half, about two-thirds, or about three-fourths) of the cDNA generated from the RNA obtained from single T cells can be used to perform a nested amplification reaction (e.g., nested PCR) designed to generate at least two amplification products within a single reaction mixture (FIG. 1). The first amplification product can include the V segment of an α chain (Vα) or the V segment of a γ chain (Vγ) for a single αβ or γδ T cell, respectively, and the second amplification product can include the V segment of an β chain (Vβ) or the V segment of a δ chain (Vδ) for that same single αβ or γδ T cell. In some cases, the first and second amplification products can encode the full-length V segments as they were present in the single T cell that provided the source RNA. For example, a human αβ T cell having a TCR with a Vα1.2 segment and a Vβ11.3 segment can be sorted into a separate well and lysed to release the T cell's RNA. That RNA can be used to generate cDNA via reverse transcription, and that generated cDNA can be used as template in a nested amplification reaction to create a first amplification product that includes a nucleic acid sequence encoding the full-length Vα1.2 segment as present in that human αβ T cell and a second amplification product that includes a nucleic acid sequence encoding the full-length Vβ11.3 segment as present in that human αβ T cell.

In some cases, the first amplification product of a nested amplification reaction provided herein can include the V and J segments of an α chain (VαJα or VJα) or the V and J segments of a γ chain (VγJγ or VJγ) for a single αβ or γδ T cell, respectively. For example, the first amplification product can encode the full-length Vα and Jα segments as they were present in the single αβ T cell that provided the source RNA, or the first amplification product can encode the full-length Vγ and Jγ segments as they were present in the single γδ T cell that provided the source RNA. In some cases, the first amplification product of a nested amplification reaction provided herein can include the leader (L) sequence and the V and J segments of an α chain (L-VαJα or L-VJα) or the L sequence and the V and J segments of a γ chain (L-VγJγ or L-VJγ) for a single αβ or γδ T cell, respectively. For example, the first amplification product can encode the full-length L sequence and the full-length Vα and Jα segments as they were present in the single αβ T cell that provided the source RNA, or the first amplification product can encode the full-length L sequence and the full-length Vγ and Jγ segments as they were present in the single γδ T cell that provided the source RNA.

In some cases, the first amplification product of a nested amplification reaction provided herein can include the V and J segments and at least a portion of the constant (C) region of an α chain (VαJαCα or VJCα) or the V and J segments and at least a portion of the C region of a γ chain (VγJγCγ or VJCγ) for a single αβ or γδ T cell, respectively. For example, the first amplification product can encode the full-length Vα and Jα segments and a least a portion of Cα as they were present in the single αβ T cell that provided the source RNA, or the first amplification product can encode the full-length Vγ and Jγ segments and a least a portion of Cγ as they were present in the single γδ T cell that provided the source RNA.

In some cases, the first amplification product of a nested amplification reaction provided herein can include the L sequence, the V and J segments, and at least a portion of the C region of an α chain (L-VαJαCα or L-VJCα) or the L sequence, the V and J segments, and at least a portion of the C region of a γ chain (L-VγJγCγ or L-VJCγ) for a single αβ or γδ T cell, respectively. For example, the first amplification product can encode the full-length L sequence, the full-length Vα and Jα segments, and a least a portion of Cα as they were present in the single αβ T cell that provided the source RNA, or the first amplification product can encode the full-length L sequence, the full-length Vγ and Jγ segments, and a least a portion of Cγ as they were present in the single γδ T cell that provided the source RNA. Examples of a first amplification product encoding the full-length L sequence, the full-length Vα and Jα segments, and a least a portion of Cα are shown on the bottom panels of FIGS. 2A and 3A.

In some cases, the second amplification product of a nested amplification reaction provided herein can include the V and D segments of an β chain (VβDβ or VDβ) or the V and D segments of a δ chain (VδDδ or VDδ) for a single αβ or γδ T cell, respectively. For example, the second amplification product can encode the full-length Vβ and Dβ segments as they were present in the single αβ T cell that provided the source RNA, or the second amplification product can encode the full-length Vδ and Dδ segments as they were present in the single γδ T cell that provided the source RNA. In some cases, the second amplification product of a nested amplification reaction provided herein can include the V, D, and J segments of an β chain (VβDβjβ or VDJβ) or the V, D, and J segments of a δ chain (VδDδJδ or VDJδ) for a single αβ or γδ T cell, respectively. For example, the second amplification product can encode the full-length Vβ, Dβ, and Jβ segments as they were present in the single αβ T cell that provided the source RNA, or the second amplification product can encode the full-length Vδ, Dδ, and Jδ segments as they were present in the single γδ T cell that provided the source RNA. In some cases, the second amplification product of a nested amplification reaction provided herein can include the L sequence and the V, D, and J segments of an β chain (L-VβDβJβ or L-VDJβ) or the L sequence and the V, D, and J segments of a δ chain (L-VδDδJδ or L-VDJδ) for a single αβ or γδ T cell, respectively. For example, the second amplification product can encode the full-length L sequence and the full-length Vβ, Dβ, and Jβ segments as they were present in the single αβ T cell that provided the source RNA, or the second amplification product can encode the full-length L sequence and the full-length Vδ, Dδ, and Jδ segments as they were present in the single γδ T cell that provided the source RNA.

In some cases, the second amplification product of a nested amplification reaction provided herein can include the V, D, and J segments and at least a portion of the C region of a β chain (VβDβJβCβ or VDJCβ) or the V, D, and J segments and at least a portion of the C region of a δ chain (VδDδJδCδ or VDJCδ) for a single αβ or γδ T cell, respectively. For example, the second amplification product can encode the full-length Vβ, Dβ, and Jβ segments and a least a portion of Cβ as they were present in the single αβ T cell that provided the source RNA, or the second amplification product can encode the full-length Vδ, Dδ, and Jδ segments and a least a portion of Cδ as they were present in the single γδ T cell that provided the source RNA.

In some cases, the second amplification product of a nested amplification reaction provided herein can include the L sequence, the V, D, and J segments, and at least a portion of the C region of an β chain (L-VβDβJβCβ or L-VDJCβ) or the L sequence, the V, D, and J segments, and at least a portion of the C region of a δ chain (L-VδDδJδCδ or L-VDJCδ) for a single αβ or γδ T cell, respectively. For example, the second amplification product can encode the full-length L sequence, the full-length VP, DP, and Jβ segments, and a least a portion of Cβ as they were present in the single αβ T cell that provided the source RNA, or the second amplification product can encode the full-length L sequence, the full-length Vδ, Dδ, and Jδ segments, and a least a portion of Cδ as they were present in the single γδ T cell that provided the source RNA. Examples of a second amplification product encoding the full-length L sequence, the full-length VP, DP, and Jβ segments, and a least a portion of Cβ are shown on the bottom panels of FIGS. 2B and 3B.

In some cases, the first and/or second amplification products of a nested amplification reaction provided herein can start from the ATG start site of the L sequence and proceed downstream into the L sequence. Examples of this are shown on the bottom panels of FIGS. 2A and 2B.

In some cases, the first and/or second amplification products of a nested amplification reaction provided herein can include a portion of the 5' untranslated region located upstream of a L sequence as that portion was present in the single T cell that provided the source RNA. Examples of this are shown on the bottom panels of FIGS. 3A and 3B. When including a portion of the 5' untranslated region located upstream of a L sequence within the first and/or second amplification products of a nested amplification reaction provided herein, any appropriate length of the 5' untranslated region can be included starting with the nucleotide preceding the ATG start site of the L sequence and working upstream. For example, from zero nucleotides to about 100 or more nucleotides (e.g., from zero nucleotides to 100 nucleotides, from zero nucleotides to 50 nucleotides, from zero nucleotides to 25 nucleotides, from zero nucleotides to 10 nucleotides, from zero nucleotides to 5 nucleotides, from zero nucleotides to 3 nucleotides, from 3 nucleotides to 100 nucleotides, from 3 nucleotides to 50 nucleotides, from 3 nucleotides to 25 nucleotides, from 3 nucleotides to 10 nucleotides, from 3 nucleotides to 5 nucleotides, from 5 nucleotides to 100 nucleotides, from 5 nucleotides to 50 nucleotides, from 5 nucleotides to 25 nucleotides, or from 5 nucleotides to 10 nucleotides) of the 5' untranslated region can be included within the first and/or second amplification products. In some cases, the first amplification product of a nested amplification reaction provided herein can include zero to about 100 or more nucleotides (e.g., from zero nucleotides to 100 nucleotides, from zero nucleotides to 50 nucleotides, from zero nucleotides to 25 nucleotides, from zero nucleotides to 10 nucleotides, from zero nucleotides to 5 nucleotides, from zero nucleotides to 3 nucleotides, from 3 nucleotides to 100 nucleotides, from 3 nucleotides to 50 nucleotides, from 3 nucleotides to 25 nucleotides, from 3 nucleotides to 10 nucleotides, from 3 nucleotides to 5 nucleotides, from 5 nucleotides to 100 nucleotides, from 5 nucleotides to 50 nucleotides, from 5 nucleotides to 25 nucleotides, or from 5 nucleotides to 10 nucleotides) of the 5' untranslated region of an α or γ chain, and the second amplification product of a nested amplification reaction provided herein can include zero to about 100 or more nucleotides (e.g., from zero nucleotides to 100 nucleotides, from zero nucleotides to 50 nucleotides, from zero nucleotides to 25 nucleotides, from zero nucleotides to 10 nucleotides, from zero nucleotides to 5 nucleotides, from zero nucleotides to 3 nucleotides, from 3 nucleotides to 100 nucleotides, from 3 nucleotides to 50 nucleotides, from 3 nucleotides to 25 nucleotides, from 3 nucleotides to 10 nucleotides, from 3 nucleotides to 5 nucleotides, from 5 nucleotides to 100 nucleotides, from 5 nucleotides to 50 nucleotides, from 5 nucleotides to 25 nucleotides, or from 5 nucleotides to 10 nucleotides) of a β or δ chain.

In one embodiment, the first and second amplification products can encode the full-length VJ segments and full-length VDJ segments as they were present in the single T cell that provided the source RNA. For example, a human αβ T cell having a TCR with a Vα1.2 segment, a Jα32 segment, a Vβ11.3 segment, a Dβ2 segment, and a Jβ1-5 segment can be sorted into a separate well and lysed to release the T cell's RNA. That RNA can be used to generate cDNA via reverse transcription, and that generated cDNA can be used as template in a nested amplification reaction to create a first amplification product that includes a nucleic acid sequence encoding the full-length Vα1.2 and Jα32 segments as present in that human αβ T cell and a second amplification product that includes a nucleic acid sequence encoding the full-length Vβ11.3, Dβ2, and Jβ1-5 segments as present in that human αβ T cell.

As another example, the first and second amplification products can encode the full-length VJ segments including the L sequence, the full-length VDJ segments including the L sequence, and at least a portion of each C region as they were present in the single T cell that provided the source RNA. For example, a human αβ T cell having a TCR with a Vα1.2 segment including the L sequence, a Jα32 segment, a Cα region, a Vβ11.3 segment including the L sequence, a Dβ2 segment, a Jβ1.5 segment, and a Cβ region can be sorted into a separate well and lysed to release the T cell's RNA. That RNA can be used to generate cDNA via reverse transcription, and that generated cDNA can be used as template in a nested amplification reaction to create a first amplification product that includes a nucleic acid sequence encoding the full-length Vα1.2 and Jα32 segments including the L sequence and at least a portion of the 5' end of Cα as present in that human αβ T cell and a second amplification product that includes a nucleic acid sequence encoding the full-length Vβ11.3, Dβ2, and Jβ1-5 segments including the L sequence and at least a portion of the 5' end of Cβ as present in that human αβ T cell.

When including a portion of a C region within the first and/or second amplification products of a nested amplification reaction provided herein, any appropriate length of the C region can be included starting from the 5' end of that C region. For example, from about 15 nucleotides to about 550 or more nucleotides (e.g., from about 15 nucleotides to about 550 nucleotides, from about 15 nucleotides to about 450 nucleotides, from about 15 nucleotides to about 400 nucleotides, from about 15 nucleotides to about 300 nucleotides, from about 15 nucleotides to about 200 nucleotides, from about 15 nucleotides to about 100 nucleotides, from about 15 nucleotides to about 50 nucleotides, from about 20 nucleotides to about 550 nucleotides, from about 20 nucleotides to about 450 nucleotides, from about 20 nucleotides to about 400 nucleotides, from about 20 nucleotides to about 300 nucleotides, from about 20 nucleotides to about 200 nucleotides, from about 20 nucleotides to about 100 nucleotides, or from about 20 nucleotides to about 50 nucleotides) of a C region can be included within the first and/or second amplification products. In some cases, the first amplification product of a nested amplification reaction provided herein can include the first 15 to about 450 nucleotides of a Cα or Cγ region, and the second amplification product of a nested amplification reaction provided herein can include the first 15 to about 550 nucleotides of a Cβ or Cδ region.

As described herein, the methods and materials provided herein can allow users to capture successfully most, if not all, functional TCRs from a sorted T cell population. For example, a nested amplification (e.g., nested PCR) procedure provided herein can include using primer collections designed to amplify every known functional V segment of the two variable chains of a particular TCR (e.g., any of the known functional V segments of the α variable and β variable chains of a particular αβ TCR or any of the known functional V segments of the γ variable and δ variable chains of a particular γδ TCR) of a mammal (e.g., a human). For humans, a nested amplification procedure provided herein can include a primer collection designed to amplify all 45 V segments of the α chain currently known to be functional and all 48 V segments of the β chain currently known to be functional. When referring to TCR V segments of the α chain herein, the shorthand abbreviation TRAV can be used. Likewise, when referring to TCR V segments of the β chain herein, the shorthand abbreviation TRBV can be used. The same is true for TCR V segments of the γ and δ chains, which can be referred to as TRGV and TRDV, respectively. The 45 TRAVs currently known to be functional in humans are listed in the second column of Table 1, while the 48 TRBVs currently known to be functional in humans are listed in the second column of Table 2.

TABLE 1

Primers targeting the 45 TRAVs currently known to be functional in humans.

| # | Target TRAV(s) | Primer Name | Sequence | SEQ ID NO: |
|---|---|---|---|---|
| 1 | TRAV1-1 TRAV1-2 | hTRAV1_12_F | TCCCTCACCCACATGAAGTGTCTAC | 1 |
| 2 | TRAV2 | hTRAV2_F | GGTGAGACCAACTGCATTTTG | 2 |
| 3 | TRAV3 | CGP_hTRAV3_F | AGAGGTGGGCTGGAAAGGAC | 3 |
| 4 | TRAV4 | hTRAV4_F | GTTGCTGCTGGGCTCATTG | 4 |
| 5 | TRAV5 | hTRAV5_F | CCAGTGGGGAGAACAATGAAGAC | 5 |
| 6 | TRAV6 | hTRAV6_F | GGTCTACATTTCAGGCCACATTTG | 6 |
| 7 | TRAV7 | hTRAV7_F | TGGTATCAAGACAAAGTATCAGGATG | 7 |
| 8 | TRAV8-1 | hTRAV8_1_F | AGAGACGCCTGCAGTGTTTC | 8 |
| 9 | TRAV8-3 | hTRAV8_3_F | GAAAAGAGCCTGCAGTGTTTC | 9 |
| 10 | TRAV8-2 TRAV8-4 TRAV8-6 | hTRAV8_246_F | CCWCTGCTCAGCCATGCTC | 10 |
| 11 | TRAV9-1 | hTRAV9_1_F | CTTCCTAACACATTCACATTTCCTG | 11 |
| 12 | TRAV9-2 | hTRAV9_2_F | CTTCCTAACACAAACTCATTTCCTG | 12 |
| 13 | TRAV10 | hTRAV10_F | CACAAGTCAACTTCTGGGAGCAG | 13 |
| 14 | TRAV12-1 TRAV12-2 TRAV12-3 | hTRAV12_123_F | CCAGGGCAGARAAGAATGATG | 14 |

TABLE 1-continued

Primers targeting the 45 TRAVs currently known to be functional in humans.

| # | Target TRAV(s) | Primer Name | Sequence | SEQ ID NO: |
|---|---|---|---|---|
| 15 | TRAV13-1 | hTRAV13_1_F | GGAGGTTGCAGGTCAATGACTGATC | 15 |
| 16 | TRAV13-2 | hTRAV13_2_F | GGAGATTGCAGGTTTATGACTGATC | 16 |
| 17 | TRAV14 | hTRAV14DV4_F | CCAGGTTCACTTCACAGTACAGAGTC | 17 |
| 18 | TRAV16 | hTRAV16_F | CAGAAAAGACCTCCAGAAAATAGCTTC | 18 |
| 19 | TRAV17 | hTRAV17_F | GCTCCATTTCAGGTCTTCTGTGATTTC | 19 |
| 20 | TRAV18 | hTRAV18_F | ACAAAACCTTCTACTGCTTCTCAG | 20 |
| 21 | TRAV19 | hTRAV19_F | TGAGACGGAGCACGGAACATTTC | 21 |
| 22 | TRAV20 | hTRAV20_F | TCGTAATTTGTTTCTAGGCTGAGATAC | 22 |
| 23 | TRAV21 | hTRAV21_F | GTGAGTCTAAGTGACAGAAGGAATG | 23 |
| 24 | TRAV22 | hTRAV22_F | GCAAGAAGGCAAAGCATCATG | 24 |
| 25 | TRAV23 | hTRAV23DV6_F | CTCTGGTGCCAGGAGGAATG | 25 |
| 26 | TRAV24 | hTRAV24_F | GGGTACGTGAGCAGGAAACATG | 26 |
| 27 | TRAV25 | hTRAV25_F | GGATGAAGAGGGAGAGGGAGATG | 27 |
| 28 | TRAV26-1 | hTRAV26_1_F | AAAACTGAACTCTGGGTCCACAATC | 28 |
| 29 | TRAV26-2 | hTRAV26_2_F | TTGGGACCTCCTCTGACCTAG | 29 |
| 30 | TRAV27 | hTRAV27_F | CACCATGTGATAGAAAGACAAGATG | 30 |
| 31 | TRAV29 | hTRAV29DV5_F | CAGCTTTCTAGGCAGGAGATAAGAC | 31 |
| 32 | TRAV30 | hTRAV30_F | TGTTAAGGAAGCCCATTCAGAAG | 32 |
| 33 | TRAV34 | hTRAV34_F | GTTTTCTAAATAGCTAAGGGATGGAG | 33 |
| 34 | TRAV35 | hTRAV35_F | GGAAATAATTCTTTGCTGATAAGGATG | 34 |
| 35 | TRAV36 | hTRAV36DV7_F | CCCAGGAAAACACACTTGATAACTG | 35 |
| 36 | TRAV38-1 | hTRAV38_1_F | CCATCAGAGCAGGAGACTTTTC | 36 |
| 37 | TRAV38-2 | hTRAV38_2DV8_F | GCAGGGACCTGTGAGCATG | 37 |
| 38 | TRAV39 | hTRAV39_F | GAACTGGACAGAAAAAAAAATGAAG | 38 |
| 39 | TRAV40 | hTRAV40_F | GCTAGGCCAGAGACACTAACAATG | 39 |
| 40 | TRAV41 | hTRAV41_F | CCGAAATCCTCCAACAGAGAC | 40 |

W = A, T; R = A, G.

TABLE 2

Primers targeting the 48 TRBVs currently known to be functional in humans.

| # | Target TRBV(s) | Primer Name | Sequence | SEQ ID NO: |
|---|---|---|---|---|
| 1 | TRBV2 | hTRBV2_F | GCCTCATTCCTGCTGTGATC | 41 |
| 2 | TRBV3 | hTRBV3_F | CTCACCACTGCAGACCAGAATC | 42 |
| 3 | TRBV4-1 TRBV4-2 TRBV4-3 | hTRBV4_123_F | ATCTCAGACCCGAGGCTAG | 43 |

TABLE 2-continued

Primers targeting the 48 TRBVs currently known to be functional in humans.

| # | Target TRBV(s) | Primer Name | Sequence | SEQ ID NO: |
|---|---|---|---|---|
| 4 | TRBV5-4 TRBV5-6 TRBV5-8 | hTRBV5_468_F | CAGAAYTCACTCGGCTCTTC | 44 |
| 5 | TRBV5-1 | hTRBV5_1_F | GCTGCCTGCCCCTTTGTG | 45 |
| 6 | TRBV5-5 | hTRBV5_5_F | GCTGCCTGCCCCACTGTG | 46 |
| 7 | TRBV6-1 TRBV6-6 TRBV6-8 TRBV6-9 | hTRBV6_1689_F | CYYCCTTGAGAGTCCTGTTC# | 47 |
| 8 | TRBV6-2 TRBV6-3 | hTRBV6_23_F | TCAGAATGACGCCCTTGAAAG | 48 |
| 9 | TRBV6-4 | hTRBV6_4_F | GTAGCATCTGCCATGAGAATC | 49 |
| 10 | TRBV6-5 | hTRBV6_5_F | CTCCGTCATGCAGCATCTG | 50 |
| 11 | TRBV7-2 TRBV7-4 | hTRBV7_24_F | CCTCTGCTCCTGCTCAYAGTGA | 51 |
| 12 | TRBV7-3 TRBV7-6 TRBV7-7 TRBV7-8 TRBV7-9 | hTRBV7_36789_F | CAGTGACMCTGATCTGGTAAAG | 52 |
| 13 | TRBV9 | hTRBV9_F | AGCCCCAAGCTAGGAGATC | 53 |
| 14 | TRBV10-1 TRBV10-2 | hTRBV10_12_F | CTGCCCTGGAGCTGAAATG | 54 |
| 15 | TRBV10-3 | hTRBV10_3_F | CTGGCCTGGACCTGAAATG | 55 |
| 16 | TRBV11-1 TRBV11-3 | hTRBV11_13_F | TCCCACYTCCTCTGCTCCTG | 56 |
| 17 | TRBV11-2 | hTRBV11_2_F | TCCCTCCTCCTCTGCTTTTG | 57 |
| 18 | TRBV12-3 TRBV12-4 | hTRBV12_34_F | TCCACATCTGCTCTCACTCTG | 58 |
| 19 | TRBV12-5 | hTRBV12_5_F | TCCTGTATTCGTGCCCACAAG | 59 |
| 20 | TRBV13 | hTRBV13_F | GCAACCTGAGCAGGGAGATG | 60 |
| 21 | TRBV14 | hTRBV14_F | TTCTCATACTTGTAAGCTCCTTCATC | 61 |
| 22 | TRBV15 | hTRBV15_F | TCATTCCTGTATGGGGTGGTATTC | 62 |
| 23 | TRBV16 | hTRBV16_F | GCCTGCTCTTCCCCTAATTCTG | 63 |
| 24 | TRBV18 | hTRBV18_F | TCCATGGCCAACTCTGCTATG | 64 |
| 25 | TRBV19 | hTRBV19_F | AGGCCCCCTTTGCACTATGAG | 65 |
| 26 | TRBV20-1 | hTRBV20_1_F | ATGGAGGCAGTGGTCACAAC | 66 |
| 27 | TRBV24-1 | hTRBV24_1_F | CCTCCATCCTGCCTCTTCATG | 67 |
| 28 | TRBV25-1 | hTRBV25_1_F | GCCCCAACTGTGCCATGAC | 68 |
| 29 | TRBV27 | hTRBV27_F | CTGAAGAGGTGGAGACGTTACAG | 69 |
| 30 | TRBV28 | hTRBV28_F | CCGGGACAATGACATCACAGAC | 70 |

TABLE 2-continued

Primers targeting the 48 TRBVs currently known to be functional in humans.

| # | Target TRBV(s) | Primer Name | Sequence | SEQ ID NO: |
|---|---|---|---|---|
| 31 | TRBV29-1 | hTRBV29_1_F | GGGAGAGGCCATCACTTGAAG | 71 |
| 32 | TRBV30 | hTRBV30_F | AAGGCTGGCTTGGATGATG | 72 |

Y = C, T; M = A, C.
When this primer preparation was used in the Example section, all four primer permutations were made and used. In some cases, this primer preparation can be replaced such that the following three primers are used: CTCCCTTGAGAGTCCTGTTC (SEQ ID NO: 280), CTTCCTTGAGAGTCCTGTTC (SEQ ID NO: 281), and CCCCCTTGAGAGTCCTGTTC (SEQ ID NO: 282).

In some cases, when using a primer set that contains primers from Table 1 as described herein, the hTRAV38_2DV8_F primer listed in Table 1 can be replaced with GGACCTGTGAGCATGGCATG (SEQ ID NO:283), GTTCAGATCAGAAGAGG-AGGCTTC (SEQ ID NO:284), or CTCAAGGTTCAGATCAGAAGAGGAG (SEQ ID NO:285).

In some cases, when using a primer set that contains primers from Table 1 as described herein, the hTRAV39_F primer listed in Table 1 can be replaced with ATCTGAGTTTTCAGTGAACTGGACAG (SEQ ID NO:286), CTCCTAAATCTGAG-TTTTCAGTGAACT (SEQ ID NO:287), or CAAGGCTCCTAAATCTGAGTTTT-CAGTG (SEQ ID NO:288).

In some cases, when using a primer set that contains primers from Table 2 as described herein, the hTRBV13_F primer listed in Table 2 can be replaced with CAC-CCCAG-GAGACCAGCAAC (SEQ ID NO:289), GGAGCAAAAGCCCTGCTTTCT (SEQ ID NO:290), or AAACGGTGAGGAGGAGCAAAAG (SEQ ID NO:291).

In some cases, when using a primer set that contains primers from Table 2 as described herein, the hTRBV14_F primer listed in Table 2 can be replaced with CTTG-TAAGCTCCTTCTTCATCTGGAAATG (SEQ ID NO:292), CAGATTTGCTTTC-CTTTTTCTCATAC (SEQ ID NO:293), or TTACAGGGCCAAGAGACAGATTTG (SEQ ID NO:294).

For mice, a nested amplification procedure provided herein can include a primer collection designed to amplify all 104 V segments of the α chain currently known to be functional and all 22 V segments of the β chain currently known to be functional. The 104 TRAVs currently known to be functional in mice are listed in the second column of Table 3, while the 22 TRBVs currently known to be functional in mice are listed in the second column of Table 4.

TABLE 3

Primers targeting the 104 TRAVs currently known to be functional in mice.

| # | Target TRAV(s) | Primer Name | Sequence | SEQ ID NO: |
|---|---|---|---|---|
| 1 | TRAV1 | mTRAV1_F | GTCAGGCTGGTGGTGTCATG | 73 |
| 2 | TRAV2 | mTRAV2_F | GGCCTGTGCTTACAAAGAGAATA | 74 |
| 3 | TRAV3<br>TRAV3D-3<br>TRAV3N-3<br>TRAV3-1<br>TRAV3-4 | mTRAV3_F | GTGGATCACAGAGGCATCYTGT | 75 |
| 4 | TRAV4-2 | mTRAV4-2_F | CTGTTGGAAATCAGCATCTTGAC | 76 |
| 5 | TRAV4-3<br>TRAV4D-3<br>TRAV4N-3<br>TRAV4-4<br>TRAV4D-4<br>TRAV4N-4 | mTRAV4-34_F | CGATTGGACAGGGGYCATG | 77 |
| 6 | TRAV5-1 | mTRAV5-1_F | GAAGCACAATGAAGACAGCTATTC | 78 |
| 7 | TRAV5D-4<br>TRAV5N-4<br>TRAV5-4 | mTRAV5D-4_F | CTGGATTTTAATTTAATTGGGAAGAG | 79 |
| 8 | TRAV6-1 | mTRAV6-1_F | GACACTGAAGATGAACTATTCTCC | 80 |

TABLE 3-continued

Primers targeting the 104 TRAVs currently known to be functional in mice.

| # | Target TRAV(s) | Primer Name | Sequence | SEQ ID NO: |
|---|---|---|---|---|
| 9 | TRAV6-2 | mTRAV6-2_F | GTTGAGGATACCACTCTGAAGATG | 81 |
| 10 | TRAV6-3 TRAV6D-3 | mTRAV6-3_F | ACTCTGGTGACACTGAAGATGAAC | 82 |
| 11 | TRAV6-4 TRAV6D-4 | mTRAV6-4_F | GAGCAGCACTCTACACTGAACATG | 83 |
| 12 | TRAV6-5 TRAV6D-5 TRAV6N-5 | mTRAV6-5_F | CACTCCAGTGGCTCAGAAAATG | 84 |
| 13 | TRAV6-6 TRAV6D-6 TRAV6N-6 | mTRAV6-6_F | CATCAAGWCCACTTTCTAGATGACA | 85 |
| 14 | TRAV6-7 TRAV6D-7 TRAV6N-7 | mTRAV6-7_F | CTGTCGAGATGGGTCTAAAGATG | 86 |
| 15 | TRAV7-1 TRAV7-4 TRAVD7-4 TRAVN7-4 | mTRAV7-14_F | AGGGAAGAGGARAGAATGAAGTC | 87 |
| 16 | TRAV7-2 TRAV7D-2 TRAV7-3 TRAV7D-3 | mTRAV7-23_F | AGGAARGARGAGAGAATGAAATC# | 88 |
| 17 | TRAV7-5 TRAV7D-5 TRAV7N-5 | mTRAV7-5_F | CCCCAGTGGAGAGAGATAAAGAG | 89 |
| 18 | TRAV7-6 TRAV7D-6 TRAV7N-6 | mTRAV7-6_F | CACTCCTTTTGCTGGCTTGA | 90 |
| 19 | TRAV8-1 TRAV8D-1 | mTRAV8-1_F | CTGGAGCTGTATCTCTTGCGA | 91 |
| 20 | TRAV8-2 TRAV8D-2 TRAV8N-2 | mTRAV8-2_F | TCCTGTGACATCAATAAAGCAAG | 92 |
| 21 | TRAV9-1 TRAV9D-1 | mTRAV9-1_F | GTTTCCAGTGTGCAGCCATG | 93 |
| 22 | TRAV9-2 TRAV9D-2 TRAV9N-2 TRAV9D-3 TRAV9-4 TRAV9D-4 TRAV9N-4 | mTRAV9-2D34_F | TTYCAAGGCTCAGCCATG | 94 |
| 23 | TRAV9-3 TRAV9N-3 | mTRAV9-3_F | AGAGCTGCAGCCTTCTCAAG | 95 |
| 24 | TRAV10 TRAV10D TRAV10N | mTRAV10_F | CCCAGGCAGGAAGAATGATG | 96 |
| 25 | TRAV11 TRAV11D | mTRAV11_F | GGCTTCTCCAGAACAACCATG | 97 |
| 26 | TRAV12N-1 TRAV12D-1 TRAV12-2 TRAV12D-2 TRAV12N-2 | mTRAV12_F | CAAGGACCAAGTGTCATTTCTTC | 98 |

TABLE 3-continued

Primers targeting the 104 TRAVs currently known to be functional in mice.

| # | Target TRAV(s) | Primer Name | Sequence | SEQ ID NO: |
|---|---|---|---|---|
| 27 | TRAV13-1 TRAV13D-1 TRAV13N-1 TRAV13-2 TRAV13D-2 TRAV13N-2 TRAV13-3 TRAV13D-3 TRAV13N-3 TRAV13-4 TRAV13D-4 TRAV13N-4 TRAV13-5 | mTRAV13_F | GGCTGGTTACTTGCTTCTGTCT | 99 |
| 28 | TRAV14-1 TRAV14D-1 TRAV14N-1 TRAV14-2 TRAV14N-2 | mTRAV14-12_F | GGAGACAAAAGGYCACCTGAGT | 100 |
| 29 | TRAV14-3/D2 | mTRAV14-3D2_F | TCAGTCTAGGAGGAATGGACAAG | 101 |
| 30 | TRAV15-1 TRAV15N-1 TRAV15-2 TRAV15D-2 TRAV15N-2 TRAV15D_DV6D-2 | mTRAV15_F | GGCAGAGCAGACACACTCATG | 102 |
| 31 | TRAV16 TRAV16D TRAV16N | mTRAV16_F | CACTCAAGACCAGAGCTAACAGTATG | 103 |
| 32 | TRAV17 | mTRAV17_F | CCTTCTCACTGCCTAGCCATG | 104 |
| 33 | TRAV19 | mTRAV19_F | AAGGAGAGATAACTCAAAGCTTCAG | 105 |
| 34 | TRAV21-DV12 | mTRAV21_F | GCTCATCCATTTGCTCTTAACTATG | 106 |

Y = C, T; W = A, T; R = A, G.
= When this primer preparation was used in the Example section, all four primer permutations were made and used. In some cases, this primer preparation can be replaced such that the following two primers are used: AGGAAGGAGGAGAGAATGAAATC (SEQ ID NO: 295) and AGGAAAGAAGAGAGAATGAAATC (SEQ ID NO: 296).

TABLE 4

Primers targeting the 22 TRBVs currently known to be functional in mice.

| # | Target TRBV(s) | Primer Name | Sequence | SEQ ID NO: |
|---|---|---|---|---|
| 1 | TRBV1 | mTRBV1_F | GGCCCACAGAGATAGAGAGAAC | 107 |
| 2 | TRBV2 | mTRBV2_F | CAGACAGCCAGGATCCAAAG | 108 |
| 3 | TRABV3 | mTRBV3_F | TGCAGTCAGTCAAGCTAGGAGAAAC | 109 |
| 4 | TRBV4 | mTRBV4_F | CCCTGCCTTGACCCAACTATG | 110 |
| 5 | TRBV5 | mTRBV5_F | ACCCGTCTGGAGCCTGATTC | 111 |
| 6 | TRBV12-1 TRBV12-2 | mTRBV12_F | CCTGAGARGAAGCATGTCTAACAC | 112 |
| 7 | TRBV13-1 TRBV13-2 TRBV13-3 | mTRBV13_F | CAARCAGGGCTGGAACATAC | 113 |
| 8 | TRBV14 | mTRBV14_F | CCCTCCTCTGCCCTCAATC | 114 |

TABLE 4-continued

Primers targeting the 22 TRBVs currently known to be functional in mice.

| # | Target TRBV(s) | Primer Name | Sequence | SEQ ID NO: |
|---|---|---|---|---|
| 9 | TRBV15 | mTRBV15_F | AAAGTCCCTTCTCTGCTCATGTAC | 115 |
| 10 | TRBV16 | mTRBV16_F | CACTGCCTCATCTTGCCATG | 116 |
| 11 | TRBV17 | mTRBV17_F | AAGACAAATATTCCTTTCCTGTTCTG | 117 |
| 12 | TRBV19 | mTRBV19_F | CAAAGAAAGTCCCTCCAAACTATG | 118 |
| 13 | TRBV20 | mTRBV20_F | TTAAGCGAAGGTGGTGTGAAGTC | 119 |
| 14 | TRBV23 | mTRBV23_F | ACAAGAAGACACCACATCCTTTG | 120 |
| 15 | TRBV24 | mTRBV24_F | TGCTGGCCTAGTGTGATCATG | 121 |
| 16 | TRBV26 | mTRBV26_F | TGAGAACACTTCAACCTTTTCGTAC | 122 |
| 17 | TRBV29 | mTRBV29_F | CACTTTCCTCAAAACCACCATG | 123 |
| 18 | TRBV30 | mTRBV30_F | GAAAGAGACCACTGCTAAAGGATG | 124 |
| 19 | TRBV31 | mTRBV31_F | AAGTGCAGAGTAGACAAGCCTAGAC | 125 |

R = A, G.

Any appropriate primer collection can be used during a first round amplification of a nested amplification reaction provided herein to amplify nucleic acid including α and β chain or γ and δ chain nucleic acid. In some cases, a primer collection can include at least one forward primer designed to amplify at least one TRAV (or at least one TRGV) and at least one forward primer designed to amplify at least one TRBV (or at least one TRGV). For humans, in general, this would mean that the forward primer collection can be designed to include at least 45 forward TRAV-specific primers (one for each of the 45 TRAVs in humans) and at least 48 forward TRBV-specific primers (one for each of the 48 TRBVs in humans), and for mice, this would mean that the forward primer collection can be designed to include at least 104 forward TRAV-specific primers (one for each of the 104 TRAVs in mice) and at least 22 forward TRBV-specific primers (one for each of the 22 TRBVs in mice). For example, for humans, one forward TRAV primer can be designed to amplify TRAV1-1, a second forward TRAV primer can be designed to amplify TRAV1-2, a third forward TRAV primer can be designed to amplify TRAV2, a fourth forward TRAV primer can be designed to amplify TRAV3, a fifth forward TRAV primer can be designed to amplify TRAV4, and so on for the α chain possibilities (see, e.g., target TRAVs listed in Table 1), and one forward TRBV primer can be designed to amplify TRBV2, a second forward TRBV primer can be designed to amplify TRBV3, a third forward TRBV primer can be designed to amplify TRBV4-1, a fourth forward TRBV primer can be designed to amplify TRBV4-2, a fifth forward TRBV primer can be designed to amplify TRBV4-3, and so on for the β chain possibilities (see, e.g., target TRBVs listed in Table 2) for a total of at least 93 forward TRAV and TRBV primers.

In some cases, when using at least one forward primer designed to amplify at least one TRAV (or at least one TRGV) and at least one forward primer designed to amplify at least one TRBV (or at least one TRDV) to have the opportunity to amplify possible combinations of α and β chains (or possible combinations of γ and δ chains) during a first round amplification of a nested amplification reaction (e.g., nested PCR) provided herein, a large number of primers can be synthesized and combined into each single first round amplification reaction. For example, when using at least 93 different forward TRAV and TRBV primers in the case of humans to have the opportunity to amplify possible combinations of human α and β chains present in the single-cell-sorted T cells (e.g., all the TRAVs and TRBVs listed in Tables 1 and 2) during a first round amplification of a nested amplification reaction (e.g., nested PCR) provided herein, a large number of primers (i.e., at least 93 in this case) can be synthesized and combined into each single first round amplification reaction. In some cases, the number of forward primers can be reduced without losing the ability to amplify possible combinations of α and β chains (or possible combinations of γ and δ chains) present in the single-cell-sorted T cells (e.g., all the TRAVs and TRBVs listed in Tables 1 and 2) during a first round amplification of a nested amplification reaction (e.g., nested PCR) provided herein. For example, a single forward TRAV primer can be designed to have the ability to amplify more than one different TRAV. An example of such a primer for humans is the hTRAV1_12_F primer (Primer #1 of Table 1), which is designed to amplify both TRAV1-2 and TRAV1-2. In some cases, a single forward TRBV primer can be designed to have the ability to amplify more than one different TRBV. Examples of such primers for humans include, without limitation, the hTRBV4_123_F primer (Primer #3 of Table 2), which is designed to amplify TRBV4-1, TRBV4-2, and TRBV4-3; the hTRBV6_23_F primer (Primer #8 of Table 2), which is designed to amplify both TRBV6-2 and TRBV6-3; the hTRBV10_12_F primer (Primer #14 of Table 2), which is designed to amplify both TRBV10-1 and TRBV10-2; and the hTRBV12_34_F primer (Primer #18 of Table 2), which is designed to amplify both TRBV12-3 and TRBV12-4.

In some cases, when using the hTRAV1_12_F primer, the hTRBV4_123_F primer, the hTRBV6_23_F primer, the hTRBV10_12_F primer, and the hTRBV12_34_F primer in combination with the other primers for each of the human TRAVs and TRBVs not targeted by those five primers, the number of forward primers to amplify all the human TRAVs and TRBVs listed in Tables 1 and 2 during a first round amplification of a nested amplification reaction (e.g., nested PCR) provided herein can be reduced from 93 forward primers to 81. Similarly, when using a single primer to target multiple TRAVs or TRBVs listed in Tables 3 and 4 as shown in Tables 3 and 4, the number of forward primers to amplify all the mouse TRAVs and TRBVs listed in Tables 3 and 4 during a first round amplification of a nested amplification reaction (e.g., nested PCR) provided herein can be reduced from 126 forward primers to 64.

Figure 5:
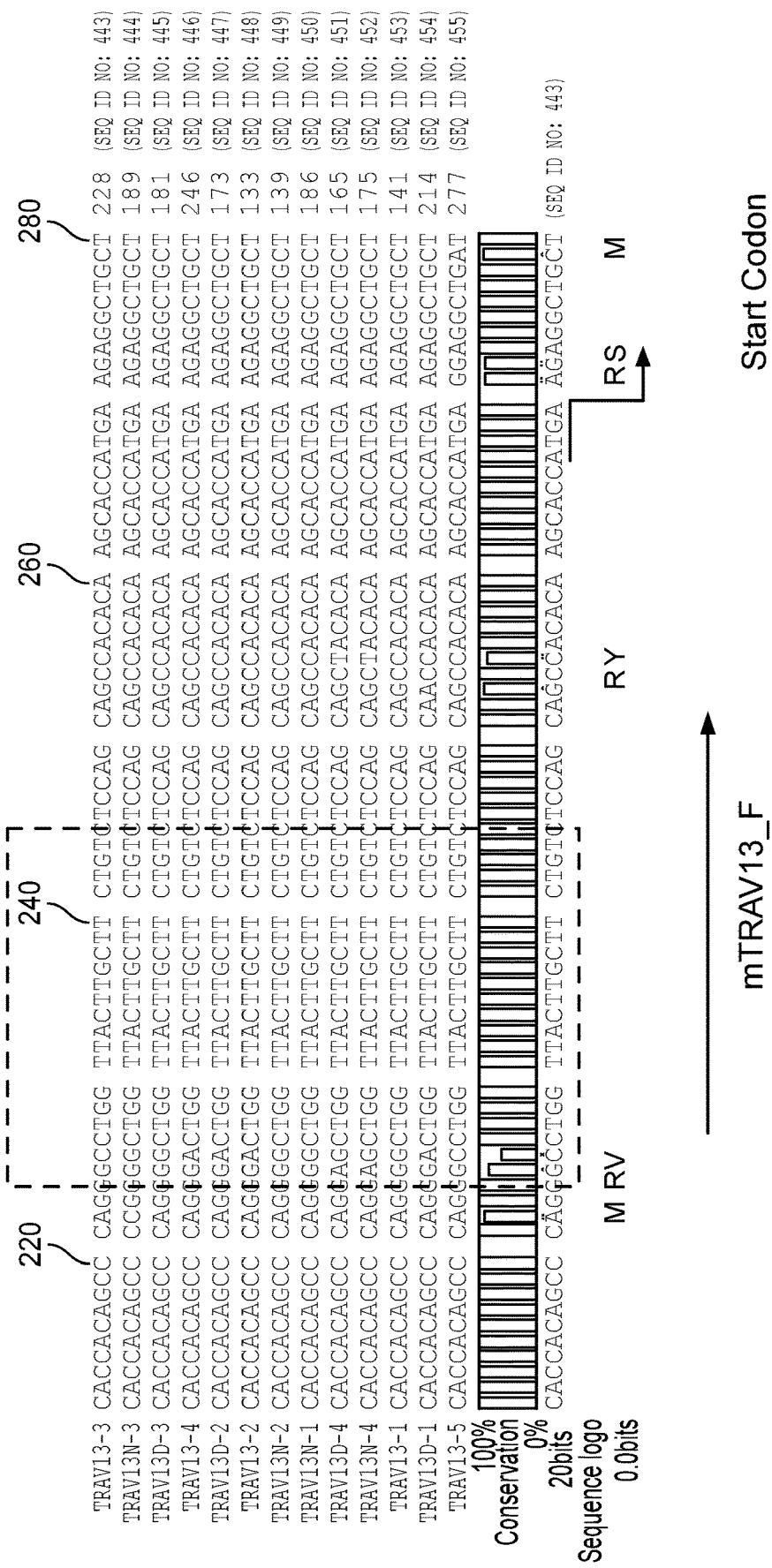
FIG. 5 is an example of an alignment used for the selection and design of primers that can amplify more than one variant. Primer sequences with homology between the different variants were selected in the regions upstream of the ATG start codon or at regions overlapping the ATG start codon. This strategy allowed the number of individual primers included in multiplexed PCR reactions to be reduced considerably, making it possible to amplify most, if not all, TCR variants. This example depicts the sequences for all 13 of the variants of the mouse TRAV13 variant group (SEQ ID NOS: 443-455, respectively, in order of appearance), and their homology upstream of the ATG start codon. In this particular example, all thirteen group members were amplified using only one forward primer (i.e., the mTRAV13_F, which has the following sequence 5'-GGCTGGTTACTTGC-TTCTGTCT-3'; SEQ ID NO:99). The location of this sequence, which is 20 nucleotides upstream of the ATG start codon, is highlighted by the dash box and arrow. Under the sequence logo, the single letter codes for positions with more than one nucleotide are provided. A IUPA-IUB table contains the code for these mixed bases.

Sequence alignments of multiple TRAV sequences (or multiple TRBV, TRGV, or TRDV sequences) can be used to select a single forward TRAV primer (or a single forward TRBV, TRGV, or TRDV primer) having the ability to amplify more than one different TRAV (or more than one different TRBV, TRGV, or TRDV). For example, with reference to FIG. 5, the nucleotide sequence of a portion of the 5' untranslated region upstream of the ATG start site, the ATG start site, and a portion of the translated region downstream of the ATG start site for multiple TRAVs (e.g., mouse TRAV13-1, TRAV13D-1, TRAV13N-1, TRAV13-2, TRAV13D-2, TRAV13N-2, TRAV13-3, TRAV13D-3, TRAV13N-3, TRAV13-4, TRAV13D-4, TRAV13N-4, and TRAV13-5) can be aligned. Once aligned, a sequence of a primer such as the sequence highlighted in the box of FIG. 5 for mTRAV13_F (SEQ ID NO:99) can be selected. In some cases, a primer sequence can be selected that lacks mismatches with respect to any of the aligned TRAV sequences (or aligned TRBV, TRGV, or TRDV sequences). As shown in FIG. 5, in some cases, the primer sequence can be selected to have a few mismatches (e.g., one or two mismatches) with respect to an aligned TRAV sequence (or an aligned TRBV, TRGV, or TRDV sequence). For example, the mTRAV13_F primer (SEQ ID NO:99) was selected to have one mismatch with respect to each of TRAV13D-1, TRAV13-2, TRAV13D-2, TRAV13-3, TRAV13-4, TRAV13D-4, TRAV13N-4, and TRAV13-5 and no mismatches with respect to the other five TRAVs shown in FIG. 5. For those primers designed to target a TRAV, TRBV, TRGV, or TRDV sequence with a few mismatches (e.g., one or two mismatches), the ability of the designed primer to amplify that target having a mismatch can be confirmed via a PCR test using that designed primer, a reverse primer, and the target. Successful generation of amplified target nucleic acid can confirm the ability of that designed primer to amplify that target even though it contains a mismatch.

In some cases, a reduction in the number of primer preparations for amplifying possible combinations of human α and β chains (or possible combinations of γ and δ chains) present in the single-cell-sorted T cells (e.g., all the TRAVs and TRBVs listed in Tables 1 and 2) can be achieved. For example, a single primer preparation can be synthesized in a manner designed to contain a mixture of two or more sequences, each targeting a different TRAV or TRBV. For example, the hTRAV8_246_F primer of Table 1 can be synthesized using the 5'-CCWCTGCTCAGCCATGCTC-3' (SEQ ID NO:10) sequence, which would result in a primer preparation having separate sequences that target TRAV8-2, TRAV8-4, and TRAV8-6. Other examples include, without limitation, the hTRAV12_123_F primer of Table 1, which can be synthesized using the 5'-CCAGGGCAGA-RAAGAATGATG-3' (SEQ ID NO:14) sequence to result in a primer preparation having separate sequences that target TRAV12-1, TRAV12-2, and TRAV12-3; the hTRBV5_468_F primer of Table 2, which can be synthesized using the 5'-CAGAAYTCACTCGGCTCTTC-3' (SEQ ID NO:44) sequence to result in a primer preparation having separate sequences that target TRBV5-4, TRBV5-6, and TRBV5-8; the hTRBV6_1689_F primer of Table 2, which can be synthesized using the 5'-CYYCCTT-GAGAGTCCTGTTC-3' (SEQ ID NO:47) sequence to result in a primer preparation having separate sequences that target TRBV6-1, TRBV6-6, TRBV6-8, and TRBV6-9; the hTRBV7_24_F primer of Table 2, which can be synthesized using the 5'-CCTCTGCTCCTGCTCAYAGTGA-3' (SEQ ID NO:51) sequence to result in a primer preparation having separate sequences that target TRBV7-2 and TRBV7-4; the hTRBV7_36789_F primer of Table 2, which can be synthesized using the 5'-CAGTGACMCTGATCTGGTAAAG-3' (SEQ ID NO:52) sequence to result in a primer preparation having separate sequences that target TRBV7-3, TRBV7-6, TRBV7-7, TRBV7-8, and TRBV7-9; and the hTRBV11_13_F primer of Table 2, which can be synthesized using the 5'-TCCCACYTCCTCTGC-TCCTG-3' (SEQ ID NO:56) sequence to result in a primer preparation having separate sequences that target TRBV11-1 and TRBV11-3.

In some cases, for humans, a primer collection for a first round amplification of a nested amplification reaction (e.g., nested PCR) provided herein can include the TRAV and TRBV primers set forth in Tables 1 and 2 or a subset of the TRAV and TRBV primers set forth in Tables 1 and 2. For example, a primer collection for a first round amplification of a nested amplification reaction (e.g., nested PCR) provided herein can include 1, 5, 10, 20, 30, 35, or more of the TRAV primers set forth in Table 1, can include 1, 5, 10, 20, 30, or more of the TRBV primers set forth in Table 2, or can include 1, 5, 10, 20, 30, 40, 50, 60, 70, or more of the TRAV and TRBV primers set forth in Tables 1 and 2. In some cases, for humans, a primer collection for a first round amplification of a nested amplification reaction (e.g., nested PCR) provided herein can include the TRAV and TRBV primers set forth in Tables 1 and 2 and no other primers with a sequence of a Vα or Vβ segment, a L sequence of a Vα or Vβ segment, or a 5' untranslated region upstream of a Vα or Vβ segment. In some case, using a reduced set of forward primer preparations such as the 72 listed in Tables 1 and 2 to have the opportunity to amplify possible combinations of human α and β chains present in the single-cell-sorted T cells (e.g., all the TRAVs and TRBVs listed in Tables 1 and 2) during a first round amplification of a nested amplification reaction (e.g., nested PCR) provided herein can result in effective amplification across many different separate locations (e.g., across many different wells) and effective downstream cloning (e.g., greater than 80, 85, 90, or 95 percent success based on number of separate locations containing single T cells).

In some cases, a primer collection for a first round amplification of a nested amplification reaction (e.g., nested PCR) provided herein can be divided into two or more subsets with each subset being used to perform a first round amplification of a nested amplification reaction (e.g., nested PCR) provided herein using a portion of the cDNA obtained from single T cells as template. In some cases, for human for example, a primer collection for a first round amplification of a nested amplification reaction (e.g., nested PCR) provided herein can be divided into two or more subsets (e.g., a first subset with only the TRAV primers listed in Table 1 and a second subset with only the TRBV primers listed in Table 2, or a first subset of the TRAV and TRBV primers set forth in Tables 1 and 2 and a second subset of the TRAV and TRBV primers set forth in Tables 1 and 2), with each subset being used to perform a first round amplification of a nested amplification reaction (e.g., nested PCR) provided herein using a portion of the cDNA obtained from single T cells as template. For example, using a portion of the cDNA obtained from single T cells, a first round amplification reaction for TRAVs using the primers listed in Table 1 together with one or more reverse primers can be performed separately from a first round amplification reaction for TRBVs with the primers listed in Table 2 together with one or more reverse primers. These separate first round amplification reactions can be followed by separate second round amplifications of a nested amplification procedure (e.g., a nested PCR procedure). For example, for the TRAVs, the primers listed in Table 5 together with one or more reverse primers can be used, and for the TRBVs, the primers listed in Table 6 together with one or more reverse primers can be used. In some cases, the separate first round amplification reactions for the same single cell can be pooled, and those pooled mixtures can be used as template for second round amplifications of a nested amplification procedure (e.g., a nested PCR procedure). For example, using a portion of the cDNA obtained from single T cells, the first round amplification reaction for TRAVs using the primers listed in Table 1 together with one or more reverse primers can be performed separately from the first round amplification reaction for TRBVs with the primers listed in Table 2 together with one or more reverse primers, followed by one mixed nested amplification reaction (e.g. nested PCR) for both TRAVs and TRBVs using the primers listed in Table 5 and Table 6 together with the reverse primers.

In some cases, where a specific TCR is identified with a unique TRAV and TRBV combination, variants within the CDR3 region can be identified using a first round amplification reaction with one forward primer specific for that particular TRAV (e.g., one of the forward primers listed Table 1) together with one or more reverse primers and one forward primer specific for that particular TRBV (e.g., one of the forward primers listed Table 2) together with one or more reverse primers. For example, forward primer hTRAV8-246_F (SEQ ID NO:10) listed in Table 1 together with one or more reverse primers and forward primer hTRBV12-34_F (SEQ ID NO: 58) listed in Table 2 together with one or more reverse primers can be used.

In some cases, where combinations of a set of TRAVs and a set of TRBVs are to be amplified only a portion of the primers listed in Table 1 and Table 2 specific for those TRAVs and TRBVs can be used.

In one embodiment, a first subset of the TRAV primers set forth in Table 1 (e.g., forward primer #'s 1-36 and 39-40 of Table 1), a second subset of the TRAV primers set forth in Table 1 (e.g., forward primer #'s 37-38 of Table 1), a first subset of the TRBV primers set forth in Table 2 (e.g., forward primer #'s 1-19 and 22-32 of Table 2), and a second subset of the TRBV primers set forth in Table 2 (e.g., forward primer #'s 21-22 of Table 2) can be used with one or more reverse primers for the TRAVs and one or more reverse primers for the TRBVs in four different combinations (e.g., first TRAV subset plus first TRBV subset, second TRAV subset plus first TRBV subset, first TRAV subset plus second TRBV subset, and second TRAV subset plus second TRBV subset) of first round amplification of a nested amplification reaction (e.g., nested PCR) provided herein. In these cases, the resulting first round reaction mixtures and be used for second round amplifications of a nested amplification procedure separately or after being pooled. Similar techniques can be used with the mouse primers of Tables 3 and 4 and/or for the second round amplifications described herein.

In some cases, for mice for example, a primer collection for a first round amplification of a nested amplification reaction (e.g., nested PCR) provided herein can include the TRAV and TRBV primers set forth in Tables 3 and 4 or a subset of the TRAV and TRBV primers set forth in Tables 3 and 4. For example, a primer collection for a first round amplification of a nested amplification reaction (e.g., nested PCR) provided herein can include 1, 5, 10, 20, 30, 35, or more of the TRAV primers set forth in Table 3, can include 1, 5, 10, 20, 30, or more of the TRBV primers set forth in Table 4, or can include 1, 5, 10, 20, 30, 40, 50, 60, 70, or more of the TRAV and TRBV primers set forth in Tables 3 and 4. In some cases, for mice, a primer collection for a first round amplification of a nested amplification reaction (e.g., nested PCR) provided herein can include the TRAV and TRBV primers set forth in Tables 3 and 4 and no other primers with a sequence of a Vα or Vβ segment, a L sequence of a Vα or Vβ segment, or a 5' untranslated region upstream of a Vα or Vβ segment. In some case, using a reduced set of forward primer preparations such as the 53 listed in Tables 3 and 4 to have the opportunity to amplify possible combinations of mouse α and β chains present in the single-cell-sorted T cells (e.g., all the TRAVs and TRBVs listed in Tables 3 and 4) during a first round amplification of a nested amplification reaction (e.g., nested PCR) provided herein can result in effective amplification across many different separate locations (e.g., across many different wells) and effective down-stream cloning (e.g., greater than 80, 85, 90, or 95 percent success based on number of separate locations containing single T cells).

In some cases, some or all the forward primers of a primer collection for a first round amplification of a nested amplification reaction (e.g., nested PCR) provided herein can be completely composed of sequence that anneals to nucleic acid of a cDNA that encodes a TCR with no more than one, two, or three mismatches (e.g., with no more than one mismatch, with no more than two mismatches, or no more than three mismatches). For example, the entire nucleic acid sequence of some or all the forward primers of a primer collection for a first round amplification of a nested amplification reaction (e.g., nested PCR) provided herein can be from a V segment, a L sequence of a V segment, or a 5' untranslated region found upstream of a V segment. In such cases, those forward primers can lack extraneous nucleic acid sequences such as primer barcode sequences or primer adapter sequences. An example of a forward Vα primer collection for a first round of a nested amplification reaction described herein where the sequence of each primer is completely composed of sequence that anneals to nucleic acid of a cDNA that encodes a TCR is shown schematically in the top panel of FIG. 2A. The same is shown for a forward Vβ primer collection for a first round of a nested amplification reaction described herein in the top panel of FIG. 2B. When using forward primers of a primer collection for a first round amplification of a nested amplification reaction (e.g., nested PCR) provided herein that lack extraneous nucleic acid sequences, highly effective amplification of nucleic acid encoding the variable chains of TCRs from single T cells can be achieved.

In some cases, each forward primer of a primer collection for a first round amplification of a nested amplification reaction (e.g., nested PCR) provided herein can composed of a sequence having most of its nucleotides being designed to anneal to a 5' untranslated region found upstream of a V segment of a cDNA that encodes a TCR. In some cases, all of the sequence of each forward primer of a primer collection for a first round amplification of a nested amplification reaction (e.g., nested PCR) provided herein can be designed to anneal to a 5' untranslated region, a 5' untranslated region plus the ATG start site, or a 5' untranslated region plus the ATG start site plus no more than five nucleotides downstream of the ATG start site. The primer collection listed in Table 1 is an example of a forward Vα primer collection for a first round of a nested amplification reaction described herein where each primer anneals to a 5' untranslated region, a 5' untranslated region plus the ATG start site, or a 5' untranslated region plus the ATG start site plus no more than five nucleotides downstream of the ATG start site, and the primer collection in Table 2 is an example of a forward Vβ primer collection for a first round of a nested amplification reaction described herein where each primer anneals to a 5' untranslated region, a 5' untranslated region plus the ATG start site, or a 5' untranslated region plus the ATG start site plus no more than five nucleotides downstream of the ATG start site.

Figure 3A:
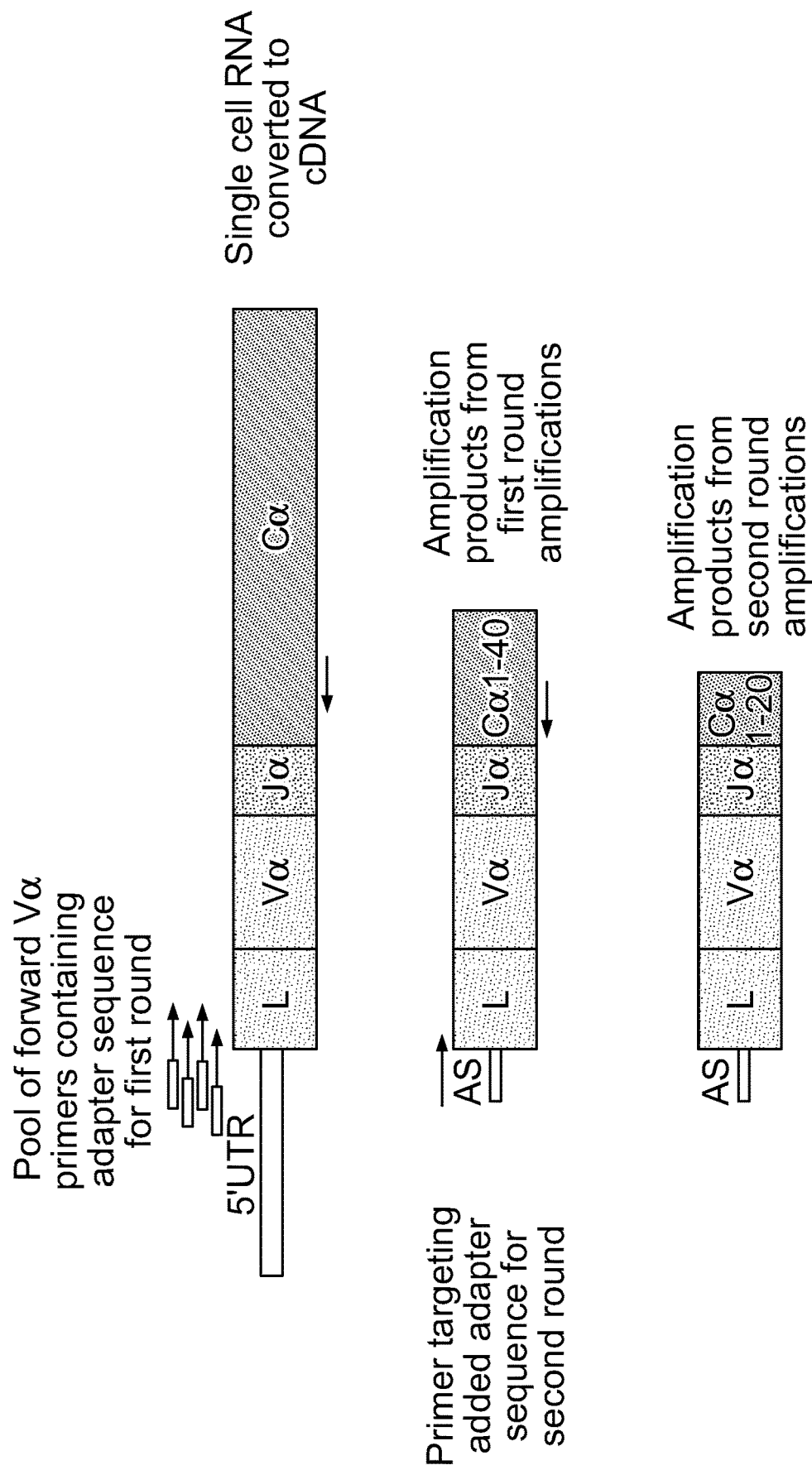
FIGS. 3A-3B are schematics of a nested PCR procedure involving the use of one pool of forward Vα primers and a primer to an adapter sequence to produce an amplification product containing a 5' added adapter sequence (AS) followed by the leader (L) sequence of a Vα segment, a Vα segment, a Jα segment, and a portion of the 5' end of Cα, according to one embodiment. In this embodiment, the primers from the pool of forward Vα primers used in the first round of PCR adds the adapter sequence, which can be used both as a primer target sequence for the second round and to clone the produced amplification product into an expression vector.
Figure 3B:
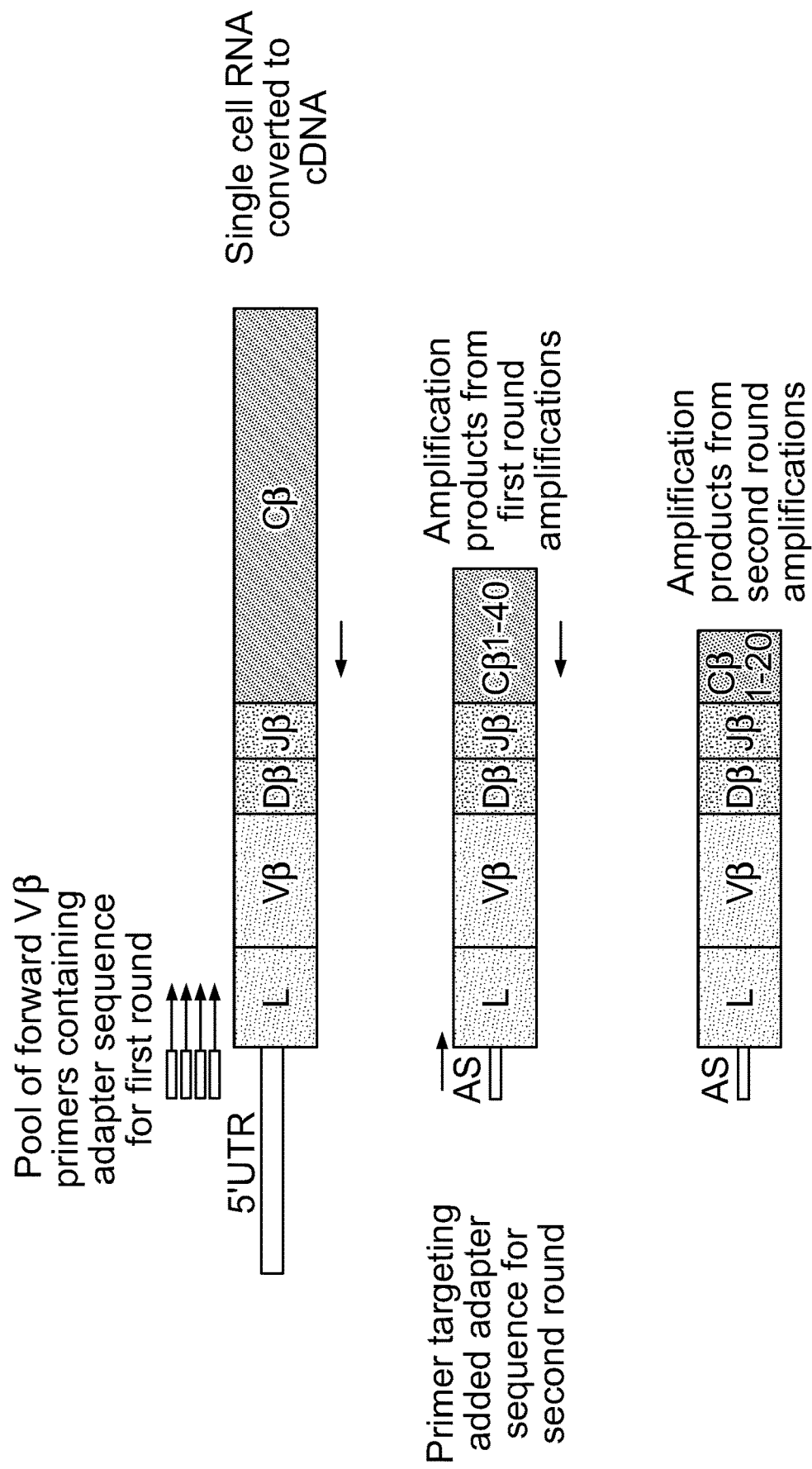

In some cases, some or all the forward primers of a primer collection for a first round amplification of a nested amplification reaction (e.g., nested PCR) provided herein can include a primer barcode sequence and/or a primer adapter sequence (see, e.g., the top panels of FIGS. 3A and 3B). For example, all the forward primers of a primer collection for a first round amplification of a nested amplification reaction (e.g., nested PCR) provided herein can have a 5' primer adapter sequence followed by the primer sequence that targets a V segment, a L sequence of a V segment, and/or a 5' untranslated region found upstream of a V segment (see, e.g., FIGS. 3A and 3B). In these cases, the second round of amplification of the nested amplification reaction, which uses the amplification products from the first round as template, can use a single forward primer specific for the adapter sequence added to all the amplification products during the first round (see, e.g., the middle panels of FIGS. 3A and 3B). In some cases, the added 5' adapter sequence from the forward primers for the first round of a nested amplification reaction provided herein can be used to assist in the cloning of the first and second amplification products into an expression vector.

The term "primer barcode sequence" as used herein refers to an identifiable nucleotide sequence that is at least about 15 nucleotides (e.g., from about 15 to about 50 nucleotides, from about 15 to about 40 nucleotides, from about 15 to about 30 nucleotides, from about 20 to about 50 nucleotides, from about 20 to about 40 nucleotides, or from about 20 to about 30 nucleotides) in length and is added to a primer (e.g., PCR primer) sequence designed to anneal to template sequence such that the produced amplification product includes both amplified template sequence and the added identifiable nucleotide sequence. When performing many amplification reactions in a multiplex format, at least one primer used at each unique location (e.g., each reaction mixture) can include a unique primer barcode sequence that allows a user to match an amplification product to its particular reaction mixture based on the sequence of the primer barcode sequence. For example, a forward primer of a primer pair designed to amplify a Vα segment can include a 5'-AAAA-3' sequence added to the 5' end of a primer specific for the Vα segment for the primer pair used in location #1 (e.g., well #1), while a forward primer of a primer pair designed to amplify the same Vα segment can include a 5'-TTTT-3' sequence added to the 5' end of the same primer specific for the Vα segment for the primer pair used in location #2 (e.g., well #2), and a forward primer of a primer pair designed to amplify the same Vα segment can include a 5'-GGGG-3' sequence added to the 5' end of the same primer specific for the Vα segment for the primer pair used in location #3 (e.g., well #3), and so on. In this case, any amplification product of that Vα segment that includes AAAA at the appropriate region of the amplification product based on the primer sequences can be identified as resulting from location #1. As described herein, in some cases, the TCR cloning methods provided herein can be performed using a nested amplification procedure (e.g., a nested PCR procedure) that includes using primers that are designed to amplify variable region sequences without including primer barcode sequences.

The term "primer adapter sequence" as used herein refers to a known nucleotide sequence that is at least about 15 nucleotides (e.g., from about 15 to about 50 nucleotides, from about 15 to about 40 nucleotides, from about 15 to about 30 nucleotides, from about 20 to about 50 nucleotides, from about 20 to about 40 nucleotides, or from about 20 to about 30 nucleotides) in length and that is added to a primer (e.g., PCR primer) sequence designed to anneal to template sequence such that the produced amplification product includes both amplified template sequence and the added known nucleotide sequence. When performing nested amplification reactions, at least one primer used during an early amplification round of a nested amplification procedure (e.g., the first round of a nested PCR procedure) can include a fixed primer adapter sequence that allows a primer for a subsequent round of the nested amplification procedure (e.g., the second round of a nested PCR procedure) to be designed to anneal to that added primer adapter sequence from the first round. This allows a user to take advantage of the fixed primer adapter sequence, which was added to the amplified template via the primers having the primer adapter sequence, for subsequent steps or procedures by designing primers to that added primer adapter sequence. As described herein, in some cases, the TCR cloning methods provided herein can be performed using a first round of a nested amplification (e.g., PCR) procedure that includes using primers that are designed to amplify variable region sequences without including primer adapter sequences.

Figure 2A:
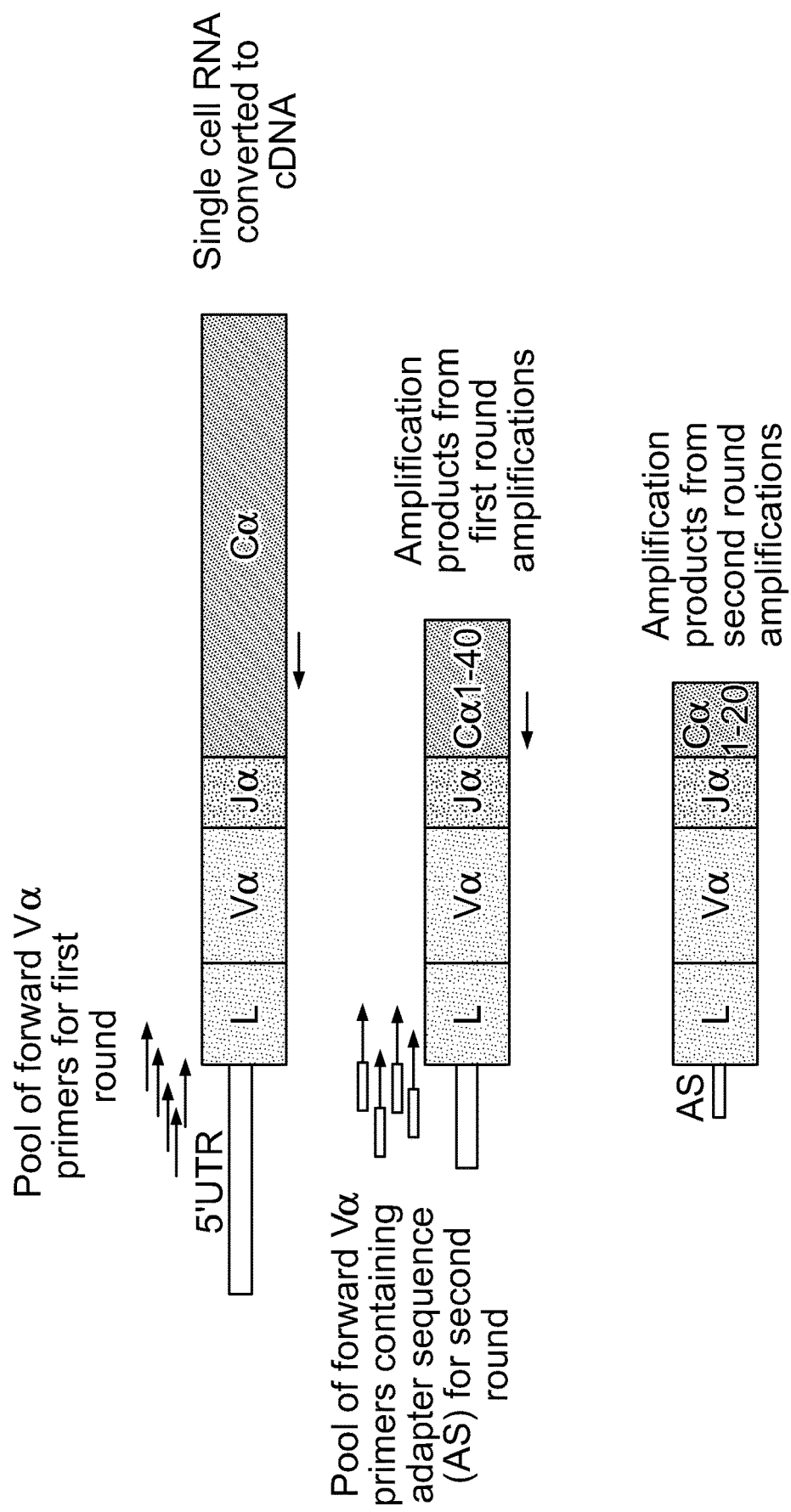
FIGS. 2A-2B are schematics of a nested PCR procedure involving the use of two separate pools of forward Vα primers to produce an amplification product containing a 5' added adapter sequence (AS) followed by the leader (L) sequence of a Vα segment, a Vα segment, a Jα segment, and a portion of the 5' end of Cα, according to one embodiment. In this embodiment, the primers from the pool of forward Vα primers for the second round of PCR adds the adapter sequence, which can be used to clone the produced amplification product into an expression vector.
Figure 2B:
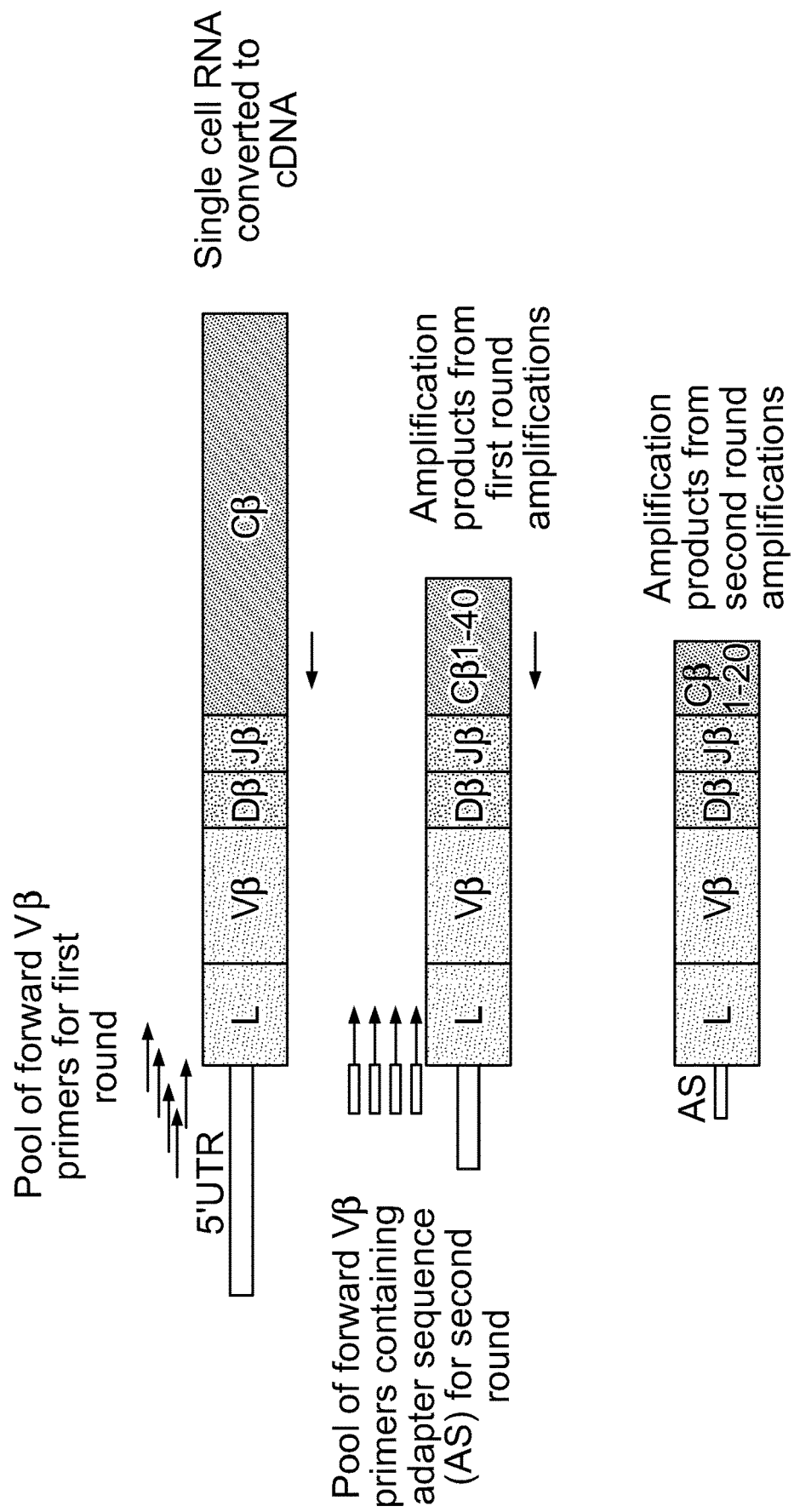

When not using these 5' primer adapter sequences on the forward primers of the first round amplification of a nested amplification reaction (e.g., nested PCR) provided herein (as shown schematically in the top panels of FIGS. 2A and 2B), then the primer collection for a second round of a nested amplification reaction (e.g., nested PCR) provided herein can be designed to include a set of forward primers specific for each variable chain (e.g., each TRAV and TRAB or each TRGV and TRDV) of TCRs in a manner similar to that of the forward primers for the first round (see, e.g., the middle panels of FIGS. 2A and 2B). For example, when the forward primers of the first round are designed to generate amplification products from the various possible variable chains without adding extra 5' sequence not found in the original cDNA used as template to the amplification products, then the forward primers for the second round can be designed to target a 5' portion of those amplification products generated during the first round.

In some cases, the forward primers of a second round of a nested amplification reaction (e.g., nested PCR) provided herein can be designed to target a sequence of a first round amplification product that includes the ATG start site of an L sequence of a V segment or is upstream of that ATG start site so the that first and second amplification products of the nested amplification reaction that are used to clone the function TCR include the ATG start site. In some cases, for humans, a primer collection for a second round amplification of a nested amplification reaction (e.g., nested PCR) provided herein can include the TRAV and TRBV primers set forth in Tables 5 and 6 or a subset of the TRAV and TRBV primers set forth in Tables 5 and 6. For example, a primer collection for a second round amplification of a nested amplification reaction (e.g., nested PCR) provided herein can include 1, 5, 10, 20, 30, 35, or more of the TRAV primers set forth in Table 5, can include 1, 5, 10, 20, 30, or more of the TRBV primers set forth in Table 6, or can include 1, 5, 10, 20, 30, 40, 50, 60, 70, or more of the TRAV and TRBV primers set forth in Tables 5 and 6. In some cases, for humans, a primer collection for a second round amplification of a nested amplification reaction (e.g., nested PCR) provided herein can include the TRAV and TRBV primers set forth in Tables 5 and 6 and no other primers with a sequence of a Vα or Vβ segment, a L sequence of a Vα or Vβ segment, or a 5' untranslated region upstream of a Vα or Vβ segment.

TABLE 5

Primers targeting the 45 TRAVs currently known to be functional in humans. Each of these primers include a primer adapter sequence (TTCAGGTGTCGTGAGGA-TCTATTTCCGGTG, SEQ ID NO: 126).

| # | Target TRAV(s) | Primer Name | Sequence | SEQ ID NO: |
|---|---|---|---|---|
| 1 | TRAV1-1 TRAV1-2 | Vect_hTRAV1_12_F | TTCAGGTGTCGTGAGGATCTATTTCCGGTG TGGTATCCTGCAGCAGATGTG | 127 |
| 2 | TRAV2 | Vect_hTRAV2_F | TTCAGGTGTCGTGAGGATCTATTTCCGGTG TGCATTTTGGCCATGGCTTTG | 128 |
| 3 | TRAV3 | Vect_hTRAV3_F | TTCAGGTGTCGTGAGGATCTATTTCCGGTG TGAGCTTAGCTGGAGCCATGG | 129 |
| 4 | TRAV4 | Vect_hTRAV4_F | TTCAGGTGTCGTGAGGATCTATTTCCGGTG ATGAGGCAAGTGGCGAGAGTG | 130 |
| 5 | TRAV5 | Vect_hTRAV5_F | TTCAGGTGTCGTGAGGATCTATTTCCGGTG ATGAAGACATTTGCTGGATTTTC | 131 |
| 6 | TRAV6 | Vect_hTRAV6_F | TTCAGGTGTCGTGAGGATCTATTTCCGGTG ATTTGGGGAGACGAATGGAGTC | 132 |
| 7 | TRAV7 | Vect_hTRAV7 | TTCAGGTGTCGTGAGGATCTATTTCCGGTG ATGGAGAAGATGCGGAGACCTGTC | 133 |
| 8 | TRAV8-1 | Vect_hTRAV8_1_F | TTCAGGTGTCGTGAGGATCTATTTCCGGTG ATGCTCCTGTTGCTCATACCAGTG | 134 |
| 9 | TRAV8-3 | Vect_hTRAV8_3_F | TTCAGGTGTCGTGAGGATCTATTTCCGGTG TTCCCTTGTTCAGCCATGCTC | 135 |
| 10 | TRAV8-2 TRAV8-4 TRAV8-6 | Vect_hTRAV8_246 | TTCAGGTGTCGTGAGGATCTATTTCCGGTG ATGCTCCTGCTGCTCCTC | 136 |
| 11 | TRAV9-1 | Vect_hTRAV9_1_F | TTCAGGTGTCGTGAGGATCTATTTCCGGTG CACCAGAGGGTCTAAAAATGAATTC | 137 |
| 12 | TRAV9-2 | Vect_hTRAV9_2_F | TTCAGGTGTCGTGAGGATCTATTTCCGGTG AAAGATGAACTATTCTCCAGGCTTAG | 138 |
| 13 | TRAV10 | Vect_hTRAV10_F | TTCAGGTGTCGTGAGGATCTATTTCCGGTG CAGAATAAAAATGAAAAAGCATCTGAC | 139 |
| 14 | TRAV12-1 TRAV12-2 TRAV12-3 | Vect_hTRAV12_123_F | TTCAGGTGTCGTGAGGATCTATTTCCGGTG TGATGAWATCCTTGAGAGTTTTACTG | 140 |
| 15 | TRAV13-1 | Vect_hTRAV13_1_F | TTCAGGTGTCGTGAGGATCTATTTCCGGTG GGAAGAACAAGGATGTCCATTC | 141 |
| 16 | TRAV13-2 | Vect_hTRAV13_2_F | TTCAGGTGTCGTGAGGATCTATTTCCGGTG ATGGCAGGCATTCGAGCTTTATTTATG | 142 |
| 17 | TRAV14 | Vect_hTRAV14D4_F | TTCAGGTGTCGTGAGGATCTATTTCCGGTG ATGTCACTTTCTAGCCTGCTGAAG | 143 |
| 18 | TRAV16 | Vect_hTRAV16_F | TTCAGGTGTCGTGAGGATCTATTTCCGGTG TGTTTCTCCACAGGTCAGACATG | 144 |
| 19 | TRAV17 | Vect_hTRAV17_F | TTCAGGTGTCGTGAGGATCTATTTCCGGTG CTGTGATTTCAATAAGGAAGAAGAATG | 145 |

TABLE 5-continued

Primers targeting the 45 TRAVs currently known to be functional in humans. Each of these primers include a primer adapter sequence (TTCAGGTGTCGTGAGGATCTATTTCCGGTG, SEQ ID NO: 126).

| # | Target TRAV(s) | Primer Name | Sequence | SEQ ID NO: |
|---|---|---|---|---|
| 20 | TRAV18 | Vect_hTRAV18_F | TTCAGGTGTCGTGAGGATCTATTTCCGGTG CATGCTGTCTGCTTCCTGCTCAG | 146 |
| 21 | TRAV19 | Vect_hTRAV19_F | TTCAGGTGTCGTGAGGATCTATTTCCGGTG CTCAGGGGAAGAGCTATGAACATG | 147 |
| 22 | TRAV20 | Vect_hTRAV20_F | TTCAGGTGTCGTGAGGATCTATTTCCGGTG GCATGGAGAAAATGTTGGAGTGTG | 148 |
| 23 | TRAV21 | Vect_hTRAV21_F | TTCAGGTGTCGTGAGGATCTATTTCCGGTG GACAGAAGGAATGGAGACCCTCTTG | 149 |
| 24 | TRAV22 | Vect_hTRAV22_F | TTCAGGTGTCGTGAGGATCTATTTCCGGTG ATGAAGAGGATATTGGGAGCTCTG | 150 |
| 25 | TRAV23 | Vect_hTRAV23DV6_F | TTCAGGTGTCGTGAGGATCTATTTCCGGTG CAGGAGGAATGGACAAGATCTTAG | 151 |
| 26 | TRAV24 | Vect_hTRAV24_F | TTCAGGTGTCGTGAGGATCTATTTCCGGTG AGGAAACATGGAGAAGAATCCTTTG | 152 |
| 27 | TRAV25 | Vect_hTRAV25_F | TTCAGGTGTCGTGAGGATCTATTTCCGGTG ATGCTACTCATCACATCAATGTTG | 153 |
| 28 | TRAV26-1 | Vect_hTRAV26_1_F | TTCAGGTGTCGTGAGGATCTATTTCCGGTG ATGAGGCTGGTGGCAAGAGTAAC | 154 |
| 29 | TRAV26-2 | Vect_hTRAV26_2_F | TTCAGGTGTCGTGAGGATCTATTTCCGGTG ATGAAGTTGGTGACAAGCATTACTG | 155 |
| 30 | TRAV27 | Vect_hTRAV27_F | TTCAGGTGTCGTGAGGATCTATTTCCGGTG GATGGTCCTGAAATTCTCCGTGTC | 156 |
| 31 | TRAV29 | Vect_hTRAV29_F | TTCAGGTGTCGTGAGGATCTATTTCCGGTG TTCACAGGAGGGATGGCCATG | 157 |
| 32 | TRAV30 | Vect_hTRAV30_F | TTCAGGTGTCGTGAGGATCTATTTCCGGTG CCATTCAGAAGCTGACTGGATATTC | 158 |
| 33 | TRAV34 | Vect_hTRAV34_F | TTCAGGTGTCGTGAGGATCTATTTCCGGTG GGGATGGAGACTGTTCTGCAAGTAC | 159 |
| 34 | TRAV35 | Vect_hTRAV35_F | TTCAGGTGTCGTGAGGATCTATTTCCGGTG ATGCTCCTTGAACATTTATTAATAATCTTG | 160 |
| 35 | TRAV36 | Vect_hTRAV36_F | TTCAGGTGTCGTGAGGATCTATTTCCGGTG ATGATGAAGTGTCCACAGGCTTTAC | 161 |
| 36 | TRAV38-1 | Vect_hTRAV38_1_F | TTCAGGTGTCGTGAGGATCTATTTCCGGTG GGGAGCGCTGTCAGCATGAC | 162 |
| 37 | TRAV38-2 | Vect_hTRAV38_2D_F | TTCAGGTGTCGTGAGGATCTATTTCCGGTG ATGGCATGCCCTGGCTTC | 163 |
| 38 | TRAV39 | Vect_hTRAV39_F | TTCAGGTGTCGTGAGGATCTATTTCCGGTG ATGAAGAAGCTACTAGCAATGATTCTGTG | 164 |
| 39 | TRAV40 | Vect_hTRAV40_F | TTCAGGTGTCGTGAGGATCTATTTCCGGTG ATGAACTCCTCTCTGGACTTTCTAATTC | 165 |

TABLE 5-continued

Primers targeting the 45 TRAVs currently known to be functional in humans. Each of these primers include a primer adapter sequence (TTCAGGTGTCGTGAGGA-TCTATTTCCGGTG, SEQ ID NO: 126).

| # | Target TRAV(s) | Primer Name | Sequence | SEQ ID NO: |
|---|---|---|---|---|
| 40 | TRAV41 | Vect_hTRAV41_F | TTCAGGTGTCGTGAGGATCTATTTCCGGTG ATGGTGAAGATCCGGCAATTTTTG | 166 |

W = A, T.

TABLE 6

Primers targeting the 48 TRBVs currently known to be functional in humans. Each of these primers include a primer adapter sequence (GTGGAAGAAAACCCCG-GTCCC, SEQ ID NO: 297).

| # | Target TRBV(s) | Primer Name | Sequence | SEQ ID NO: |
|---|---|---|---|---|
| 1 | TRBV2 | Vect_hTRBV2_F | GTGGAAGAAAACCCCGGTCCC ATGGATACCTGGCTCGTATGC | 167 |
| 2 | TRBV3 TRBV4-1 TRBV4-2 TRBV4-3 | Vect_hTRBV3, hTRBV4_123_F | GTGGAAGAAAACCCCGGTCCC ATGGGCTGCAGGCTSCTCTG | 168 |
| 3 | TRBV5-4 TRBV5-5 TRBV5-6 | Vect_hTRBV5_456_F | GTGGAAGAAAACCCCGGTCCC ATGGGCCCYGGGCTCCTC | 169 |
| 4 | TRBV5-1 | Vect_hTRBV5_1_F | GTGGAAGAAAACCCCGGTCCC ATGGGCTCCAGGCTGCTCTG | 170 |
| 5 | TRBV5-8 | Vect_hTRBV5_8_F | GTGGAAGAAAACCCCGGTCCC ATGGGACCCAGGCTCCTCTTC | 171 |
| 6 | TRBV6-2 TRBV6-3 TRBV6-8 | Vect_hTRBV6_238_F | GTGGAAGAAAACCCCGGTCCC ATGAGTCTCGGGCTCCTGTG | 172 |
| 7 | TRBV6-1 TRBV6-9 | Vect_hTRBV6_19_F | GTGGAAGAAAACCCCGGTCCC ATGAGTATCGGGCTCCTGTG | 173 |
| 8 | TRBV6-5 TRBV6-6 | Vect_hTRBV6_56_F | GTGGAAGAAAACCCCGGTCCC ATGAGCATCGGACTCCTGTG | 174 |
| 9 | TRBV6-4 | Vect_hTRBV6_4_F | GTGGAAGAAAACCCCGGTCCC ATGAGAATCAGGCTCCTGTGCTG | 175 |
| 10 | TRBV7-2 TRBV7-3 TRBV7-4 TRBV7-8 TRBV11-2 | Vect_hTRBV7_2348, hTRBV11_2_F | GTGGAAGAAAACCCCGGTCCC ATGGGCACCAGGCTCCTCTTC | 176 |
| 11 | TRBV7-6 TRBV7-7 | Vect_hTRBV7_67_F | GTGGAAGAAAACCCCGGTCCC ATGGGYACCAGTCTCCTATG | 177 |
| 12 | TRBV7-9 | Vect_hTRBV7_9_F | GTGGAAGAAAACCCCGGTCCC ATGGGTACCAGCCTCCTCTG | 178 |
| 13 | TRBV9 | Vect_hTRBV9_F | GTGGAAGAAAACCCCGGTCCC ATGGGCTTCAGGCTCCTCTG | 179 |
| 14 | TRBV10-1 TRBV10-2 | Vect_hTRBV10_12_F | GTGGAAGAAAACCCCGGTCCC ATGGGCACSAGGCTCTTCTTC | 180 |
| 15 | TRBV10-3 | Vect_hTRBV10_3_F | GTGGAAGAAAACCCCGGTCCC ATGGGCACAAGGTTGTTCTTC | 181 |
| 16 | TRBV11-1 | Vect_hTRBV11_1_F | GTGGAAGAAAACCCCGGTCCC ATGAGTACCAGGCTTCTCTGCTG | 182 |

TABLE 6-continued

Primers targeting the 48 TRBVs currently known to be functional in humans. Each of these primers include a primer adapter sequence (GTGGAAGAAAACCCCG-GTCCC, SEQ ID NO: 297).

| # | Target TRBV(s) | Primer Name | Sequence | SEQ ID NO: |
|---|---|---|---|---|
| 17 | TRBV11-3 | Vect_hTRBV11_3_F | GTGGAAGAAAACCCCGGTCCC ATGGGTACCAGGCTCCTCTG | 183 |
| 18 | TRBV12-3 TRBV12-4 | Vect_hTRBV12_34_F | GTGGAAGAAAACCCCGGTCCC ATGGACTCCTGGACCTTCTGCTG | 184 |
| 19 | TRBV12-5 | Vect_hTRBV12_5_F | GTGGAAGAAAACCCCGGTCCC ATGGCTACCAGGCTCCTCTG | 185 |
| 20 | TRBV13 | Vect_hTRBV13_F | GTGGAAGAAAACCCCGGTCCC ATGCTTAGTCCTGACCTGCCTGAC | 186 |
| 21 | TRBV14 | Vect_hTRBV14_F | GTGGAAGAAAACCCCGGTCCC ATGGTTTCCAGGCTTCTCAGTTTAG | 187 |
| 22 | TRBV15 | Vect_hTRBV15_F | GTGGAAGAAAACCCCGGTCCC ATGGGTCCTGGGCTTCTCCAC | 188 |
| 23 | TRBV16 | Vect_hTRBV16_F | GTGGAAGAAAACCCCGGTCCC ATGAGCCCAATATTCACCTGCATC | 189 |
| 24 | TRBV18 | Vect_hTRBV18_F | GTGGAAGAAAACCCCGGTCCC ATGGACACTAGAGTACTCTGCTGTG | 190 |
| 25 | TRBV19 | Vect_hTRBV19_F | GTGGAAGAAAACCCCGGTCCC ATGAGTAACCAGGTGCTCTGCTG | 191 |
| 26 | TRBV20 | Vect_hTRBV20_F | GTGGAAGAAAACCCCGGTCCC ATGCTGCTGCTTCTGCTGCTTC | 192 |
| 27 | TRBV24 | Vect_hTRBV24_F | GTGGAAGAAAACCCCGGTCCC ATGGCCTCCCTGCTCTTCTTC | 193 |
| 28 | TRBV25 | Vect_hTRBV25_F | GTGGAAGAAAACCCCGGTCCC ATGACTATCAGGCTCCTCTGCTAC | 194 |
| 29 | TRBV27 | Vect_hTRBV27_F | GTGGAAGAAAACCCCGGTCCC ATGGGCCCCAGCTCCTTG | 195 |
| 30 | TRBV28 | Vecct_hTRBV28_F | GTGGAAGAAAACCCCGGTCCC ATGGGAATCAGGCTCCTCTGTC | 196 |
| 31 | TRBV29 | Vect_hTRBV29_F | GTGGAAGAAAACCCCGGTCCC ATGCTGAGTCTTCTGCTCCTTCTC | 197 |
| 32 | TRBV30 | Vect_hTRBV30_F | GTGGAAGAAAACCCCGGTCCC ATGCTCTGCTCTCTCCTTGCCCTTC | 198 |

S = C, G; Y = C, T.

In some cases, for mice, a primer collection for a second round amplification of a nested amplification reaction (e.g., nested PCR) provided herein can include the TRAV and TRBV primers set forth in Tables 7 and 8 or a subset of the TRAV and TRBV primers set forth in Tables 7 and 8. For example, a primer collection for a second round amplification of a nested amplification reaction (e.g., nested PCR) provided herein can include 5, 10, 20, 30, 35, or more of the TRAV primers set forth in Table 7, can include 5, 10, 20, 30, or more of the TRBV primers set forth in Table 8, or can include 5, 10, 20, 30, 40, 50, 60, 70, or more of the TRAV and TRBV primers set forth in Tables 7 and 8. In some cases, for mice, a primer collection for a second round amplification of a nested amplification reaction (e.g., nested PCR) provided herein can include the TRAV and TRBV primers set forth in Tables 7 and 8 and no other primers with a sequence of a Vα or Vβ segment, a L sequence of a Vα or Vβ segment, or a 5' untranslated region upstream of a Vα or Vβ segment.

TABLE 7

Primers targeting the 104 TRAVs currently known to be functional in mice. Each of these primers include a primer adapter sequence (TCTCTAGGCGCCGG-AATTCA, SEQ ID NO: 298).

| # | Target TRAV(s) | Primer Name | Sequence | SEQ ID NO: |
|---|---|---|---|---|
| 1 | TRAV1 | Vect_mTRAV1 | TCTCTAGGCGCCGGAATTCA ATGCTGCAGATGTGGGGGTTTG | 199 |
| 2 | TRAV2 | Vect_mTRAV2 | TCTCTAGGCGCCGGAATTCA ATGAAGCAGGTGGCAAAAGTGA | 200 |
| 3 | TRAV3 TRAV3D-3 TRAV3N-3 TRAV3-1 TRAV3-4 | Vect_mTRAV3 | TCTCTAGGCGCCGGAATTCA ATGAARACRGTGACTGGACCTT# | 201 |
| 4 | TRAV4-2 | Vect_mTRAV4-2 | TCTCTAGGCGCCGGAATTCA ATGGAGAGGAGCCCGGGA | 202 |
| 5 | TRAV4N-3 TRAV4-4 TRAV4D-4 TRAV4N-4 | Vect_mTRAV4-34 | TCTCTAGGCGCCGGAATTCA ATGSAGAGGAACCTGGGAGCTG | 203 |
| 6 | TRAV4-3 TRAV4D-3 | Vect_mTRAV4-3 | TCTCTAGGCGCCGGAATTCA ATGSAGAGGAACCTGGTTGCTG | 204 |
| 7 | TRAV5-1 | Vect_mTRAV5-1 | TCTCTAGGCGCCGGAATTCA ATGAAGACAGCTATCCATGCTT | 205 |
| 8 | TRAV5D-4 TRAV5N-4 TRAV5-4 | Vect_mTRAV5-4DN | TCTCTAGGCGCCGGAATTCA ATGAAAACAYAYGCTYCTACATTATTC## | 206 |
| 9 | TRAV6-1 TRAV6-2 TRAV6-3 TRAV6D-3 | Vect_mTRAV6-123 | TCTCTAGGCGCCGGAATTCA ATGAACWMTTCYCCAGCTTTAGTGAC### | 207 |
| 10 | TRAV6-4 TRAV6D-4 | Vect_mTRAV6-4 | TCTCTAGGCGCCGGAATTCA ATGAATACTTCTCCAGTTTTAGTRAC | 208 |
| 11 | TRAV6-5 TRAV6D-5 TRAV6N-5 | Vect_mTRAV6-5 | TCTCTAGGCGCCGGAATTCA ATGAACCTTTRTCCTGAACTGG | 209 |
| 12 | TRAV6-6 TRAV6D-6 TRAV6N-6 | Vect_mTRAV6-6 | TCTCTAGGCGCCGGAATTCA ATGGACTYTTCACCAGGCTTCG | 210 |
| 13 | TRAV6-7 TRAV6D-7 TRAV6N-7 | Vect_mTRAV6-7 | TCTCTAGGCGCCGGAATTCA ATGAACTCTTCTCCAGGCTTCA | 211 |
| 14 | TRAV7-1 | Vect_mTRAV7-1 | TCTCTAGGCGCCGGAATTCA ATGAAGTCCTTGTGTGTTTCAC | 212 |
| 15 | TRAV7-2 TRAV7-4 TRAV7D-4 TRAV7-5 TRAV7D-5 TRAV7N-5 | Vect_mTRAV7-2345 | TCTCTAGGCGCCGGAATTCA ATGAAGTCCTTGAGTGTTTYACTAG | 213 |
| 16 | TRAV7D-2 TRAV7-3 TRAV7D-3 TRAV7N-4 | Vect_mTRAV7-23N4 | TCTCTAGGCGCCGGAATTCA ATGAAGTCCTTKAGTRTTTCCCTAG* | 214 |
| 17 | TRAV7-6 TRAV7D-6 TRAV7N-6 | Vect_mTRAV7-6 | TCTCTAGGCGCCGGAATTCA ATGCATTCCTTACATGTTTCAC | 215 |
| 18 | TRAV8-1 TRAV8D-1 | Vect_mTRAV8-1 | TCTCTAGGCGCCGGAATTCA ATGCACAGCCTCCTRGGGTTGT | 216 |

TABLE 7-continued

Primers targeting the 104 TRAVs currently known to be functional in mice. Each of these primers include a primer adapter sequence (TCTCTAGGCGCCGG-AATTCA, SEQ ID NO: 298).

| # | Target TRAV(s) | Primer Name | Sequence | SEQ ID NO: |
|---|---|---|---|---|
| 19 | TRAV8-2<br>TRAV8D-2<br>TRAV8N-2 | Vect_mTRAV8-2 | TCTCTAGGCGCCGGAATTCA<br>ATGAACAGATTCCTGGGAATAT | 217 |
| 20 | TRAV9-1<br>TRAV9D-1 | Vect_mTRAV9-1 | TCTCTAGGCGCCGGAATTCA<br>ATGCTCCTGGTYCTCATCTCGT | 218 |
| 21 | TRAV9-2<br>TRAV9D-2<br>TRAV9N-2<br>TRAV9D-3<br>TRAV9-4<br>TRAV9D-4<br>TRAV9N-4<br>TRAV9-3<br>TRAV9N-3 | Vect_mTRAV9-234 | TCTCTAGGCGCCGGAATTCA<br>ATGCTCCTGGYRCTCCTC** | 219 |
| 22 | TRAV10<br>TRAV10D<br>TRAV10N | Vect_mTRAV10 | TCTCTAGGCGCCGGAATTCA<br>ATGAAGACATCCCTCCACACTG | 220 |
| 23 | TRAV11<br>TRAV11D | Vect_mTRAV11 | TCTCTAGGCGCCGGAATTCA<br>ATGAAAAAGTGCCTTAGTGCCT | 221 |
| 24 | TRAV12-1<br>TRAV12N-1<br>TRAV12-2<br>TRAV12-3<br>TRAV12N-3 | Vect_mTRAV12-123 | TCTCTAGGCGCCGGAATTCA<br>ATGCRTCCTGTCACCTGCTCAG | 222 |
| 25 | TRAV12D-1<br>TRAV12D-3 | Vect_mTRAV12D-13 | TCTCTAGGCGCCGGAATTCA<br>ATGCGTCCTGWCACCTCCTCAG | 223 |
| 26 | TRAV12D-2<br>TRAV12N-2 | Vect_mTrAV12-2 | TCTCTAGGCGCCGGAATTCA<br>ATGCGTCCTGRCACCTGCTCAG | 224 |
| 27 | TRAV13-2<br>TRAV13D-2<br>TRAV13-5 | Vect_mTRAV13-25 | TCTCTAGGCGCCGGAATTCA<br>ATGARGAGGCTGMTGTGTTCTC*** | 225 |
| 28 | TRAV13N-1<br>TRAV13N-2<br>TRAV13-3<br>TRAV13D-3<br>TRAV13N-3<br>3TRAV13-4<br>TRAV13D-4<br>TRAV13N-4 | Vect_mTRAV13-1234 | TCTCTAGGCGCCGGAATTCA<br>ATGAAGAGGCTGCTGTGCTCTC | 226 |
| 29 | TRAV13-1 | Vect_mTRAV13-1 | TCTCTAGGCGCCGGAATTCA<br>ATGAACAGGCTGCTGTGCTCTC | 227 |
| 30 | TRAV13D-1 | Vect_mTRAV13D-1 | TCTCTAGGCGCCGGAATTCA<br>ATGAAGAGGCTGCTGAGCTCTC | 228 |
| 31 | TRAV14-2<br>TRAV14N-2<br>TRAV14-3/D2 | Vect_mTRAV14-23 | TCTCTAGGCGCCGGAATTCA<br>ATGGACAAGATCCTGACAGCAT | 229 |
| 32 | TRAV14N-1 | Vect_TRAV14N-1 | TCTCTAGGCGCCGGAATTCA<br>ATGGACAAGATCCTGACAGCAA | 230 |
| 33 | TRAV14D-1 | Vect_mTRAV14-1 | TCTCTAGGCGCCGGAATTCA<br>ATGGACACGATCCTGACAGCAT | 231 |
| 34 | TRAV14-1 | Vect_mTRAV14D-1 | TCTCTAGGCGCCGGAATTCA<br>ATGGACAAGATTCTGACAGCAT | 232 |

TABLE 7-continued

Primers targeting the 104 TRAVs currently known to be functional in mice. Each of these primers include a primer adapter sequence (TCTCTAGGCGCCGG-AATTCA, SEQ ID NO: 298).

| # | Target TRAV(s) | Primer Name | Sequence | SEQ ID NO: |
|---|---|---|---|---|
| 35 | TRAV15-1 TRAV15N-1 TRAV15-2 TRAV15D-2 TRAV15N-2 TRAV15D_DV6D-2 | Vect_mTRAV15 | TCTCTAGGCGCCGGAATTCA ATGCCTCCTCASAGCCTG | 233 |
| 36 | TRAV16 TRAV16D TRAV16N | Vect_mTRAV16 | TCTCTAGGCGCCGGAATTCA ATGCTGATTCTAAGCCTGTTGG | 234 |
| 37 | TRAV17 | Vect_mTRAV17 | TCTCTAGGCGCCGGAATTCA ATGTTCCCAGTGACCATTCTGC | 235 |
| 38 | TRAV19 | Vect_mTRAV19 | TCTCTAGGCGCCGGAATTCA ATGACTGGTTTCCTGAAGGCCT | 236 |
| 39 | TRAV21-DV12 | Vect_mTRAV21 | TCTCTAGGCGCCGGAATTCA ATGGGATGTGTGAGTGGAATTG | 237 |

Y = C, T; M = A, C; W = A, T; R = A, G; K = G, T.
= When this primer preparation was used in the Example section, all four primer permutations were made and used. In some cases, this primer preparation can be replaced such that the following three primers are used: TCTCTAGGCGCCGGAA-TTCAATGAAGACGGTGACTGGACCTT (SEQ ID NO: 299), TCTCTAGGC-GCCGGAATTCAATGAAGACAGTGACTGGACCTT (SEQ ID NO: 300), and TCTCTAGGCGCCGGAAT-TCAATGAAAACAGTGACTGGACCTT (SEQ ID NO: 301).
= When this primer preparation was used in the Example section, all eight primer permutations were made and used. In some cases, this primer preparation can be replaced such that the following three primers are used: TCTCTAGGCGCCGGAAT-TCAATGAAAACATACGCTCCTACATTATTC (SEQ ID NO: 302), TCTCTAG-GCGCCGGAATTCAATGAAAACATATGCTCCTACATTATTC (SEQ ID NO: 303), and CTCTAGGCGCCGGAATTCAATGAAAACATGCTTC-TACATTATTC (SEQ ID NO: 304).
= When this primer preparation was used in the Example section, all primer permutations were made and used. In some cases, this primer preparation can be replaced such that the following four primers are used: TCTCTAGGCGCCGGAATT-CAATGAACCATTCCCCAGCTTTAGTGAC (SEQ ID NO: 305), TCTCTAGG-CGCCGGAATTCAATGAACCTTTCTCCAGCTTTAGTGAC (SEQ ID NO: 306), TCTCTAGGCGCCGAATTCAATGAACCATTCTCCAGCTTTAGTGAC (SEQ ID NO: 307), TCTCTAGGCGCCGGAATTCAAT-GAACTATTCTCCAGCTTTAGT-GAC (SEQ ID NO: 308).
* = When this primer preparation was used in the Example section, all four primer permutations were made and used. In some cases, this primer preparation can be replaced such that the following two primers are used: TCTCTAGGCGCCGG-AATTCAATGAAGTCCTTGAGTGTTTCCCTAG (SEQ ID NO: 309) and TCTC-TAGGCGCCGGAATTCAATGAAGTCCTTTAGTATTTCCCTAG (SEQ ID NO: 310).
** = When this primer preparation was used in the Example section, only the following three primers were made, combined, and used: TCTCTAGGCGCCGGAATTCAA-TGCTCCTGGCACTCCTC (SEQ ID NO: 311), TCTCTAGGCGCCGGAATTCAA-TGCTCCTGGCGCTCCTC (SEQ ID NO: 312), and TCTCTAGGCGCCGGAATT-CAATGCTCCTGGTGCTCCTC (SEQ ID NO: 313). In some cases, this three primer mixture can be replaced such that all four primer permutations are made and used.
*** = When this primer preparation was used in the Example section, only the following two primers were made, combined, and used: TCTCTAGGCGCCGGAATT-CAATGAAGAGGCTGCTGTTCTC (SEQ ID NO: 314) and TCTCTAGGCGCC-GGAATTCAATGAGGAGGCTGATGTGTTCTC (SEQ ID NO: 315). In some cases, this three primer mixture can be replaced such that all four primer permutations are made and used.

TABLE 8

Primers targeting the 22 TRBVs currently known to be functional in mice. Each of these primers include a primer adapter sequence (TGGAAGAAAACCC-CGGTCCC, SEQ ID NO: 316).

| # | Target TRBV(s) | Primer Name | Sequence | SEQ ID NO: |
|---|---|---|---|---|
| 1 | TRBV1 | Vect_mTRBV1 | TGGAAGAAAACCCCGGTCCC ATGTGGCAGTTTTGCATTCTGT | 238 |
| 2 | TRBV2 | Vect_mTRBV2 | TGGAAGAAAACCCCGGTCCC ATGGGCTCCATTTTCCTCAGTT | 239 |
| 3 | TRABV3 | Vect_mTRBV3 | TGGAAGAAAACCCCGGTCCC ATGGATATCTGGCTTCTAGGTT | 240 |
| 4 | TRBV4 | Vect_mTRBV4 | TGGAAGAAAACCCCGGTCCC ATGGGCTGTAGGCTCCTAAGCT | 241 |
| 5 | TRBV5 | Vect_mTRBV5 | TGGAAGAAAACCCCGGTCCC ATGAGCTGCAGGCTTCTCCTCT | 242 |

TABLE 8-continued

Primers targeting the 22 TRBVs currently known to be functional in mice. Each of these primers include a primer adapter sequence (TGGAAGAAAACCC-CGGTCCC, SEQ ID NO: 316).

| # | Target TRBV(s) | Primer Name | Sequence | SEQ ID NO: |
|---|---|---|---|---|
| 6 | TRBV12-1 | Vect_mTRBV12-1 | TGGAAGAAAACCCCGGTCCC ATGTCTAACACTGTCCTCGCTG | 243 |
| 7 | TRBV12-2 | Vect_mTRBV12-2 | TGGAAGAAAACCCCGGTCCC ATGTCTAACACTGCCTTCCCTG | 244 |
| 8 | TRBV13-1 | Vect_mTRBV13-1 | TGGAAGAAAACCCCGGTCCC ATGGGCTCCAGGCTCTTTCTGG | 245 |
| 9 | TRBV13-2 | Vect_mTRBV13-2 | TGGAAGAAAACCCCGGTCCC ATGGGCTCCAGGCTCTTCTTCG | 246 |
| 10 | TRBV13-3 | Vect_mTRBV13-3 | TGGAAGAAAACCCCGGTCCC ATGGGCTCCAGACTCTTCTTTG | 247 |
| 11 | TRBV14 | Vect_mTRBV14 | TGGAAGAAAACCCCGGTCCC ATGGGCACCAGGCTTCTT | 248 |
| 12 | TRBV15 | Vect_mTRBV15 | TGGAAGAAAACCCCGGTCCC ATGGGCATCCAGACCCTCTGTT | 249 |
| 13 | TRBV16 | Vect_mTRBV16 | TGGAAGAAAACCCCGGTCCC ATGGCCCCCAGGCTCCTTTTC | 250 |
| 14 | TRBV17 | Vect_mTRBV17 | TGGAAGAAAACCCCGGTCCC ATGGATCCTAGACTTCTTTGCT | 251 |
| 15 | TRBV19 | Vect_mTRBV19 | TGGAAGAAAACCCCGGTCCC ATGAACAAGTGGGTTTTCTGCT | 252 |
| 16 | TRBV20 | Vect_mTRBV20 | TGGAAGAAAACCCCGGTCCC ATGTTACTGCTTCTATTACTTCTGG | 253 |
| 17 | TRBV23 | Vect_mTRBV23 | TGGAAGAAAACCCCGGTCCC ATGGGTGCACGGCTCATTTGCTAT | 254 |
| 18 | TRBV24 | Vect_mTRBV24 | TGGAAGAAAACCCCGGTCCC ATGGGTGCAAGACTGCTC | 255 |
| 19 | TRBV26 | Vect_mTRBV26 | TGGAAGAAAACCCCGGTCCC ATGGCTACAAGGCTCCTCTGTTA | 256 |
| 20 | TRBV29 | Vect_mTRBV29 | TGGAAGAAAACCCCGGTCCC ATGAGAGTTAGGCTCATCTCTG | 257 |
| 21 | TRBV30 | Vect_mTRBV30 | TGGAAGAAAACCCCGGTCCC ATGTGGACATTCCTGCTACTTC | 258 |
| 22 | TRBV31 | Vect_mTRBV31 | TGGAAGAAAACCCCGGTCCC ATGCTGTACTCTCTCCTTGCCT | 259 |

In some cases, a primer collection for a second round amplification of a nested amplification reaction (e.g., nested PCR) provided herein can be divided into two or more subsets with each subset being used to perform a second round amplification of a nested amplification reaction (e.g., nested PCR) provided herein using a portion of a resulting amplification reaction from a first round amplification as template. In some cases, for human for example, a primer collection for a second round amplification of a nested amplification reaction (e.g., nested PCR) provided herein can be divided into two or more subsets (e.g., a first subset of the TRAV and TRBV primers set forth in Tables 5 and 6 and a second subset of the TRAV and TRBV primers set forth in Tables 5 and 6), with each subset being used to perform a second round amplification of a nested amplification reaction (e.g., nested PCR) provided herein using a portion of a resulting amplification reaction from a first round amplification as template. In some cases, for mice, a primer collection for a second round amplification of a nested amplification reaction (e.g., nested PCR) provided herein can be divided into two or more subsets (e.g., a first subset of the TRAV and TRBV primers set forth in Tables 7 and 8 and a second subset of the TRAV and TRBV primers set forth in Tables 7 and 8), with each subset being used to perform a second round amplification of a nested amplification reaction (e.g., nested PCR) provided herein using a portion of a resulting amplification reaction from a first round amplification as template. The results of these separate second round amplifications of a nested amplification reaction (e.g., nested PCR) for cDNA obtained from the same single T cell can be combined, and the combination can be used to assemble an expression vector as described herein.

In some cases, the forward primers for the second round of a nested amplification reaction provided herein can be designed to include a primer barcode sequence and/or a primer adapter sequence (see, e.g., the middle panels of FIGS. 2A and 2B). For example, all the forward primers of a primer collection for a second round amplification of a nested amplification reaction (e.g., nested PCR) provided herein can have a 5' primer adapter sequence followed by the primer sequence that targets a V segment, a L sequence of a V segment, and/or a 5' untranslated region found upstream of a V segment (see, e.g., FIGS. 2A and 2B). In some cases, the added 5' adapter sequence from the forward primers for the second round of a nested amplification reaction provided herein can be used to assist in the cloning of the first and second amplification products into an expression vector. In some cases, any one or more of the primer sequences set forth in Tables 5-8 can be designed to include a primer adapter sequence at the 5' end of the sequence shown to create a forward primer for the second round of a nested amplification reaction provided herein as shown, for example, in FIGS. 2A and 2B. For example, all the primer sequences set forth in Tables 5 and 6 can be designed to include a primer adapter sequence at the 5' end of the sequence shown.

Any appropriate primer adapter sequence can be added to a primer such as a first round primer, in which case the primer adapter sequence can serve as a target for the forward primer of the second round of a nested amplification procedure described herein and as an overlap sequence to assist with cloning the first and second amplification products into an expression vector, or a second round primer, in which case the primer adapter sequence can serve as an overlap sequence to assist with cloning the first and second amplification products into an expression vector. In some cases, a primer adapter sequence can be from about 15 to about 50 nucleotides (e.g., from about 15 to about 45 nucleotides, from about 15 to about 40 nucleotides, from about 15 to about 30 nucleotides, from about 20 to about 50 nucleotides, from about 20 to about 40 nucleotides, or from about 20 to about 30 nucleotides) in length. Examples of primer adapter sequences that can be used as described herein include, without limitation,

```
                                      (SEQ ID NO: 260)
TTCAGGTGTCGTGAGGATCTATTTCCGGTG;

(SEQ ID NO: 261)
GTGGAAGAAAACCCCGGTCCC;

(SEQ ID NO: 262)
TCTCTAGGCGCCGG-AATTCA;
and (SEQ ID NO: 263)
TGGAAGAAAACCCCGGTCCC.
```

As described herein, a primer collection for a first round amplification of a nested amplification reaction (e.g., nested PCR) provided herein can include a pool of forward primers to target TRAVs (or TRGVs) and a pool of forward primers to target TRBVs (or TRDVs). Such a primer collection can include at least one reverse primer for each pool of forward primers. For example, a primer collection for a first round amplification of a nested amplification reaction (e.g., nested PCR) provided herein for αβ TCRs (or γδ TCRs) can include a set of forward TRAV primers (or forward TRGV primers) as described herein, one or more reverse primers designed to pair with one or more of those forward TRAV primers (or those forward TRGV primers) to generate an amplification product having a sequence of a TRAV (or a TRGV), a set of forward TRBV primers (or forward TRDV primers) as described herein, and one or more reverse primers designed to pair with one or more of those forward TRBV primers (or those forward TRDV primers) to generate an amplification product having a sequence of a TRBV (or a TRDV). In general, reverse primers designed to pair with one or more forward TRAV primers (or forward TRGV primers) within a primer collection for a first round amplification of a nested amplification reaction provided herein for αβ TCRs (or γδ TCRs) can be designed to be specific for a sequence of a C region of an α chain (or a sequence of a C region of a γ chain). In some cases, one Cα (or Cγ) reverse primer or more than one Cα (or Cγ) reverse primer (e.g., two, three, four, five, or more Cα (or Cγ) reverse primers) can be used for a first round amplification of a nested amplification reaction provided herein for αβ TCRs (or γδ TCRs). Likewise, reverse primers designed to pair with one or more forward TRBV primers (or forward TRDV primers) within a primer collection for a first round amplification of a nested amplification reaction provided herein for αβ TCRs (or γδ TCRs) can be designed to be specific for a sequence of a C region of an β chain (or a sequence of a C region of a δ chain). In some cases, one Cβ (or Cδ) reverse primer or more than one Cβ (or Cδ) reverse primer (e.g., two, three, four, five, or more Cβ (or Cδ) reverse primers) can be used for a first round amplification of a nested amplification reaction provided herein for αβ TCRs (or γδ TCRs).

In some cases, a primer collection for a first round amplification of a nested amplification reaction (e.g., nested PCR) provided herein for αβ TCRs (or γδ TCRs) can include a set of forward TRAV primers (or forward TRGV primers) as described herein, a single reverse primer designed to pair with each of those forward TRAV primers (or those forward TRGV primers) to generate an amplification product having a sequence of a TRAV (or a TRGV), a set of forward TRBV primers (or forward TRDV primers) as described herein, and a single reverse primer designed to pair with each of those forward TRBV primers (or those forward TRDV primers) to generate an amplification product having a sequence of a TRBV (or a TRDV).

In general, reverse primers for a primer collection for a first round amplification of a nested amplification reaction (e.g., nested PCR) provided herein can be designed to be specific for a C region that is from about 15 nucleotides to about 550 nucleotides (e.g., from about 15 nucleotides to about 500 nucleotides, from about 15 nucleotides to about 450 nucleotides, from about 15 nucleotides to about 400 nucleotides, from about 15 nucleotides to about 300 nucleotides, from about 15 nucleotides to about 200 nucleotides, from about 15 nucleotides to about 100 nucleotides, from about 15 nucleotides to about 50 nucleotides, from about 20 nucleotides to about 550 nucleotides, from about 20 nucleotides to about 450 nucleotides, from about 20 nucleotides to about 400 nucleotides, from about 20 nucleotides to about 300 nucleotides, from about 20 nucleotides to about 200 nucleotides, from about 20 nucleotides to about 100 nucleotides, or from about 20 nucleotides to about 50 nucleotides) from the 5' most nucleotide of that targeted C region. For example, a Cα reverse primer can be designed to be specific for a nucleotide sequence that is from about nucleotide 15 to about nucleotide 450 of a Cα region. For humans and mice, examples of such Cα reverse primers include, without limitation, the Cα reverse primers set forth in Table 9. A Cβ reverse primer can be designed to be specific for a nucleotide sequence that is from about nucleotide 15 to about nucleotide 550 of a Cβ region. For humans and mice, examples of such Cβ reverse primers include, without limitation, the Cβ reverse primers set forth in Table 10.

TABLE 9

Exemplary first round reverse primers targeting Cα of human or mice.

| # | Primer Name | Sequence | SEQ ID NO: |
|---|---|---|---|
| 1 | hTRAC (for human) | CACATCAGAATCCTTACTTTGTGACAC | 264 |
| 2 | hTRACf (for human) | ATCGGTGAATAGGCAGACAGACTTG | 265 |
| 3 | mTRAC (for mice) | TCTTGGAATCCATAGCTTTCATG | 266 |

TABLE 10

Exemplary first round reverse primers targeting Cβ of human or mice.

| # | Primer Name | Sequence | SEQ ID NO: |
|---|---|---|---|
| 1 | hTRBC (for human) | CATTCACCCACCAGCTCAG | 267 |
| 2 | hTRBCf (for human) | GTGTGGGAGATCTCTGCTTCTG | 268 |
| 3 | mTRBC (for mice) | CCACGTGGTCAGGGAAGAAG | 269 |

As described herein, a primer collection for a second round amplification of a nested amplification reaction (e.g., nested PCR) provided herein can include a pool of forward primers to target TRAVs (or TRGVs) and a pool of forward primers to target TRBVs (or TRDVs), for example, when primer adapter sequences are not used during the first round as shown in, for example, FIGS. 2A and 2B. Such a primer collection can include at least one reverse primer for each pool of forward primers. For example, a primer collection for a second round amplification of a nested amplification reaction (e.g., nested PCR) provided herein for αβ TCRs (or γδ TCRs) can include a set of forward TRAV primers (or forward TRGV primers) as described herein, one or more reverse primers designed to pair with one or more of those forward TRAV primers (or those forward TRGV primers) to generate the first amplification product having a sequence of a TRAV (or a TRGV), a set of forward TRBV primers (or forward TRDV primers) as described herein, and one or more reverse primers designed to pair with one or more of those forward TRBV primers (or those forward TRDV primers) to generate the second amplification product having a sequence of a TRBV (or a TRDV). In general, reverse primers designed to pair with one or more forward TRAV primers (or forward TRGV primers) within a primer collection for a second round amplification of a nested amplification reaction provided herein for αβ TCRs (or γδ TCRs) can be designed to be specific for a sequence of a C region of an α chain (or a sequence of a C region of a γ chain). In some cases, one Cα (or Cγ) reverse primer or more than one Cα (or Cγ) reverse primer (e.g., two, three, four, five, or more Cα (or Cγ) reverse primers) can be used for a second round amplification of a nested amplification reaction provided herein for αβ TCRs (or γδ TCRs). Likewise, reverse primers designed to pair with one or more forward TRBV primers (or forward TRDV primers) within a primer collection for a second round amplification of a nested amplification reaction provided herein for αβ TCRs (or γδ TCRs) can be designed to be specific for a sequence of a C region of an β chain (or a sequence of a C region of a δ chain). In some cases, one Cβ (or Cδ) reverse primer or more than one co (or Cδ) reverse primer (e.g., two, three, four, five, or more Cβ (or Cδ) reverse primers) can be used for a second round amplification of a nested amplification reaction provided herein for αβ TCRs (or γδ TCRs).

In some cases, a primer collection for a second round amplification of a nested amplification reaction (e.g., nested PCR) provided herein for αβ TCRs (or γδ TCRs) can include a set of forward TRAV primers (or forward TRGV primers) as described herein, a single reverse primer designed to pair with each of those forward TRAV primers (or those forward TRGV primers) to generate the first amplification product having a sequence of a TRAV (or a TRGV), a set of forward TRBV primers (or forward TRDV primers) as described herein, and a single reverse primer designed to pair with each of those forward TRBV primers (or those forward TRDV primers) to generate the second amplification product having a sequence of a TRBV (or a TRDV).

In general, reverse primers for a primer collection for a second round amplification of a nested amplification reaction (e.g., nested PCR) provided herein can be designed to be specific for a C region that is from about 15 nucleotides to about 550 nucleotides (e.g., from about 15 nucleotides to about 500 nucleotides, from about 15 nucleotides to about 450 nucleotides, from about 15 nucleotides to about 400 nucleotides, from about 15 nucleotides to about 300 nucleotides, from about 15 nucleotides to about 200 nucleotides, from about 15 nucleotides to about 100 nucleotides, from about 15 nucleotides to about 50 nucleotides, from about 20 nucleotides to about 550 nucleotides, from about 20 nucleotides to about 450 nucleotides, from about 20 nucleotides to about 400 nucleotides, from about 20 nucleotides to about 300 nucleotides, from about 20 nucleotides to about 200 nucleotides, from about 20 nucleotides to about 100 nucleotides, or from about 20 nucleotides to about 50 nucleotides) from the 5' most nucleotide of that targeted C region, provided that it is within the site of the reverse primer that was used for the first round when a fully-nested amplification procedure is used. In some cases, a nested amplification procedure described herein can be semi-nested, in which case one or more of the reverse primers for the first and second rounds of amplification can be the same. For example, a Cα reverse primer can be designed to be specific for a nucleotide sequence that is from about nucleotide 1 to about nucleotide 30 of a Cα region when the reverse primer used for the first round was designed to be specific for a sequence that is from about nucleotide 40 to about nucleotide 70 of a Cα region in a fully-nested amplification procedure. For humans and mice, examples of such Cα reverse primers include, without limitation, the Cα reverse primers set forth in Table 11. A Cβ reverse primer can be designed to be specific for a nucleotide sequence that is from about nucleotide 1 to about nucleotide 549 of a Cβ region provided that that site is within the site of the reverse primer used during the first round in a fully-nested amplification procedure. For humans and mice, examples of such Cβ reverse primers include, without limitation, the Cβ reverse primers set forth in Table 12.

TABLE 11

Exemplary second round reverse primers targeting Cα of human or mice.

| # | Primer Name | Sequence | SEQ ID NO: |
|---|---|---|---|
| 1 | hTRACn (for human) | GACTTGTCACTGGATTTAGAGTCTC | 270 |
| 2 | mTRACn (for mice) | AGGTTCTGGGTTCTGGATGT | 271 |

TABLE 12

Exemplary second round reverse primers targeting Cβ of human or mice.

| # | Primer Name | Sequence | SEQ ID NO: |
|---|---|---|---|
| 1 | hTRBCn (for human) | TGCTTCTGATGGCTCAAACAC | 272 |
| 2 | mTRBCn (for mice) | GGAGTCACATTTCTCAGATCCT | 273 |

As also described herein, a primer collection for a second round amplification of a nested amplification reaction (e.g., nested PCR) provided herein can include (a) one or more forward primers designed to target a primer adapter sequence that was added to the TRAV (or TRGV) amplification products during the first round when primer adapter sequences are used during the first round as shown in, for example, FIG. 3A, (b) one or more reverse primers to pair with the one or more forward primers of (a), (c) one or more forward primers designed to target a primer adapter sequence that was added to the TRBV (or TRDV) amplification products during the first round when primer adapter sequences are used during the first round as shown in, for example, FIG. 3B, and (d) one or more reverse primers to pair with the one or more forward primers of (c).

In one embodiment, a first round amplification of a nested amplification reaction (e.g., nested PCR) provided herein can be performed using a primer collection that includes the primers set forth in Tables 1 and 2 together with the hTRAC primer of Table 9 as a reverse primer to pair with the forward primers of Table 1 and the hTRBC primer of Table 10 as a reverse primer to pair with the forward primers of Table 2 (see, e.g., the top panels of FIGS. 2A and 2B). The amplification products of this first round can be used as template in a second round amplification. The second round can be performed using a primer collection that includes the primers set forth in Table 5 (with the addition of a primer adapter sequence at the 5' end), the primers set forth in Table 6 (with the addition of a primer adapter sequence at the 5' end different from the adapter sequence used with the Table 5 primers), the hTRACn primer of Table 11 as a reverse primer to pair with the forward primers of Table 5, and the hTRBCn primer of Table 12 as a reverse primer to pair with the forward primers of Table 6 (see, e.g., the middle panels of FIGS. 2A and 2B). This second round amplification can result in a first amplification product that includes an adapter sequence, the entire L sequence of a Vα segment, a Vα segment, a Jα segment, and a 5' portion of a Cα region and a second amplification product that includes a different adapter sequence, the entire L sequence of a Vβ segment, a Vβ segment, a Dβ segment, a Jβ segment, and a 5' portion of a Cβ region (see, e.g., the bottom panels of FIGS. 2A and 2B). The first and second amplification products can be used as described herein to assemble an expression vector having the ability to express a functional TCR that was cloned from a single T cell.

Any appropriate polymerase enzyme (e.g., thermostable polymerase enzyme) can be used to perform the first and/or second rounds of a nested amplification reaction provided herein. Examples of polymerase enzymes that can be used as described herein included, without limitation, Taq DNA polymerase (available commercially from ThermoFisher Scientific), Phusion DNA polymerase (available commercially from ThermoFischer Scientific), Pfu Turbo DNA polymerase (available commercially from Agilent), Q5 High Fidelity DNA polymerase (available commercially from New England Biolabs), and MyFi DNA polymerase (available commercially from Bioline). Other ingredients for performing a first and/or second rounds of a nested amplification reaction provided herein can include, without limitation, the appropriate polymerase buffer, $MgCl_2$, DMSO, and dNTPs.

The first and/or second rounds of a nested amplification reaction provided herein can be performed by contacting the template with a thermostable polymerase (e.g., Taq polymerase) in the presence of a primer collection as described herein, dNTPs, and optionally a detergent (e.g., a non-denaturing detergent) and subjecting the reaction mixture to thermal cycling conditions such as 40 cycles of 98° C. for 1 minute, 53° C. for 30 seconds, and 72° C. for 40 seconds.

In some cases, the forward primers of a first and/or second round of a nested amplification reaction (e.g., nested PCR) provided herein can be designed to target amplification of V segments without amplifying L sequences of those V segments. In such cases, a heterologous leader sequence can be used in place of the L sequences of those V segments to promote expression of the cloned TCRs on the surface of cells. Such heterologous leader sequences can be provided during the amplification procedure and/or during the assembly of the expression vector. Examples of heterologous leader sequences that can be used as described herein include, without limitation, leader sequences that encode a MLTASLLRAVIASICVVSSM (SEQ ID NO:317) sequence for mouse TRAVs, a MSTRLLCWMALCLLGALS (SEQ ID NO:318) sequence for mouse TRBVs, a MLQMWGFVLYLFLMVGAA (SEQ ID NO:319) sequence for human TRAVs, and a MWQFCILCLCVL-MASVAT (SEQ ID NO:320) sequence for human TRBVs.

Once the first amplification product containing a Vα segment (or Vγ segment) such as a first amplification product containing the entire L sequence of a Vα segment, a Vα segment, a Jα segment, and a 5' portion of a Cα region and a second amplification product containing a Vβ segment (or Vδ segment) such as a second amplification product containing the entire L sequence of a Vβ segment, a Vβ segment, a Dβ segment, a Jβ segment, and a 5' portion of a Cβ region (see, e.g., the bottom panels of FIG. 2A, 2B, 3A or 3B) are generated, they can be cloned into an expression vector in a manner such that a functional TCR having the α and β variable region combination (or γ and δ variable region combination) as present in the single T cell source is expressed.

Any appropriate cloning technique can be used to assemble an expression vector designed to express functional TCRs cloned from single T cells. In some cases, cloning steps can be performed from the point of obtaining the first and second amplification products to the point of obtaining assembled expression vectors having the ability to express functional TCRs cloned from single T cells without using a restriction enzyme. In such cases, the cloning technique can be referred to herein as a "seamless" cloning technique. Examples of seamless cloning techniques that can be used to arrange a first amplification product into a complete α (or γ) chain (e.g., a full-length L sequence, a full-length Vα segment, a full-length Jα segment, and a full-length Cα region) and to arrange a second amplification product into a complete β (or δ) chain (e.g., a full-length L sequence, a full-length Vβ segment, a full-length Dβ segment, a full-length Jβ segment, and a full-length Cβ region) in a manner that creates an expression vector designed to express functional TCRs cloned from single T cells include, without limitation, exonuclease-based cloning techniques such as Gibson assembly techniques, High-5 assembly techniques, and Ligation Independent Cloning (LIC) techniques and exonuclease independent cloning techniques such as the Golden Gate assembly techniques and the univector plasmid-fusion assembly techniques.

With reference to FIG. 1, a Gibson assembly technique can be performed using the first and second amplification products from a nested amplification reaction provided herein, a separate cloning fragment, and an expression vector designed to receive the first and second amplification products. In some cases, the first amplification product can be designed to have a 5' sequence that overlaps with a portion of the expression vector prepared to receive the first amplification product. This 5' overlapping sequence can be added to the first amplification product via a primer adapter sequence as described herein. The first amplification product also can be designed to have a 3' sequence that overlaps with a 5' portion of the separate cloning fragment. For example, a 3' portion of Cα (or Cγ) of the first amplification product can overlap with a 5' portion of Cα (or Cγ) of the separate cloning fragment. In some cases, as shown in FIG. 1, for example, this separate cloning fragment can be designed to provide any 3' portion of a full-length α chain (or γ chain) that is missing from the first amplification product. In the case of FIG. 1, the separate cloning fragment is providing the remainder of the Cα region.

The second amplification product can be designed to have a 5' sequence that overlaps with a 3' sequence of the separate cloning fragment such that the second amplification fragment can be attached to the separate cloning fragment. This 5' overlapping sequence of the second amplification product can be added to the second amplification product via a primer adapter sequence as described herein. The second amplification product also can be designed to have a 3' sequence that overlaps with a portion of the expression vector prepared to receive the second amplification product. As shown in FIG. 1, this portion of the expression vector can be designed to provide any 3' portion of a full-length β chain (or δ chain) that is missing from the second amplification product. In the case of FIG. 1, the expression vector to receive the second amplification product is providing the remainder of the Cβ region.

When the first and second amplification products from a nested amplification reaction provided herein, a separate cloning fragment, and an expression vector prepared to receive the first and second amplification products, each having the overlapping sequences, for example, as shown in FIG. 1, are incubated together with a 5' exonuclease enzyme, a DNA polymerase enzyme, and a DNA ligase enzyme to perform Gibson assembly, an assembled expression vector can be produced with the first amplification product being followed by the separate cloning fragment which is followed by the second amplification product and then vector sequence.

In some cases, the vector sequence upstream of the first amplification product can be a promoter sequence designed to drive expression of the assembled nucleic acid encoding the α chain (or γ chain) of a TCR. Any type of promoter sequence can be used. Examples of promoter sequences that can be used include, without limitation, without limitation, CMV promoter sequences for high expression, MCSV promoter sequences for high expression, E1Fa promoter sequences for moderate expression, PGK promoter sequences for moderate expression, and UbC promoter sequences for low expression.

In some cases, the separate cloning fragment can be designed to encode a self-cleaving peptide such as a 2A peptide such that it is located between the nucleic acid encoding an α chain (or γ chain) and the nucleic acid encoding a β chain (or δ chain) in the assembled vector. In these cases, only one promoter is needed to drive expression of both the α and β chains (or γ and δ chains). Examples of 2A peptides that can be used as described herein include, without limitation, a 2A peptide of foot-and-mouth disease virus, a 2A peptide of equine rhinitis A virus, a 2A peptide of *Thosea asigna* virus, and a 2A peptide of porcine teschovirus-1. The amino acid sequence of exemplary 2A polypeptides are provided in Table 13. Examples of separate cloning fragments that can be used in a Gibson assembly technique provided herein to obtain an expression vector that expresses a cloned human or mouse TCR include, without limitation, those set forth in Table 14. In some cases, a linker sequence can be included upstream of the sequence encoding a self-cleaving peptide (e.g., the sequence encoding a 2A peptide). Such a linker sequence can have a length that maintains the reading frame for the sequence encoding a self-cleaving peptide. For example, the linker can be from about 3 to about 45 nucleotides (e.g., 27 nucleotides) in length.

TABLE 13

Exemplary 2A peptides.

| # | Peptide Name | Sequence | SEQ ID NO: |
|---|---|---|---|
| 1 | P2A | GSGATNFSLLKQAGDVEENPGP | 274 |
| 2 | T2A | GSGEGRGSLLTCGDVEENPGP | 275 |
| 3 | E2A | GSGQCTNYALLKLAGDVESNPGP | 276 |
| 4 | F2A | GSGVKQTLNFDLLKLAGDVESNPGP | 277 |

TABLE 14

Exemplary separate cloning fragments.

| # | Name | Sequence | SEQ ID NO: |
|---|---|---|---|
| 1 | Human INSERT_B | 5'-AGACTCTAAATCCAGTGACAAGT CTGTCTGCCTATTCACCGATTTTGATTCTCAAACA AATGTGTCACAAAGTAAGGATTCTGATGTGTATA TCACAGACAAAACTGTGCTAGACATGAGGTCTAT GGACTTCAAGAGCAACAGTGCTGTGGCCTGGAGC AACAAATCTGACTTTGCATGTGCAAACGCCTTCA ACAACAGCATTATTCCAGAAGACACCTTCTTCCC CAGCCCAGAAAGTTCCTGTGATGTCAAGCTGGTC GAGAAAAGCTTTGAAACAGATACGAACCTAAAC TTTCAAAACCTGTCAGTGATTGGGTTCCGAATCCT CCTCCTGAAAGTGGCCGGGTTTAATCTGCTCATG ACGCTGCGGCTGTGGTCCAGCGGCTCCGGAGCCA | 321 |

TABLE 14-continued

Exemplary separate cloning fragments.

| # | Name | Sequence | SEQ ID NO: |
|---|------|----------|------------|
|   |      | CGAACTTCTCTCTGTTAAAGCAAGCAGGAGACGT GGAAGAAAACCCCGGTCCC-3' |   |
| 2 | Mouse INSERT_B | 5'-ACATCCAGAACCCAGAACCTGCTG TGTACCAGTTAAAAGATCCTCGGTCTCAGGACAG CACCCTCTGCCTGTTCACCGACTTTGACTCCCAAA TCAATGTGCCGAAAACCATGGAATCTGGAACGTT CATCACTGACAAAACTGTGCTGGACATGAAAGCT ATGGATTCCAAGAGCAATGGGGCCATTGCCTGGA GCAACCAGACAAGCTTCACCTGCCAAGATATCTT CAAAGAGACCAACGCCACCTACCCCAGTTCAGAC GTTCCCTGTGATGCCACGTTGACCGAGAAAAGCT TTGAAACAGATATGAACCTAAACTTTCAAAACCT GTCAGTTATGGGACTCCGAATCCTCCTGCTGAAA GTAGCGGGATTTAACCTGCTCATGACGCTGAGGC TGTGGTCCAGTGGCTCCGGAGCCACGAACTTCTC TCTGTTAAAGCAAGCAGGAGACGTGGAAGAAAA CCCCGGTCCC-3' | 322 |

When using a self-cleaving peptide such as a 2A peptide, the expression vector can drive transcription of transcripts that encode the α chain (or γ chain) followed by the self-cleaving peptide (e.g., a 2A peptide) followed by the β chain (or δ chain). During translation of these transcripts, the growing polypeptide can be cleaved at the 2A peptide with translation continuing through the β chain (or δ chain). When designing an expression vector to express the α and β chains (or the γ and δ chains) as a multicistronic unit the nucleic acid encoding the two TCR chains and the self-cleaving peptide (e.g., a 2A peptide) can be designed such that they are in translational frame with each other.

In some cases, an Internal Ribosome Entry Site (IRES) can be used in place of a self-cleaving peptide. Examples of IRES sequences include, without limitation, an Encephalomyocrditis virus (EMCV) IRES (e.g., IRES2), a Hepatitis C virus (HCV) IRES, a Picorna virus IRES, and a Pestivirus IRES.

In some cases, a separate promoter sequence can be used in place of self-cleaving peptide or an IRES. In these cases, one promoter sequence can drive expression of an α chain (or γ chain), and a separate promoter sequence can drive expression of a β chain (or δ chain). These two promoter sequences can be the same or different.

Any appropriate 5' exonuclease enzyme, DNA polymerase enzyme, and DNA ligase enzyme can be used to perform a Gibson assembly technique provided herein. Examples of 5' exonuclease enzymes that can be used as described herein include, without limitation, T5 exonucleases (available commercially from New England Biolabs). Examples of DNA polymerase enzymes that can be used as described herein include, without limitation, Phusion DNA polymerases (available commercially from ThermoFisher Scientific), Pfu Turbo DNA polymerases (available commercially from Agilent), and Q5 High Fidelity DNA polymerases (available commercially from New England Biolabs). Examples of DNA ligase enzymes that can be used as described herein include, without limitation, T4 DNA ligases (available commercially from ThermoFischer Scientific), T3 DNA ligases (available commercially from New England Biolabs), T7 DNA ligases (available commercially from New England Biolabs), and HiFi Taq DNA ligases (available commercially from New England Biolabs). Other ingredients for performing a Gibson assembly technique provided herein can include, without limitation, dNTPS, $MgCl_2$, DTT, PEG-8000, and NAD.

In general, a Gibson assembly technique can be used to join any appropriate double-stranded DNA fragments having overlapping sequences. Briefly, an enzyme with 5' exonuclease activity chews back the 5' ends. When the overlapping sequences anneal, the DNA polymerase fills in the sequence extending from the 3' end, and the DNA ligase seals the nicks, thereby joining the two overlapping fragments.

A Gibson assembly technique provided herein can be performed by contacting the first and second amplification products, a separate cloning fragment, and a prepared vector (e.g., a vector opened to receive an insert), each having their overlapping sequences as described herein, with enzymes having 5' exonuclease activity, DNA polymerase activity, and DNA ligase activity in the presence of a reaction mixture containing dNTPS, $MgCl_2$, DTT, PEG-8000, and NAD and incubating the reaction mixture isothermally from about 40 to about 60° C. (e.g., from about 45 to about 55° C., from about 48 to about 52° C., or at about 50° C.) for about 10 to about 120 minutes (e.g., for about 10 to about 90 minutes, for about 10 to about 60 minutes, for about 10 to about 45 minutes, for about 15 to about 90 minutes, for about 15 to about 60 minutes, or for about 15 to about 45 minutes).

In some cases, restriction endonuclease cloning can be used to arrange a first amplification product into a complete α (or γ) chain (e.g., a full-length L sequence, a full-length Vα segment, a full-length Jα segment, and a full-length Cα region) and to arrange a second amplification product into a complete β (or δ) chain (e.g., a full-length L sequence, a full-length Vβ segment, a full-length Dβ segment, a full-length Jβ segment, and a full-length Cβ region) within an expression vector in a manner such that both are expressed. For example, restriction endonuclease cloning can be used to assemble an expression vector to have a promotor sequence followed by nucleic acid encoding an α chain (or γ chain) followed by nucleic acid encoding a self-cleaving peptide (or IRES) or nucleic acid of a second promoter sequence followed by nucleic acid encoding a β chain (or δ chain).

When describing the arrangement of the expression vectors provided herein and the components used to assemble those expression vectors (e.g., the first and second amplification products), the α chain (or γ chain) is described as being upstream of the β chain (or δ chain). This is not a requirement as the expression vector can be designed to express the α and β chains (or γ and δ chains) in either order. For example, an expression vector can be constructed using the methods and materials provided herein such that a promoter sequence drives expression of a transcript that starts with nucleic acid encoding a β chain (or δ chain) followed by nucleic acid encoding a self-cleaving peptide (or IRES) or nucleic acid of a second promoter sequence followed by nucleic acid encoding an α chain (or γ chain).

Any appropriate vector designed to drive polypeptide expression can be used to assemble an expression vector provided herein. For example, lentiviral vectors can be used to make an expression vector having the ability to express functional TCRs that are cloned from single T cells as described herein. Other vectors that can be used to make the expression vectors described herein include, without limitation, viral based vectors such as herpesviral vectors, adenoviral vectors, adeno associated viral vectors, or retroviral vectors, or other DNA or RNA cell expression vectors that can be introduced into target cells. In some cases, lentiviral vectors such as pLVX-IRES (commercially available from Clontech) or retroviral vectors such as pMIG II (commercially available from Addgene) can be used to assemble an expression vector having the ability to express function TCRs that are cloned from single T cells as described herein.

Once an expression vector is assembled to include the sequences for a TCR cloned from single T cells as described herein, that vector can be used to make additional copies of itself. For example, bacteria can be transformed to replicate the assembled expression vector. In such cases, the expression vector can be designed to include a bacterial origin of replication.

Figure 4:
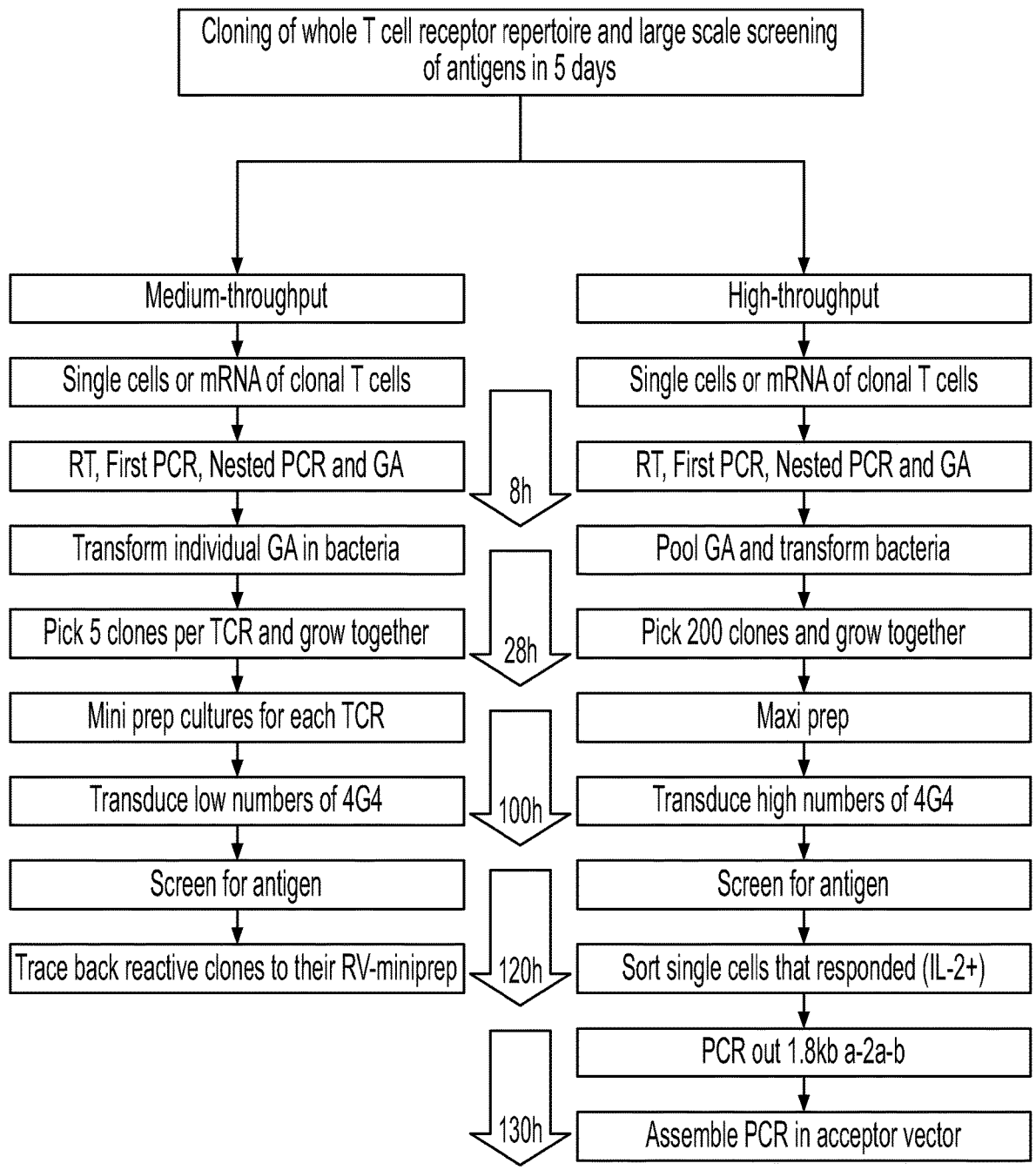
FIG. 4 is a flowchart of two exemplary screening procedures that can be performed using the methods and materials described herein to obtain desired TCR clones quickly using the methods and materials provided herein. In some cases, these screening procedures can be carried out from the step of sorting the original T cells into single sorted cells prior to TCR cloning to the step of isolating particular TCR clones having a desired antigen specificity from an antigen screen without performing nucleic acid sequencing, without performing restriction endonuclease cleavage steps, or without performing either nucleic acid sequencing or restriction endonuclease cleavage steps.

The assembled expression vectors provided herein can be used to screen the cloned TCRs for TCRs of interest using any appropriate method. For example, the methods shown in FIG. 4 can be performed to screen cloned TCRs provided herein.

In some cases, each assembled expression vector can be expanded individually such that each nucleic acid preparation of an expression vector is for a single T cell. In these cases, any particular TCRs identified as being of interest based on, for example, downstream TCR screening and analysis can be traced back to a nucleic acid preparation for that TCR.

In some cases, two or more (e.g., tens, hundreds, thousands, or more) assembled expression vectors can be pooled and expanded as a pool. In these cases, the pooled nucleic acid can be used to perform downstream screening and analysis of pools of cells expressing any of the cloned TCRs. Those cells identified as expressing a particular TCR of interest can be isolated, and the particular expression vector (or all or part of the TCR-encoding nucleic acid) contained within that cell can be retrieved. For example, in one embodiment, a pool of different expression vectors provided herein, each encoding a particular TCR cloned from a single T cell, can be delivered to a population of cells (e.g., cells lacking native TCRs) such that each cell is transfected to express the TCR provided to it by the expression vector it receives. The pool of cells expressing the different cloned TCRs then can be assessed to identify cells expressing TCRs of interest. Those cells that are expressing a TCR of interest can be isolated. Once isolated, the cell can be assessed to determine the identity of the TCR. For example, nucleic acid sequencing can be performed to identify the TCR. In some cases, the nucleic acid encoding the TCR can be isolated from the isolated cells. For example, one or more amplification reactions (e.g., PCR) can be performed to obtain one or more amplification products that include nucleic acid encoding all or a portion of the TCR.

The methods and materials provided herein are described with a focus on obtaining an expression vector having the ability to express a cloned TCR obtained from a single T cell. In some cases, the methods and materials provided herein can be performed in a manner designed to produce a vector encoding the TCRs as described herein except that that vector need not be an expression vector. For example, a cloning vector such as pUC19 or a PCR TOPO vector can be used to assemble a nucleic acid construct encoding an α chain (or γ chain), a β chain (or δ chain), and optionally a self-cleaving peptide (or IRES) and/or promotor sequences as describe herein. In such cases, the assembled construct can be moved from the cloning vector to an expression vector if expression is later desired. If expression is not desired, then the vector containing the assembled construct can be used as is. For example, nucleic acid sequencing can be performed using such vectors to obtain sequence information about paired α and β chains (or γ and δ chains) obtained from single T cells. In some cases, nucleic acid sequencing can be performed using the first and/or second amplification products described herein to obtain sequence information about the α and/or β chains (or γ and/or δ chains) obtained from single T cells.

The methods and materials provided herein are described with a focus on obtaining an expression vector having the ability to express a cloned TCR that contains α and β (or γ and δ) C regions. In some cases, the methods and materials provided herein can be performed in a manner designed to produce vectors (e.g., expression vectors) encoding the TCRs as described herein except that a different signaling domain or a domain that results in soluble TCRs being expressed is added. In some cases, the methods and materials provided herein can be performed in a manner designed to produce vectors (e.g., expression vectors) encoding the TCRs as described herein except that all or a portion of the α and/or β (or γ and/or δ) C regions are replaced with a different signaling domain or with a domain that results in soluble TCRs being expressed. For example, a vector (e.g., expression vector) provided herein can be assembled such that nucleic acid encoding a signaling domain (e.g., a CD3-zeta signaling domain) replaces the stop codon of the α or β (or γ or δ) C region of a cloned TCR and added in frame with the constant region. Examples of signaling domains that can be added to, or used in place of, all or a portion of the α and/or β (or γ and/or δ) C regions of a cloned TCR provided herein include, without limitation, CD3-zeta signaling domains (Ohno et al., *The EMBO Journal*, 12:4357-66 (1993); Exley et al., *Journal Biol. Chem.*, 269: 15140-6 (1994); and Maher et al., *Nat. Biotechnol.*, 20:70-5 (2002)), CD28 signaling domains (Maher et al., *Nat. Biotechnol.*, 20:70-5 (2002); and Tian et al., *Proc. Natl. Acad. Sci. USA*, 112:E1594-603 (2015)), co-stimulatory TNFR family signaling domains (e.g., OX-40, 4-1BB, CD30, CD27, and GITR signaling domains; Arch et al., *Mol. Cell. Biol.*, 18:558-65 (1998); Croft, *Cytok. Growth Factor Rev.*, 14:265-73 (2003); and Watts, *Ann. Rev. Immunol.*, 23:23-68 (2005)), CD278 signaling domains (Bertram et al., *Eur. J. Immunol.*, 32:3376-85 (2002); and Gigoux et al., *Proc. Natl. Acad. Sci. USA*, 106:20371-6 (2009)), and combinations thereof. Examples of domains and/or mutations having the ability, individually or in combination, to result in soluble TCRs being expressed and that can be used to replace the α and/or β (or γ and/or δ) C regions (or a portion thereof) of a cloned TCR or that can be added to the C regions of a cloned TCR include, without limitation, biotinylation target motifs placed on the α and/or β (or γ and/or δ) C regions (Laugel et al., *J. Biol. Chem.*, 280:1882-92 (2005)), one or more Ig domains in place of one or both C regions, mutation of the C region sequence such that additional cysteine residues are expressed in both the α and β (or γ and δ) C regions (Laugel et al., *J. Biol. Chem.*, 280:1882-92 (2005)), deletion of the transmembrane and intracellular domains of one or both constant regions, Jun-Zipper domains added to α and β C regions, and Fos-Zipper domains added to γ and δ C regions (Willcox et al., *Protein Sci.*, 8:2418-23 (1999)). In some cases, a FLAG tag or a His tag can be added to one or both C regions to promote protein purification. In some cases, the internal cytoplasmic tail of one or both C regions can be removed to promote cell free expression of the TCR chains (Walseng et al., *PloS One*, 10:e0119559 (2015)).

Once an assembled expression vector described herein or a pool of different expression vectors described herein is prepared, it can be introduced into cells such that the cells express the provided TCR. Any appropriate cell can be used. In some cases, expression vectors described herein can be introduced into cells (e.g., T cells) that do not express endogenous TCRs. For example, expression vectors provided herein can be introduced into T cells (e.g., human T cells) that were engineered to lack expression of an endogenous α chain (or γ chain) of a TCR, to lack expression of an endogenous β chain (or δ chain) of a TCR, or to lack expression of both endogenous α and β chains (or both endogenous γ and δ chains) of a TCR. Any appropriate method can be used to generate T cells that lack expression of one or both chains of an endogenous TCR. For example, gene editing techniques such as those that involve using Clustered Regularly Interspaced Short Palindromic Repeats (CRISPR) technology or Transcription Activator-Like Effector Nuclease (TALEN) technology can be used to interfere with the expression of one or both chains of an endogenous TCR.

In some cases, natural killer (NK) cells can be used. For example, expression vectors described herein can be introduced into NK cells that were engineered to express the CD3 chains of the TCR complex (e.g., the CD3ε, CD3γ, CD3ζ, and optionally CD3δ). In such cases, the exogenously provided TCRs can be expressed on the surface of the NK cells in combination with the exogenously provided CD3 complex.

In some cases, expression vectors provided herein can be introduced into T cells (e.g., human T cells) that express an endogenous TCR. In such cases, a portion of the TCRs present on the surface of such T cells can be endogenous TCRs, a portion of the TCRs present on the surface of such T cells can be exogenously provided TCRs (e.g., TCRs generated from the two TCR chains encoded by the introduced expression vector), and a portion of the TCRs present on the surface of such T cells can have one endogenous provided TCR chain and one exogenously provided TCR chain.

In some cases, the constant regions of the α and β chains (or γ and δ chains) encoded by an expression vector provided herein can be engineered to include sequences that encode one or more cysteine residues to increase the pairing of those chains with each other when expressed within a cell (e.g., a cell that expresses an endogenous TCR). For example, the TCR sequences obtained from single-cell-sorted T cells as described herein can be assembled into expression vectors such that each encoded constant region of an expression vector includes introduced cysteine residues that increase the pairing of those chains with each other when expressed within a cell (e.g., a cell that expresses an endogenous TCR). Examples of such cysteine residues include, without limitation, those described elsewhere (Kuball et al., *Blood*, 109:2331-2338 (2007)).

In some cases, an expression vector provided herein can be introduced into a T cell from a species that is different from the species used to clone the TCR sequences of that expression vector. For example, expression vectors provided herein that express TCRs having variable regions obtained from mouse T cells can be introduced into T cells from a species other than a mouse species (e.g., human T cells).

In some cases, an expression vector provided herein can be engineered to express a chimeric TCR having variable regions from one species (e.g., human) and constant regions from a different species (e.g., mouse). In such cases, the expression vector can be introduced into a T cell from a species that is different from the species of the constant regions. For example, an expression vector engineered to express a chimeric TCR having human variable regions and mouse constant regions can be introduced into human T cells (e.g., human T cells expressing endogenous TCRs). In such cases, the exogenously provided human/mouse chimeric TCRs can be expressed and assembled into functional TCRs on the surface of the human T cells as described elsewhere (Cohen et al., *Cancer Res.*, 66(17):8878-8886 (2006)).

In some cases, an expression vector provided herein that expresses a cloned TCR having αβ constant regions can be introduced into γδ T cells having endogenous γδ TCRs. In these cases, the two chains of the exogenous TCR can pair properly through the αβ constant regions with little, or no, interference from the endogenous γ and δ TCR chains. In some cases, an expression vector provided herein that expresses a cloned TCR having γδ constant regions can be introduced into αβ T cells having endogenous αβ TCRs. In these cases, the two chains of the exogenous TCR can pair properly through the γδ constant regions with little, or no, interference from the endogenous α and β TCR chains.

In some cases, an expression vector provided herein can be engineered to express a TCR having γδ variable regions obtained from a single γδ T cell and αβ constant regions. In such cases, the expression vector can be introduced into γδ T cells having endogenous γδ TCRs. In these cases, the two chains of the exogenous TCR can pair properly through the αβ constant regions even though those TCRs contain γδ variable regions.

In some cases, an expression vector provided herein can be engineered to express a TCR having αβ variable regions obtained from a single αβ T cell and γδ constant regions. In such cases, the expression vector can be introduced into αβT cells having endogenous αβ TCRs. In these cases, the two chains of the exogenous TCR can pair properly through the γδ constant regions even though those TCRs contain variable regions. This proper pairing can occur with little, or no, interference from the endogenous α and β TCR chains.

In some cases, an expression vector provided herein can be engineered to express a TCR having γδ variable regions obtained from a single γδ T cell and αβ constant regions. In such cases, the expression vector can be introduced into γδ T cells having endogenous γδ TCRs. In these cases, the two chains of the exogenous TCR can pair properly through the αβ constant regions even though those TCRs contain γδ variable regions.

As described herein, once an assembled expression vector or a pool of different expression vectors is prepared, it can be introduced into cells such that the cells express the provided TCR. Any appropriate cell can be used. For example, expression vectors provided herein can be introduced into immortal human T cell lines such as Jurkat cells, Molt cell lines, or cell lines derived from these sources. In some cases, sub-strains of Jurkat or Molt cell lines that do not express endogenous arranged TCRs can be used (Minowada et al., *Haematol. Blood Transfus.*, 32:233-236 (1989); Zhang et al., *PLoS Pathog.*, 6(7):e1001018 (2010)). In some cases, murine cell lines can be used to express human or mouse TCRs. In some cases, cell lines designed to express exogenous CD3 nucleic acid such as 4G4 cell lines, BW5147 cell lines, or 58 hybridoma cell lines transformed to express CD3 genes can be used.

Selection of TCRs that are relevant to a specific patient or disease being treated can be identified before and after TCR cloning. Detection of the appropriate TCR can begin with the sorting steps. For example, prior to sorting, a screen can be performed by culturing the cells for a period of time (e.g., four hours) with antigen presenting cells (APCs) pulsed with one or more antigens (e.g., antigens of a vaccine such as a prostate tumor vaccine, a minor histocompatibility antigen vaccine, or an anti-viral vaccine such as a flu vaccine). Examples of APCs that can be used include, without limitation, immortal cell lines known to express MEW 1 and/or 2 and peripheral blood monocytes that have been differentiated into professional APCs and expanded by stimulation with TLR ligands and cultured with IL-4 and GM-CSF. Following stimulation, the peripheral blood can be stained to identify T cells. Within that group of T cells, activated T cells can be identified based on the expression of markers such as CD62L, CD127, CD69, CD44, and CD45RA/RO.

Once the cells exposed to the one or more antigens are sorted into single T cells as described herein and the cDNA generated, up to about 80 percent of the cDNA generated from the single T cells can be used for qPCR without interfering with the efficiency of the TCR cloning. In some cases, stimulated T cells can be screened for the upregulation of effector molecules such IFN-γ, IL-2, TNF-α, and other molecules known to be expressed directly after stimulation. By normalizing the expression of these cells to one or more housekeeping genes on a single cell level, the wells containing single T cells with TCRs specific for the antigens used to stimulate the T cell population can be identified. In some cases, the cloning steps can be continued for those TCRs obtained from T cells identified as having TCRs specific for the antigens used to stimulate the T cell population.

Once expression vectors are assembled, the TCRs they are designed to express can be tested for functionality and antigen specificity. Functionality and antigen specificity can be confirmed by expressing the assembled TCRs in either cell lines or primary cells. In some cases, cells expressing a cloned TCR can be screened using any appropriate method to identify cloned TCRs of interest. For example, particular antigen peptide-tetramer complexes can be used to stain cells expressing TCRs having the ability to bind to that complex. In some cases, assembled expression vectors provided herein can be introduced into reporter cells engineered to provide an identifiable signal upon successful activation of a cloned and functional TCR.

In some cases, a cell line can be designed to express a marker polypeptide (e.g., luciferase) under the control of a NFAT response element can be used to identify functional TCRs. NFAT is transcription factor that is sequestered in the nucleus until a signal such TCR ligation leads to its dephosphorylation and subsequent transportation to nucleus (Crabtree et al., Cell, 109(Suppl):S67-79 (2002)). NFAT will then bind NFAT response elements and lead to expression the marker polypeptide encoded by the nucleic acid sequence downstream of that NFAT response element. In some cases, a commercially available immortal T cell line such as a Jurkat cell line that contains a NFAT response element upstream of nucleic acid encoding luciferase (Promega; Catalog No. J1621) can be used to identify functional TCRs. Upon TCR ligation of a functional TCR, these cells can express luciferase. As described herein, 4G4 NFAT-RE cells can be transfected with retroviral vectors that express cloned TCRs as described herein and those cells can be stimulated in 384-well plates that are coated with anti-CD3 antibodies. In these cases, stimulated cells can express luciferase, which can be detected within 4 hours of stimulation. This system can allow for the rapid screening of more than 360 viral vectors per 384-well plate for the expression of functional TCRs. In such cases, 24 wells can be used for positive and negative assay controls.

In some cases, an assay that confirms antigen specificity of a cloned TCR can be performed. For example, cells can be cultured with APCs that have been pulsed with antigenic peptides or infected with viral vectors that express the target genes or transfected with plasmids that express suspected target genes. Examples of target genes include, without limitation, tumor associated antigens, vaccine associated antigens, and pathogenic virus associated antigens. As with the assessment of TCR functionality, specificity can be assessed using the NFAT response element luciferase assay with the exception that the specific antigen within an appropriate MHC molecule is used instead of anti-CD3 antibodies to stimulate the TCRs being tested. The MHC molecules expressed by cell lines described herein can be load with specific peptides by either placing peptides directly in culture or transfecting the MHC-expressing cells with a vector (e.g., a plasmid) that expresses one or more peptides of interest. In some cases, the peptide (or antigen expression vector) can be tittered to control for different TCR affinities and different peptide/MHC affinities.

In some cases, TCR expression, functionality, and/or specificity can be assessed simultaneously by flow cytometry. By replacing the luciferase protein of a NFAT response element reporter system with a fluorescent protein (e.g., eGFP or tdTomato), a cloned TCR expressed from an expression vector provided herein can be assessed for proper expression, functionality, and/or specificity in transfected cells. Briefly, cell line containing a NFAT response element reporter system that controls expression of a fluorescent protein can be transfected with an expression vector provided herein that expresses a cloned TCR. The cell line then can be incubated with antigen pulsed APCs or APC cell lines. The cells then can be assessed by flow cytometry for expression of the fluorescent marker. The presence of a fluorescent protein after stimulation can indicate that the introduced TCR is expressed, functional, and specific for the antigen used to stimulate the cells. In some cases, an expression vector provided herein that expresses a cloned TCR can include nucleic acid encoding a marker polypeptide that can be used as an indicator to track which cells receive the expression vector. Expression vectors and cell lines can be chosen so that the reporter polypeptide expressed by the cell line and the indicator expressed by the expression vector will not interfere with each other.

In some cases, these flow cytometric assessments can be combined with another round of single cell sorting. For example, antigen responsive cells (e.g., those expressing a fluorescent marker in response to stimulation with a specific antigen plus MCH) can be sorted into 384-well plates, and an amplification reaction (e.g., PCR) can be performed to amplify the TCR constructs introduced into these cells.

This method of sorting can be used to screen multiple expression vectors simultaneously. Briefly, reporter cells can be transfected with expression vectors provided herein to express the cloned TCRs. The reporter cells can be transfected with a single expression vector, however, multiple cultures can be infected (each with a different expression vector). These cultures can be combined and then incubated with APCs having the desired antigen or antigens for between about 4 to 12 hours. After this time, the cultures can be assessed by flow cytometry, and the cells expressing a fluorescent marker via an NFAT response element can be sorted into single wells. Those cells can be cloned and used as therapeutic TCR vectors. In some cases, this process can be used to screen hundreds of expression vectors designed to express cloned TCRs simultaneously.

In some cases, primary T cells can be used to screen the specificity of cloned TCRs encoded by expression vectors provided herein. In some cases, the primary T cells can be screened for the ability to kill target cells (e.g., particular cancer cells). For example, cloned MHC class I-restricted TCRs can be transferred into cytotoxic lymphocytes (either primary cells differentiated into CTLs or expanded primary natural killer (NK) cells transformed to express CD3 gene(s)) and then co-cultured with labeled target cells. These target cells can be expanded tumor cells (e.g., tumor cells expanded from biopsy samples of tumor resection), MHC class I-expressing cells that were pulsed with antigens derived from tumor samples, and/or MHC class I-expressing cell lines that were transfected with antigen plasmids that express tumor specific genes. In these cases, CTL activity can be measured by loading target cells with either radioactive isotope such as chromium 51 or dye and measuring the release of the loaded marker following incubation (Rowe et al., *Toxicol. Appl. Pharmacol.*, 221:179-88 (2007)). When interested in the specificity of the TCR and the ability of that TCR to facilitate a lytic hit in effector cells, degranulation can be measured as an effective assessment of the cytotoxic potential of TCR transformed effector cells. Following incubation of effector cells with target, perforin or granzyme B ELISAs can be performed. Measuring CD107a expression on the surface of the effector cells (Betts et al., *Methods Cell Biol.*, 75:497-512 (2004)) and cell death of target by flow cytometry can be used to assess the cytotoxic potential of the effector cell population.

In some cases, expansion of cells in response to known or suspected antigens following TCR stimulation can be used to assess antigen specific activation of cloned TCRs. The ability of the TCR vectors described herein to drive proliferation of primary mammalian (e.g., human) T cells can be measured with CFSE or another cell proliferation dye (Lyons, *Immunol. Cell. Biol.*, 77:509-15 (1999)). Measurement of cell proliferation can be used to determine antigen specify of vector based TCRs. Briefly, primary T cells can be infected with TCR-expressing vectors provided herein that have been validated for function and TCR chain pairing. The primary T cells can be labeled with CFSE and incubated with APCs pulsed with one or more antigenic peptides or a vector that expresses one or more antigenic proteins. Primary T cells receiving a TCR vector that is specific for the antigen being expressed by the APCs will divide and thus dilute the CFSE dye. Those cells that express lower amounts of CFSE (i.e., divided more) can be isolated via single cell sorting, and the assembled nucleic acid encoding the $\alpha\beta$ TCR (or $\gamma\delta$ TCR) can be amplified (e.g., PCR amplified) from a single cell.

The methods and materials provided herein can be used to obtain many different cloned TCRs. Once obtained, they can be screened to identify those that can be used to treat various conditions such as autoimmunity, cancer, an organ transplant rejection, a viral infection, a bacterial infection, an inflammatory process that can be regulated by T cells (e.g., inflammatory bowel disease, psoriasis, vasculitis, atherosclerosis, non-infectious hepatitis, or autoimmune cholangitis). For example, in some cases, tumor-infiltrating T cells can be isolated from a human patient having cancer. Those T cells can be used as described herein to generate a collection of hundreds or thousands of different cloned TCRs from that human quickly. Then, those cloned TCRs can be quickly screened to identify a population of cloned TCRs having the ability to kill the cancer cells also obtained from that patient. Those cloned and identified TCRs can be used to generate additional cell lines that express those TCRs and can be used to treat that human. In some cases, all these steps from obtaining the source T cells to using cells transfected with an expression vector encoding a therapeutically effective TCR that was cloned as described herein as a therapeutic agent can be performed without determining the sequence identity of the therapeutically effective TCR.

In some cases, the methods provided herein can be performed without performing nucleic acid sequencing, without performing restriction endonuclease cleavage steps, without performing other steps or techniques as described herein, and/or without using particular reagents or materials as described herein. For example, in some cases, the methods used to obtain a collection of expression vectors designed to express cloned TCRs obtained from single T cells as described herein can be carried out from the point of sorting T cells into single T cells to the point of having the assembled expression vectors without performing any nucleic acid sequencing. In some cases, the methods provided herein can include obtaining a collection of expression vectors designed to express cloned TCRs obtained from single T cells and identifying particular TCRs from that collection of expression vectors without performing any nucleic acid sequencing. For example, TCRs having a particular function can be cloned and identified using the methods and materials provided herein without performing any nucleic acid sequencing of the TCR sequence.

As described herein, in some cases, the methods used to obtain a collection of expression vectors designed to express cloned TCRs obtained from single T cells can be carried out from the point of sorting T cells into single T cells to the point of having the assembled expression vectors without performing any restriction endonuclease cleavage reaction for cloning or otherwise. For example, a seamless cloning technique can be used to assemble expression vectors from the first and second amplification products.

Also as described herein, in some cases, the methods used to obtain a collection of expression vectors designed to express cloned TCRs obtained from single T cells can be carried out from the point of sorting T cells into single T cells to the point of having the assembled expression vectors without performing a first round amplification of a nested amplification (e.g., PCR) procedure within a reaction mixture that is designed to amplify only nucleic acid of one type of variable chain (e.g., designed to amplify only nucleic acid of $\alpha$ variable chains and not $\beta$ variable chains (or vice versa), or designed to amplify only nucleic acid of $\gamma$ variable chains and not $\delta$ variable chains (or vice versa)). For example, a first round amplification of a nested amplification (e.g., PCR) procedure can be performed within a reaction mixture designed to amplify both $\alpha$ and $\beta$ variable chain nucleic acid (or both $\gamma$ and $\delta$ variable chain nucleic acid) within that reaction mixture.

As described herein, in some cases, the methods used to obtain a collection of expression vectors designed to express cloned TCRs obtained from single T cells can be carried out from the point of sorting T cells into single T cells to the point of having the assembled expression vectors without performing a second round amplification of a nested amplification (e.g., PCR) procedure within a reaction mixture that is designed to amplify only nucleic acid of one type of variable chain (e.g., designed to amplify only nucleic acid of $\alpha$ variable chains and not $\beta$ variable chains (or vice versa), or designed to amplify only nucleic acid of $\gamma$ variable chains and not $\delta$ variable chains (or vice versa)). For example, a second round amplification of a nested amplification (e.g., PCR) procedure can be performed within a reaction mixture designed to amplify both $\alpha$ and $\beta$ variable chain nucleic acid (or both $\gamma$ and $\delta$ variable chain nucleic acid) within that reaction mixture.

In some cases, as described herein, the methods used to obtain a collection of expression vectors designed to express cloned TCRs obtained from single T cells can be carried out from the point of sorting T cells into single T cells to the point of having the assembled expression vectors without performing a first round amplification of a nested amplification (e.g., PCR) procedure using a first round primer collection where the primers specific for amplifying nucleic acid of α variable chain (e.g., an α, β, γ, or δ variable chain) include an extraneous nucleic acid sequence (e.g., a primer barcode sequence or a primer adapter sequence). For example, a first round primer collection can include primers having a sequence specific for amplifying nucleic acid of α variable chain (e.g., an α, β, γ, or δ variable chain) while lacking extraneous nucleic acid sequences (e.g., a primer barcode sequence or a primer adapter sequence) that are longer than five contiguous nucleotides, that are not complementary to the variable chain being amplified, and that are attached to a nucleic acid sequence complementary to the variable chain being amplified.

In some cases, as described herein, the methods used to obtain a collection of expression vectors designed to express cloned TCRs obtained from single T cells can be carried out from the point of sorting T cells into single T cells to the point of having the assembled expression vectors without performing a nested amplification (e.g., PCR) procedure designed to produce an amplification product containing less than the full-length coding region of α variable chain (e.g., an α, β, γ, or δ variable chain) such as an amplification product containing a CDR3 region α variable chain (e.g., an α, β, γ, or δ variable chain) in the absence of a CDR1 region or in the absence of both a CDR1 region and a CDR2 region. For example, a nested amplification (e.g., PCR) procedure provided herein can be designed to amplify a first amplification product containing the full-length α variable chain (or full-length γ variable chain) and a second amplification product containing the full-length β variable chain (or full-length δ variable chain).

In some embodiments, the methods used to obtain a collection of expression vectors designed to express cloned TCRs obtained from single T cells can be carried out from the point of sorting T cells into single T cells to the point of having the assembled expression vectors (a) without performing any nucleic acid sequencing, (b) without performing any restriction endonuclease cleavage reaction for cloning or otherwise, (c) without performing a first round amplification of a nested amplification (e.g., PCR) procedure within a reaction mixture that is designed to amplify only nucleic acid of one type of variable chain (e.g., designed to amplify only nucleic acid of α variable chains and not β variable chains (or vice versa), or designed to amplify only nucleic acid of γ variable chains and not δ variable chains (or vice versa)), (d) without performing a second round amplification of a nested amplification (e.g., PCR) procedure within a reaction mixture that is designed to amplify only nucleic acid of one type of variable chain (e.g., designed to amplify only nucleic acid of α variable chains and not β variable chains (or vice versa), or designed to amplify only nucleic acid of γ variable chains and not δ variable chains (or vice versa)), (e) without performing a first round amplification of a nested amplification (e.g., PCR) procedure using a first round primer collection where the primers specific for amplifying nucleic acid of α variable chain (e.g., an α, β, γ, or δ variable chain) include an extraneous nucleic acid sequence (e.g., a primer barcode sequence or a primer adapter sequence) that is longer than five contiguous nucleotides, that is not complementary to the variable chain being amplified, and that is attached to a nucleic acid sequence complementary to the variable chain being amplified, and/or (f) without performing a nested amplification (e.g., PCR) procedure designed to produce an amplification product containing less than the full-length coding region of α variable chain (e.g., an α, β, γ, or δ variable chain) such as an amplification product containing a CDR3 region α variable chain (e.g., an α, β, γ, or δ variable chain) in the absence of a CDR1 region or in the absence of both a CDR1 region and a CDR2 region. In some cases, the methods described herein (e.g., the multiplexed methods described herein) can be performed such that any one or more of the exclusionary items of (a) through (f) from the previous sentence are met from the point of cell sorting to the point of obtaining expression vectors capable of expressing functional TCRs. Examples of combinations of such exclusionary items that can be met when performing a method described herein (e.g., a multiplexed method described herein) from the point of cell sorting to the point of obtaining the expression vectors include, without limitation, (a) and (b); (a) and (c); (a) and (d); (a) and (e); (a) and (f); (b) and (c); (b) and (d); (b) and (e); (b) and (f); (c) and (d); (c) and (e); (c) and (f); (d) and (e); (d) and (f); (a), (b), and (c); (a), (b), and (d); (a), (b), and (e); (a), (b), and (f); (a), (c), and (d); (a), (c), and (e); (a), (c), and (f); (a), (d), and (e); (a), (d), and (f); (a), (e), and (f); (b), (c), and (d); (b), (c), and (e); (b), (c), and (f); (b), (d), and (e); (b), (d), and (f); (b), (e), and (f); (c), (d), and (e); (c), (d), and (f); (c), (e), and (f); (d), (e), and (f); (a), (b), (c), and (d); (a), (b), (c), and (e); (a), (b), (c), and (f); (a), (b), (d), and (e); (a), (b), (d), and (f); (a), (b), (e), and (f); (a), (c), (d), and (e); (a), (c), (d), and (f); (a), (c), (e), and (f); (a), (d), (e), and (f); (b), (c), (d), and (e); (b), (c), (d), and (f); (b), (c), (e), and (f); (b), (d), (e), and (f); (c), (d), (e), and (f); (a), (b), (c), (d), and (e); (a), (b), (c), (d), and (f); (a), (b), (c), (e), and (f); (a), (b), (d), (e), and (f); (a), (c), (d), (e), and (f); and (a), (b), (c), (d), (e), and (f). For example, the methods described herein (e.g., the multiplexed methods described herein) can be performed (a) without performing any nucleic acid sequencing and (b) without performing any restriction endonuclease cleavage reactions from the point of cell sorting to the point of obtaining expression vectors capable of expressing functional TCRs. In some cases, the methods described herein (e.g., the multiplexed methods described herein) can be performed without performing a first round amplification of a nested amplification procedure using a first round primer collection where the primers specific for amplifying nucleic acid of α variable chain (e.g., an α, β, γ, or δ variable chain) include an extraneous nucleic acid sequence (e.g., a primer barcode sequence or a primer adapter sequence) that is longer than five contiguous nucleotides, that is not complementary to the variable chain being amplified, and that is attached to a nucleic acid sequence complementary to the variable chain being amplified.

This document also provides kits for obtaining nucleic acid encoding a TCR from a single T cell and arranging that nucleic acid to form nucleic acid vectors successfully designed to express a TCR (e.g., a fully intact TCR such as a fully intact TCR having the variable chain combination as present in that single T cell). For example, a kit provided herein can include a primer collection for carrying out a first round amplification of a nested amplification reaction (e.g., nested PCR) described herein in combination with a primer collection for carrying out a second round amplification of a nested amplification reaction (e.g., nested PCR) described herein.

In one embodiment, a kit provided herein can include (a) a primer collection for carrying out a first round amplification of a nested amplification reaction (e.g., nested PCR) described herein, (b) a primer collection for carrying out a second round amplification of a nested amplification reaction (e.g., nested PCR) described herein, and (c) a cloning fragment and/or a vector. In this case, the primer collections can have the ability, during a nested amplification reaction, to create a first amplification product containing nucleic acid encoding a L sequence, a Vα segment (or Vγ segment), a Jα segment (or Jγ segment), and at least a portion of a Cα region (or Cγ region) and a second amplification product containing nucleic acid encoding a L sequence, a Vβ segment (or Vδ segment), a Dβ segment (or Dδ segment), a Jβ segment (or J3 segment), and at least a portion of a Cβ region (or Cδ region). In those cases where the kit includes a cloning fragment, the cloning fragment can contain nucleic acid encoding a portion of a C region of a TCR (e.g., a portion of a Cα region, a Cγ region, a Cβ region, or a Cδ region). In those cases where the kit includes a vector, the vector can include nucleic acid encoding a portion of a TCR (e.g., a portion of a Cα region, a Cγ region, a Cβ region, or a Cδ region).

In some cases, a kit provided herein can include a primer collection that includes a first primer set for carrying out a first round amplification of a nested amplification reaction (e.g., nested PCR) described herein and a second primer set for carrying out a second round amplification of a nested amplification reaction (e.g., nested PCR) described herein, where (a) at least one of the primers of the first primer set is set forth in Table 1 or Table 2 (e.g., hTRAV1_12_F, hTRBV4_123_F, hTRBV10_12_F, and/or hTRBV12_34_F) or (b) at least one of the primers of the second primer set is set forth in Table 5 or Table 6 (e.g., Vect_hTRAV1_12_F, Vect_hTRAV8_246, Vect_hTRBV4_123_F, Vect_hTRBV6_23_F, Vect_hTRBV6_89_F, Vect_hTRBV7_2348_F, and/or Vect_hTRBV12_34_F). In this case, one or more of the primers of the first primer set (e.g., all the forward primers of the first set) can lack adapter sequences, and one or more primers of the second primer set (e.g., all the forward primers of the second set) can include adapter sequences. In some cases, such a kit can include reverse primers for the first and second rounds of amplification. Other optional ingredients for the kit can include reverse transcription primers (e.g., random oligomers), a reverse transcriptase enzyme, a DNA polymerase enzyme for PCR (e.g., Taq polymerase, buffers, a cloning fragment, an expression vector (e.g., a lentiviral vector) configured to receive nucleic acid encoding a TCR, a 5' exonuclease enzyme, a DNA polymerase for performing Gibson assembly reactions, a DNA ligase enzyme, and combinations thereof. For example, a kit provided herein can include a primer collection as described herein in combination with a cloning fragment and/or an expression vector configured to receive nucleic acid encoding a TCR. As described herein, a cloning fragment can include nucleic acid encoding a portion of a TCR and nucleic acid encoding a self-cleaving peptide (or IRES). In some cases, a cloning fragment can include nucleic acid encoding a portion of a TCR and a promoter sequence. In some cases, an expression vector (e.g., a lentiviral vector) can be configured to include nucleic acid encoding at least a portion of a TCR as described herein.

In another example, a kit provided herein can include a primer collection that includes (a) a first set of primers as set forth in Table 1, (b) a second set of primers as set forth in Table 2, (c) a reverse primer for each of the first and second sets, (d) third set of primers as set forth in Table 5 (with the addition of a primer adapter sequence at the 5' end), (e) a fourth set of primers as set forth in Table 6 (with the addition of a primer adapter sequence at the 5' end different from the adapter sequence used with third set of primers), and (f) a reverse primer for each of the third and fourth sets.

This document also provided reaction mixtures. For example, in one embodiment, a reaction mixture provided herein can include (a) a first amplification product containing nucleic acid encoding a L sequence, a Vα segment (or Vγ segment), a Jα segment (or Jγ segment), and at least a portion of a Cα region (or Cγ region) and (b) a second amplification product containing nucleic acid encoding a L sequence, a Vβ segment (or Vδ segment), a Dβ segment (or Dδ segment), a Jβ segment (or Jδ segment), and at least a portion of a Cβ region (or Cδ region). In this embodiment, the reaction mixture can optionally include a cloning fragment and/or a vector. In those cases where the reaction mixture includes a cloning vector, the cloning fragment can contain nucleic acid encoding a portion of a C region of a TCR (e.g., a portion of a Cα region, a Cγ region, a Cβ region, or a Cδ region). In those cases where the reaction mixture includes a vector, the vector can include nucleic acid encoding a portion of a TCR (e.g., a portion of a Cα region, a Cγ region, a Cβ region, or a Cδ region).

In another example, a reaction mixture provided herein can include (a) a primer collection for performing a second round of a nested amplification reaction (e.g., nested PCR) provided herein, (b) a first amplification product containing nucleic acid encoding a L sequence, a Vα segment (or Vγ segment), a Jα segment (or Jγ segment), and at least a portion of a Cα region (or Cγ region), and (c) a second amplification product containing nucleic acid encoding a L sequence, a Vβ segment (or Vδ segment), a Dβ segment (or Dδ segment), a Jβ segment (or Jδ segment), and at least a portion of a Cβ region (or Cδ region). In this embodiment, the reaction mixture can optionally include a polymerase enzyme (e.g., Taq polymerase).

This document also provides collections of nucleic acid primers designed to carry out a nested amplification procedure having the ability to generate first and second amplification products described herein. For example, a collection of nucleic acid primers provided herein can be designed to carry out a nested amplification procedure having the ability to generate (a) a first amplification product containing nucleic acid encoding a L sequence, a Vα segment (or Vγ segment), a Jα segment (or Jγ segment), and at least a portion of a Cα region (or Cγ region) and (b) a second amplification product containing nucleic acid encoding a L sequence, a Vβ segment (or Vδ segment), a Dβ segment (or Dδ segment), a Jβ segment (or Jδ segment), and at least a portion of a Cβ region (or Cδ region).

In some cases, a collection of nucleic acid primers provided herein can include a primer collection that includes a first primer set for carrying out a first round amplification of a nested amplification reaction (e.g., nested PCR) described herein and a second primer set for carrying out a second round amplification of a nested amplification reaction (e.g., nested PCR) described herein, where (a) at least one of the primers of the first primer set is set forth in Table 1 or Table 2 (e.g., hTRAV1_12_F, hTRBV4_123_F, hTRBV10_12_F, and/or hTRBV12_34_F) or (b) at least one of the primers of the second primer set is set forth in Table 5 or Table 6 (e.g., Vect_hTRAV1_12_F, Vect_hTRAV8_246, Vect_hTRBV4_123_F, Vect_hTRBV6_23_F, Vect_hTRBV6_89_F, Vect_hTRBV7_2348_F, and/or Vect_hTRBV12_34_F). In this case, one or more of the primers of the first primer set (e.g., all the forward primers of the first set) can lack adapter sequences, and one or more primers of the second primer set (e.g., all the forward primers of the second set) can include adapter sequences. In some cases, a collection of primers provided herein can include reverse primers for the first and second rounds of amplification.

In another example, a collection of primers provided herein can include (a) a first set of primers as set forth in Table 1, (b) a second set of primers as set forth in Table 2, (c) a reverse primer for each of the first and second sets, (d) third set of primers as set forth in Table 5 (with the addition of a primer adapter sequence at the 5' end), (e) a fourth set of primers as set forth in Table 6 (with the addition of a primer adapter sequence at the 5' end different from the adapter sequence used with third set of primers), and (f) a reverse primer for each of the third and fourth sets.

This document also provides methods for making the kits described herein, the reaction mixtures described herein, and the collections of nucleic acid primers described herein. For example, the ingredients of a kit described herein can be obtained and arranged into a package to form a kit described herein. In some cases, each ingredient of a kit described herein can be housed within a separate container with the package. To make a reaction mixture described herein, the ingredients of a reaction mixture described herein can be combined into a single reaction vessel. For example, the ingredients of a reaction mixture described herein can be combined into a single well of a multi-well plate. To make a collection of nucleic acid primers described herein, the primers of a collection described herein can be combined into a single reaction vessel. For example, each primer of collection of nucleic acid primers described herein can be combined into a single well of a multi-well plate.

The invention will be further described in the following examples, which do not limit the scope of the invention described in the claims.

EXAMPLES

Example 1—Sorting T Cells and Obtaining cDNA from Single T Cells

Amplifying the individual pairs of the TCR α and β chains using the methods and materials described herein involved plating of single T cells accurately, extracting RNA efficiently, and preserving the integrity of the RNA. To confirm each of these, a mouse hybridoma T cell line, 1B9, which expresses the mTRAV6-7 α chain and the mTRBV17 β chain, was used. Serial two-fold limited cell dilution down to 0.08 cells per well was used, and the detection of the mouse GAPDH mRNA was detected using real time qPCR. qPCR reactions were performed in a Biorad CFX384 real time instrument utilizing a KAPA SYBR Green FAST kit (obtained commercially from Kapa Biosystems), a forward primer (5'-TCCCACTCTTCCACCTTCGA-3'; SEQ ID NO:323), and a reverse primer (5'-AGTTGGGA-TAGGGCCTCTCTT-3'; SEQ ID NO:324). PCR conditions included 10 minutes at 95° C. for DNA polymerase activation followed by 55 cycles of 10 seconds at 95° C. for denaturation and 30 seconds at 60° C. for annealing/extension. A melting curve analysis was performed to establish specificity.

Using GAPDH as a readout, effective conditions were determined to be as follows: one 1B9 cell/well suspended in 1 μL of PBS containing 1 mg/mL Bovine Serum Albumin (obtained commercially from Ambion) and lysed using 1 μL of 0.3% IGEPAL CA-630 (obtained commercially from Sigma). cDNA was produced by the addition of 1 μL of Random Hexamers (obtained commercially available Promega), 1 μL of dNTPs (obtained commercially from Bio-line), 1 μL of RNase OUT (obtained commercially from Promega), 1 μL DTT, 2 μL of 5× buffer, and 1 μL of Superscript IV (obtained commercially from ThermoFisher Scientific) to a total volume of 10 μL. cDNA synthesis was carried by incubating at 25° C. for 10 minutes for primer binding, at 50° C. for 40 minutes for extension, and at 85° C. for 5 minutes for heat inactivation of the enzyme.

Using a forward primer for mTRBV17 (SEQ ID NO:251) with a corresponding reverse primer (mTRBCn; SEQ ID NO:273), amplification of the mouse TRBV17 β chain from the cDNA produced from the serial dilution of cells was performed using Phusion (a proofreading DNA polymerase) to reduce mutations incorporated during the amplification stage and to be compatible with subsequent cloning steps.

Figure 6A:
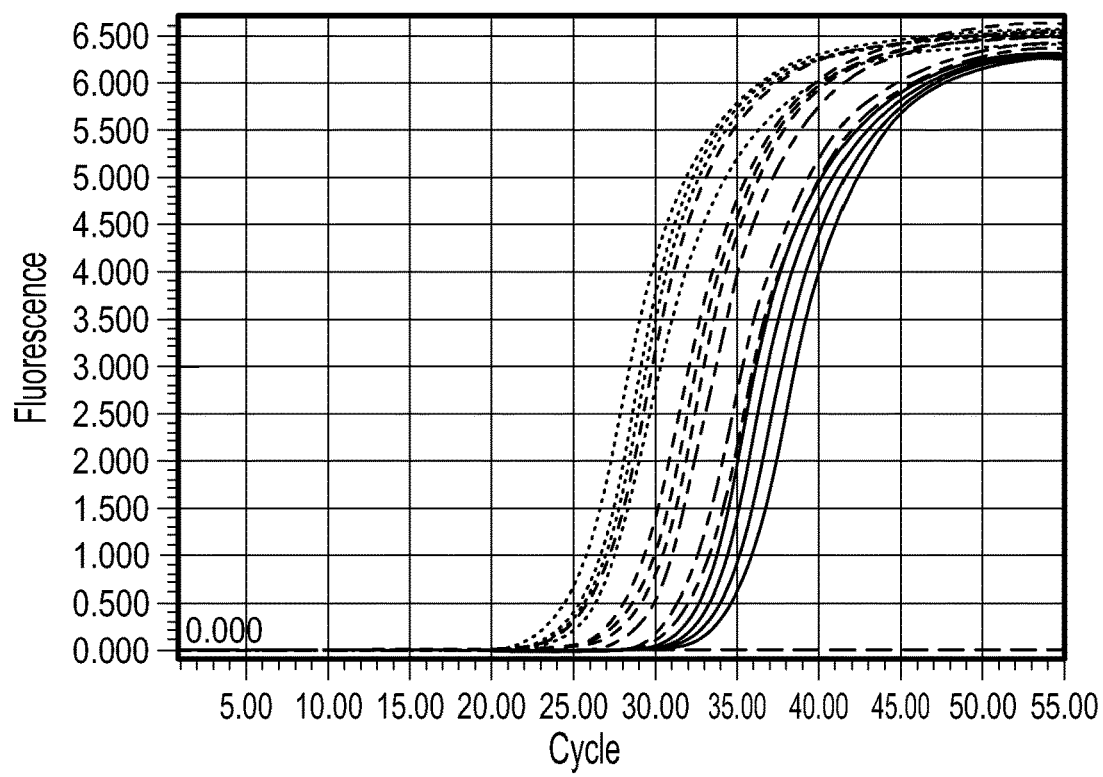
Figure 6B:
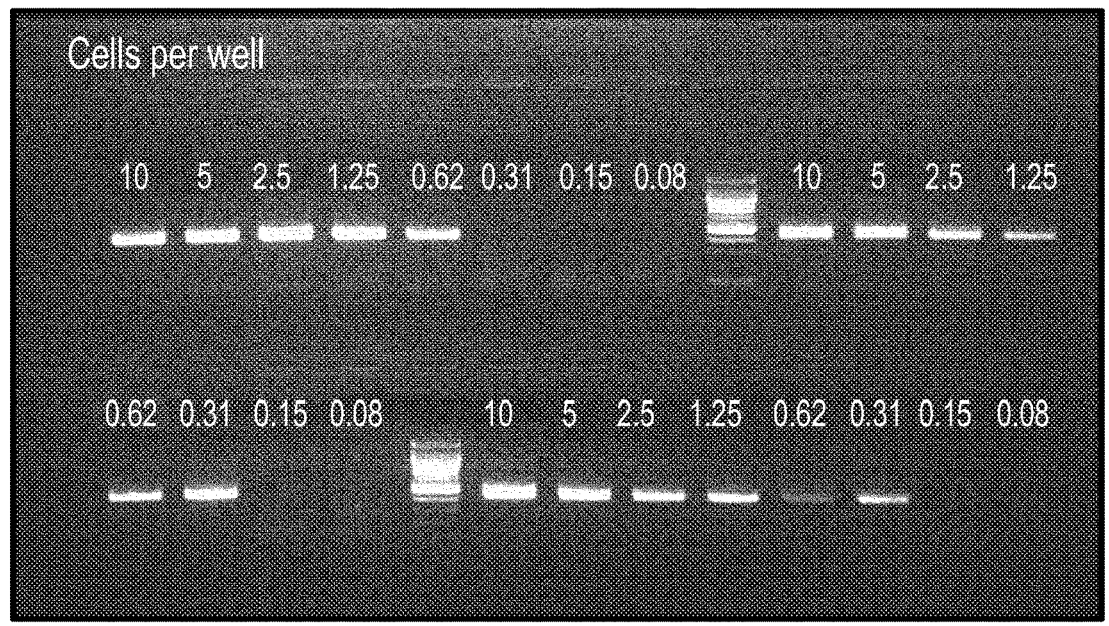

As shown in FIGS. 6A and 6B using a serial dilution from 10 cells down to 0.08 cells per well in a 384 well PCR plate, RNA was extracted efficiently from single cells located in wells containing a single cell, and cDNA was successfully obtained from that RNA. Using 5 μL of the cDNA reaction, GAPDH was detected down to an estimated 0.31 cell/well (FIG. 6A). In parallel, using the other half of the cDNA reaction, mTRBV17 was amplified in all the wells that tested positive for GAPDH, again down to the estimated 0.31 cells/well (FIG. 6B). Each dilution was tested in triplicates (FIG. 6B).

To confirm that these conditions were able to amplify TCR chains from single cells, single 1B9 cells were plated in a 384 well plate using a micromanipulator and a glass pipette monitored under a microscope. In this example, 22 out of 24 single 1B9 cells resulted in amplification of their specific mTRBV17 β chain following cell lysis to release RNA and reverse transcription to convert the RNA into cDNA (FIG. 6C).

After confirming effective amplification of TCR chains from single cells, single 1B9 cells were sorted into separate wells of a 384-well plate using a FACS sorter. mTRBV17 amplification was used as a readout to confirm successful amplification from single T cells sorted using a cell sorter. The cell sorter was a BD FACSAria sorter configured with a 100-micron nozzle and set to 25 psi for efficient plating in 384 well plates. In this example, 22 out of 24 wells containing 1B9 single cells sorted by the BD FACSAria cell sorter resulted in amplification of their specific mTRBV17 β chain following cell lysis to release RNA and reverse transcription to convert the RNA into cDNA (FIG. 6D).

These results demonstrate that the methods and materials described herein can be used to sort single T cells into separate locations (e.g., to obtain one T cell/well), to obtain RNA from those single T cells, and to convert that RNA into cDNA in a manner that allows for amplification of TCR sequences from that cDNA.

Example 2—Confirming Amplification Efficiencies of First Round Amplification Primers A panel of primers was synthesized for the amplification of all the human hTRAVs and hTRBVs listed in Tables 1 and 2. Human peripheral blood mononuclear cells (PBMCs) were isolated from the blood of a healthy donor using density gradient centrifugation. In brief, 35 mL of freshly isolated blood was carefully layered on the top of 15 mL of Ficoll-Paque PLUS (obtained commercially from GE Life-Sciences) and centrifuged for 30 minutes at 400×g at room temperature in a swinging bucket rotor without brake. The mononuclear cell layer was isolated, and platelets were removed by centrifuging twice at 100×g for 7 minutes. Total RNA from $10^7$ human mononuclear cells was isolated using an RNeasy kit (obtained commercially from Qiagen). cDNA was synthesized using a Superscript IV reverse transcriptase, and each individual primer listed in Tables 1 and 2 was tested for its amplification efficiency to amplify the corresponding variant. For the hTRAVs forward primers listed in Table 1, the hTRACf reverse primer (SEQ ID NO:265) was used. For the hTRBVs forward primers listed in Table 2, the hTRBC reverse primer (SEQ ID NO:268) was used. The PCR amplification reactions used the Phusion DNA polymerase.

Figure 7:
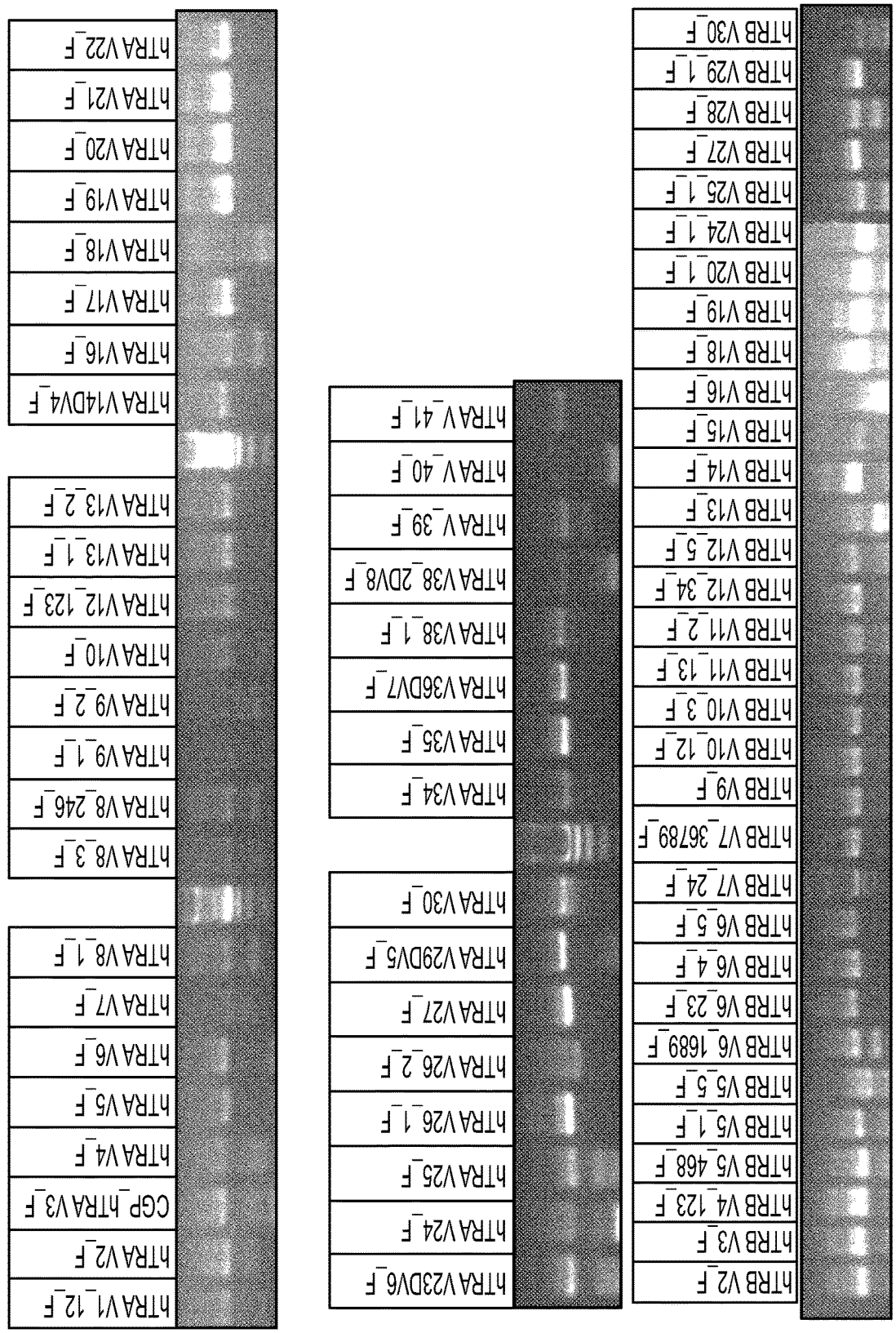
FIG. 7 shows the amplification efficiency of the human primers listed in Table 1 to amplify the corresponding human TCR α variants (top panels) and that of the human primers listed in Table 2 to amplify the corresponding TCR β variants (bottom panel). Human peripheral blood mononuclear cells (PBMCs) were isolated from a healthy donor using density gradient centrifugation. RNA was isolated using a RNAeasy Qiagen kit and converted to cDNA using Superscript IV for the reverse transcription. For the hTRAV primers listed in Table 1, hTRACf (SEQ ID NO:265) was used as a reverse primer. For the hTRBVs primers listed in Table 2, hTRBCf (SEQ ID NO:268) was used as a reverse primer.

All hTRAV primers were capable of amplifying corresponding hTRAVs, generating DNA products ranging from 463 basepairs to 569 basepairs in length (FIG. 7). Similarly, all hTRBV primers were capable of amplifying corresponding hTRBVs, generating DNA products ranging from 561 basepairs to 636 basepairs in length (FIG. 7).

Figure 8:
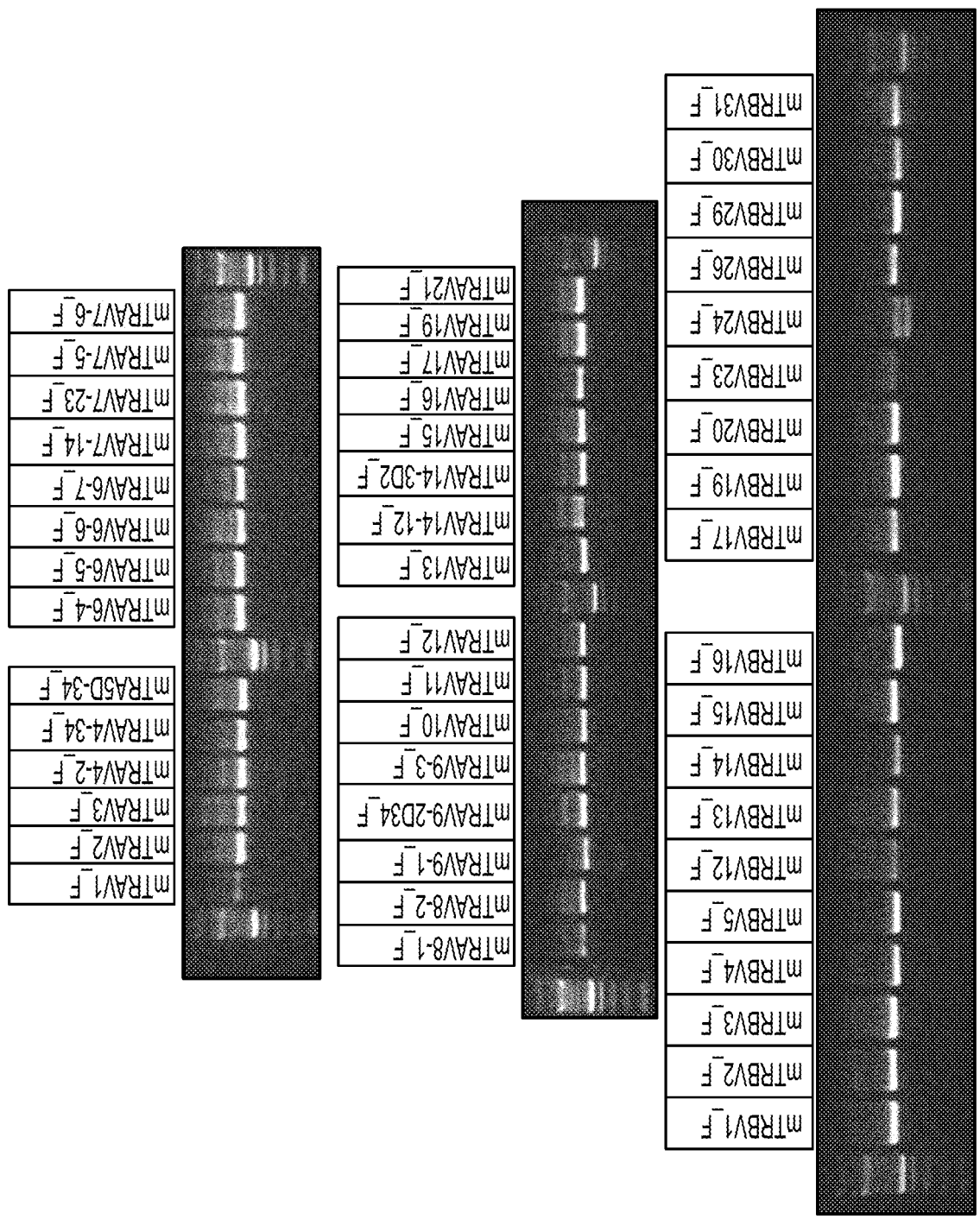
FIG. 8 shows the amplification efficiency of the mouse primers listed in Table 3 to amplify the corresponding mouse TCR α variants (top panels) and that of the mouse primers listed in Table 2 to amplify the corresponding mouse TCR β variants (bottom panel). Lymphocytes were isolated from the thymus of young C57/BL6 mouse, and RNA was isolated using a RNAeasy kit. The RNA was converted into cDNA using Superscript IV for the reverse transcription. For the mTRAV primers listed in Table 3, mTRAC (SEQ ID NO:266) was used as a reverse primer. For the mTRBV primers listed in Table 4, mTRBC (SEQ ID NO:269) was used as a reverse primer.

To confirm the amplification efficiency of first round mouse primers listed in Tables 3 and 4, a similar approach was used. Briefly, lymphocytes were isolated from the thymus of a young BL6 mouse, and total RNA was isolated using the RNeasy Qiagen kit. cDNA was produced using Superscript IV, and amplification efficiency was tested in a PCR reaction using Phusion as a thermostable DNA polymerase and the corresponding mTRAC reverse primer (SEQ ID NO:266) and the corresponding mTRBC reverse primer (SEQ ID NO:269). All the mTRAV forward primers of Table 3, except the mTRAV5-1, mTRAV6-1, mTRAV6-2, and mTRAV6-3 primers, were shown to amplify corresponding mTRAVs via gel electrophoresis (FIG. 8). The mTRAV6-1, mTRAV6-2, and mTRAV6-3 primers were confirmed to amplify corresponding mTRAVs via sequencing of amplified products. From this data, it appeared that the mTRAV5-1 variant might be rare in the mouse repertoire. All the mTRBV forward primers were shown to amplify corresponding mTRBVs via gel electrophoresis (FIG. 8). This also was confirmed via sequencing.

Example 3—Performing Nested Amplification Procedures to Obtain Mouse TCR Sequences The primers listed in Tables 3 and 4 were used to perform amplification of mouse TCRs. Naïve CD8$^+$ splenocytes from a C57BL/6 mouse were sorted and single cell plated using the FACS Aria in two 384-well PCR plates containing 1 µL of PBS and 1 mg/mL ultra-pure BSA. cDNA was synthesized using the methods described in Example 1, and 5 µL of the cDNA reaction was used to amplify the α and TCR chain pairs.

In the first PCR amplification step, all the primers listed on Table 3 and Table 4 were combined into one PCR reaction including the two specific reverse primers (mTRAC, SEQ ID NO:266; and mTRBC, SEQ ID NO:269) at 200 nM for each individual primer. PCR was performed in a 25 µL reaction in the presence of 200 nM dNTPs and 1.5 mM MgCl$_2$ using 1 unit of the Phusion DNA polymerase per reaction. The thermocycling conditions included 1 minute at 98° C., 10 seconds at 98° C., 30 seconds at 55° C., and 40 seconds at 72° C. for a total of 30 cycles.

Following the first round amplification, two separate "nested" PCR reactions were performed for the separate amplification of the α and β chains. Briefly, 1 µL of the first amplification was amplified either with a mixture of all primers listed in Table 7 plus the mTRACn primer (SEQ ID NO:271) as the reverse primer for the nested amplification of the mTRAVs or a mixture of all primers listed in Table 8 plus the mTRBCn primer (SEQ ID NO:273) as the reverse primer for the nested amplification of the mTRBVs. PCR was performed in a 25 µL reaction in the presence of 200 nM dNTPs and 1.5 mM MgCl$_2$, using 1 unit of the Phusion DNA polymerase per reaction. The thermocycling conditions included 1 minute at 98° C., 10 seconds at 98° C., 30 seconds at 55° C., and 40 seconds at 72° C. for a total of 45 cycles and included at the end a 10-minute incubation at 72° C.

Figure 9A:
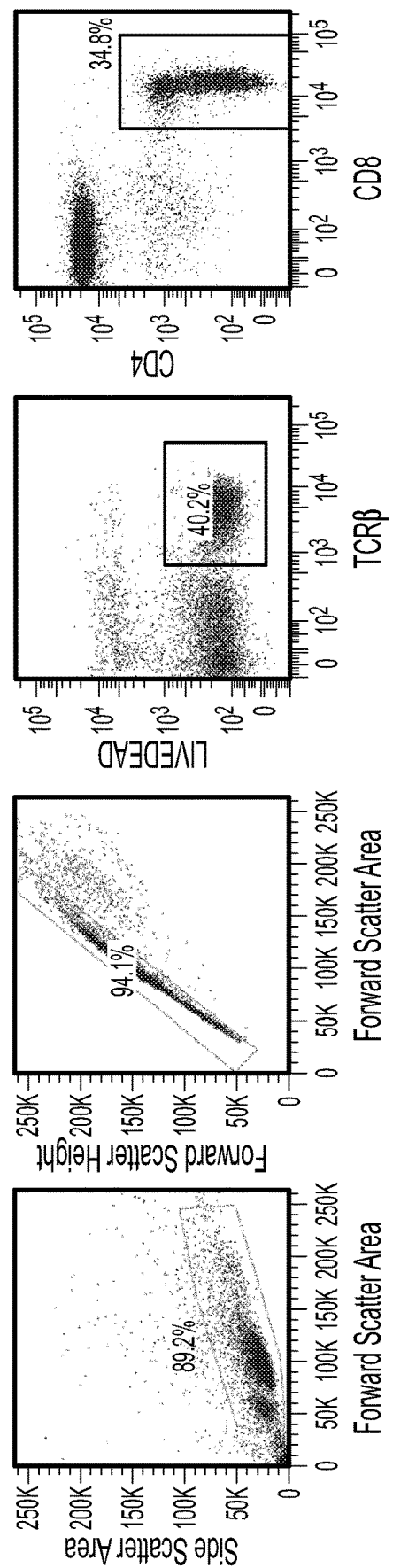
FIGS. 9A and 9B show amplification efficiencies of obtaining amplification products for subsequent cloning and identify sequences for α and β chains of the whole mouse T cell receptor repertoire.
Figure 9B:
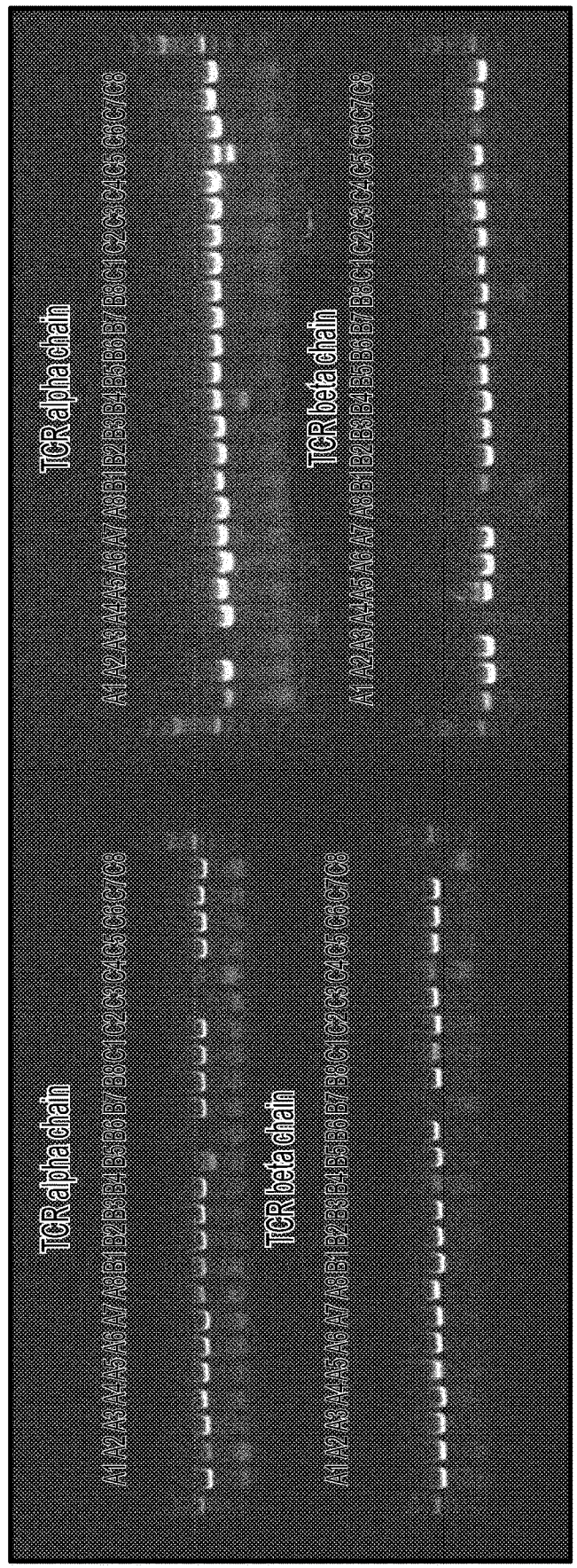

The staining and selection of CD8$^+$/TCR β$^+$ T cells that were sorted in the two 384-well plates were shown in FACS scans (FIG. 9A). In addition, amplification reactions for the first 24 wells having a single T-cell/well from the plate #1 and for the first 24 wells having a single T cell/well from plate #2 were analyze by ethidium bromide gel electrophoresis (FIG. 9B). The ability of these methods to amplify TCR α and β chain pairs from single T cells was confirmed (FIG. 9B). The amplified DNA products exhibited different sizes as expected between the mTRAVs and mTRBVs, indicating specificity of the amplification and not amplification due to DNA contamination (FIG. 9B). In total, 45 out 48 α chains were amplified, 44 out of 48 β chains amplified, and 41 out of 48 TCR pairs were amplified, reaching 85.4 percent efficiency. These PCR amplified products were in enough quantities, were specific, and lacked non-specific amplified bands, making them suitable for downstream high throughput cloning of functional TCRs. Upon sequencing of the amplified products, a large variety of different TCRs were identified with examples of clonality as determined by their sequence at the CDR3 region.

This approach was performed multiple times using different sources of mouse T cells and the primers set forth Tables 3 and 4 as forward primers and two reverse primers (SEQ ID NOs:266 and 269) for first round amplifications. Two separate second round amplifications were performed with each using a portion of the resulting first round amplification reaction mixtures. One included the primers set forth in Table 7 as forward primers together with a reverse primer (SEQ ID NO:271), and the other included the primers set forth in Table 8 as forward primers together with a reverse primer (SEQ ID NO:273). Over 400 different amplification products were sequenced. From these sequencing results, successful amplification from all TRAV primers of Tables 3 and 7 (except for primers specific for TRAV5-1) was confirmed. The sequencing results also confirmed successful amplification of all 22 mTRBVs. In some cases, the amplification products were cloned into expression vectors (e.g., retroviral vectors). Five of these expression vectors were introduced into cells, and expression of functional cloned TCRs was confirmed via stimulation with anti-CD3 antibodies. One of these five was described in greater detail in Examples 5 and 6.

Example 4—Assessing Gene Expression Levels in Single T Cells

Due to the high efficiency of the RNA extraction and cDNA conversion, a portion of the generated cDNA (e.g., about half) was used successfully to obtain TCR chain pairs from single T cells. This left about half for further characterization of the status of these single T cells using gene expression analysis with either a pre-amplification step or directly from the generated cDNA.

A screen for specific TCRs can be performed using several screening assays to confirm hits. In some cases, gene expression can be performed in parallel with cloning the TCRs to determine the activation status of the individual T cells. Even though this can be addressed by FACS, using, e.g., upregulation of CD69 expression, identification of activation genes in a secondary screening assay can be used to further confirm positive hits.

Figure 10:
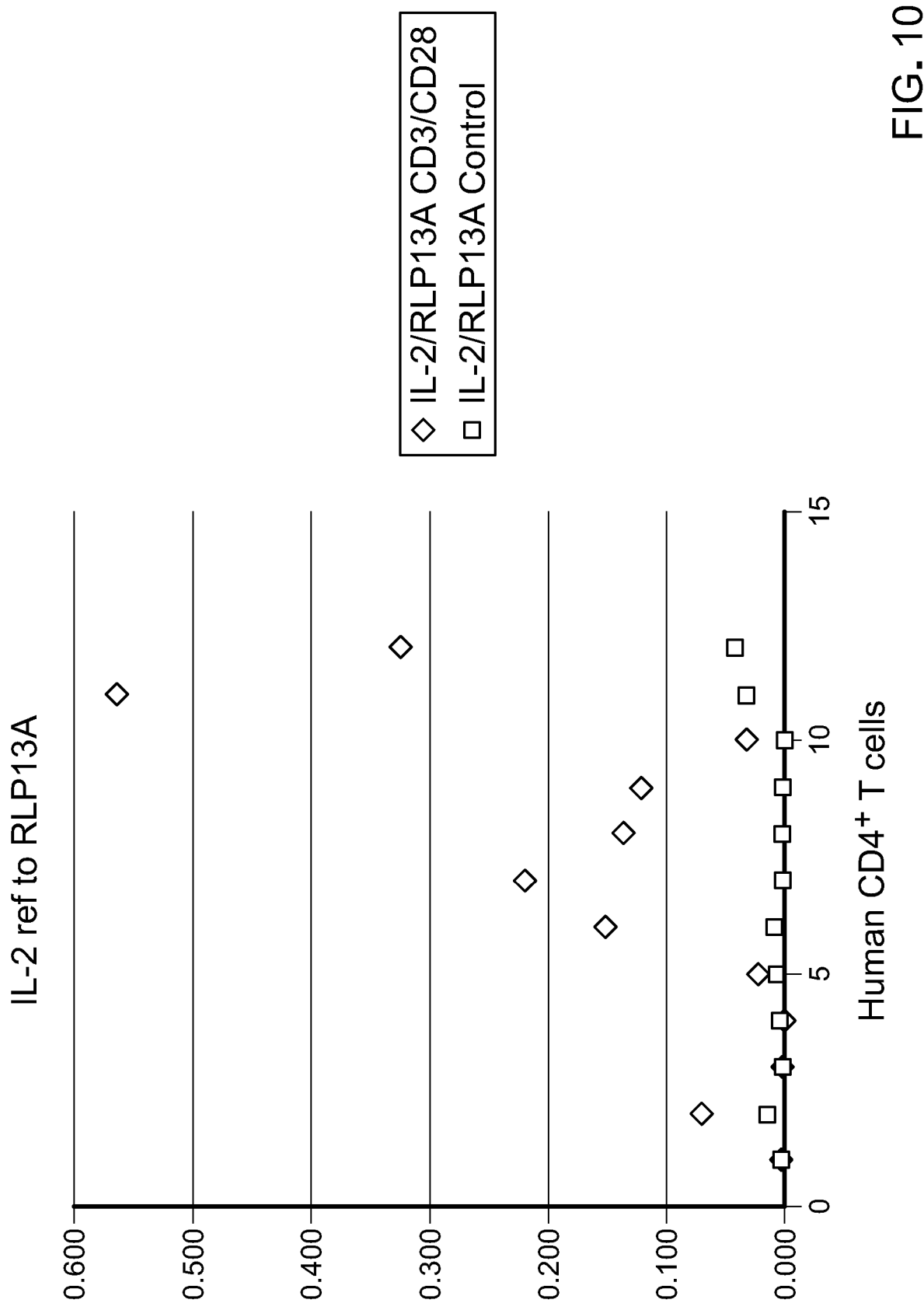
FIG. 10 is a graph plotting IL-2 expression for single T cells. CD4$^+$ human T cells were isolated by positive selection from PBMCs using BD iMag streptavidin beads and a biotinylated human anti-CD4 antibody. Cells were culture for 5 days and activated for 16 hours with anti-CD3/anti-CD28 DYNA beads to imitate the activation of T cells by antigen presenting cells (APCs) or unstimulated control cells. Following the 16-hour incubation, CD4$^+$ cells were sorted as a single per well in a 384-well PCR plate. RNA extraction and cDNA conversion were completed. One fifth of the cDNA (2 µL) was used for gene expression analysis of human IL-2 and compared to the expression of RLP13A, which was used as a reference gene for normalization using real time PCR. Performing qPCR in a fraction of cDNA generated from single cells, activated cells were identified based on their IL-2 levels, which ranged from a twofold increase to several hundred-fold increase compared to unstimulated control single cells.

CD4+ human T cells were isolated by positive selection from PBMCs using BD iMag streptavidin beads and a biotinylated human anti-CD4 antibody. Cells were cultured with RPMI 1640, 10% FCS, and 1% PS/Glu medium for 5 days. Subsequently, the CD4+ cells were activated for 16 hours at 37° C. with anti-CD3/anti-CD28 antibodies coupled to DYNA beads to imitate the activation of T cells by antigen presenting cells (APCs). Following activation, the positive selected CD4+ cells were plated at one T cell/well in a 384-well PCR plate using a micromanipulator with each well containing 1 μL of PBS, 1 mg/mL ultra-pure BSA. RNA was extracted, and cDNA generated in a 10 μL reaction as described herein. 2 μL of the resulting cDNA mixture were utilized for the gene expression analysis of human IL-2 compared to RLP13A expression as a reference gene for normalization. The qPCR reactions were performed in a Biorad CFX384 real time instrument utilizing a KAPA SYBR Green FAST kit (obtained commercially from Kapa Biosystems), using an IL-2 forward primer (5'-AGG-GATCTGAAACAACATTC-3', SEQ ID NO:325), an IL-2 reverse primer (5'-GCCTGATATGTTTTAAGTGGG-3', SEQ ID NO:326), an RLP13A forward primer (5'-GTCT-GAAGCCTACAAGAAAG-3', SEQ ID NO:327), and an RLP13A reverse primer (5'-TGTCAATTTTCTTCTC-CACG-3', SEQ ID NO:328). PCR conditions included 10 minutes at 95° C. for DNA polymerase activation, 10 seconds at 95° C. for denaturation, and 30 seconds at 60° C. for annealing/extension for a total of 45 cycles, followed by a melting curve analysis to establish specificity. The fold increase in IL-2 expression normalized with RLP13A reference gene was determined. Upon activation with the anti-CD3/anti-CD28 beads, IL-2 expression varied from no stimulation to a several hundred-fold increase, confirming that this assay can be used to distinguish single sorted T cells that responded to a particular stimulation from those that did not (FIG. 10).

Example 5—Cloning TCRs

Wild-type female C57Bl/6 mice were vaccinated with an H60 peptide (LTFNYRNL (SEQ ID NO: 278)) or an OVA peptide (SINFEKL (SEQ ID NO: 279)) conjugated to an anti-DEC205 antibody as described elsewhere (Li et al., Blood, 118:5965-76 (2011)). At 7 days post vaccination, spleens and lymph nodes were harvested, worked into single cell suspensions, and stained with fluorescently labeled antibodies for anti-TCRβ (clone H57 conjugated to PerCp Cy5.5 Biolegend), anti-CD8a (clone 53-6.7 conjugated to PE, Biolegend or clone 53-6.7 conjugated to AF488), anti-CD44 (clone IM7 conjugated to either AF647 or AF488), and in the case of the H60 isolation only anti-CD4 (clone GK1.5 conjugated to PE-Cy7, Biolegend). The single cell suspensions also were stained with a V450 conjugate MHC-I tetramer loaded with either the H60 peptide or the OVA peptide.

Following surface staining, the cells were washed once in PBS and stained with Ghost 780 (Tonbo) for 30 minutes at room temperature in PBS. Cells were washed twice and suspended in sterile PBS. Cells from separate mice were not pooled prior to being sorted. Cells from individual mice were sorted into different plates or different sections of shared plates. The vaccine activated antigen specific cells (CD8+, TCRβ+, CD44$^{hi}$, OVA or H60 Tetramer+) from two H60 vaccinated mice and four OVA vaccinated mice were sorted into multiple 384-well plates as described herein. The relative binding of the tetramer by CD44$^{hi}$ CD8+ splenocytes was assessed by flow cytometry (FIGS. 11A and 11B). Total cDNA was produced using random hexamers (Promega) and Superscript IV (Thermo Fisher). The quality of cDNA was confirmed by qPCR for GAPDH (forward primer: 5'-TCC-CACTCTTCCACCTTCGA-3', SEQ ID NO:329; and reverse primer: 5'-AGTTGGATAGGGCCTCTCTT-3', SEQ ID NO:330) using KAPA SYBR FAST qPCR Master Mix (Sigma Aldrich). Each well was processed such that the TCR α and β chains were amplified for each well. The murine specific forward primers set forth in Tables 3 and 4 together with reverse primers (SEQ ID NOs: 266 and 269) were used together in first round amplifications. For the second round, a portion of the first round PCR product was used to amplify TCRα or TCRβ chains in two separate reactions using a multiplex of all the primers included in Table 7 plus a reverse primer (SEQ ID NO:271) in one reaction and all the primer listed in Table 8 plus a reverse primer (SEQ ID NO:273) in the other reaction.

A subset of the TCR α and β positive wells were sequenced using the Sanger Sequencing method (Genewiz). Two primers (SEQ ID NOs:263 and 262) were used as sequencing primers, and the results were analyzed using SnapGene software (SnapGene). The results of the cloning (FIG. 11C) indicated the presence of unique clonal cell populations.

Based on the sequencing, TCR α and β pairs were cloned into Tdtomato expressing retroviral constructs. Briefly, five TCR α and β pairs from the H60 sort were assembled into a retroviral vector along with the Mouse INSERT_B of Table 14 using a Gibson Cloning Kit (New England Biolabs). The assembled vectors were grown up as a plasmid in NEB 5α competent cells (New England Biolabs) and selected based on ampicillin resistance. Platinum-E retroviral packaging cells (PLAT-E cells) were grown up as per manufactures' instructions (Cell Biolabs Inc) and transfected with TCR containing plasmids using a LipoJet In Vitro Transfection Kit (Signa Gen Laboratories). At 48 hours post-transfection, the supernatants from transfected PLAT-E cell cultures were harvested.

Figure 11D:
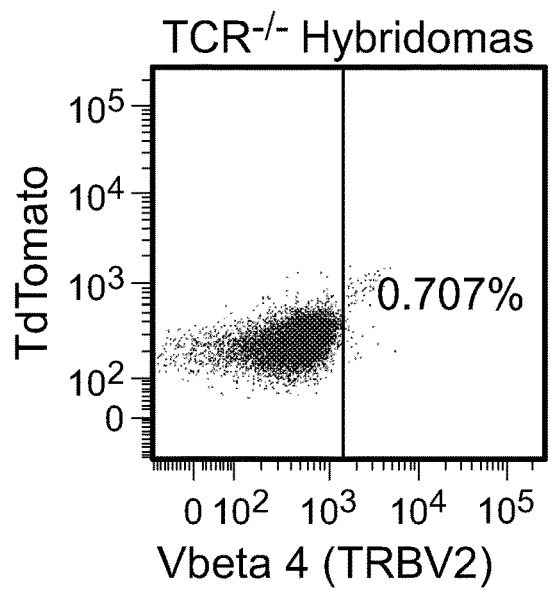
Figure 11E:
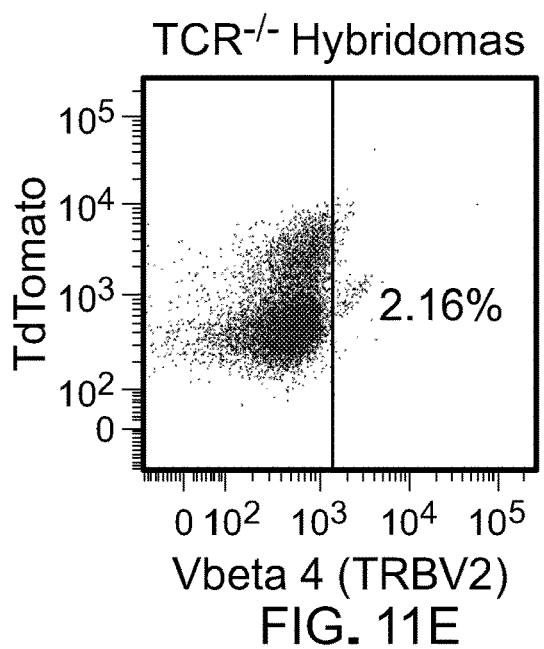
Figure 11F:
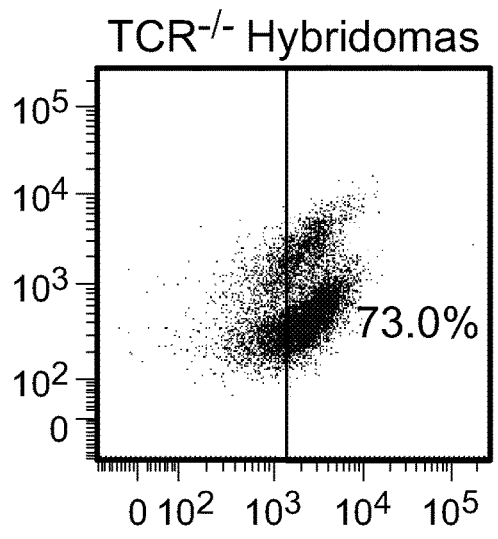
Figure 13:
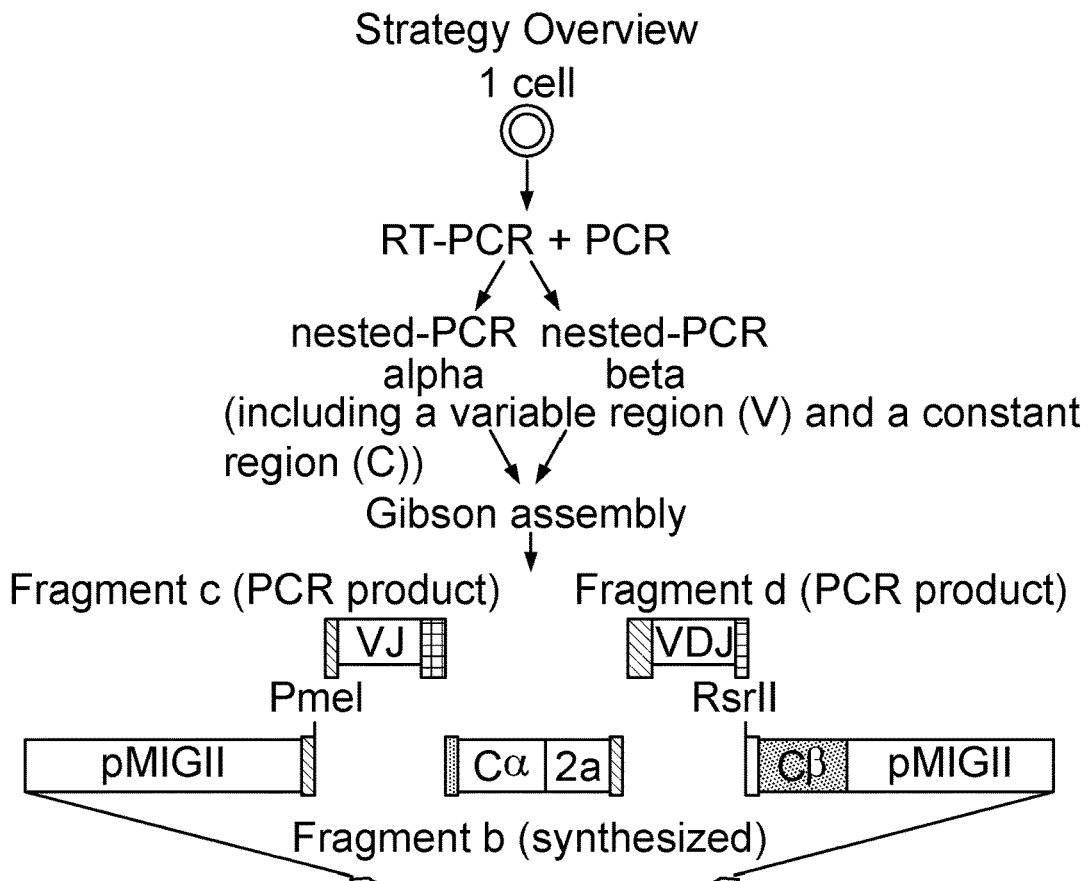
FIG. 13 is a schematic representation of an overview of one embodiment set forth in Example 7.

A TCRα⁻β⁻ hybridoma cell line was infected with individual retroviral vectors that contained either TCR genes isolated and expanded from H60-tetramer binding CD8 cells or TCR gene vectors assembled using another primer set. At two, four, and six days post-infection, the cells were assessed by flow cytometry for the expression of TCR β and tdtomato. All five TCRs selected for amplification from the H60 sort successfully expressed a TCR on the surface of the hybridoma cell line. At six days post-infection, the Tdtomato+ cells were sorted out using bulk-sorting techniques, and the cells expressed both the Tdtomato gene and the surface TCR for over two months. Two of the H60 TCRβ cells were identified as expressing the TRVB2 gene (which encodes the TCRVβ 4 gene). The specificity of the sequence and the fidelity of the virus production was tested by staining the cells lines infected with TRVB2 containing virus with anti-TCRVβ4 (clone KT4, biotin labeled, BD Biosciences). Staining was assessed using an LSR II (BD Bioscience). The staining results indicated that TCRs (in this case an H60 derived TCR Vβ4) that were cloned and selected through staining or sequencing were selectively expressed (FIGS. 11D-F). These transformed cells lines stably expressed the selected TCR for over two months.

Example 6—Expressing Functional TCRs Cloned from Single T Cells

Using a Lipojet transfection Kit (Signa Gen Laboratories), 4G4 cells were transfected with a NFAT-RE driven luciferase reporter plasmid containing a hygromycin resistance gene. Two days after transfection, 4G4 were placed into culture with 1 mg/mL concentration of hygromycin. This concentration killed 100% of untransfected 4G4 cells within ten days. The hygromycin resistant 4G4 cells were repeatedly subcloned and stimulated with PMA/I in order to induce NFAT driven luciferase. Luciferase activity was measure in 384 well, opaque white tissue culture treated plates (Greiner) using a BioGlow Luciferase Assay Kit (Promega). Sub-lines of hygromycin resistant cells were selected for low luciferase background expression and high inducible luciferase expression.

The 4G4 cells were infected with two different TCR-expressing retroviral vectors that were assembled using Gibson assembly using TCR sequences obtained from single cell sorted T cells. The viruses were generated using PLAT-E cells. One TCR-expressing vector was generated from the single cell sorting of primary T cells and contained a Tdtomato-expressing viral backbone. The other TCR-expressing vector was generated from a TCR obtained from ex vivo expanded T cells and contained an eGFP expressing backbone.

In order to determine the specificity and efficiency of retroviral transfection and TCR expression, background levels were obtained by staining uninfected cells with anti-TCRβ (clone H57) and assessing them for the expression of tdtomato and TCR. Unifected 4G4 cells did not express TCRβ (FIG. 12A, Left Panel). Virally infected cells stained 24 hours after infection for TCRβ and both eGFP and tdtomato expression (dependent on the viral vector used) were assessed. At 24 hours post-infection, there were detectable levels of surface TCR and eGFP expression (FIG. 12A, Right Panel).

Luciferase reporter cells were infected the TCR expressing viruses. One day after the cells were infected, the 4G4 cells were placed into 384-well opaque white tissue culture treated plates (Greiner). The individual wells of white opaque tissue culture treated 384-well plates were coated with varying concentrations of anti-murine CD3 antibodies and incubated overnight at 4° C. (Clone 2C11, BD Biosceinces). The wells were washed twice with PBS, and $3 \times 10^4$ 4 G4 cells from culture were infected with TCR expressing viral vectors, which were plated in a total volume of 40 μL of culture media. Flow cytometry analysis of infected 4G4 cultures found that infection efficiencies were less than 80% in most cases and judge by Tdtomato or eGFP expression. TCR expression on the surface of the cells was measure by staining anti-murine TCR β clone H57 (Biolegend).

After 3.5 hours in culture with anti-CD3, 40 μL of the BioGlow substrate (Promega) was added to each well, and the plates were incubated 10 minutes at room temperature. Relative light units were measured over a period of 100 ms using a SpectaMax i3 (Molecular Devices).

Uninfected cells expressed some luciferase as measure by the RLU above zero (FIG. 12B). However, the uninfected cells were unresponsive to anti-CD3 stimulation. Infected cell cultures were very responsive to anti-CD3 stimulation (FIG. 12B).

Example 7—Compositions and Methods for the Simultaneous Capture of Full-Length T Cell Receptor Variable Regions from a Single T Cell Background The quest to clone the genes that encode for the TCR and its discovery dates back more than 30 years ago. Isolating, characterizing and re-expressing TCRs represents a major goal for understanding diseases caused by T cells as well as employing T cells with defined TCR as therapy to cure cancer. Thus, such methods have both research/basic and therapeutic implications.

Currently, in a common method to identify T cell clones specific for a defined antigen, T cells are isolated from an organism and expanded in vitro in the presence of the antigen and/or nonspecific stimuli and pro-inflammatory cytokines. They are then cloned cellularly and/or immortalized as T cell hybridomas by fusing with a continuous T cell tumor line that lacks its own TCR expression. This is a biased method because T cells with lower affinity for the antigen may be overgrown by T cells that have higher affinity for that same antigen, leaving low affinity TCRs undiscovered. Also many T cells that are isolated from tissues or solid tumors will not expand well in vitro and their TCR specificities will be missed. Moreover, it is low throughput, slow, and labor intensive.

An approach that partially solves these issues is to perform immunizations in vivo and sort single T cells that show expression of activation markers or bind defined MHC-tetramers that are pre-loaded with specific known peptide antigenic targets. The disadvantage of the former approach is that many T cells showing activation markers were stimulated by bystander mechanisms and are not specific for the antigen. The use of tetramers is an advance, but is limited in that there is only a limited number of tetramers available and they can be laborious and expensive to produce; further, they are HLA/MHC restricted and they may lack sensitivity to pull out lower affinity T cells. The tetramer approach also can only isolate cells that have known, predefined specificities and cannot be used for discovery of T cells and their receptors that recognize unknown but important antigenic peptides.

T cells that are so-isolated are typically then subjected to TCR sequencing. Capturing the sequence across the VDJ border of TCRβ and VJ border of TCRVα fully specifies the TCR and therefore is a "hook" for immortalizing (with some further effort) each T cell; this is necessary because the cells themselves have not been immortalized. This in turn is typically accomplished by using a pool of published primers that bind in the variable region of the alpha (Vα) and beta (Vβ) chains and primers that bind the constant part for alpha and beta chains followed by nested PCR. Until recently T cell repertoires have actually been usually analyzed by sequencing either Vβ or Vα from pools of cells, even using high throughput sequencing (HTS). However, while this method assesses diversity and origin, it loses the single-cell pairing of Vα/Vβ that only together can determine specificity.

Hence in the last few years a few methods and papers have emerged to capture linked Vα/Vβ from single T cells. Such methods, depending how they are configured, are low to medium-throughput and expensive ($3-7 per sequence; considering both alpha and beta chains $6-14 per TCR). Such sequences do identify the needed information, but they are not the full length Vα/Vβ. Therefore, this full-length sequence must be reconstructed if the goal is expression: either a PCR specific for each TCR must be performed (ordering primers for each TCR would cost around $5 per primer and $20 per TCR) or complete alpha and beta sequences must be synthesized ($160-200 per TCR). Once both Vα and Vβ sequences are amplified/synthesized they can finally be cloned into vectors of choice. There is no technique developed so far that allows one to perform unbiased high throughput identification and cloning of any single T cell isolated from tissues or blood suitable for high throughput screening of antigens or application in therapy.

The compositions, vectors, and methods disclosed in this Example 7 can address these and other needs.

Summary

Provided within this Example 7 are methods of assembling a TCR expression vector comprising a full-length Vα and a full-length Vβ from a single T cell (or a homogenous T cell population) in a single vector. Also provided within this Example 7 are methods of assembling a TCR expression vector comprising a full-length Vγ and a full-length Vδ from a single T cell (or a homogenous T cell population) into a single vector. The TCR can be readily expressed without further cloning steps.

In one aspect, provided within this Example 7 is a method for assembling a TCR expression vector comprising a Vα region and a Vβ region from a single T cell (or a homogenous population of T cells), comprising the steps:
  a. obtaining a linearized vector comprising a 5' end, a 3' end, and a first polynucleotide sequence encoding TCR Cβ;
  b. obtaining a fragment b polynucleotide sequence; wherein the fragment b polynucleotide sequence comprises a second polynucleotide sequence encoding TCR Cα operably linked to a third polynucleotide sequence encoding 2A;
  c. obtaining RNA from a single T cell (or a homogenous population of T cells);
  d. performing a one-step reverse transcriptase-polymerase chain reaction (RT-PCR) to amplify a first set of TCR Vα amplicon products, comprising the steps:
    i. performing a reverse transcription of the RNA into cDNA;
    ii. performing a polymerase chain reaction on the cDNA, using;
      1. a first forward Vα primer, wherein the first forward Vα primer comprises at the 5' end a first nucleotide sequence that is complementary to a second nucleotide sequence at the 5' end of the linearized vector; wherein the first nucleotide sequence is operably linked to a first leader sequence of a Vα gene; and
      2. a first reverse Cα primer, having a third nucleotide sequence that is complementary to a fourth nucleotide sequence at the 5' end of fragment b;
  e. performing a one-step reverse transcriptase-polymerase chain reaction (RT-PCR) to amplify a first set of TCR amplicon products, comprising the steps:
    i. performing a reverse transcription of the RNA into cDNA;
    ii. performing a polymerase chain reaction on the cDNA, using;
      1. a first forward Vβ primer, wherein the first forward Vβ primer comprises at the 5' end a fifth nucleotide sequence that is complementary to a sixth nucleotide sequence at the 3' end of the fragment b; wherein the fifth nucleotide sequence is operably linked to a second leader sequence of a Vβ gene; and
      2. a first reverse Cβ primer, having a seventh nucleotide sequence that is complementary to an eighth nucleotide sequence at the 3' end the linearized vector;
  f. performing a nested polymerase chain reaction on the first set of TCR Vα amplicon products to amplify a second set of TCR Vα amplicon products, using:
    i. a second forward Vα primer comprising a ninth nucleotide sequence that contains a portion of the first nucleotide sequence of the first forward Vα primer; and
    ii. a second reverse Cα primer having a tenth nucleotide sequence that is complementary to an eleventh nucleotide sequence at the 5' end of fragment b;
  g. performing a nested polymerase chain reaction on the first set of TCR Vβ amplicon to amplify a second set of TCR β amplicon products, using:
    i. a second forward Vβ primer having a twelfth nucleotide sequence at its 5' end that contains a portion of the fifth nucleotide sequence of the first forward Vβ primer; and
    ii. a second reverse Cβ primer having a thirteenth nucleotide sequence that is complementary to a fourteenth nucleotide sequence at to the 3' end of the linearized vector;
  h. assembling the TCR expression vector by ligation in a 5' to 3' direction, of the following:
    i. the 5' end of the linearized vector;
    ii. the second set of TCR Vα amplicon products;
    iii. the fragment b polynucleotide sequence;
    iv. the second set of TCR amplicon products; and
    v. the 3' end of the linearized vector.

In another aspect, provided within this Example 7 is a method for assembling a TCR expression vector comprising a Vα region and a Vβ region from a single T cell (or a homogenous population of T cells), comprising the steps:
  a. obtaining a linearized vector comprising a 5' end, a 3' end, and a first polynucleotide sequence encoding TCR Cβ;
  b. obtaining a fragment b polynucleotide sequence; wherein the fragment b polynucleotide sequence comprises a second polynucleotide sequence encoding TCR Cα operably linked to a third polynucleotide sequence encoding 2A;
  c. obtaining RNA from a single T cell (or a homogenous population of T cells);
  d. performing a one-step reverse transcriptase-polymerase chain reaction (RT-PCR) to amplify a first set of TCR Vα amplicon products, comprising the steps:
    i. performing a reverse transcription of the RNA into cDNA;
    ii. performing a polymerase chain reaction on the cDNA, using;
      1. a plurality of first forward Vα primers, wherein the first forward Vα primers comprise at the 5' end a first nucleotide sequence that is complementary to a second nucleotide sequence at the 5' end of the linearized vector; wherein the first nucleotide sequence is operably linked to a plurality of first leader sequences of Vα genes; and
      2. a first reverse Cα primer, having a third nucleotide sequence that is complementary to a fourth nucleotide sequence at the 5' end of fragment b;
  e. performing a one-step reverse transcriptase-polymerase chain reaction (RT-PCR) to amplify a first set of TCR amplicon products, comprising the steps:
    i. performing a reverse transcription of the RNA into cDNA;
    ii. performing a polymerase chain reaction on the cDNA, using;
      1. a plurality of first forward Vβ primers, wherein the first forward Vβ primers comprise at the 5' end a fifth nucleotide sequence that is complementary to a sixth nucleotide sequence at the 3' end of the fragment b; wherein the fifth nucleotide sequence is operably linked to a plurality of second leader sequences of Vβ genes; and
    2. a first reverse Cβ primer, having a seventh nucleotide sequence that is complementary to an eighth nucleotide sequence at the 3' end the linearized vector;
f. performing a nested polymerase chain reaction on the first set of TCR Vα amplicon products to amplify a second set of TCR Vα amplicon products, using:
    i. a second forward Vα primer comprising a ninth nucleotide sequence that contains a portion of the first nucleotide sequence of the first forward Vα primer; and
    ii. a second reverse Cα primer having a tenth nucleotide sequence that is complementary to an eleventh nucleotide sequence at the 5' end of fragment b;
g. performing a nested polymerase chain reaction on the first set of TCR amplicon to amplify a second set of TCR β amplicon products, using:
    i. a second forward Vβ primer having a twelfth nucleotide sequence at its 5' end that contains a portion of the fifth nucleotide sequence of the first forward Vβ primer; and
    ii. a second reverse Cβ primer having a thirteenth nucleotide sequence that is complementary to a fourteenth nucleotide sequence at to the 3' end of the linearized vector;
h. assembling the TCR expression vector by ligation, in a 5' to 3' direction, of the following:
    i. the 5' end of the linearized vector;
    ii. the second set of TCR Vα amplicon products;
    iii. the fragment b polynucleotide sequence;
    iv. the second set of TCR Vβ amplicon products; and
    v. the 3' end of the linearized vector.

In one aspect, provided within this Example 7 is a method for assembling a TCR expression vector comprising a Vγ region and a Vδ region from a single T cell (or a homogenous population of T cells), comprising the steps:
    a. obtaining a linearized vector comprising a 5' end, a 3' end, and a first polynucleotide sequence encoding TCR Cδ;
    b. obtaining a fragment b polynucleotide sequence; wherein the fragment b polynucleotide sequence comprises a second polynucleotide sequence encoding TCR Cγ operably linked to a third polynucleotide sequence encoding 2A;
    c. obtaining RNA from a single T cell (or a homogenous population of T cells);
    d. performing a one-step reverse transcriptase-polymerase chain reaction (RT-PCR) to amplify a first set of TCR Vγ amplicon products, comprising the steps:
        i. performing a reverse transcription of the RNA into cDNA;
        ii. performing a polymerase chain reaction on the cDNA, using;
            1. a first forward Vγ primer, wherein the first forward Vγ primer comprises at the 5' end a first nucleotide sequence that is complementary to a second nucleotide sequence at the 5' end of the linearized vector; wherein the first nucleotide sequence is operably linked to a first leader sequence of a Vγ gene; and
            2. a first reverse Cγ primer, having a third nucleotide sequence that is complementary to a fourth nucleotide sequence at the 5' end of fragment b;
    e. performing a one-step reverse transcriptase-polymerase chain reaction (RT-PCR) to amplify a first set of TCR Vδ amplicon products, comprising the steps:
        i. performing a reverse transcription of the RNA into cDNA;
        ii. performing a polymerase chain reaction on the cDNA, using;
            1. a first forward Vδ primer, wherein the first forward Vδ primer comprises at the 5' end a fifth nucleotide sequence that is complementary to a sixth nucleotide sequence at the 3' end of the fragment b; wherein the fifth nucleotide sequence is operably linked to a second leader sequence of a Vδ gene; and
            2. a first reverse Cδ primer, having a seventh nucleotide sequence that is complementary to an eighth nucleotide sequence at the 3' end the linearized vector;
    f. performing a nested polymerase chain reaction on the first set of TCR Vγ amplicon products to amplify a second set of TCR Vγ amplicon products, using:
        i. a second forward Vγ primer comprising a ninth nucleotide sequence that contains a portion of the first nucleotide sequence of the first forward Vγ primer; and
        ii. a second reverse Cγ primer having a tenth nucleotide sequence that is complementary to an eleventh nucleotide sequence at the 5' end of fragment b;
    g. performing a nested polymerase chain reaction on the first set of TCR Vδ amplicon to amplify a second set of TCR δ amplicon products, using:
        i. a second forward Vδ primer having a twelfth nucleotide sequence at its 5' end that contains a portion of the fifth nucleotide sequence of the first forward Vδ primer; and
        ii. a second reverse Cδ primer having a thirteenth nucleotide sequence that is complementary to a fourteenth nucleotide sequence at to the 3' end of the linearized vector;
    h. assembling the TCR expression vector by ligation, in a 5' to 3' direction, of the following:
        i. the 5' end of the linearized vector;
        ii. the second set of TCR Vγ amplicon products;
        iii. the fragment b polynucleotide sequence;
        iv. the second set of TCR Vδ amplicon products; and
        v. the 3' end of the linearized vector.

In another aspect, provided within this Example 7 is a method for assembling a TCR expression vector comprising a Vγ region and a Vδ region from a single T cell (or a homogenous population of T cells), comprising the steps:
    a. obtaining a linearized vector comprising a 5' end, a 3' end, and a first polynucleotide sequence encoding TCR Cβ;
    b. obtaining a fragment b polynucleotide sequence; wherein the fragment b polynucleotide sequence comprises a second polynucleotide sequence encoding TCR Cγ operably linked to a third polynucleotide sequence encoding 2A;
    c. obtaining RNA from a single T cell (or a homogenous population of T cells);
    d. performing a one-step reverse transcriptase-polymerase chain reaction (RT-PCR) to amplify a first set of TCR Vγ amplicon products, comprising the steps:
        i. performing a reverse transcription of the RNA into cDNA;
        ii. performing a polymerase chain reaction on the cDNA, using;

1. a plurality of first forward Vγ primers, wherein the first forward Vγ primers comprise at the 5' end a first nucleotide sequence that is complementary to a second nucleotide sequence at the 5' end of the linearized vector; wherein the first nucleotide sequence is operably linked to a plurality of first leader sequences of Vγ genes; and
2. a first reverse Cγ primer, having a third nucleotide sequence that is complementary to a fourth nucleotide sequence at the 5' end of fragment b;
e. performing a one-step reverse transcriptase-polymerase chain reaction (RT-PCR) to amplify a first set of TCR Vδ amplicon products, comprising the steps:
  i. performing a reverse transcription of the RNA into cDNA;
  ii. performing a polymerase chain reaction on the cDNA, using;
    1. a plurality of first forward Vδ primers, wherein the first forward Vδ primers comprise at the 5' end a fifth nucleotide sequence that is complementary to a sixth nucleotide sequence at the 3' end of the fragment b; wherein the fifth nucleotide sequence is operably linked to a plurality of second leader sequences of Vδ genes; and
    2. a first reverse Cδ primer, having a seventh nucleotide sequence that is complementary to an eighth nucleotide sequence at the 3' end the linearized vector;
f. performing a nested polymerase chain reaction on the first set of TCR Vγ amplicon products to amplify a second set of TCR Vγ amplicon products, using:
  i. a second forward Vγ primer comprising a ninth nucleotide sequence that contains a portion of the first nucleotide sequence of the first forward Vγ primer; and
  ii. a second reverse Cγ primer having a tenth nucleotide sequence that is complementary to an eleventh nucleotide sequence at the 5' end of fragment b;
g. performing a nested polymerase chain reaction on the first set of TCR Vδ amplicon to amplify a second set of TCR δ amplicon products, using:
  i. a second forward Vδ primer having a twelfth nucleotide sequence at its 5' end that contains a portion of the fifth nucleotide sequence of the first forward Vδ primer; and
  ii. a second reverse Cδ primer having a thirteenth nucleotide sequence that is complementary to a fourteenth nucleotide sequence at to the 3' end of the linearized vector;
h. assembling the TCR expression vector by ligation, in a 5' to 3' direction, of the following:
  i. the 5' end of the linearized vector;
  ii. the second set of TCR Vγ amplicon products;
  iii. the fragment b polynucleotide sequence;
  iv. the second set of TCR Vδ amplicon products; and
  v. the 3' end of the linearized vector.

In one embodiment, steps (d) and (e) are performed in a single reaction. In one embodiment, steps (f) and (g) are performed in a single reaction.

In one embodiment, the assembling of the TCR expression vector by ligation comprises a seamless cloning method that utilizes short regions of homology. In one embodiment, the assembling of the TCR expression vector by ligation comprises a Gibson assembly method.

In one embodiment, the first nucleotide sequence is 15 to 25 nucleotides in length. In one embodiment, the first nucleotide sequence is 20 nucleotides in length.

In one embodiment, the fifth nucleotide sequence is 15 to 25 nucleotides in length. In one embodiment, the fifth nucleotide sequence is 20 nucleotides in length.

In one embodiment, the ninth nucleotide sequence is 15 to 25 nucleotides in length. In one embodiment, the ninth nucleotide sequence is 18 nucleotides in length.

In one embodiment, the twelfth nucleotide sequence is 15 to 25 nucleotides in length. In one embodiment, the twelfth nucleotide sequence is 18 nucleotides in length.

In one embodiment, the linearized vector comprises pMIGII.

In one embodiment, the third polynucleotide sequence encoding 2A is selected from a nucleotide sequence encoding for a 2A peptide sequence, wherein the 2A peptide sequence is selected from SEQ ID NO:331, SEQ ID NO:332, SEQ ID NO:333, SEQ ID NO:334, or SEQ ID NO:335. In one embodiment, the third polynucleotide sequence encoding 2A is selected from a nucleotide sequence encoding for a 2A peptide sequence, wherein the 2A peptide sequence is selected from SEQ ID NO:332, SEQ ID NO:333, SEQ ID NO:334, or SEQ ID NO:335. In one embodiment, the third polynucleotide sequence encoding 2A is selected from a nucleotide sequence encoding for a 2A peptide sequence, wherein the 2A peptide sequence is SEQ ID NO:335.

In one embodiment, the third polynucleotide sequence encoding 2A is SEQ ID NO:336.

In one embodiment, the T cell is from a human. In one embodiment, the T cell is from a mouse.

In one embodiment, the RNA is obtained directly from the T-cell as part of a one-step RT-PCR reaction. In one embodiment, the RNA is obtained and isolated from the T-cell prior to the RT-PCR reaction.

Description

Provided within this Example 7 are methods of assembling a TCR expression vector comprising a full-length Vα and a full-length Vβ from a single T cell (or a homogenous T cell population) in a single vector. Also provided within this Example 7 are methods of assembling a TCR expression vector comprising a full-length Vγ and a full-length Vδ from a single T cell (or a homogenous T cell population) into a single vector. The TCR can be readily expressed without further cloning steps. See, e.g., FIGS. 13-23.

Terms used throughout this application are to be construed with ordinary and typical meaning to those of ordinary skill in the art. However, the following terms are given a particular definition as defined below.

As used in the specification and claims, the singular form "a," "an," and "the" include plural references unless the context clearly dictates otherwise. For example, the term "a cell" includes a plurality of cells, including mixtures thereof.

The terms "about" and "approximately" are defined as being "close to" as understood by one of ordinary skill in the art. In one non-limiting embodiment, the terms are defined to be within 10%. In another non-limiting embodiment, the terms are defined to be within 5%. In still another non-limiting embodiment, the terms are defined to be within 1%.

The terms "cell," "cell line," and "cell culture" include progeny. It is also understood that all progeny may not be precisely identical in DNA content, due to deliberate or inadvertent mutations. Variant progeny within a population, which population has the same TCR expression of as screened for in the originally engineered cell population, are included.

As used herein, the term "comprising" is intended to mean that the compositions and methods include the recited elements, but not excluding others. "Consisting essentially of"

when used to define compositions and methods, shall mean excluding other elements of any essential significance to the combination. Thus, a composition consisting essentially of the elements as defined herein would not exclude trace contaminants from the isolation and purification method and pharmaceutically acceptable carriers, such as phosphate buffered saline, preservatives, and the like. "Consisting of" shall mean excluding more than trace elements of other ingredients and substantial method steps for administering the compositions of this invention. Embodiments defined by each of these transition terms are within the scope of this invention.

A "control" is an alternative subject or sample used in an experiment for comparison purposes. A control can be "positive" or "negative."

The term "fragment b" refers herein to a DNA polynucleotide sequence comprising in a 5' to 3' direction a Cα polynucleotide and a viral 2a polynucleotide, wherein fragment b is joinable on both its 5' and 3' ends with amplicon products of this Example 7 using a Gibson assembly method. In one embodiment, fragment b is as shown in SEQ ID NO:337. As used herein, "gene expression" and "protein expression" refer to the process by which polynucleotides are transcribed into mRNA and the process by which the transcribed mRNA is subsequently being translated into peptides, polypeptides, or proteins, respectively. If the polynucleotide is derived from genomic DNA, expression may include splicing of the mRNA in a eukaryotic cell. "Gene overexpression" refers to the overproduction of the mRNA transcribed from the gene, at a level that is 2.5 times higher, 5 times higher, or 10 times higher than the expression level detected in a control sample. "Protein overexpression" includes the overproduction of the protein product encoded by a gene at a level that is 2.5 times higher, 5 times higher, or 10 times higher than the expression level detected in a control sample.

As used herein "surface expression" refers to the process by which polypeptides are translocated to the surface of a cell such that at least a portion of the polypeptide is located at the exterior of the cell surface. "Surface overexpression" includes an increase in the amount of a particular polypeptide at the exterior surface of a cell, at a level that is 2.5 times higher, 5 times higher, or 10 times higher than the surface expression level detected in a control sample.

The term "Gibson assembly method" as used in Example 7 refers to a method that provides for directional closing of multiple DNA fragments known to those of skill in the art that was first described in Gibson D G, Young L, et al. (2009) Enzymatic assembly of DNA molecules up to several hundred kilobases. Nature Methods, 6(5):343-345. The Gibson assembly method makes use of DNA fragments and an acceptor vector designed with overlapping sequences at the locations that are to be joined, along with an exonuclease, a ligase and a polymerase.

The term "identity" or "homology" shall be construed to mean the percentage of nucleotide bases or amino acid residues in the candidate sequence that are identical with the bases or residues of a corresponding sequence to which it is compared, after aligning the sequences and introducing gaps, if necessary to achieve the maximum percent identity for the entire sequence, and not considering any conservative substitutions as part of the sequence identity. Neither N- nor C-terminal extensions nor insertions shall be construed as reducing identity or homology. A polynucleotide or polynucleotide region (or a polypeptide or polypeptide region) that has a certain percentage (for example, 80%, 85%, 90%, or 95%) of "sequence homology" to another sequence means that, when aligned, that percentage of bases (or amino acids) are the same in comparing the two sequences. This alignment and the percent homology or sequence identity can be determined using software programs known in the art. In one embodiment, default parameters are used for alignment. In one embodiment, a BLAST program is used with default parameters. In one embodiment, BLAST programs BLASTN and BLASTP are used with the following default parameters: Genetic code=standard; filter=none; strand=both; cutoff=60; expect=10; Matrix=BLOSUM62; Descriptions=50 sequences; sort by=HIGH SCORE; Databases=non-redundant, GenBank+EMBL+DDBJ+PDB+GenBank CDS translations+SwissProtein+SPupdate+PIR.

"Mammal" for purposes of treatment as used in Example 7 refers to any animal classified as a mammal, including human, domestic and farm animals, nonhuman primates, and zoo, sports, or pet animals, such as dogs, horses, cats, cows, etc.

The terms "polynucleotide" and "oligonucleotide" are used interchangeably, and refer to a polymeric form of nucleotides of any length, either deoxyribonucleotides or ribonucleotides, or analogs thereof. Polynucleotides may have any three-dimensional structure, and may perform any function, known or unknown. The following are non-limiting examples of polynucleotides: a gene or gene fragment, exons, introns, messenger RNA (mRNA), transfer RNA, ribosomal RNA, ribozymes, cDNA, recombinant polynucleotides, branched polynucleotides, plasmids, vectors, isolated DNA of any sequence, isolated RNA of any sequence, nucleic acid probes, and primers. A polynucleotide may comprise modified nucleotides, such as methylated nucleotides and nucleotide analogs. If present, modifications to the nucleotide structure may be imparted before or after assembly of the polymer. The sequence of nucleotides may be interrupted by non-nucleotide components. A polynucleotide may be further modified after polymerization, such as by conjugation with a labeling component. The term also refers to both double- and single-stranded molecules. Unless otherwise specified or required, any embodiment of this invention that is a polynucleotide encompasses both the double-stranded form and each of two complementary single-stranded forms known or predicted to make up the double-stranded form. A polynucleotide is composed of a specific sequence of four nucleotide bases: adenine (A); cytosine (C); guanine (G); thymine (T); and uracil (U) for thymine (T) when the polynucleotide is RNA. Thus, the term "polynucleotide sequence" is the alphabetical representation of a polynucleotide molecule. This alphabetical representation can be input into databases in a computer having a central processing unit and used for bioinformatics applications such as functional genomics and homology searching.

The term "polypeptide" is used in its broadest sense to refer to a compound of two or more subunit amino acids, amino acid analogs, or peptidomimetics. The subunits may be linked by peptide bonds. In another embodiment, the subunit may be linked by other bonds, e.g. ester, ether, etc. As used herein the term "amino acid" refers to either natural and/or unnatural or synthetic amino acids, including glycine and both the D or L optical isomers, and amino acid analogs and peptidomimetics. A peptide of three or more amino acids is commonly called an oligopeptide if the peptide chain is short. If the peptide chain is long, the peptide is commonly called a polypeptide or a protein.

A "primer" is a short polynucleotide, generally with a free 3'-OH group that binds to a target or "template" potentially present in a sample of interest by specifically hybridizing with the target, and thereafter promoting polymerization of a polynucleotide complementary to the target. "Primer specificity" refers to the ability of the primer to bind specifically to the target. Primer specificity is determined by the polynucleotide region within the primer that hybridizes to the target, also referred to herein as the "hybridizing region."

A "polymerase chain reaction" ("PCR") is a reaction in which replicate copies are made of a target polynucleotide using a "pair of primers" or a "set of primers" consisting of a "forward" and a "reverse" primer, and a catalyst of polymerization, such as a DNA polymerase, and typically a thermally-stable polymerase enzyme. In some embodiments, the forward primers bind specifically to a T cell leader sequence, resulting in an amplicon product that comprises the leader sequence. Methods for PCR are well known in the art, and taught, for example in "PCR: A PRACTICAL APPROACH" (M. MacPherson et al., IRL Press at Oxford University Press (1991)). The term "RT-PCR" refers herein to a reverse transcription PCR process wherein a RNA molecule, for example, mRNA, is reverse transcribed into a cDNA molecule that is then amplified as known by one of skill in the art. The term "nested PCR" refers herein to a PCR process that follows a first PCR process and uses at least one different primer than the first process in order to amplify a target that lies within the product of the first PCR process. In some embodiments, the first PCR process is an RT-PCR process. All processes of producing replicate copies of a polynucleotide, such as PCR or gene cloning, are collectively referred to herein as "replication."

The term "subject" is defined herein to include animals such as mammals, including, but not limited to, primates (e.g., humans), cows, sheep, goats, horses, dogs, cats, rabbits, rats, mice and the like. In some embodiments, the subject is a human.

The term "T cell" refers herein to a lymphocyte that expresses a T cell receptor. T cells include CD4$^+$ T cells, CD8$^+$ T cells, and NK T cells. CD4$^+$ T cell subsets included within the definition of T cells are Th1, Th2, Th9, Th22, Treg, and Tfh. CD8$^+$ T cells include both memory and effector cell subsets.

The term "T cell receptor" is used interchangeably with the term "TCR." Although these terms typically refer to a complex of integral membrane proteins that participate in the activation of T cells in response to an antigen (alpha (α) chain (or gamma (γ) chain), beta (β) chain (or delta (δ) chain), two zeta (ζ) chains, CD3 delta (δ) chain, CD3 (ε) chain, and CD3 (γ) chain), as used herein, the terms "T cell receptor" and "TCR" refer to the alpha (α) (or gamma (γ)) and beta (β) (or delta (δ)) chains (polypeptides) of a TCR. A "TCR α polynucleotide" encodes a TCR α chain (including α variable region (V) and a constant region (C)), whereas a "TCR β polynucleotide" encodes a TCR β chain (including α variable region (V) and a constant region (C)). Accordingly, a "Vα polynucleotide" refers herein to a polynucleotide that encodes a TCR α chain variable region polypeptide. A "Cα polynucleotide" refers herein to a polynucleotide that encodes a TCR α chain constant region polypeptide. A "Vβ polynucleotide" refers to a polynucleotide that encodes a TCR β chain variable region polypeptide. A "Cβ polynucleotide" refers herein to a polynucleotide that encodes a TCR β chain constant region polypeptide. In some embodiments, the encoded polypeptides are full length polypeptides. In other embodiments, the encoded polypeptides are fragments. It should be understood that a Vα polynucleotide comprises both a TCR Vα polynucleotide and a TCR Jα polynucleotide. It should be further understood that a Vβ polynucleotide comprises all of a TCR Vβ polynucleotide, a TCR Dβ polynucleotide, and a TCR Jβ polynucleotide. In one embodiment, the Cβ polynucleotide sequence is SEQ ID NO:338.

The term "expression vector" as used in Example 7 means a DNA construct containing a DNA sequence which is operably linked to a suitable control sequence capable of effecting the expression of the DNA in a suitable host. Such control sequences include a promoter to effect transcription, an optional operator sequence to control such transcription, a sequence encoding suitable mRNA ribosome binding sites, and sequences which control the termination of transcription and translation. The expression vector may be a plasmid, a phage particle, or simply a potential genomic insert. Once transformed into a suitable host, the expression vector may replicate and function independently of the host genome, or may in some instances, integrate into the genome itself. A plasmid is the most commonly used form of expression vector, however, the invention is intended to include such other forms of expression vectors which serve equivalent function as and which are, or become, known in the art.

The term "2a polynucleotide" refers herein to a polynucleotide that encodes a 2A peptide or a 2A peptide consensus motif of Asp-Val/Ile-Glu-X-Asn-Pro-Gly-Pro (SEQ ID NO:331). 2A peptides include, but are not limited to, 2A peptide of foot-and-mouth disease virus (VKQTLNFDLLKLAGDVESNPGP, SEQ ID NO:332), 2A peptide of equine rhinitis A virus (QCTNYALLKLAGD-VESNPGP, SEQ ID NO:333), 2A peptide of *Thosea asigna* virus (EGRGSLLTCGDVEENPGP, SEQ ID NO:334), 2A peptide of porcine teschovirus-1 (ATNFSLLKQAGD-VEENPGP, SEQ ID NO:335).

Methods

Provided in Example 7 are methods of assembling a TCR expression vector by capturing a full-length Vα and a full-length Vβ from a single T cell (or a homogenous T cell population) in a single vector. Also provided in Example 7 are methods of assembling a TCR expression vector comprising capturing a full-length Vγ and a full-length Vδ from a single T cell (or a homogenous T cell population) into a single vector. The TCR can be readily expressed without further cloning steps.

Disclosed in Example 7 are methods that allow for rapid cloning of any known or unknown TCR in any vector. These methods are less expensive than prior art methods and unbiased. In some embodiments, these methods allow for fast and inexpensive amplification of intact TCRs of any T cell and direct seamless cloning of the products in a vector of choice. The applications of these methods and materials are numerous such as medium to high-throughput isolation and cloning of TCRs into retroviral vectors for screening of antigen and/or for the generation of retrogenic or transgenic mice.

The methods described in Example 7 are adapted for the human system by designing a set of primers specific for human α and β chains and by using a vector (for example, a retroviral vector or provirus) suitable to infect human cells. In some embodiments, these methods can be used for immunotherapy of cancer. This is accomplished by cloning TCRs from a high number of tumor infiltrating cells (TILs) into an acceptor retroviral vector with the ultimate goal of transducing patient lymphocytes to be used for immunotherapy. In some embodiments, the methods disclosed in Example 7 are used to clone high numbers of TCR from inflamed tissue of autoimmune patients to screen for autoantigens. With this knowledge, strategies are employed to either neutralize that antigen or the specific autoreactive T cells that are recognizing it. In another embodiment, TCRs are cloned from a T cell taken from a solid organ graft such as liver, kidney, lung or intestine that are undergoing rejection by the host. Such TCRs can be used to study the rejection process, monitor the rejection process, and to introduce these T cells into host human T cells that have regulatory function that can be used to treat rejection.

In one aspect, provided in Example 7 is a method for assembling a TCR expression vector comprising a Vα region and a Vβ region from a single T cell (or a homogenous population of T cells), comprising the steps:
  a. obtaining a linearized vector comprising a 5' end, a 3' end, and a first polynucleotide sequence encoding TCR Cβ;
  b. obtaining a fragment b polynucleotide sequence; wherein the fragment b polynucleotide sequence comprises a second polynucleotide sequence encoding TCR Cα operably linked to a third polynucleotide sequence encoding 2A;
  c. obtaining RNA from a single T cell (or a homogenous population of T cells);
  d. performing a one-step reverse transcriptase-polymerase chain reaction (RT-PCR) to amplify a first set of TCR Vα amplicon products, comprising the steps:
    i. performing a reverse transcription of the RNA into cDNA;
    ii. performing a polymerase chain reaction on the cDNA, using;
      1. a first forward Vα primer, wherein the first forward Vα primer comprises at the 5' end a first nucleotide sequence that is complementary to a second nucleotide sequence at the 5' end of the linearized vector; wherein the first nucleotide sequence is operably linked to a first leader sequence of a Vα gene; and
      2. a first reverse Cα primer, having a third nucleotide sequence that is complementary to a fourth nucleotide sequence at the 5' end of fragment b;
  e. performing a one-step reverse transcriptase-polymerase chain reaction (RT-PCR) to amplify a first set of TCR amplicon products, comprising the steps:
    i. performing a reverse transcription of the RNA into cDNA;
    ii. performing a polymerase chain reaction on the cDNA, using;
      1. a first forward Vβ primer, wherein the first forward Vβ primer comprises at the 5' end a fifth nucleotide sequence that is complementary to a sixth nucleotide sequence at the 3' end of the fragment b; wherein the fifth nucleotide sequence is operably linked to a second leader sequence of a Vβ gene; and
      2. a first reverse Cβ primer, having a seventh nucleotide sequence that is complementary to an eighth nucleotide sequence at the 3' end the linearized vector;
  f. performing a nested polymerase chain reaction on the first set of TCR Vα amplicon products to amplify a second set of TCR Vα amplicon products, using:
    i. a second forward Vα primer comprising a ninth nucleotide sequence that contains a portion of the first nucleotide sequence of the first forward Vα primer; and
    ii. a second reverse Cα primer having a tenth nucleotide sequence that is complementary to an eleventh nucleotide sequence at the 5' end of fragment b;
  g. performing a nested polymerase chain reaction on the first set of TCR amplicon to amplify a second set of TCR β amplicon products, using:
    i. a second forward Vβ primer having a twelfth nucleotide sequence at its 5' end that contains a portion of the fifth nucleotide sequence of the first forward Vβ primer; and
    ii. a second reverse Cβ primer having a thirteenth nucleotide sequence that is complementary to a fourteenth nucleotide sequence at to the 3' end of the linearized vector;
  h. assembling the TCR expression vector by ligation (for example, a seamless cloning method or a Gibson assembly method), in a 5' to 3' direction, of the following:
    i. the 5' end of the linearized vector;
    ii. the second set of TCR Vα amplicon products;
    iii. the fragment b polynucleotide sequence;
    iv. the second set of TCR amplicon products; and
    v. the 3' end of the linearized vector.

In another aspect, provided in Example 7 is a method for assembling a TCR expression vector comprising a Vα region and a Vβ region from a single T cell (or a homogenous population of T cells), comprising the steps:
  a. obtaining a linearized vector comprising a 5' end, a 3' end, and a first polynucleotide sequence encoding TCR Cβ;
  b. obtaining a fragment b polynucleotide sequence; wherein the fragment b polynucleotide sequence comprises a second polynucleotide sequence encoding TCR Cα operably linked to a third polynucleotide sequence encoding 2A;
  c. obtaining RNA from a single T cell (or a homogenous population of T cells);
  d. performing a one-step reverse transcriptase-polymerase chain reaction (RT-PCR) to amplify a first set of TCR Vα amplicon products, comprising the steps:
    i. performing a reverse transcription of the RNA into cDNA;
    ii. performing a polymerase chain reaction on the cDNA, using;
      1. a plurality of first forward Vα primers, wherein the first forward Vα primers comprise at the 5' end a first nucleotide sequence that is complementary to a second nucleotide sequence at the 5' end of the linearized vector; wherein the first nucleotide sequence is operably linked to a plurality of first leader sequences of Vα genes; and
      2. a first reverse Cα primer, having a third nucleotide sequence that is complementary to a fourth nucleotide sequence at the 5' end of fragment b;
  e. performing a one-step reverse transcriptase-polymerase chain reaction (RT-PCR) to amplify a first set of TCR amplicon products, comprising the steps:
    i. performing a reverse transcription of the RNA into cDNA;
    ii. performing a polymerase chain reaction on the cDNA, using;
      1. a plurality of first forward Vβ primers, wherein the first forward Vβ primers comprise at the 5' end a fifth nucleotide sequence that is complementary to a sixth nucleotide sequence at the 3' end of the fragment b; wherein the fifth nucleotide sequence is operably linked to a plurality of second leader sequences of Vβ genes; and 2. a first reverse Cβ primer, having a seventh nucleotide sequence that is complementary to an eighth nucleotide sequence at the 3' end the linearized vector;
f. performing a nested polymerase chain reaction on the first set of TCR Vα amplicon products to amplify a second set of TCR Vα amplicon products, using:
  i. a second forward Vα primer comprising a ninth nucleotide sequence that contains a portion of the first nucleotide sequence of the first forward Vα primer; and
  ii. a second reverse Cα primer having a tenth nucleotide sequence that is complementary to an eleventh nucleotide sequence at the 5' end of fragment b;
g. performing a nested polymerase chain reaction on the first set of TCR amplicon to amplify a second set of TCR β amplicon products, using:
  i. a second forward Vβ primer having a twelfth nucleotide sequence at its 5' end that contains a portion of the fifth nucleotide sequence of the first forward Vβ primer; and
  ii. a second reverse Cβ primer having a thirteenth nucleotide sequence that is complementary to a fourteenth nucleotide sequence at to the 3' end of the linearized vector;
h. assembling the TCR expression vector by ligation (for example, a seamless cloning method or a Gibson assembly method), in a 5' to 3' direction, of the following:
  i. the 5' end of the linearized vector;
  ii. the second set of TCR Vα amplicon products;
  iii. the fragment b polynucleotide sequence;
  iv. the second set of TCR amplicon products; and
  v. the 3' end of the linearized vector.

In one aspect, provided in Example 7 is a method for assembling a TCR expression vector comprising a Vγ region and a Vδ region from a single T cell (or a homogenous population of T cells), comprising the steps:
a. obtaining a linearized vector comprising a 5' end, a 3' end, and a first polynucleotide sequence encoding TCR Cβ;
b. obtaining a fragment b polynucleotide sequence; wherein the fragment b polynucleotide sequence comprises a second polynucleotide sequence encoding TCR Cγ operably linked to a third polynucleotide sequence encoding 2A;
c. obtaining RNA from a single T cell (or a homogenous population of T cells);
d. performing a one-step reverse transcriptase-polymerase chain reaction (RT-PCR) to amplify a first set of TCR Vγ amplicon products, comprising the steps:
  i. performing a reverse transcription of the RNA into cDNA;
  ii. performing a polymerase chain reaction on the cDNA, using;
    1. a first forward Vγ primer, wherein the first forward Vγ primer comprises at the 5' end a first nucleotide sequence that is complementary to a second nucleotide sequence at the 5' end of the linearized vector; wherein the first nucleotide sequence is operably linked to a first leader sequence of a Vγ gene; and
    2. a first reverse Cγ primer, having a third nucleotide sequence that is complementary to a fourth nucleotide sequence at the 5' end of fragment b;
e. performing a one-step reverse transcriptase-polymerase chain reaction (RT-PCR) to amplify a first set of TCR Vδ amplicon products, comprising the steps:
  i. performing a reverse transcription of the RNA into cDNA;
  ii. performing a polymerase chain reaction on the cDNA, using;
    1. a first forward Vδ primer, wherein the first forward Vδ primer comprises at the 5' end a fifth nucleotide sequence that is complementary to a sixth nucleotide sequence at the 3' end of the fragment b; wherein the fifth nucleotide sequence is operably linked to a second leader sequence of a Vδ gene; and
    2. a first reverse Cδ primer, having a seventh nucleotide sequence that is complementary to an eighth nucleotide sequence at the 3' end the linearized vector;
f. performing a nested polymerase chain reaction on the first set of TCR Vγ amplicon products to amplify a second set of TCR Vγ amplicon products, using:
  i. a second forward Vγ primer comprising a ninth nucleotide sequence that contains a portion of the first nucleotide sequence of the first forward Vγ primer; and
  ii. a second reverse Cγ primer having a tenth nucleotide sequence that is complementary to an eleventh nucleotide sequence at the 5' end of fragment b;
g. performing a nested polymerase chain reaction on the first set of TCR Vδ amplicon to amplify a second set of TCR δ amplicon products, using:
  i. a second forward Vδ primer having a twelfth nucleotide sequence at its 5' end that contains a portion of the fifth nucleotide sequence of the first forward Vδ primer; and
  ii. a second reverse Cδ primer having a thirteenth nucleotide sequence that is complementary to a fourteenth nucleotide sequence at to the 3' end of the linearized vector;
h. assembling the TCR expression vector by ligation (for example, a seamless cloning method or a Gibson assembly method), in a 5' to 3' direction, of the following:
  i. the 5' end of the linearized vector;
  ii. the second set of TCR Vγ amplicon products;
  iii. the fragment b polynucleotide sequence;
  iv. the second set of TCR Vδ amplicon products; and
  v. the 3' end of the linearized vector.

In another aspect, provided in Example 7 is a method for assembling a TCR expression vector comprising a Vγ region and a Vδ region from a single T cell (or a homogenous population of T cells), comprising the steps:
a. obtaining a linearized vector comprising a 5' end, a 3' end, and a first polynucleotide sequence encoding TCR Cβ;
b. obtaining a fragment b polynucleotide sequence; wherein the fragment b polynucleotide sequence comprises a second polynucleotide sequence encoding TCR Cγ operably linked to a third polynucleotide sequence encoding 2A;
c. obtaining RNA from a single T cell (or a homogenous population of T cells);
d. performing a one-step reverse transcriptase-polymerase chain reaction (RT-PCR) to amplify a first set of TCR Vγ amplicon products, comprising the steps:
  i. performing a reverse transcription of the RNA into cDNA;

ii. performing a polymerase chain reaction on the cDNA, using;
  1. a plurality of first forward Vγ primers, wherein the first forward Vγ primers comprise at the 5' end a first nucleotide sequence that is complementary to a second nucleotide sequence at the 5' end of the linearized vector; wherein the first nucleotide sequence is operably linked to a plurality of first leader sequences of Vγ genes; and
  2. a first reverse Cγ primer, having a third nucleotide sequence that is complementary to a fourth nucleotide sequence at the 5' end of fragment b;
e. performing a one-step reverse transcriptase-polymerase chain reaction (RT-PCR) to amplify a first set of TCR Vδ amplicon products, comprising the steps:
  i. performing a reverse transcription of the RNA into cDNA;
  ii. performing a polymerase chain reaction on the cDNA, using;
    1. a plurality of first forward Vδ primers, wherein the first forward Vδ primers comprise at the 5' end a fifth nucleotide sequence that is complementary to a sixth nucleotide sequence at the 3' end of the fragment b; wherein the fifth nucleotide sequence is operably linked to a plurality of second leader sequences of Vδ genes; and
    2. a first reverse Cδ primer, having a seventh nucleotide sequence that is complementary to an eighth nucleotide sequence at the 3' end the linearized vector;
f. performing a nested polymerase chain reaction on the first set of TCR Vγ amplicon products to amplify a second set of TCR Vγ amplicon products, using:
  i. a second forward Vγ primer comprising a ninth nucleotide sequence that contains a portion of the first nucleotide sequence of the first forward Vγ primer; and
  ii. a second reverse Cγ primer having a tenth nucleotide sequence that is complementary to an eleventh nucleotide sequence at the 5' end of fragment b;
g. performing a nested polymerase chain reaction on the first set of TCR Vδ amplicon to amplify a second set of TCR δ amplicon products, using:
  i. a second forward Vδ primer having a twelfth nucleotide sequence at its 5' end that contains a portion of the fifth nucleotide sequence of the first forward Vδ primer; and
  ii. a second reverse Cδ primer having a thirteenth nucleotide sequence that is complementary to a fourteenth nucleotide sequence at to the 3' end of the linearized vector;
h. assembling the TCR expression vector by ligation (for example, a seamless cloning method or a Gibson assembly method), in a 5' to 3' direction, of the following:
  i. the 5' end of the linearized vector;
  ii. the second set of TCR Vγ amplicon products;
  iii. the fragment b polynucleotide sequence;
  iv. the second set of TCR Vδ amplicon products; and
  v. the 3' end of the linearized vector.

In one embodiment, steps (d) and (e) are performed in a single reaction. In one embodiment, steps (f) and (g) are performed in a single reaction.

In one embodiment, the assembling of the TCR expression vector by ligation comprises a seamless cloning method that utilizes short regions of homology. In one embodiment, the assembling of the TCR expression vector by ligation comprises a Gibson assembly method.

In one embodiment, the first nucleotide sequence is 15 to 25 nucleotides in length. In one embodiment, the first nucleotide sequence is 20 nucleotides in length.

In one embodiment, the fifth nucleotide sequence is 15 to 25 nucleotides in length. In one embodiment, the fifth nucleotide sequence is 20 nucleotides in length.

In one embodiment, the ninth nucleotide sequence is 15 to 25 nucleotides in length. In one embodiment, the ninth nucleotide sequence is 18 nucleotides in length.

In one embodiment, the twelfth nucleotide sequence is 15 to 25 nucleotides in length. In one embodiment, the twelfth nucleotide sequence is 18 nucleotides in length.

In one embodiment, the first nucleotide sequence is perfectly complementary to the second nucleotide sequence at the 5' end of the linearized vector. In one embodiment, the third nucleotide sequence is perfectly complementary to the fourth nucleotide sequence at the 5' end of fragment b.

In one embodiment, the fifth nucleotide sequence is perfectly complementary to the sixth nucleotide sequence at the 3' end of the fragment b. In one embodiment, the seventh nucleotide sequence is perfectly complementary to the eighth nucleotide sequence at the 3' end the linearized vector. In one embodiment, the tenth nucleotide sequence is perfectly complementary to the eleventh nucleotide sequence at the 5' end of fragment b. In one embodiment, the thirteenth nucleotide sequence is perfectly complementary to the fourteenth nucleotide sequence at to the 3' end of the linearized vector.

In one embodiment, the plurality of first forward Vα primers comprises SEQ ID NO:345 to SEQ ID NO:416 (72 primers total). In one embodiment, the plurality of first forward Vβ primers comprises SEQ ID NO:417 to SEQ ID NO:441 (25 primers total).

In one embodiment, the linearized vector comprises pMIGII.

In one embodiment, the third polynucleotide sequence encoding 2A is selected from SEQ ID NO:331, SEQ ID NO:332, SEQ ID NO:333, SEQ ID NO:334, or SEQ ID NO:335. In one embodiment, the third polynucleotide sequence encoding 2A is selected from SEQ ID NO:332, SEQ ID NO:333, SEQ ID NO:334, or SEQ ID NO:335. In one embodiment, the third polynucleotide sequence encoding 2A is SEQ ID NO:335.

In alternate embodiments, the methods herein can use a linker sequence comprising any self-cleavable peptide, instead of a 2A sequence.

In some embodiments, the methods disclosed herein use primers that comprise the entire leader sequence in the 5' "first" primer for each Vα and VP.

In some embodiments, the TCR expression vector constructs may be cloned in different arrangements. For example, the TCR expression vector may be assembled by ligation (for example, a seamless cloning method or a Gibson assembly method), in a 5' to 3' direction, the following:
  i. the 5' end of the linearized vector;
  ii. the second set of TCR amplicon products;
  iii. the fragment b polynucleotide sequence;
  iv. the second set of TCR Vα amplicon products; and
  v. the 3' end of the linearized vector.

In some embodiments, the TCR expression vector may be assembled by ligation (for example, a seamless cloning method or a Gibson assembly method), in a 5' to 3' direction, the following:

i. the 5' end of the linearized vector;
ii. the second set of TCR Vδ amplicon products;
iii. the fragment b polynucleotide sequence;
iv. the second set of TCR Vγ amplicon products; and
v. the 3' end of the linearized vector.

In one embodiment, the T cell is from a human. In one embodiment, the T cell is from a mouse.

In other embodiments, the TCR α and β RNA are obtained from a clonal population rather than from a single T cell.

In some embodiments, either or both the TCR α and TCR β RNA is exposed to a plurality of the first forward Vα primer, each primer having a same terminal 5' end and a different primer specificity. As used herein, "primer specificity" refers to the ability of the primer to bind specifically to the target TCR α or TCR β RNA. Primer specificity is determined by the polynucleotide region within the primer that hybridizes to the TCR α or TCR β RNA, also referred to herein as the "hybridizing region."

The expression vector used in accordance with the methods can be any appropriate expression vector known to one of skill in the art. In some embodiments, the expression vector is a viral vector. In some embodiments, the expression vector is a retroviral vector. In some embodiments, the expression vector is an adenoviral vector. In some embodiments, the expression vector is pMIGII (Holst et al., *Nat. Protoc.*, 1(1):406-17 (2006)).

Primer Generation

An algorithm was developed using the matlab code language for the generation of primers for given DNA sequences obtained in a raw text format from internet-based genome databases. This method can be easily adapted for other forms of inputs. The IMGT database was used to generate lists in text format of all annotated functional mouse Vα and Vβ chains. The user was able to set up one or two desired temperature ranges of melting temperatures for the primers and a desired range of number of nucleotides as well. In addition, the user can add any fixed nucleotide sequence on the 5' side of the resulting primers. In this example, the fixed nucleotide sequences were the 20 nucleotides added to the primers for Vα and Vβ having homology to the acceptor vector or fragment b, respectively. Once the input parameters were set, the program scanned the raw text containing hundreds or even thousands of DNA sequences, automatically recognizing each sequence name and the sequence linked to it and determining an optimum primer within the given input constrains for each sequence. The program uses the nearest-neighbor method (Santa Lucia, J Jr. (1998) "A unified view of polymer, dumbbell, and oligonucleotide DNA nearest-neighbor thermodynamics." *Proc. Natl. Acad. Sci. USA* 95, 1460-1465) to calculate melting temperatures and build primers with as close of a melting temperature to each other as possible.

As an output, the program automatically saves a series of lists in text files:
1. A full result report listing all primers and their features as melting temperature, temperature range, if the primer can be fit or not within the desired parameters and a general statement about how many primers succeeded and how many are repeated primers.
2. A list with only the non-repeated primers and all its features.
3. A list with only the repeated primers and all its features.
4. A list of the primers names
5. A buy-list for ordering primers
6. A statistical analysis with histograms about the distribution of primers over their melting temperatures, their size and over which temperature range they belong.

The whole calculation process is virtually instantaneous, saving the user from days of work and making it possible to quickly try different possibilities for the desired final primers.

Assembly of TCR Expression Vectors

Figure 14:
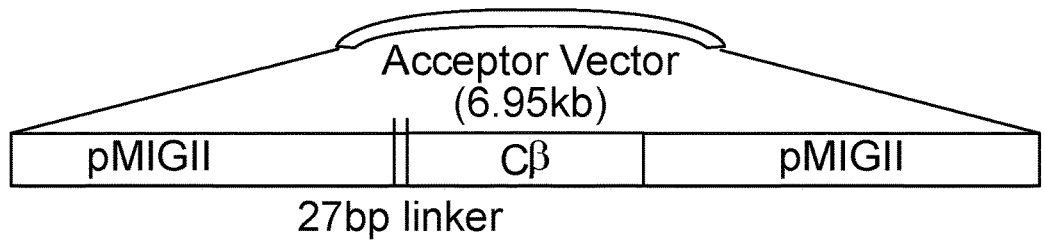
FIG. 14 is a schematic representation of the acceptor vector based on the pMIGII retroviral vector. A synthesized DNA fragment comprising a 27 nucleotide linker containing restriction recognition sites for PmeI and RsrII and the constant region of the TCR β chain was assembled in the pMIGII retroviral vector using the Gibson assembly cloning method. The resulting vector is 6.95 kb in length.
Figure 15:
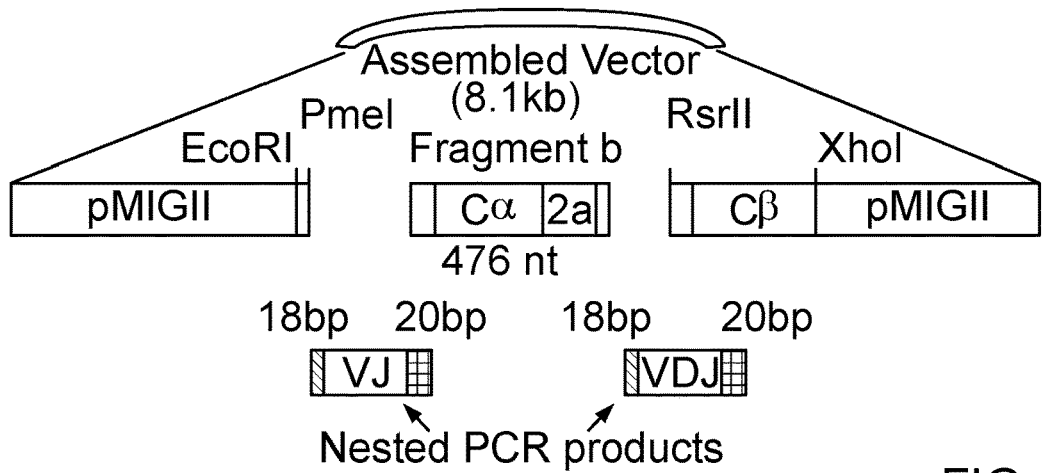
FIG. 15 is a schematic representation of the linearized acceptor vector to be assembled with fragment b and the nested α and β PCR products. The acceptor vector linearized with the restriction enzymes PmeI and RsrII is assembled in a single Gibson reaction with fragment b, containing the TCR α constant region and the 2a element, and the α VJ and β VDJ nested PCR products of the unknown TCRs. The resulting retroviral vector size (roughly 8.1 kb) will vary slightly according with the length of the assembled α and β chain.

The method described in the "Primer Generation" section was used to create a set of forward primers that together can bind to all leader sequences of the Vα repertoire as well as of the Vβ repertoire of any mouse strain annotated in the IMGT databank to date. The sequences of these Vα and Vβ primers are provided in SEQ ID NOs:345-416 and SEQ ID NOs:417-441, respectively. These primers, in combination with reverse primers that bind the constant region of α and β (SEQ ID NO:339 and SEQ ID NO:340, respectively), can be used either with mRNA of a clonal population or with single cells in a one-step RT-PCR reaction to amplify a full-length, expressible V sequences. On the 5' end of each forward primer there is a fixed 20 nucleotide segment that has homology to the vector or to a DNA fragment that contains the constant region of the alpha chain and a 2a element downstream of it (hereafter "fragment b") (see FIG. 15). In one example, the invariant 20 nucleotides of the Vα primers have homology to the 5' end of a linearized acceptor vector based on the pMIGII retroviral vector and the invariant 20 nucleotides of the Vβ primers are homologous to the 3' end of fragment b (FIGS. 14 and 15). The linearized acceptor vector contains the constant region of the beta chain on its 3' end.

After the RT-PCR, the sample is split, and a nested PCR is done for α and β chains with 18 nucleotide forward primers that bind either to the invariant part of Vα or Vβ and nested reverse primers for Cα and Cβ. After completion of the nested PCR, the products containing Vα plus 20 nucleotides of Cα and Vβ plus 20 nucleotides of Cβ are assembled in the linearized acceptor vector together with fragment b in a total reaction of 10 μL using the Gibson assembly method. As an example, 50 ng of linearized (acceptor) vector, 10 ng of alpha amplicon, 10 ng of beta amplicon, and 10 ng of fragment b (total mix of 10 μL) are added to 10 μL of 2× Gibson assembly enzymes (Kit from NEB) and incubated for 1 hour at 50° C.

Characterization of TCR Expression Vectors

Figure 16:
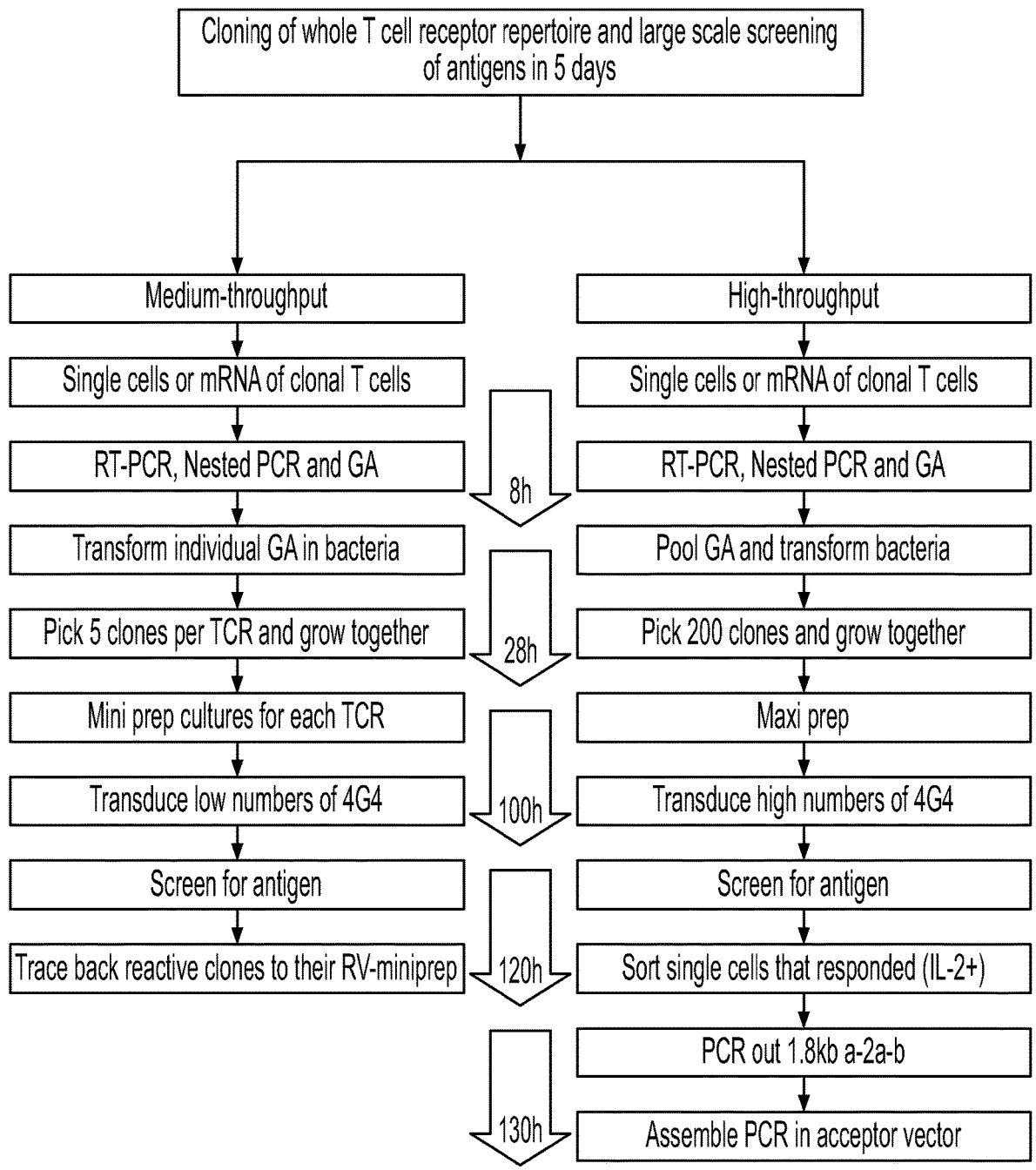
FIG. 16 is a diagram illustrating two different cloning strategies downstream of a Gibson assembly (GA). The flow chart on the left depicts the medium-throughput strategy (strategy 1) and on the right is the high-throughput strategy (strategy 2).
Figure 17:
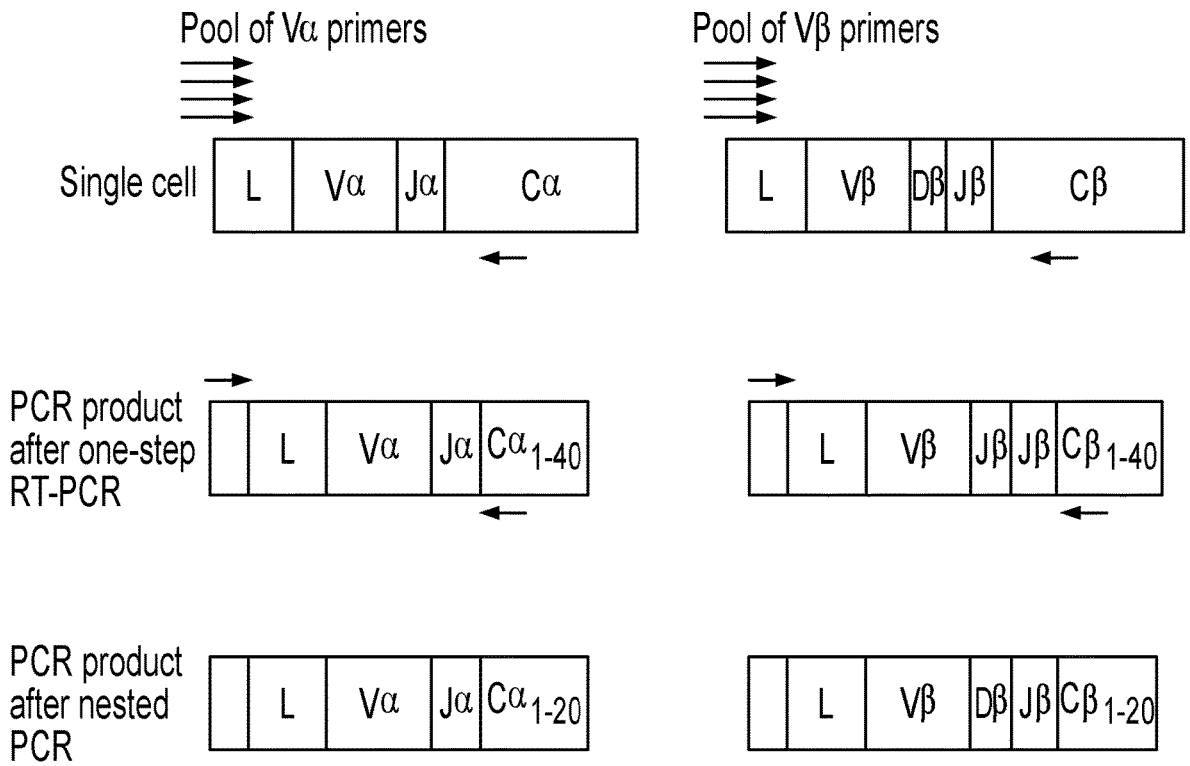
FIG. 17 is PCR strategy set forth in Example 7 for amplifying any VαJα and VβDβJβ from rearranged cDNA. RT-PCR of either RNA from a single T cell or RNA of clonal T cells is performed using a pool of forward primers that bind the leader sequence of a multitude of Vα and Vβ gene segments and two reverse primers that bind either Cα or Cβ. All Vα primers at the 5' end possess a common sequence of 20 nt that overlaps with the 5' end of the linearized pMIGII and all Vβ primers contain at the 5' end a common sequence of 20 nt that overlaps with the 3' end of fragment b. A second PCR called "nested PCR" is done with forward primers that bind the last 18 nt of either Vα or Vβ common sequences and reverse primers that bind the first 20 nt of either Cα or Cβ. Both Vα and Vβ amplicons contain, respectively, 18 nt overlap to either the vector or fragment b, VαJα and VβDβJβ with intact leader sequences and the first 20 nt of either Cα or Cβ.
Figure 18:
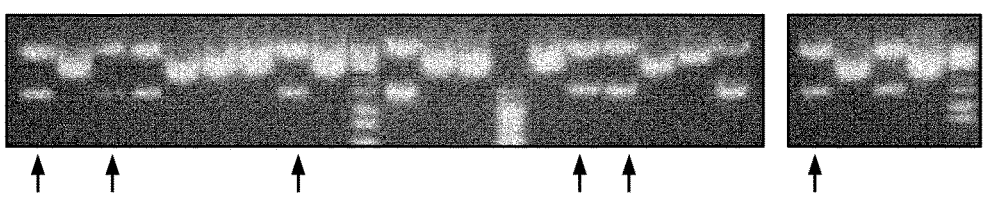
FIG. 18 shows a ClaI restriction digestion for screening of positive assembled vectors after Gibson assembly for Example 7. The expected bands size after digestion are around 6700 nt and 1400 nt. The gel shows that around 50% efficiency for cloning of the TCRs of 13C2 and 1B9 T cell hybridoma.
Figure 19A:
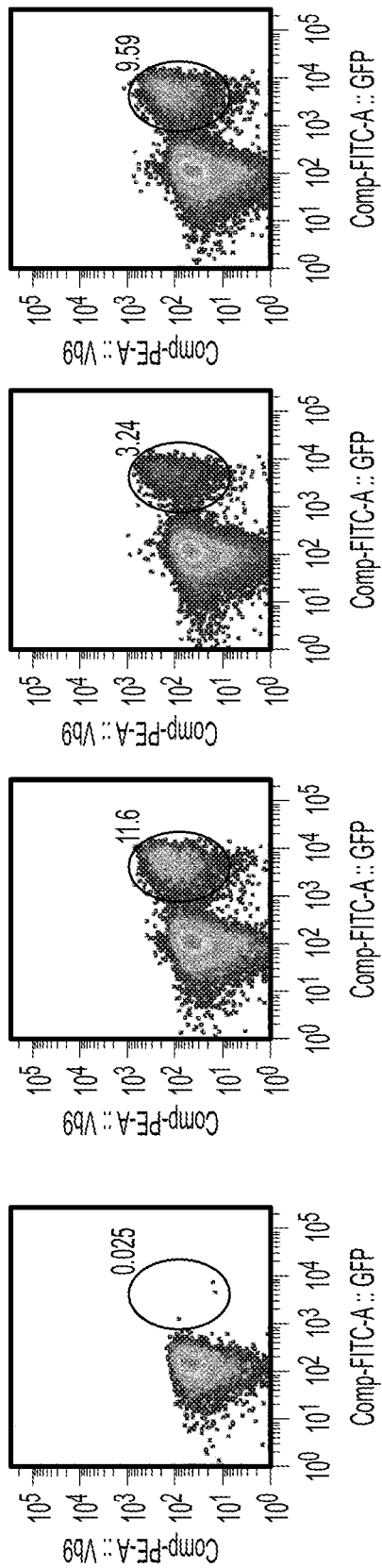
FIGS. 19A-19C show TCR expression and T cell function. Three assembled retroviral vectors of each 13C2 or 1B9 TCRs were transduced in 4G4 cells. 13C2 (A) and 1B9 (B) TCRs expression on the membrane of 4G4 cells were assessed by flow cytometry. Double positive staining of GFP (contained in the RV vector) and the respective Vβ indicates percentage of cells expressing the TCR. (C) IL-2 secretion of 4G4 transduced with either 1B9 or 13C2 and stimulated with AM14Vk8R B cells, that can present PL2-3 antigens, and PL2-3 (black bars) or irrelevant anti-IgM (white bars). Shown are stimulations with three transduction event for each TCR.
Figure 19B:
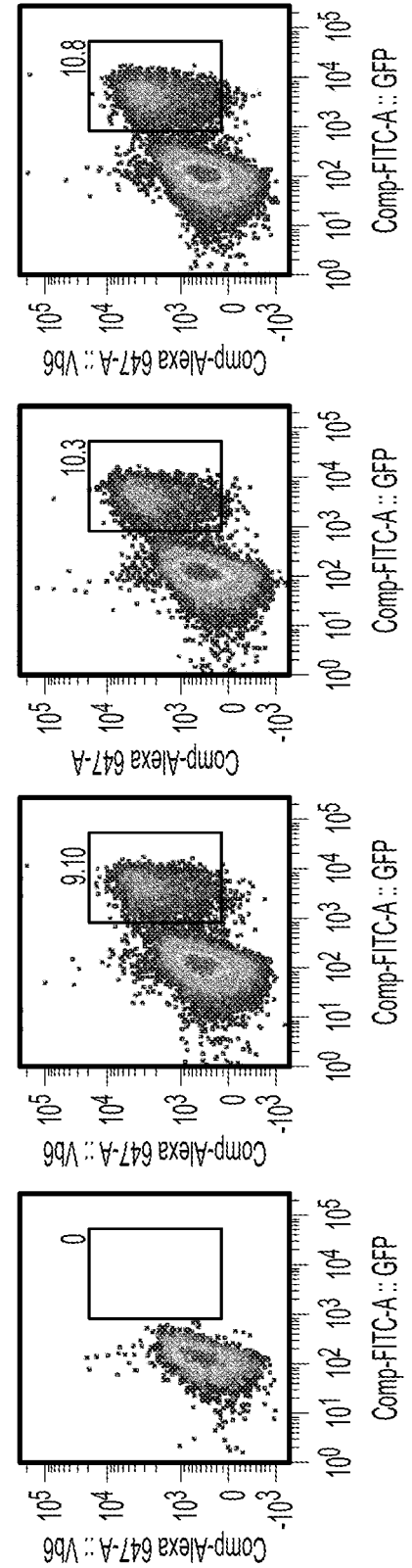
Figure 19C:
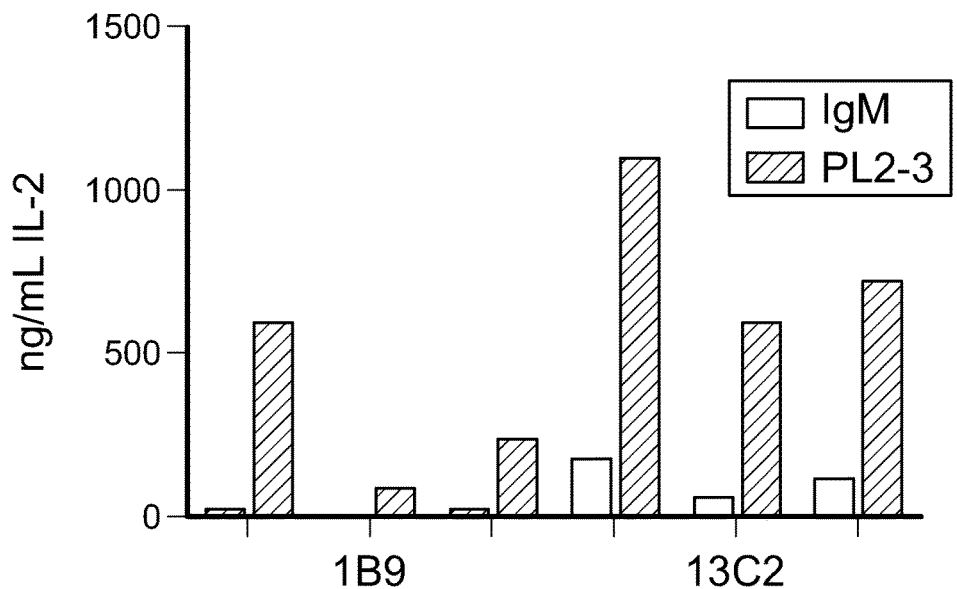
Figure 20:
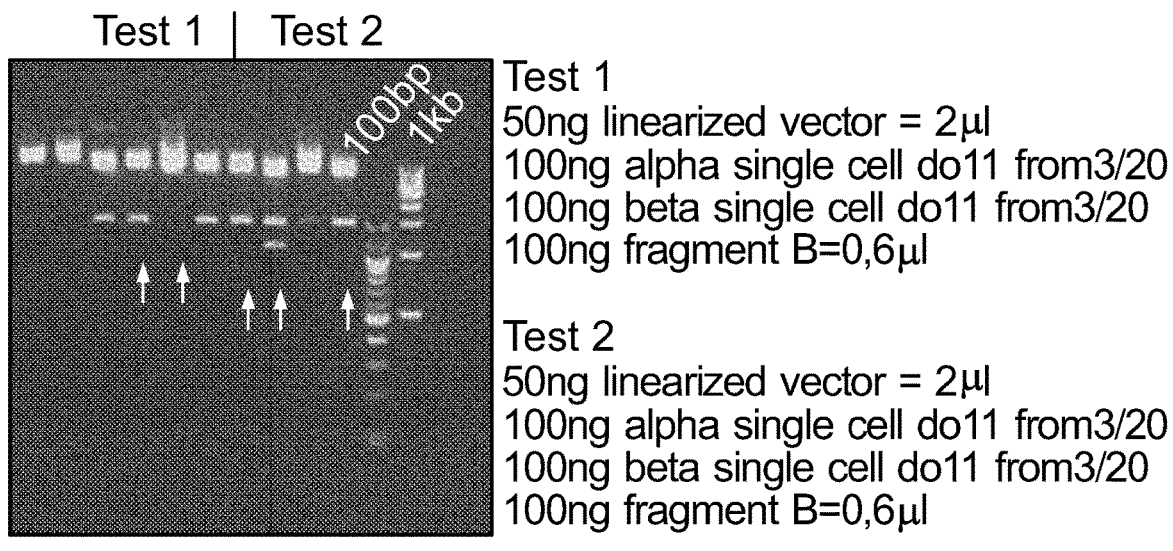
FIG. 20 is a gel showing Gibson assembly. Shown are two tests for Gibson assembly using different DNA concentrations and DO11.10 TCR. Arrows point to correct ClaI digestion pattern and correct assembled pMIGII vector and DO11.10 TCR.
Figure 21:
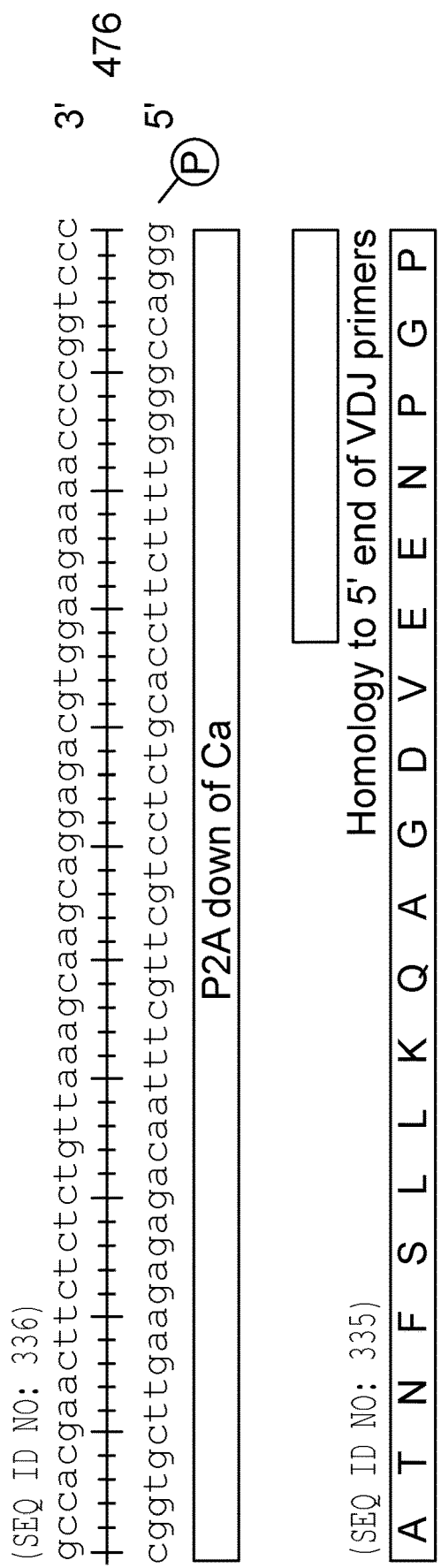
FIG. 21 is a schematic illustrating a P2A nucleotide (SEQ ID NO: 336) and amino acid sequence (SEQ ID NO: 335). Approximate region of homology (overlap) to the (plurality of) first forward Vβ primers is shown.

There are two downstream strategies that can be taken following the creation of the TCR expression vector, taking note that now the Vα/Vβ of each single cell is linked in one circular DNA fragment (FIG. 16).

Strategy 1 consists of keeping the Gibson assembly reactions of each TCR separated and transforming each as single reactions in *E. coli*. The steps from the first RT-PCR to the Gibson assembly and transformation in *E. coli* are completed in roughly 8 hours. The next day, 5 colonies of each TCR are grown together in 5-10 mL LB medium containing ampicillin, and plasmid mini-prep is performed for each TCR. Because the Gibson assembly reaction results in approximately 30-50% positive clones, roughly at least 1 of the 5 colonies contains retroviral vector with correct α and β inserts. PlatE cells grown on 12-well plates are then transfected with 2-5 μg of each plasmid pool and 1.4-3.6 μg Ecohelper plasmid in 1-1.5 mL DMEM medium. 24 hours later 0.5-1×10$^5$ 4 G4 TCRα$^{-/-}$ CD4$^+$ cells are transduced with 1-1.5 mL RV supernatant from each PlatE well in 12-wells or with 1 mL in 48 well-plates. The following day, the transduction using virus supernatant is repeated.

Detection of TCR expression on the membrane and screening for the antigen occurs on the third or fourth day. When a single correct RV vector is preferred instead of a pool (which may contain incorrectly assembled and/or empty acceptor vectors), the pool is transformed back into bacteria, and bacterial colonies are screened for the correct insertion of α and β chains by digesting the plasmid with EcoRI and XhoI. After digestion, the size of the fragment (or of the sum of fragments if alpha or/and beta possesses a EcoRI or/and XhoI restriction sites) containing the correctly assembled α and β products must be around 1.8 kb, and the size of the vector backbone must be around 6.3 kb. This strategy is suited for medium-throughput cloning of unknown T cells and screening of antigens.

Strategy 2 is designed to address high-throughput purposes. In this strategy, the Gibson assembly reaction of each TCR is pooled (maximum of 40 TCR per pool), and 8 μL is transformed in 120 μL chemical competent *E. coli*. The bacteria are plated on LB-agar containing ampicillin. As soon as 12 hours after plating, bacterial colonies are picked to grow in liquid LB containing ampicillin. No more than 200 colonies (1 colony/2.5 mL LB medium) are picked and grown together overnight in 500 mL LB medium. Because the Gibson assembly reaction provides approximately 30-50% positive clones, the 200 colonies picked contain 60 to 100 retroviral vectors with correct α and β inserts, and theoretically at least 1 correct retroviral per input TCR (40 per pool, as above). Roughly 12 hours later, a maxi prep is performed to isolate the plasmid DNA library. PlatE cells grown for 12 hours in 6 T175 flasks containing 20 mL DMEM medium each are transfected with 25 μg Eco-helper plasmid and 35 μg of the plasmid library per flask using lipid transfection reagents. 24 hours later, 5 T75 flasks, each with 2×10$^6$ exponentially growing 4G4 TCRα$^{-/-}$ CD4$^+$ cells (alternatively other CD4$^+$ such as B3Z/lacZ or CD8$^+$ cell lines can be used) are transduced with 20 mL virus supernatant. The following day, the transduction using virus supernatant was repeated.

Detection of TCR expression on the membrane and screening for the antigen specificity occurs on the third-fourth day. 4G4 cells that have undergone TCR-dependent recognition of antigen secreted IL-2 (note that other recipient indicator cells can easily be used). Reactive 4G4 cells are sorted as single cells based on surface IL-2 capture or other means. The Vα-2a-Vβ transgene (approximately 1850 bp) in these cells are amplified by performing a PCR with primers designed to bind the genome integrated provirus 20 nucleotides upstream of EcoRI and 20 nucleotides downstream of the XhoI restriction sites. To obtain a retroviral vector carrying the functional and antigen specific TCR, the Vα-2a-Vβ transgene can be rapidly assembled in the assembly vector that was cut with EcoRI and XhoI. This strategy is well suited for high-throughput cloning of TCRs of unknown specificity followed by large scale screening of candidate antigens. The libraries that are made also can be amplified and reused.

Additional sequences used in the methods disclosed herein:

Nucleotide sequence encoding self-cleavable peptide 2A in FASTA format (SEQ ID NO: 336):
5'-GCCACGAACTTCTCTCTGTTAAAGCAAGCAGGAGACGTGGAAGAAA
ACCCCGGTCCC-3'

Nucleotide sequence encoding Fragment b in FASTA format (SEQ ID NO: 337):
5'-ACATCCAGAACCCAGAACCTGCTGTGTACCAGTTAAAAGATCCTCGG
TCTCAGGACAGCACCCTCTGCCTGTTCACCGACTTTGACTCCCAAATCAA
TGTGCCGAAAACCATGGAATCTGGAACGTTCATCACTGACAAAACTGTGC
TGGACATGAAAGCTATGGATTCCAAGAGCAATGGGGCCATTGCCTGGAGC
AACCAGACAAGCTTCACCTGCCAAGATATCTTCAAAGAGACCAACGCCAC
CTACCCCAGTTCAGACGTTCCCTGTGATGCCACGTTGACCGAGAAAAGCT
TTGAAACAGATATGAACCTAAACTTTCAAAACCTGTCAGTTATGGGACTC
CGAATCCTCCTGCTGAAAGTAGCGGGATTTAACCTGCTCATGACGCTGAG
GCTGTGGTCCAGTGGCTCCGGAGCCACGAACTTCTCTCTGTTAAAGCAAG
CAGGAGACGTGGAAGAAAACCCCGGTCCC-3'

Nucleotide sequence encoding Cβ in FASTA format (SEQ ID NO: 338):
5'-AGGATCTGAGAAATGTGACTCCACCCAAGGTCTCCTTGTTTGAGCCA
TCAAAAGCAGAGATTGCAAACAAACAAAAGGCTACCCTCGTGTGCTTGGC
CAGGGGCTTCTTCCCTGACCACGTGGAGCTGAGCTGGTGGGTGAATGGCA
AGGAGGTCCACAGTGGGGTCAGCACGGACCCTCAGGCCTACAAGGAGAGC
AATTATAGCTACTGCCTGAGCAGCCGCCTGAGGGTCTCTGCTACCTTCTG
GCACAATCCTCGAAACCACTTCCGCTGCCAAGTGCAGTTCCATGGGCTTT
CAGAGGAGGACAAGTGGCCAGAGGGCTCACCCAAACCTGTCACACAGAAC
ATCAGTGCAGAGGCCTGGGGCCGAGCAGACTGTGGAATCACTTCAGCATC
CTATCATCAGGGGGTTCTGTCTGCAACCATCCTCTATGAGATCCTACTGG
GGAAGGCCACCCTATATGCTGTGCTGGTCAGTGGCCTGGTGCTGATGGCC
ATGGTCAAGAAAAAAAAATTCCTGA-3'

First reverse Cα primer (SEQ ID NO: 339):
GTCAAAGTCGGTGAACAGGC

First reverse Cβ primer (SEQ ID NO: 340):
TTGGGTGGAGTCACATTTCTC

Nested reverse primer for Cα (second reverse Cα primer)(SEQ ID NO: 341):
AGGTTCTGGGTTCTGGATGT Nested reverse primer for Cβ (second reverse Cβ primer)(SEQ ID NO: 342):
GGAGTCACATTTCTCAGATCCT Nested forward alpha (second forward Vα primer) (SEQ ID NO: 343):
TCTAGGCGCCGGAATTCA Nested forward beta (second forward Vβ primer) (SEQ ID NO: 344):
GAAGAAAACCCCGGTCCC Primers alpha (Vα) pool (plurality of first forward Vα primers) (SEQ ID NO: 345 to SEQ ID NO: 416):
ATN-a1:
tctctaggcgccggaattcaatgctgcagatgtggggtttg (SEQ ID NO: 345)

-continued

ATN-a2:
tctctaggcgccggaattcaatgaagacatcccttcacactg (SEQ ID NO: 346)

ATN-a3:
tctctaggcgccggaattcaatggataaaacatcccttcaca (SEQ ID NO: 347)

ATN-a4:
tctctaggcgccggaattcaatggattaagacatcccttcac (SEQ ID NO: 348)

ATN-a5:
tctctaggcgccggaattcaatgaaaaagtgccttagtgcct (SEQ ID NO: 349)

ATN-a6:
tctctaggcgccggaattcaatgaaaaagcgcctgagtgcct (SEQ ID NO: 350)

ATN-a7:
tctctaggcgccggaattcaatgaaaaagtgcctgagtgcct (SEQ ID NO: 351)

ATN-a8:
tctctaggcgccggaattcaatgcgtcctgtcacctgctcag (SEQ ID NO: 352)

ATN-a9:
tctctaggcgccggaattcaatgaacatgcatcctgtcacct (SEQ ID NO: 353)

ATN-a10:
tctctaggcgccggaattcaatgcgtcctggcacctgc (SEQ ID NO: 354)

ATN-a11:
tctctaggcgccggaattcaatgcgtcctgacacctgctcag (SEQ ID NO: 355)

ATN-a12:
tctctaggcgccggaattcaatgaacatgcgtcctgtcacct (SEQ ID NO: 356)

ATN-a13:
tctctaggcgccggaattcaatgcgtcctgtcacctcctcag (SEQ ID NO: 357)

ATN-a14:
tctctaggcgccggaattcaatgcgtcctgacacctcctcag (SEQ ID NO: 358)

ATN-a15:
tctctaggcgccggaattcaatgaacaggctgctgtgctctc (SEQ ID NO: 359)

ATN-a16:
tctctaggcgccggaattcaatgaagaggctgctgtgttctc (SEQ ID NO: 360)

ATN-a17:
tctctaggcgccggaattcaatgaagaggctgctgtgctctc (SEQ ID NO: 361)

ATN-a18:
tctctaggcgccggaattcaatgaagaggctgatgtgctctc (SEQ ID NO: 362)

ATN-a19:
tctctaggcgccggaattcaatgaggaggctgatgtgttctc (SEQ ID NO: 363)

ATN-a20:
tctctaggcgccggaattcaatgaagaggctgctgagctctc (SEQ ID NO: 364)

ATN-a21:
tctctaggcgccggaattcaatgaagaggctagtgtgttctc (SEQ ID NO: 365)

ATN-a22:
tctctaggcgccggaattcaatgaaaaggctgctgtgctctc (SEQ ID NO: 366)

ATN-a23:
tctctaggcgccggaattcaatggacaagatcctgacagcaa (SEQ ID NO: 367)

ATN-a24:
tctctaggcgccggaattcaatggacacgatcctgacagcat (SEQ ID NO: 368)

ATN-a25:
tctctaggcgccggaattcaatggacaagatcctgacagcat (SEQ ID NO: 369)

ATN-a26:
tctctaggcgccggaattcaatggacaagattctgacagcat (SEQ ID NO: 370)

ATN-a27:
tctctaggcgccggaattcaatggacaagaacctgacagcat (SEQ ID NO: 371)

ATN-a28:
tctctaggcgccggaattcaatgcctcctcacagcctg (SEQ ID NO: 372)

ATN-a29:
tctctaggcgccggaattcaatgcctcctcagagcctg (SEQ ID NO: 373)

ATN-a30:
tctctaggcgccggaattcaatgcctcctcacagcctgttct (SEQ ID NO: 374)

ATN-a31:
tctctaggcgccggaattcaatgctgattctaagcctgttgg (SEQ ID NO: 375)

ATN-a32:
tctctaggcgccggaattcaatgttcctagtgaccattctgc (SEQ ID NO: 376)

ATN-a33:
tctctaggcgccggaattcaatgttcccagtgaccattctgc (SEQ ID NO: 377)

ATN-a34:
tctctaggcgccggaattcaatgactggcttcctgaaggcct (SEQ ID NO: 378)

ATN-a35:
tctctaggcgccggaattcaatgaagcaggtggcaaaagtga (SEQ ID NO: 379)

ATN-a36:
tctctaggcgccggaattcaatgggatgtgtgagtggaattg (SEQ ID NO: 380)

ATN-a37:
tctctaggcgccggaattcaatgaagacagtgactggacctt (SEQ ID NO: 381)

ATN-a38:
tctctaggcgccggaattcaatgaagacggtgactggacctt (SEQ ID NO: 382)

ATN-a39:
tctctaggcgccggaattcaatgaaaacagtgactggacctt (SEQ ID NO: 383)

ATN-a40:
tctctaggcgccggaattcaatggagaggagcccggga (SEQ ID NO: 384)

ATN-a41:
tctctaggcgccggaattcaatggagaggaacctggttgctg (SEQ ID NO: 385)

ATN-a42:
tctctaggcgccggaattcaatgcagaggaacctgggagctg (SEQ ID NO: 386)

ATN-a43:
tctctaggcgccggaattcaatgcagaggaacctggttgctg (SEQ ID NO: 387)

ATN-a44:
tctctaggcgccggaattcaatggagaggaacctgggagctg (SEQ ID NO: 388)

ATN-a45:
tctctaggcgccggaattcaatgaagacagctattcatgctt (SEQ ID NO: 389)

ATN-a46:
tctctaggcgccggaattcaatgaaaacatacgctcctacat (SEQ ID NO: 390)

ATN-a47:
tctctaggcgccggaattcaatgaaaacatatgctcctacattattca (SEQ ID NO: 391)

ATN-a48:
tctctaggcgccggaattcaatgaactattctccagctttagtg (SEQ ID NO: 392)

ATN-a49:
tctctaggcgccggaattcaatgaacacttctccagctttag (SEQ ID NO: 393)

ATN-a50:
tctctaggcgccggaattcaatgaacaattccccagctttag (SEQ ID NO: 394)

ATN-a51:
tctctaggcgccggaattcaatgaatacttctccagttttagtaact (SEQ ID NO: 395)

ATN-a52:
tctctaggcgccggaattcaatgaacctttatcctgaactgg (SEQ ID NO: 396)

ATN-a53:
tctctaggcgccggaattcaatgaacctttgtcctgaactgg (SEQ ID NO: 397)

ATN-a54:
tctctaggcgccggaattcaatggactcttctccaggcttcg (SEQ ID NO: 398)

ATN-a55:
tctctaggcgccggaattcaatgaactcttctccaggcttca (SEQ ID NO: 399)

ATN-a56:
tctctaggcgccggaattcaatgaatacttctccagttttagtga (SEQ ID NO: 400)

ATN-a57:
tctctaggcgccggaattcaatggacttttctccaggcttcg (SEQ ID NO: 401)

ATN-a58:
tctctaggcgccggaattcaatgaagtccttgtgtgtttcac (SEQ ID NO: 402)

ATN-a59:
tctctaggcgccggaattcaatgaaatccttgagtgtttcact (SEQ ID NO: 403)

ATN-a60:
tctctaggcgccggaattcaatgaaatcctttagtatttccctagtg (SEQ ID NO: 404)

ATN-a61:
tctctaggcgccggaattcaatgaaatccttgagtgttttccc (SEQ ID NO: 405)

ATN-a62:
tctctaggcgccggaattcaatgcattccttacatgtttcac (SEQ ID NO: 406)

ATN-a63:
tctctaggcgccggaattcaatggtacaaacacagatgttct (SEQ ID NO: 407)

ATN-a64:
tctctaggcgccggaattcaatgaaatccttgagtgttttactagt (SEQ ID NO: 408)

ATN-a65:
tctctaggcgccggaattcaatgcacagcctcctgggg (SEQ ID NO: 409)

ATN-a66:
tctctaggcgccggaattcaatgaacagattcctgggaatat (SEQ ID NO: 410)

ATN-a67:
tctctaggcgccggaattcaatgcacagcctcctagggttgt (SEQ ID NO: 411)

ATN-a68:
tctctaggcgccggaattcaatgctcctggtcctcatctcgt (SEQ ID NO: 412)

ATN-a69:
tctctaggcgccggaattcaatgctcctggttctcatctcgt (SEQ ID NO: 413)

ATN-a70:
tctctaggcgccggaattcaatgctcctggtgctcctc (SEQ ID NO: 414)

ATN-a71:
tctctaggcgccggaattcaatgctcctggcgctcctc (SEQ ID NO: 415)

ATN-a72:
tctctaggcgccggaattcaatgctcctggcactcctc (SEQ ID NO: 416)

Primers beta (Vβ) pool (plurality of first forward Vβ primers)(SEQ ID NO: 417 to SEQ ID NO: 441):
ATN-b1:
tggaagaaaaccccggtcccatgtggcagttttgcattctgt (SEQ ID NO: 417)

ATN-b2:
tggaagaaaaccccggtcccatgccacggacaccaggc (SEQ ID NO: 418)

ATN-b3:
tggaagaaaaccccggtcccatgtctaacactgtcctcgctg (SEQ ID NO: 419)

ATN-b4:
tggaagaaaaccccggtcccatgtctaacactgccttccctg (SEQ ID NO: 420)

ATN-b5:
tggaagaaaaccccggtcccatgtgtaatactaccctccttaatttt (SEQ ID NO: 421)

ATN-b6:
tggaagaaaaccccggtcccatgggctccaggctattctgg (SEQ ID NO: 422)

ATN-b7:
tggaagaaaaccccggtcccatgggctccaggctcttcttcg (SEQ ID NO: 423)

ATN-b8:
tggaagaaaaccccggtcccatgggctccagactcttctttg (SEQ ID NO: 424)

ATN-b9:
tggaagaaaaccccggtcccatgggcaccaggcttctt (SEQ ID NO: 425)

ATN-b10:
tggaagaaaaccccggtcccatgggcatccagaccctctgtt (SEQ ID NO: 426)

ATN-b11:
tggaagaaaaccccggtcccatggccccaggctccttttc (SEQ ID NO: 427)

ATN-b12:
tggaagaaaaccccggtcccatggatcctagacttctttgct (SEQ ID NO: 428)

ATN-b13:
tggaagaaaaccccggtcccatgaacaagtgggttttctgct (SEQ ID NO: 429)

ATN-b14:
tggaagaaaaccccggtcccatgggctccattttcctcagtt (SEQ ID NO: 430)

ATN-b15:
tggaagaaaaccccggtcccatgttactgcttctattacttctgg (SEQ ID NO: 431)

ATN-b16:
tggaagaaaaccccggtcccatgggtgcacggctcatttgctat (SEQ ID NO: 432)

ATN-b17:
tggaagaaaaccccggtcccatgggtgcaagactgctc (SEQ ID NO: 433)

ATN-b18:
tggaagaaaaccccggtcccatgactgccaagttcatgcatt (SEQ ID NO: 434)

ATN-b19:
tggaagaaaaccccggtcccatggtcaccagtctctcaagat (SEQ ID NO: 435)

ATN-b20:
tggaagaaaaccccggtcccatgagagttaggctcatctctg (SEQ ID NO: 436)

ATN-b21:
tggaagaaaaccccggtcccatggatatctggcttctaggtt (SEQ ID NO: 437)

ATN-b22:
tggaagaaaaccccggtcccatgctgtactctctccttgcct (SEQ ID NO: 438)

ATN-b23:
tggaagaaaaccccggtcccatgggctgtaggctcctaagct (SEQ ID NO: 439)

ATN-b24:
tggaagaaaaccccggtcccatgagctgcaggcttctcctct (SEQ ID NO: 440)

-continued

ATN-b25:
tggaagaaaacccggtcccatgggctgaaaaatgctctgct (SEQ ID NO: 441)

This document also provides:

Paragraph #1. A method for assembling a T cell receptor expression vector comprising a Vα region and a Vβ region from a single T cell, comprising the steps:
 a. obtaining a linearized vector comprising a 5' end, a 3' end, and a first polynucleotide sequence encoding TCR Cβ;
 b. obtaining a fragment b polynucleotide sequence; wherein the fragment b polynucleotide sequence comprises a second polynucleotide sequence encoding TCR Cα operably linked to a third polynucleotide sequence encoding 2A;
 c. obtaining RNA from a single T cell;
 d. performing a one-step reverse transcriptase-polymerase chain reaction (RT-PCR) to amplify a first set of TCR Vα amplicon products, comprising the steps:
  i. performing a reverse transcription of the RNA into cDNA;
  ii. performing a polymerase chain reaction on the cDNA, using;
   1. a first forward Vα primer, wherein the first forward Vα primer comprises at the 5' end a first nucleotide sequence that is complementary to a second nucleotide sequence at the 5' end of the linearized vector; wherein the first nucleotide sequence is operably linked to a first leader sequence of a Vα gene; and
   2. a first reverse Cα primer, having a third nucleotide sequence that is complementary to a fourth nucleotide sequence at the 5' end of fragment b;
 e. performing a one-step reverse transcriptase-polymerase chain reaction (RT-PCR) to amplify a first set of TCR amplicon products, comprising the steps:
  i. performing a reverse transcription of the RNA into cDNA;
  ii. performing a polymerase chain reaction on the cDNA, using;
   1. a first forward Vβ primer, wherein the first forward Vβ primer comprises at the 5' end a fifth nucleotide sequence that is complementary to a sixth nucleotide sequence at the 3' end of the fragment b; wherein the fifth nucleotide sequence is operably linked to a second leader sequence of a Vβ gene; and
   2. a first reverse Cβ primer, having a seventh nucleotide sequence that is complementary to an eighth nucleotide sequence at the 3' end the linearized vector;
 f. performing a nested polymerase chain reaction on the first set of TCR Vα amplicon products to amplify a second set of TCR Vα amplicon products, using:
  i. a second forward Vα primer comprising a ninth nucleotide sequence that contains a portion of the first nucleotide sequence of the first forward Vα primer; and
  ii. a second reverse Cα primer having a tenth nucleotide sequence that is complementary to an eleventh nucleotide sequence at the 5' end of fragment b;
 g. performing a nested polymerase chain reaction on the first set of TCR amplicon to amplify a second set of TCR β amplicon products, using:
  i. a second forward Vβ primer having a twelfth nucleotide sequence at its 5' end that contains a portion of the fifth nucleotide sequence of the first forward Vβ primer; and
  ii. a second reverse Cβ primer having a thirteenth nucleotide sequence that is complementary to a fourteenth nucleotide sequence at to the 3' end of the linearized vector;
 h. assembling the TCR expression vector by ligation, in a 5' to 3' direction, of the following:
  i. the 5' end of the linearized vector;
  ii. the second set of TCR Vα amplicon products;
  iii. the fragment b polynucleotide sequence;
  iv. the second set of TCR amplicon products; and
  v. the 3' end of the linearized vector.

2. The method of Paragraph #1, wherein steps (d) and (e) are performed in a single reaction.

3. The method of Paragraph #1 or Paragraph #2, wherein steps (f) and (g) are performed in a single reaction.

4. The method of any one of Paragraph #1 to #3, wherein the assembling of the TCR expression vector by ligation comprises a seamless cloning method that utilizes short regions of homology.

5. The method of any one of Paragraph #1 to #3, wherein the assembling of the TCR expression vector by ligation comprises a Gibson assembly method.

6. The method of any one of Paragraph #1 to #5, wherein the first nucleotide sequence is 15 to 25 nucleotides in length.

7. The method of any one of Paragraph #1 to #5, wherein the first nucleotide sequence is 20 nucleotides in length.

8. The method of any one of Paragraph #1 to #7, wherein the fifth nucleotide sequence is 15 to 25 nucleotides in length.

9. The method of any one of Paragraph #1 to #7, wherein the fifth nucleotide sequence is 20 nucleotides in length.

10. The method of any one of Paragraph #1 to #9, wherein the ninth nucleotide sequence is 15 to 25 nucleotides in length.

11. The method of any one of Paragraph #1 to #9, wherein the ninth nucleotide sequence is 18 nucleotides in length.

12. The method of any one of Paragraph #1 to #11, wherein the twelfth nucleotide sequence is 15 to 25 nucleotides in length.

13. The method of any one of Paragraph #1 to #11, wherein the twelfth nucleotide sequence is 18 nucleotides in length.

14. The method of any one of Paragraph #1 to #13, wherein the linearized vector comprises pMIGII.

15. The method of any one of Paragraph #1 to #14, wherein the third polynucleotide sequence encoding 2A is selected from SEQ ID NO:332, SEQ ID NO:333, SEQ ID NO:334, or SEQ ID NO:335.

16. The method of any one of Paragraph #1 to #15, wherein the T cell is from a human.

17. The method of any one of Paragraph #1 to #15, wherein the T cell is from a mouse.

Paragraph #18. A method for assembling a T cell receptor (TCR) expression vector comprising a Vα region and a Vβ region from a single T cell, comprising the steps:
 a. obtaining a linearized vector comprising a 5' end, a 3' end, and a first polynucleotide sequence encoding TCR Cβ;
 b. obtaining a fragment b polynucleotide sequence; wherein the fragment b polynucleotide sequence comprises a second polynucleotide sequence encoding TCR Cα operably linked to a third polynucleotide sequence encoding 2A;
 c. obtaining RNA from a single T cell;

d. performing a one-step reverse transcriptase-polymerase chain reaction (RT-PCR) to amplify a first set of TCR Vα amplicon products, comprising the steps:
  i. performing a reverse transcription of the RNA into cDNA;
  ii. performing a polymerase chain reaction on the cDNA, using;
    1. a plurality of first forward Vα primers, wherein the first forward Vα primers comprise at the 5' end a first nucleotide sequence that is complementary to a second nucleotide sequence at the 5' end of the linearized vector; wherein the first nucleotide sequence is operably linked to a plurality of first leader sequences of Vα genes; and
    2. a first reverse Cα primer, having a third nucleotide sequence that is complementary to a fourth nucleotide sequence at the 5' end of fragment b;
e. performing a one-step reverse transcriptase-polymerase chain reaction (RT-PCR) to amplify a first set of TCR amplicon products, comprising the steps:
  i. performing a reverse transcription of the RNA into cDNA;
  ii. performing a polymerase chain reaction on the cDNA, using;
    1. a plurality of first forward Vβ primers, wherein the first forward Vβ primers comprise at the 5' end a fifth nucleotide sequence that is complementary to a sixth nucleotide sequence at the 3' end of the fragment b; wherein the fifth nucleotide sequence is operably linked to a plurality of second leader sequences of Vβ genes; and
    2. a first reverse Cβ primer, having a seventh nucleotide sequence that is complementary to an eighth nucleotide sequence at the 3' end the linearized vector;
f. performing a nested polymerase chain reaction on the first set of TCR Vα amplicon products to amplify a second set of TCR Vα amplicon products, using:
  i. a second forward Vα primer comprising a ninth nucleotide sequence that contains a portion of the first nucleotide sequence of the first forward Vα primer; and
  ii. a second reverse Cα primer having a tenth nucleotide sequence that is complementary to an eleventh nucleotide sequence at the 5' end of fragment b;
g. performing a nested polymerase chain reaction on the first set of TCR amplicon to amplify a second set of TCR β amplicon products, using:
  i. a second forward Vβ primer having a twelfth nucleotide sequence at its 5' end that contains a portion of the fifth nucleotide sequence of the first forward Vβ primer; and
  ii. a second reverse Cβ primer having a thirteenth nucleotide sequence that is complementary to a fourteenth nucleotide sequence at to the 3' end of the linearized vector;
h. assembling the TCR expression vector by ligation, in a 5' to 3' direction, of the following:
  i. the 5' end of the linearized vector;
  ii. the second set of TCR Vα amplicon products;
  iii. the fragment b polynucleotide sequence;
  iv. the second set of TCR amplicon products; and
  v. the 3' end of the linearized vector.
19. The method of Paragraph #18, wherein steps (d) and (e) are performed in a single reaction.
20. The method of Paragraph #18 or Paragraph #19, wherein steps (f) and (g) are performed in a single reaction.
21. The method of any one of Paragraph #18 to #20, wherein the assembling of the TCR expression vector by ligation comprises a seamless cloning method that utilizes short regions of homology.
22. The method of any one of Paragraph #18 to #20, wherein the assembling of the TCR expression vector by ligation comprises a Gibson assembly method.
23. The method of any one of Paragraph #18 to #22, wherein the first nucleotide sequence is 15 to 25 nucleotides in length.
24. The method of any one of Paragraph #18 to #22, wherein the first nucleotide sequence is 20 nucleotides in length.
25. The method of any one of Paragraph #18 to #24, wherein the fifth nucleotide sequence is 15 to 25 nucleotides in length.
26. The method of any one of Paragraph #18 to #24, wherein the fifth nucleotide sequence is 20 nucleotides in length.
27. The method of any one of Paragraph #18 to #26, wherein the ninth nucleotide sequence is 15 to 25 nucleotides in length.
28. The method of any one of Paragraph #18 to #26, wherein the ninth nucleotide sequence is 18 nucleotides in length.
29. The method of any one of Paragraph #18 to #28, wherein the twelfth nucleotide sequence is 15 to 25 nucleotides in length.
30. The method of any one of Paragraph #18 to #28, wherein the twelfth nucleotide sequence is 18 nucleotides in length.
31. The method of any one of Paragraph #18 to #30, wherein the linearized vector comprises pMIGII.
32. The method of any one of Paragraph #18 to #31, wherein the third polynucleotide sequence encoding 2A is selected from SEQ ID NO:332, SEQ ID NO:333, SEQ ID NO:334, or SEQ ID NO:335.
33. The method of any one of Paragraph #18 to #32, wherein the T cell is from a human.
34. The method of any one of Paragraph #18 to #32, wherein the T cell is from a mouse.

Example 8—Paragraphs Outlining Other Embodiments Provided Herein

This document also provides:
Paragraph #35. A method for obtaining a plurality of nucleic acid vectors containing nucleic acid encoding functional T cell receptors, wherein said method comprises:
(a) obtaining a device comprising a plurality of separate locations, wherein each of said separate locations contains cDNA generated from RNA obtained from a single T cell that was sorted into said separate locations,
(b) performing a nested amplification procedure using said cDNA of each of said plurality of separate locations as template to obtain a first amplification product and a second amplification product for said cDNA of each of said plurality of separate locations, wherein said first amplification product comprises nucleic acid encoding a Vα or Vγ segment, and wherein said second amplification product comprises nucleic acid encoding a Vβ or Vδ segment, and
(c) assembling said first amplification product and said second amplification product for said cDNA of each of said plurality of separate locations into a nucleic acid vector to obtain an assembled nucleic acid vector for said cDNA of each of said plurality of separate locations, wherein said assembled nucleic acid vector for said cDNA of each of said plurality of separate locations comprises nucleic acid encoding a functional T cell receptor comprising a signaling domain.

36. The method of Paragraph #35, wherein said plurality is greater than 50.
37. The method of Paragraph #35, wherein said plurality is greater than 500.
38. The method of Paragraph #35, wherein said plurality is greater than 5000.
39. The method of any one of Paragraphs #35-38, wherein said plurality of nucleic acid vectors is a plurality of nucleic acid expression vectors.
40. The method of any one of Paragraphs #35-39, wherein said device comprises a multi-well plate.
41. The method of Paragraph #40, wherein said multi-well plate is a 96-well plate, a 384-well plate, or a 1536-well plate.
42. The method of any one of Paragraphs #35-41, wherein said cDNA generated from RNA obtained from a single T cell single comprises cDNA generated from RNA obtained from a single human T cell.
43. The method of any one of Paragraphs #35-42, wherein said first amplification product comprises nucleic acid encoding an L sequence of a Vα or Vγ segment.
44. The method of any one of Paragraphs #35-43, wherein said first amplification product comprises nucleic acid encoding a Jα or Jγ segment.
45. The method of any one of Paragraphs #35-44, wherein said first amplification product comprises nucleic acid encoding a 5' portion of a Cα or Cγ region.
46. The method of any one of Paragraphs #35-45, wherein said first amplification product comprises nucleic acid encoding an L sequence of a Vα or Vγ segment, a Jα or Jγ segment, and a 5' portion of a Cα or Cγ region.
47. The method of any one of Paragraphs #35-46, wherein said second amplification product comprises nucleic acid encoding an L sequence of a Vβ or Vδ segment.
48. The method of any one of Paragraphs #35-47, wherein said second amplification product comprises nucleic acid encoding a Dβ or Dδ segment.
49. The method of any one of Paragraphs #35-48, wherein said second amplification product comprises nucleic acid encoding a Jβ or Jδ segment.
50. The method of any one of Paragraphs #35-49, wherein said second amplification product comprises nucleic acid encoding a 5' portion of a Cβ or Cδ region.
51. The method of any one of Paragraphs #35-50, wherein said second amplification product comprises nucleic acid encoding an L sequence of a Vβ or Vδ segment, a Dβ or Dδ segment, a Jβ or Jδ segment, and a 5' portion of a Cβ or Cδ region.
52. The method of any one of Paragraphs #35-51, wherein said first amplification product comprises an adapter sequence added to an amplified template sequence of said cDNA via a second round amplification of said nested amplification procedure.
53. The method of any one of Paragraphs #35-52, wherein said second amplification product comprises an adapter sequence added to an amplified template sequence of said cDNA via a second round amplification of said nested amplification procedure.
54. The method of any one of Paragraphs #35-53, wherein said first amplification product comprises a first adapter sequence added to an amplified template sequence of said cDNA via a second round amplification of said nested amplification procedure, and wherein said second amplification product comprises a second adapter sequence added to an amplified template sequence of said cDNA via a second round amplification of said nested amplification procedure, wherein said first and second adapter sequence are different.
55. The method of any one of Paragraphs #35-54, wherein said functional T cell receptor of each of said assembled nucleic acid vector comprises a Vα/Vβ combination or Vγ/Vδ combination as present in said single T cell originating said RNA.
56. The method of any one of Paragraphs #35-55, wherein said functional T cell receptor of each of said assembled nucleic acid vector comprises (a) a full-length α variable region and a full-length β variable region or (b) a full-length γ variable region and a full-length δ variable region.
57. The method of any one of Paragraphs #35-56, wherein said functional T cell receptor of each of said assembled nucleic acid vector comprises (a) a full-length α variable region and a full-length β variable region as present in said single T cell originating said RNA or (b) a full-length γ variable region and a full-length δ variable region as present in said single T cell originating said RNA.
58. The method of any one of Paragraphs #35-57, wherein said functional T cell receptor of each of said assembled nucleic acid vector comprises (a) a full-length α constant region and a full-length β constant region or (b) a full-length γ constant region and a full-length δ constant region.
59. The method of any one of Paragraphs #35-58, wherein each of said assembled nucleic acid vector comprises a nucleic acid sequence encoding a self-cleaving peptide or an internal ribosome entry site (IRES).
60. The method of any one of Paragraphs #35-59, wherein said method comprises sorting single T cells into said separate locations.
61. The method of any one of Paragraphs #35-60, wherein said method comprises performing a reverse transcription reaction to obtain said cDNA.
62. The method of any one of Paragraphs #35-61, wherein said assembling step comprises seamless cloning.
63. The method of any one of Paragraphs #35-62, wherein each of said assembled nucleic acid vector is obtained without performing nucleic acid sequencing.
64. The method of any one of Paragraphs #35-63, wherein each of said assembled nucleic acid vector is obtained without performing a restriction endonuclease cleavage reaction.
65. The method of any one of Paragraphs #35-64, wherein said heterologous signaling domain is a CD3-zeta signaling domain, a CD28 signaling domain, an OX-40 signaling domain, a 4-1BB signaling domain, a CD30 signaling domain, a CD27 signaling domain, or a GITR signaling domain.
66. The method of any one of Paragraphs #35-65, wherein said heterologous signaling domain is attached to a constant region of said functional T cell receptor.

Paragraph #67. A method for obtaining a plurality of nucleic acid vectors containing nucleic acid encoding soluble T cell receptors, wherein said method comprises:
(a) obtaining a device comprising a plurality of separate locations, wherein each of said separate locations contains cDNA generated from RNA obtained from a single T cell that was sorted into said separate locations,
(b) performing a nested amplification procedure using said cDNA of each of said plurality of separate locations as template to obtain a first amplification product and a second amplification product for said cDNA of each of said plurality of separate locations, wherein said first amplification product comprises nucleic acid encoding a Vα or Vγ segment, and wherein said second amplification product comprises nucleic acid encoding a Vβ or Vδ segment, and (c) assembling said first amplification product and said second amplification product for said cDNA of each of said plurality of separate locations into a nucleic acid vector to obtain an assembled nucleic acid vector for said cDNA of each of said plurality of separate locations, wherein said assembled nucleic acid vector for said cDNA of each of said plurality of separate locations comprises nucleic acid encoding a soluble T cell receptor.

68. The method of Paragraph #67, wherein said plurality is greater than 50.

69. The method of Paragraph #67, wherein said plurality is greater than 500.

70. The method of Paragraph #67, wherein said plurality is greater than 5000.

71. The method of any one of Paragraphs #67-70, wherein said plurality of nucleic acid vectors is a plurality of nucleic acid expression vectors.

72. The method of any one of Paragraphs #67-71, wherein said device comprises a multi-well plate.

73. The method of Paragraph #72, wherein said multi-well plate is a 96-well plate, a 384-well plate, or a 1536-well plate.

74. The method of any one of Paragraphs #67-73, wherein said cDNA generated from RNA obtained from a single T cell single comprises cDNA generated from RNA obtained from a single human T cell.

75. The method of any one of Paragraphs #67-74, wherein said first amplification product comprises nucleic acid encoding an L sequence of a Vα or Vγ segment.

76. The method of any one of Paragraphs #67-75, wherein said first amplification product comprises nucleic acid encoding a Jα or Jγ segment.

77. The method of any one of Paragraphs #67-76, wherein said first amplification product comprises nucleic acid encoding a 5' portion of a Cα or Cγ region.

78. The method of any one of Paragraphs #67-77, wherein said first amplification product comprises nucleic acid encoding an L sequence of a Vα or Vγ segment, a Jα or Jγ segment, and a 5' portion of a Cα or Cγ region.

79. The method of any one of Paragraphs #67-78, wherein said second amplification product comprises nucleic acid encoding an L sequence of a Vβ or Vδ segment.

80. The method of any one of Paragraphs #67-79, wherein said second amplification product comprises nucleic acid encoding a Dβ or Dδ segment.

81. The method of any one of Paragraphs #67-80, wherein said second amplification product comprises nucleic acid encoding a Jβ or Jδ segment.

82. The method of any one of Paragraphs #67-81, wherein said second amplification product comprises nucleic acid encoding a 5' portion of a Cβ or Cδ region.

83. The method of any one of Paragraphs #67-82, wherein said second amplification product comprises nucleic acid encoding an L sequence of a Vβ or Vδ segment, a Dβ or Dδ segment, a Jβ or Jδ segment, and a 5' portion of a Cβ or Cδ region.

84. The method of any one of Paragraphs #67-83, wherein said first amplification product comprises an adapter sequence added to an amplified template sequence of said cDNA via a second round amplification of said nested amplification procedure.

85. The method of any one of Paragraphs #67-84, wherein said second amplification product comprises an adapter sequence added to an amplified template sequence of said cDNA via a second round amplification of said nested amplification procedure.

86. The method of any one of Paragraphs #67-85, wherein said first amplification product comprises a first adapter sequence added to an amplified template sequence of said cDNA via a second round amplification of said nested amplification procedure, and wherein said second amplification product comprises a second adapter sequence added to an amplified template sequence of said cDNA via a second round amplification of said nested amplification procedure, wherein said first and second adapter sequence are different.

87. The method of any one of Paragraphs #67-86, wherein said soluble T cell receptor of each of said assembled nucleic acid vector comprises a Vα/Vβ combination or Vγ/Vδ combination as present in said single T cell originating said RNA.

88. The method of any one of Paragraphs #67-87, wherein said soluble T cell receptor of each of said assembled nucleic acid vector comprises (a) a full-length α variable region and a full-length β variable region or (b) a full-length γ variable region and a full-length δ variable region.

89. The method of any one of Paragraphs #67-88, wherein said soluble T cell receptor of each of said assembled nucleic acid vector comprises (a) a full-length α variable region and a full-length β variable region as present in said single T cell originating said RNA or (b) a full-length γ variable region and a full-length δ variable region as present in said single T cell originating said RNA.

90. The method of any one of Paragraphs #67-89, wherein said soluble T cell receptor of each of said assembled nucleic acid vector comprises (a) a full-length α constant region and a full-length β constant region or (b) a full-length γ constant region and a full-length δ constant region.

91. The method of any one of Paragraphs #67-90, wherein each of said assembled nucleic acid vector comprises a nucleic acid sequence encoding a self-cleaving peptide or an internal ribosome entry site (IRES).

92. The method of any one of Paragraphs #67-91, wherein said method comprises sorting single T cells into said separate locations.

93. The method of any one of Paragraphs #67-92, wherein said method comprises performing a reverse transcription reaction to obtain said cDNA.

94. The method of any one of Paragraphs #67-93, wherein said assembling step comprises seamless cloning.

95. The method of any one of Paragraphs #67-94, wherein each of said assembled nucleic acid vector is obtained without performing nucleic acid sequencing.

96. The method of any one of Paragraphs #67-95, wherein each of said assembled nucleic acid vector is obtained without performing a restriction endonuclease cleavage reaction.

97. The method of any one of Paragraphs #67-96, wherein said heterologous soluble T cell receptor lacks a transmembrane domain and/or lacks an intracellular domain of its α chain (or γ) chain.

98. The method of any one of Paragraphs #67-97, wherein said heterologous soluble T cell receptor lacks a transmembrane domain and/or lacks an intracellular domain of its chain (or δ) chain.

99. The method of any one of Paragraphs #67-98, wherein said heterologous soluble T cell receptor lacks a transmembrane domain and/or lacks an intracellular domain of both its α chain and β chain (or both its γ chain and δ chain).

100. The method of any one of Paragraphs #67-99, wherein said heterologous soluble T cell receptor lacks a transmembrane domain and lacks an intracellular domain of both its α chain and β chain (or both its γ chain and δ chain).

Paragraph #101. A composition comprising one or more primers as set forth in any one of Tables 1-12.

102. The composition of Paragraph #101, wherein said composition comprises one or more primers (e.g., at least 1, 5, 10, 15, or 20 primers) as set forth in Table 1.

103. The composition of Paragraph #101, wherein said composition comprises one or more primers (e.g., at least 1, 5, 10, 15, or 20 primers) as set forth in Table 2.

104. The composition of Paragraph #101, wherein said composition comprises one or more primers (e.g., at least 1, 5, 10, 15, or 20 primers) as set forth in Table 3.

105. The composition of Paragraph #101, wherein said composition comprises one or more primers (e.g., at least 1, 5, 10, 15, or 20 primers) as set forth in Table 4.

106. The composition of Paragraph #101, wherein said composition comprises one or more primers (e.g., at least 1, 5, 10, 15, or 20 primers) as set forth in Table 5.

107. The composition of Paragraph #101, wherein said composition comprises one or more primers (e.g., at least 1, 5, 10, 15, or 20 primers) as set forth in Table 6.

108. The composition of Paragraph #101, wherein said composition comprises one or more primers (e.g., at least 1, 5, 10, 15, or 20 primers) as set forth in Table 7.

109. The composition of Paragraph #101, wherein said composition comprises one or more primers (e.g., at least 1, 5, 10, 15, or 20 primers) as set forth in Table 8.

110. The composition of Paragraph #101, wherein said composition comprises one or two of the primers as set forth in Table 9.

111. The composition of Paragraph #101, wherein said composition comprises one or two of the primers as set forth in Table 10.

112. The composition of Paragraph #101, wherein said composition comprises one of the primers as set forth in Table 11. 113. The composition of Paragraph #101, wherein said composition comprises one of the primers as set forth in Table 12.

Paragraph #114. A composition comprising one or more primers as set forth in SEQ ID NOs:283-294.

Paragraph #115. A composition comprising one or more primers as set forth in SEQ ID NOs:283-288 and one or more primers (e.g., at least 1, 5, 10, 15, or 20 primers) as set forth Table 1.

Paragraph #116. A composition comprising one or more primers as set forth in SEQ ID NOs:289-294 and one or more primers (e.g., at least 1, 5, 10, 15, or 20 primers) as set forth Table 2.

Paragraph #117. A method for obtaining a plurality of nucleic acid vectors containing nucleic acid encoding functional T cell receptors, wherein said method comprises:

(a) sorting T cells into a plurality of separate locations of a device (e.g., a multi-welled plate such as 384-well plate) to obtain one sorted T cell per each of said plurality of separate locations, (b) lysing each of said sorted T cells of said plurality of separate locations to release RNA, (c) generating cDNA from said released RNA, (d) performing a nested amplification procedure using said cDNA of each of said plurality of separate locations as template to obtain a first amplification product and a second amplification product for said cDNA of each of said plurality of separate locations, wherein said first amplification product comprises nucleic acid encoding a Vα or Vγ segment, and wherein said second amplification product comprises nucleic acid encoding a Vβ or Vδ segment, and (e) assembling said first amplification product and said second amplification product for said cDNA of each of said plurality of separate locations into a nucleic acid vector to obtain an assembled nucleic acid vector for said cDNA of each of said plurality of separate locations, wherein said assembled nucleic acid vector for said cDNA of each of said plurality of separate locations comprises nucleic acid encoding a functional T cell receptor.

Paragraph #118. A method for expressing cloned T cell receptors from a plurality of nucleic acid vectors containing nucleic acid encoding functional T cell receptors, wherein said method comprises:

(a) obtaining a device comprising a plurality of separate locations, wherein each of said separate locations contains cDNA generated from RNA obtained from a single T cell that was sorted into said separate locations, (b) performing a nested amplification procedure using said cDNA of each of said plurality of separate locations as template to obtain a first amplification product and a second amplification product for said cDNA of each of said plurality of separate locations, wherein said first amplification product comprises nucleic acid encoding a Vα or Vγ segment, and wherein said second amplification product comprises nucleic acid encoding a Vβ or Vδ segment, (c) assembling said first amplification product and said second amplification product for said cDNA of each of said plurality of separate locations into a nucleic acid vector to obtain an assembled nucleic acid vector for said cDNA of each of said plurality of separate locations, thereby obtaining a collection of different assembled nucleic acid vectors, wherein each assembled nucleic acid vector for said cDNA of said plurality of separate locations comprises nucleic acid encoding a functional T cell receptor, and (d) introducing said collection of different assembled nucleic acid vectors into cells, wherein said cells express a functional T cell receptor from an introduced vector.

119. The method of Paragraph #118, wherein said method comprises screening said cells for T cell receptor activity.

120. The method of Paragraph #118 or Paragraph #119, wherein said method comprises sorting said cells after said introducing step.

Paragraph #121. A method for expressing cloned T cell receptors from a plurality of nucleic acid vectors containing nucleic acid encoding functional T cell receptors, wherein said method comprises:

(a) sorting T cells into a plurality of separate locations of a device (e.g., a multi-welled plate such as 384-well plate) to obtain one sorted T cell per each of said plurality of separate locations, (b) lysing each of said sorted T cells of said plurality of separate locations to release RNA, (c) generating cDNA from said released RNA, (d) performing a nested amplification procedure using said cDNA of each of said plurality of separate locations as template to obtain a first amplification product and a second amplification product for said cDNA of each of said plurality of separate locations, wherein said first amplification product comprises nucleic acid encoding a Vα or Vγ segment, and wherein said second amplification product comprises nucleic acid encoding a Vβ or Vδ segment, (e) assembling said first amplification product and said second amplification product for said cDNA of each of said plurality of separate locations into a nucleic acid vector to obtain an assembled nucleic acid vector for said cDNA of each of said plurality of separate locations, thereby obtaining a collection of different assembled nucleic acid vectors, wherein each assembled nucleic acid vector for said cDNA of said plurality of separate locations comprises nucleic acid encoding a functional T cell receptor, and (f) introducing said collection of different assembled nucleic acid vectors into cells, wherein said cells express a functional T cell receptor from an introduced vector.

122. The method of Paragraph #121, wherein said method comprises screening said cells for T cell receptor activity.
123. The method of Paragraph #121 or Paragraph #122, wherein said method comprises sorting said cells after said introducing step.

Other Embodiments

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A method for obtaining a plurality of nucleic acid vectors containing nucleic acid encoding functional T cell receptors, wherein said method comprises:
  (a) obtaining a device comprising a plurality of separate locations, wherein each of said separate locations contains cDNA generated from RNA obtained from a single T cell that was sorted into said separate locations,
  (b) performing a nested amplification procedure using said cDNA of each of said plurality of separate locations as template to obtain a first amplification product and a second amplification product for said cDNA of each of said plurality of separate locations, wherein said first amplification product comprises nucleic acid encoding a full-length α variable (Vα) or γ variable (Vγ) segment, and wherein said second amplification product comprises nucleic acid encoding a full-length β variable (Vβ) or δ variable (Vδ) segment, and
  (c) assembling said first amplification product and said second amplification product for said cDNA of each of said plurality of separate locations into a nucleic acid vector to obtain an assembled nucleic acid vector for said cDNA of each of said plurality of separate locations, wherein said assembled nucleic acid vectors for said cDNA of each of said plurality of separate locations comprise nucleic acid encoding a functional T cell receptor,
  wherein said functional T cell receptor of each of said assembled nucleic acid vectors comprises (i) a full-length α variable region and a full-length β variable region as present in said single T cell originating said RNA or (ii) a full-length γ variable region and a full-length δ variable region as present in said single T cell originating said RNA.

2. The method of claim 1, wherein said plurality of separate locations is greater than 50.

3. The method of claim 1, wherein said plurality of nucleic acid vectors is a plurality of nucleic acid expression vectors.

4. The method of claim 1, wherein said device comprises a multi-well plate.

5. The method of claim 1, wherein said cDNA generated from RNA obtained from a single T cell comprises cDNA generated from RNA obtained from a single human T cell.

6. The method of claim 1, wherein said first amplification product comprises nucleic acid encoding said full-length Vα segment.

7. The method of claim 1, wherein said first amplification product comprises nucleic acid encoding said full-length Vγ segment.

8. The method of claim 1, wherein said first amplification product comprises nucleic acid encoding a 5' portion of an α constant (Cα) region.

9. The method of claim 1, wherein said first amplification product comprises nucleic acid encoding a 5' portion of a γ constant (Cγ) region.

10. The method of claim 1, wherein said second amplification product comprises nucleic acid encoding said full-length Vβ segment.

11. The method of claim 1, wherein said second amplification product comprises nucleic acid encoding said full-length Vδ segment.

12. The method of claim 1, wherein said second amplification product comprises nucleic acid encoding a 5' portion of a β constant (Cβ) region.

13. The method of claim 1, wherein said second amplification product comprises nucleic acid encoding a 5' portion of a δ constant (Cδ) region.

14. The method of claim 1, wherein said first amplification product comprises an adapter sequence added to an amplified template sequence of said cDNA via a second round amplification of said nested amplification procedure.

15. The method of claim 1, wherein said second amplification product comprises an adapter sequence added to an amplified template sequence of said cDNA via a second round amplification of said nested amplification procedure.

16. The method of claim 1, wherein said first amplification product comprises a first adapter sequence added to an amplified template sequence of said cDNA via a second round amplification of said nested amplification procedure, and wherein said second amplification product comprises a second adapter sequence added to an amplified template sequence of said cDNA via a second round amplification of said nested amplification procedure, wherein said first and second adapter sequence are different.

17. The method of claim 1, wherein said functional T cell receptor of each of said assembled nucleic acid vectors comprises (a) a full-length α constant region and a full-length β constant region or (b) a full-length γ constant region and a full-length δ constant region.

18. The method of claim 1, wherein each of said assembled nucleic acid vectors comprises a nucleic acid sequence encoding a self-cleaving peptide or an internal ribosome entry site (IRES).

19. The method of claim 1, wherein said method further comprises sorting single T cells into said separate locations prior to step (a).

20. The method of claim 1, wherein said method further comprises performing a reverse transcription reaction to obtain said cDNA prior to step (a).

21. The method of claim 1, wherein said assembling step comprises seamless cloning.

22. The method of claim 1, wherein each of said assembled nucleic acid vectors is obtained without performing nucleic acid sequencing.

23. The method of claim 1, wherein each of said assembled nucleic acid vectors is obtained without performing a restriction endonuclease cleavage reaction.

* * * * *

UNITED STATES PATENT AND TRADEMARK OFFICE
CERTIFICATE OF CORRECTION

Page 1 of 1

PATENT NO. : 10,876,111 B2
APPLICATION NO. : 15/826671
DATED : December 29, 2020
INVENTOR(S) : Shlomchik et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 29 days.

Signed and Sealed this
Twenty-seventh Day of June, 2023

Katherine Kelly Vidal
*Director of the United States Patent and Trademark Office*

SEQUENCE LISTING

```
<160> NUMBER OF SEQ ID NOS: 457

<210> SEQ ID NO 1
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1
tccctcaccc acatgaagtg tctac                                             25

<210> SEQ ID NO 2
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 2
ggtgagacca actgcatttt g                                                 21

<210> SEQ ID NO 3
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 3
agaggtgggc tggaaaggac                                                   20

<210> SEQ ID NO 4
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 4
gttgctgctg ggctcattg                                                    19

<210> SEQ ID NO 5
<211> LENGTH: 23
<212> TYPE: DNA
<213> ORGANISM: Artificial Sequence
<220> FEATURE:
<223> OTHER INFORMATION: Description of Artificial Sequence: Synthetic
      primer
```

```
<400> SEQUENCE: 5
ccagtgggga gaacaatgaa gac                                           23

<210> SEQ ID NO 6
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 6
ggtctacatt tcaggccaca tttg                                          24

<210> SEQ ID NO 7
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 7
tggtatcaag acaaagtatc aggatg                                        26

<210> SEQ ID NO 8
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 8
agagacgcct gcagtgtttc                                               20

<210> SEQ ID NO 9
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 9
gaaaagagcc tgcagtgttt c                                             21

<210> SEQ ID NO 10
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 10
ccwctgctca gccatgctc                                                19

<210> SEQ ID NO 11
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 11
```
cttcctaaca cattcacatt tcctg                                         25

<210> SEQ ID NO 12
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 12
cttcctaaca caaactcatt tcctg                                         25

<210> SEQ ID NO 13
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 13
cacaagtcaa cttctgggag cag                                           23

<210> SEQ ID NO 14
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 14
ccagggcaga raagaatgat g                                             21

<210> SEQ ID NO 15
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 15
ggaggttgca ggtcaatgac tgatc                                         25

<210> SEQ ID NO 16
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 16
ggagattgca ggtttatgac tgatc                                         25

<210> SEQ ID NO 17
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 17
ccaggttcac ttcacagtac agagtc                                    26

<210> SEQ ID NO 18
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 18
cagaaaagac ctccagaaaa tagcttc                                   27

<210> SEQ ID NO 19
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 19
gctccatttc aggtcttctg tgatttc                                   27

<210> SEQ ID NO 20
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 20
acaaaacctt ctactgcttc tcag                                      24

<210> SEQ ID NO 21
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 21
tgagacggag cacggaacat ttc                                       23

<210> SEQ ID NO 22
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 22
tcgtaatttg tttctaggct gagatac                                   27

<210> SEQ ID NO 23
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 23
gtgagtctaa gtgacagaag gaatg                                     25

<210> SEQ ID NO 24
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 24
gcaagaaggc aaagcatcat g                                              21

<210> SEQ ID NO 25
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 25
ctctggtgcc aggaggaatg                                                20

<210> SEQ ID NO 26
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 26
gggtacgtga gcaggaaaca tg                                             22

<210> SEQ ID NO 27
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 27
ggatgaagag ggagagggag atg                                            23

<210> SEQ ID NO 28
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 28
aaaactgaac tctgggtcca caatc                                          25

<210> SEQ ID NO 29
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 29
ttgggacctc ctctgaccta g                                              21

```
<210> SEQ ID NO 30
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 30
caccatgtga tagaaagaca agatg                                          25

<210> SEQ ID NO 31
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 31
cagctttcta ggcaggagat aagac                                          25

<210> SEQ ID NO 32
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 32
tgttaaggaa gcccattcag aag                                            23

<210> SEQ ID NO 33
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 33
gttttctaaa tagctaaggg atggag                                         26

<210> SEQ ID NO 34
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 34
ggaaataatt ctttgctgat aaggatg                                        27

<210> SEQ ID NO 35
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 35
cccaggaaaa cacacttgat aactg                                          25
```

<210> SEQ ID NO 36
<211> LENGTH: 22
<212> TYPE: DNA
<213> ORGANISM: Artificial Sequence
<220> FEATURE:
<223> OTHER INFORMATION: Description of Artificial Sequence: Synthetic primer

<400> SEQUENCE: 36
ccatcagagc aggagacttt tc                                            22

<210> SEQ ID NO 37
<211> LENGTH: 19
<212> TYPE: DNA
<213> ORGANISM: Artificial Sequence
<220> FEATURE:
<223> OTHER INFORMATION: Description of Artificial Sequence: Synthetic primer

<400> SEQUENCE: 37
gcagggacct gtgagcatg                                                19

<210> SEQ ID NO 38
<211> LENGTH: 26
<212> TYPE: DNA
<213> ORGANISM: Artificial Sequence
<220> FEATURE:
<223> OTHER INFORMATION: Description of Artificial Sequence: Synthetic primer

<400> SEQUENCE: 38
gaactggaca gaaaaaaaaa atgaag                                        26

<210> SEQ ID NO 39
<211> LENGTH: 24
<212> TYPE: DNA
<213> ORGANISM: Artificial Sequence
<220> FEATURE:
<223> OTHER INFORMATION: Description of Artificial Sequence: Synthetic primer

<400> SEQUENCE: 39
gctaggccag agacactaac aatg                                          24

<210> SEQ ID NO 40
<211> LENGTH: 21
<212> TYPE: DNA
<213> ORGANISM: Artificial Sequence
<220> FEATURE:
<223> OTHER INFORMATION: Description of Artificial Sequence: Synthetic primer

<400> SEQUENCE: 40
ccgaaatcct ccaacagaga c                                             21

<210> SEQ ID NO 41
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 41
gcctcattcc tgctgtgatc                                               20

<210> SEQ ID NO 42

<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 42
ctcaccactg cagaccagaa tc                                              22

<210> SEQ ID NO 43
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 43
atctcagacc cgaggctag                                                  19

<210> SEQ ID NO 44
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 44
cagaaytcac tcggctcttc                                                 20

<210> SEQ ID NO 45
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 45
gctgcctgcc cctttgtg                                                   18

<210> SEQ ID NO 46
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 46
gctgcctgcc ccactgtg                                                   18

<210> SEQ ID NO 47
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 47
cyyccttgag agtcctgttc                                                 20

<210> SEQ ID NO 48
<211> LENGTH: 21

```
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 48
tcagaatgac gcccttgaaa g                                                21

<210> SEQ ID NO 49
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 49
gtagcatctg ccatgagaat c                                                21

<210> SEQ ID NO 50
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 50
ctccgtcatg cagcatctg                                                   19

<210> SEQ ID NO 51
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 51
cctctgctcc tgctcayagt ga                                               22

<210> SEQ ID NO 52
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 52
cagtgacmct gatctggtaa ag                                               22

<210> SEQ ID NO 53
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 53
agccccaagc taggagatc                                                   19

<210> SEQ ID NO 54
<211> LENGTH: 19
<212> TYPE: DNA
```

<213> ORGANISM: Artificial Sequence
<220> FEATURE:
<223> OTHER INFORMATION: Description of Artificial Sequence: Synthetic
      primer

<400> SEQUENCE: 54
ctgccctgga gctgaaatg                                                    19

<210> SEQ ID NO 55
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 55
ctggcctgga cctgaaatg                                                    19

<210> SEQ ID NO 56
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 56
tcccacytcc tctgctcctg                                                   20

<210> SEQ ID NO 57
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 57
tccctcctcc tctgcttttg                                                   20

<210> SEQ ID NO 58
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 58
tccacatctg ctctcactct g                                                 21

<210> SEQ ID NO 59
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 59
tcctgtattc gtgcccacaa g                                                 21

<210> SEQ ID NO 60
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 60
gcaacctgag cagggagatg                                              20

<210> SEQ ID NO 61
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 61
ttctcatact tgtaagctcc ttcatc                                       26

<210> SEQ ID NO 62
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 62
tcattcctgt atggggtggt attc                                         24

<210> SEQ ID NO 63
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 63
gcctgctctt cccctaattc tg                                           22

<210> SEQ ID NO 64
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 64
tccatggcca actctgctat g                                            21

<210> SEQ ID NO 65
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 65
aggcccsctt tgcactatga g                                            21

<210> SEQ ID NO 66
<211> LENGTH: 20
<212> TYPE: DNA
<213> ORGANISM: Artificial Sequence
<220> FEATURE:

```
<223> OTHER INFORMATION: Description of Artificial Sequence: Synthetic
      primer

<400> SEQUENCE: 66
atggaggcag tggtcacaac                                                20

<210> SEQ ID NO 67
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 67
cctccatcct gcctcttcat g                                              21

<210> SEQ ID NO 68
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 68
gccccaactg tgccatgac                                                 19

<210> SEQ ID NO 69
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 69
ctgaagaggt ggagacgtta cag                                            23

<210> SEQ ID NO 70
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 70
ccgggacaat gacatcacag ac                                             22

<210> SEQ ID NO 71
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 71
gggagaggcc atcacttgaa g                                              21

<210> SEQ ID NO 72
<211> LENGTH: 19
<212> TYPE: DNA
<213> ORGANISM: Artificial Sequence
<220> FEATURE:
<223> OTHER INFORMATION: Description of Artificial Sequence: Synthetic
``` primer

<400> SEQUENCE: 72
aaggctggct tggatgatg                                              19

<210> SEQ ID NO 73
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 73
gtcaggctgg tggtgtcatg                                             20

<210> SEQ ID NO 74
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 74
ggcctgtgct tacaaagaga ata                                         23

<210> SEQ ID NO 75
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 75
gtggatcaca gaggcatcyt gt                                          22

<210> SEQ ID NO 76
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 76
ctgttggaaa tcagcatctt gac                                         23

<210> SEQ ID NO 77
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 77
cgattggaca ggggycatg                                              19

<210> SEQ ID NO 78
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 78
gaagcacaat gaagacagct attc                                            24

<210> SEQ ID NO 79
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 79
ctggatttta atttaattgg gaagag                                          26

<210> SEQ ID NO 80
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 80
gacactgaag atgaactatt ctcc                                            24

<210> SEQ ID NO 81
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 81
gttgaggata ccactctgaa gatg                                            24

<210> SEQ ID NO 82
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 82
actctggtga cactgaagat gaac                                            24

<210> SEQ ID NO 83
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 83
gagcagcact ctacactgaa catg                                            24

<210> SEQ ID NO 84
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 84
cactccagtg gctcagaaaa tg                                              22

<210> SEQ ID NO 85
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 85
catcaagwcc actttctaga tgaca                                           25

<210> SEQ ID NO 86
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 86
ctgtcgagat gggtctaaag atg                                             23

<210> SEQ ID NO 87
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 87
agggaagagg aragaatgaa gtc                                             23

<210> SEQ ID NO 88
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 88
aggaargarg agagaatgaa atc                                             23

<210> SEQ ID NO 89
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 89
ccccagtgga gagagataaa gag                                             23

<210> SEQ ID NO 90
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 90 cactccttttt gctggcttga                                          20

<210> SEQ ID NO 91
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 91
ctggagctgt atctcttgcg a                                         21

<210> SEQ ID NO 92
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 92
tcctgtgaca tcaataaagc aag                                       23

<210> SEQ ID NO 93
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 93
gtttccagtg tgcagccatg                                           20

<210> SEQ ID NO 94
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 94
ttycaaggct cagccatg                                             18

<210> SEQ ID NO 95
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 95
agagctgcag ccttctcaag                                           20

<210> SEQ ID NO 96
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 96

```
cccaggcagg aagaatgatg                                                20
```

<210> SEQ ID NO 97
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 97

```
ggcttctcca gaacaaccat g                                              21
```

<210> SEQ ID NO 98
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 98

```
caaggaccaa gtgtcatttc ttc                                            23
```

<210> SEQ ID NO 99
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 99

```
ggctggttac ttgcttctgt ct                                             22
```

<210> SEQ ID NO 100
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 100

```
ggagacaaaa ggycacctga gt                                             22
```

<210> SEQ ID NO 101
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 101

```
tcagtctagg aggaatggac aag                                            23
```

<210> SEQ ID NO 102
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 102

```
ggcagagcag acacactcat g                                              21
```

```
<210> SEQ ID NO 103
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 103
cactcaagac cagagctaac agtatg                                          26

<210> SEQ ID NO 104
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 104
ccttctcact gcctagccat g                                               21

<210> SEQ ID NO 105
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 105
aaggagagat aactcaaagc ttcag                                           25

<210> SEQ ID NO 106
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 106
gctcatccat ttgctcttaa ctatg                                           25

<210> SEQ ID NO 107
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 107
ggcccacaga gatagagaga ac                                              22

<210> SEQ ID NO 108
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 108
cagacagcca ggatccaaag                                                 20
```

<210> SEQ ID NO 109
<211> LENGTH: 25
<212> TYPE: DNA
<213> ORGANISM: Artificial Sequence
<220> FEATURE:
<223> OTHER INFORMATION: Description of Artificial Sequence: Synthetic primer

<400> SEQUENCE: 109
tgcagtcagt caagctagga gaaac                                          25

<210> SEQ ID NO 110
<211> LENGTH: 21
<212> TYPE: DNA
<213> ORGANISM: Artificial Sequence
<220> FEATURE:
<223> OTHER INFORMATION: Description of Artificial Sequence: Synthetic primer

<400> SEQUENCE: 110
ccctgccttg acccaactat g                                              21

<210> SEQ ID NO 111
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 111
acccgtctgg agcctgattc                                                20

<210> SEQ ID NO 112
<211> LENGTH: 24
<212> TYPE: DNA
<213> ORGANISM: Artificial Sequence
<220> FEATURE:
<223> OTHER INFORMATION: Description of Artificial Sequence: Synthetic primer

<400> SEQUENCE: 112
cctgagarga agcatgtcta acac                                           24

<210> SEQ ID NO 113
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 113
caarcagggc tggaacatac                                                20

<210> SEQ ID NO 114
<211> LENGTH: 19
<212> TYPE: DNA
<213> ORGANISM: Artificial Sequence
<220> FEATURE:
<223> OTHER INFORMATION: Description of Artificial Sequence: Synthetic primer

<400> SEQUENCE: 114
ccctcctctg ccctcaatc                                                 19

<210> SEQ ID NO 115
<211> LENGTH: 24
<212> TYPE: DNA
<213> ORGANISM: Artificial Sequence
<220> FEATURE:
<223> OTHER INFORMATION: Description of Artificial Sequence: Synthetic primer

<400> SEQUENCE: 115
aaagtccctt ctctgctcat gtac                                      24

<210> SEQ ID NO 116
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 116
cactgcctca tcttgccatg                                           20

<210> SEQ ID NO 117
<211> LENGTH: 26
<212> TYPE: DNA
<213> ORGANISM: Artificial Sequence
<220> FEATURE:
<223> OTHER INFORMATION: Description of Artificial Sequence: Synthetic primer

<400> SEQUENCE: 117
aagacaaata ttcctttcct gttctg                                    26

<210> SEQ ID NO 118
<211> LENGTH: 24
<212> TYPE: DNA
<213> ORGANISM: Artificial Sequence
<220> FEATURE:
<223> OTHER INFORMATION: Description of Artificial Sequence: Synthetic primer

<400> SEQUENCE: 118
caaagaaagt ccctccaaac tatg                                      24

<210> SEQ ID NO 119
<211> LENGTH: 23
<212> TYPE: DNA
<213> ORGANISM: Artificial Sequence
<220> FEATURE:
<223> OTHER INFORMATION: Description of Artificial Sequence: Synthetic primer

<400> SEQUENCE: 119
ttaagcgaag gtggtgtgaa gtc                                       23

<210> SEQ ID NO 120
<211> LENGTH: 23
<212> TYPE: DNA
<213> ORGANISM: Artificial Sequence
<220> FEATURE:
<223> OTHER INFORMATION: Description of Artificial Sequence: Synthetic primer

<400> SEQUENCE: 120
acaagaagac accacatcct ttg                                       23

<210> SEQ ID NO 121

<211> LENGTH: 21
<212> TYPE: DNA
<213> ORGANISM: Artificial Sequence
<220> FEATURE:
<223> OTHER INFORMATION: Description of Artificial Sequence: Synthetic primer

<400> SEQUENCE: 121
tgctggccta gtgtgatcat g         21

<210> SEQ ID NO 122
<211> LENGTH: 25
<212> TYPE: DNA
<213> ORGANISM: Artificial Sequence
<220> FEATURE:
<223> OTHER INFORMATION: Description of Artificial Sequence: Synthetic primer

<400> SEQUENCE: 122
tgagaacact tcaacctttt cgtac     25

<210> SEQ ID NO 123
<211> LENGTH: 22
<212> TYPE: DNA
<213> ORGANISM: Artificial Sequence
<220> FEATURE:
<223> OTHER INFORMATION: Description of Artificial Sequence: Synthetic primer

<400> SEQUENCE: 123
cactttcctc aaaaccacca tg        22

<210> SEQ ID NO 124
<211> LENGTH: 24
<212> TYPE: DNA
<213> ORGANISM: Artificial Sequence
<220> FEATURE:
<223> OTHER INFORMATION: Description of Artificial Sequence: Synthetic primer

<400> SEQUENCE: 124
gaaagagacc actgctaaag gatg      24

<210> SEQ ID NO 125
<211> LENGTH: 25
<212> TYPE: DNA
<213> ORGANISM: Artificial Sequence
<220> FEATURE:
<223> OTHER INFORMATION: Description of Artificial Sequence: Synthetic primer

<400> SEQUENCE: 125
aagtgcagag tagacaagcc tagac     25

<210> SEQ ID NO 126
<211> LENGTH: 30
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 126
ttcaggtgtc gtgaggatct atttccggtg    30

<210> SEQ ID NO 127
<211> LENGTH: 51

<212> TYPE: DNA
<213> ORGANISM: Artificial Sequence
<220> FEATURE:
<223> OTHER INFORMATION: Description of Artificial Sequence: Synthetic
      primer

<400> SEQUENCE: 127
ttcaggtgtc gtgaggatct atttccggtg tggtatcctg cagcagatgt g          51

<210> SEQ ID NO 128
<211> LENGTH: 51
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 128
ttcaggtgtc gtgaggatct atttccggtg tgcattttgg ccatggcttt g          51

<210> SEQ ID NO 129
<211> LENGTH: 51
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 129
ttcaggtgtc gtgaggatct atttccggtg tgagcttagc tggagccatg g          51

<210> SEQ ID NO 130
<211> LENGTH: 51
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 130
ttcaggtgtc gtgaggatct atttccggtg atgaggcaag tggcgagagt g          51

<210> SEQ ID NO 131
<211> LENGTH: 53
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 131
ttcaggtgtc gtgaggatct atttccggtg atgaagacat ttgctggatt ttc        53

<210> SEQ ID NO 132
<211> LENGTH: 52
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 132
ttcaggtgtc gtgaggatct atttccggtg atttggggag acgaatggag tc         52

<210> SEQ ID NO 133
<211> LENGTH: 54
<212> TYPE: DNA

<213> ORGANISM: Artificial Sequence
<220> FEATURE:
<223> OTHER INFORMATION: Description of Artificial Sequence: Synthetic
      primer

<400> SEQUENCE: 133
ttcaggtgtc gtgaggatct atttccggtg atggagaaga tgcggagacc tgtc       54

<210> SEQ ID NO 134
<211> LENGTH: 54
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 134
ttcaggtgtc gtgaggatct atttccggtg atgctcctgt tgctcatacc agtg       54

<210> SEQ ID NO 135
<211> LENGTH: 51
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 135
ttcaggtgtc gtgaggatct atttccggtg ttcccttgtt cagccatgct c          51

<210> SEQ ID NO 136
<211> LENGTH: 48
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 136
ttcaggtgtc gtgaggatct atttccggtg atgctcctgc tgctcctc              48

<210> SEQ ID NO 137
<211> LENGTH: 55
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 137
ttcaggtgtc gtgaggatct atttccggtg caccagaggg tctaaaaatg aattc      55

<210> SEQ ID NO 138
<211> LENGTH: 56
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 138
ttcaggtgtc gtgaggatct atttccggtg aaagatgaac tattctccag gcttag     56

<210> SEQ ID NO 139
<211> LENGTH: 57
<212> TYPE: DNA
<213> ORGANISM: Artificial Sequence

```
<220> FEATURE:
<223> OTHER INFORMATION: Description of Artificial Sequence: Synthetic
      primer

<400> SEQUENCE: 139
ttcaggtgtc gtgaggatct atttccggtg cagaataaaa atgaaaaagc atctgac        57

<210> SEQ ID NO 140
<211> LENGTH: 56
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 140
ttcaggtgtc gtgaggatct atttccggtg tgatgawatc cttgagagtt ttactg        56

<210> SEQ ID NO 141
<211> LENGTH: 52
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 141
ttcaggtgtc gtgaggatct atttccggtg ggaagaacaa ggatgtccat tc            52

<210> SEQ ID NO 142
<211> LENGTH: 57
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 142
ttcaggtgtc gtgaggatct atttccggtg atggcaggca ttcgagcttt atttatg       57

<210> SEQ ID NO 143
<211> LENGTH: 54
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 143
ttcaggtgtc gtgaggatct atttccggtg atgtcacttt ctagcctgct gaag          54

<210> SEQ ID NO 144
<211> LENGTH: 53
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 144
ttcaggtgtc gtgaggatct atttccggtg tgtttctcca caggtcagac atg           53

<210> SEQ ID NO 145
<211> LENGTH: 57
<212> TYPE: DNA
<213> ORGANISM: Artificial Sequence
<220> FEATURE:
```

```
<223> OTHER INFORMATION: Description of Artificial Sequence: Synthetic
      primer

<400> SEQUENCE: 145
ttcaggtgtc gtgaggatct atttccggtg ctgtgatttc aataaggaag aagaatg          57

<210> SEQ ID NO 146
<211> LENGTH: 53
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 146
ttcaggtgtc gtgaggatct atttccggtg catgctgtct gcttcctgct cag              53

<210> SEQ ID NO 147
<211> LENGTH: 54
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 147
ttcaggtgtc gtgaggatct atttccggtg ctcagggaa gagctatgaa catg              54

<210> SEQ ID NO 148
<211> LENGTH: 54
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 148
ttcaggtgtc gtgaggatct atttccggtg gcatggagaa aatgttggag tgtg             54

<210> SEQ ID NO 149
<211> LENGTH: 55
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 149
ttcaggtgtc gtgaggatct atttccggtg gacagaagga atggagaccc tcttg            55

<210> SEQ ID NO 150
<211> LENGTH: 54
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 150
ttcaggtgtc gtgaggatct atttccggtg atgaagagga tattgggagc tctg             54

<210> SEQ ID NO 151
<211> LENGTH: 54
<212> TYPE: DNA
<213> ORGANISM: Artificial Sequence
<220> FEATURE:
<223> OTHER INFORMATION: Description of Artificial Sequence: Synthetic
```

-continued primer

<400> SEQUENCE: 151
ttcaggtgtc gtgaggatct atttccggtg caggaggaat ggacaagatc ttag         54

<210> SEQ ID NO 152
<211> LENGTH: 55
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 152
ttcaggtgtc gtgaggatct atttccggtg aggaaacatg gagaagaatc ctttg        55

<210> SEQ ID NO 153
<211> LENGTH: 54
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 153
ttcaggtgtc gtgaggatct atttccggtg atgctactca tcacatcaat gttg         54

<210> SEQ ID NO 154
<211> LENGTH: 53
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 154
ttcaggtgtc gtgaggatct atttccggtg atgaggctgg tggcaagagt aac          53

<210> SEQ ID NO 155
<211> LENGTH: 55
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 155
ttcaggtgtc gtgaggatct atttccggtg atgaagttgg tgacaagcat tactg        55

<210> SEQ ID NO 156
<211> LENGTH: 54
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 156
ttcaggtgtc gtgaggatct atttccggtg gatggtcctg aaattctccg tgtc         54

<210> SEQ ID NO 157
<211> LENGTH: 51
<212> TYPE: DNA
<213> ORGANISM: Artificial Sequence
<220> FEATURE:
<223> OTHER INFORMATION: Description of Artificial Sequence: Synthetic
      primer -continued

<400> SEQUENCE: 157
ttcaggtgtc gtgaggatct atttccggtg ttcacaggag ggatggccat g    51

<210> SEQ ID NO 158
<211> LENGTH: 55
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 158
ttcaggtgtc gtgaggatct atttccggtg ccattcagaa gctgactgga tattc    55

<210> SEQ ID NO 159
<211> LENGTH: 55
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 159
ttcaggtgtc gtgaggatct atttccggtg gggatggaga ctgttctgca agtac    55

<210> SEQ ID NO 160
<211> LENGTH: 60
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 160
ttcaggtgtc gtgaggatct atttccggtg atgctccttg aacatttatt aataatcttg    60

<210> SEQ ID NO 161
<211> LENGTH: 55
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 161
ttcaggtgtc gtgaggatct atttccggtg atgatgaagt gtccacaggc tttac    55

<210> SEQ ID NO 162
<211> LENGTH: 50
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 162
ttcaggtgtc gtgaggatct atttccggtg gggagcgctg tcagcatgac    50

<210> SEQ ID NO 163
<211> LENGTH: 48
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 163
ttcaggtgtc gtgaggatct atttccggtg atggcatgcc ctggcttc                48

<210> SEQ ID NO 164
<211> LENGTH: 59
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 164
ttcaggtgtc gtgaggatct atttccggtg atgaagaagc tactagcaat gattctgtg    59

<210> SEQ ID NO 165
<211> LENGTH: 58
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 165
ttcaggtgtc gtgaggatct atttccggtg atgaactcct ctctggactt tctaattc     58

<210> SEQ ID NO 166
<211> LENGTH: 54
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 166
ttcaggtgtc gtgaggatct atttccggtg atggtgaaga tccggcaatt tttg         54

<210> SEQ ID NO 167
<211> LENGTH: 42
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 167
gtggaagaaa accccggtcc catggatacc tggctcgtat gc                      42

<210> SEQ ID NO 168
<211> LENGTH: 41
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 168
gtggaagaaa accccggtcc catgggctgc aggctsctct g                       41

<210> SEQ ID NO 169
<211> LENGTH: 39
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 169
gtggaagaaa accccggtcc catgggcccy gggctcctc            39

<210> SEQ ID NO 170
<211> LENGTH: 41
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 170
gtggaagaaa accccggtcc catgggctcc aggctgctct g            41

<210> SEQ ID NO 171
<211> LENGTH: 42
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 171
gtggaagaaa accccggtcc catgggaccc aggctcctct tc            42

<210> SEQ ID NO 172
<211> LENGTH: 41
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 172
gtggaagaaa accccggtcc catgagtctc gggctcctgt g            41

<210> SEQ ID NO 173
<211> LENGTH: 41
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 173
gtggaagaaa accccggtcc catgagtatc gggctcctgt g            41

<210> SEQ ID NO 174
<211> LENGTH: 41
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 174
gtggaagaaa accccggtcc catgagcatc ggactcctgt g            41

<210> SEQ ID NO 175
<211> LENGTH: 44
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 175
gtggaagaaa accccggtcc catgagaatc aggctcctgt gctg         44

<210> SEQ ID NO 176
<211> LENGTH: 42
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 176
gtggaagaaa accccggtcc catgggcacc aggctcctct tc           42

<210> SEQ ID NO 177
<211> LENGTH: 41
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 177
gtggaagaaa accccggtcc catgggyacc agtctcctat g            41

<210> SEQ ID NO 178
<211> LENGTH: 41
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 178
gtggaagaaa accccggtcc catgggtacc agcctcctct g            41

<210> SEQ ID NO 179
<211> LENGTH: 41
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 179
gtggaagaaa accccggtcc catgggcttc aggctcctct g            41

<210> SEQ ID NO 180
<211> LENGTH: 42
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 180
gtggaagaaa accccggtcc catgggcacs aggctcttct tc           42

<210> SEQ ID NO 181
<211> LENGTH: 42
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 181
gtggaagaaa accccggtcc catgggcaca aggttgttct tc           42

<210> SEQ ID NO 182
<211> LENGTH: 44
<212> TYPE: DNA
<213> ORGANISM: Artificial Sequence
<220> FEATURE:
<223> OTHER INFORMATION: Description of Artificial Sequence: Synthetic primer

<400> SEQUENCE: 182
gtggaagaaa accccggtcc catgagtacc aggcttctct gctg         44

<210> SEQ ID NO 183
<211> LENGTH: 41
<212> TYPE: DNA
<213> ORGANISM: Artificial Sequence
<220> FEATURE:
<223> OTHER INFORMATION: Description of Artificial Sequence: Synthetic primer

<400> SEQUENCE: 183
gtggaagaaa accccggtcc catgggtacc aggctcctct g            41

<210> SEQ ID NO 184
<211> LENGTH: 44
<212> TYPE: DNA
<213> ORGANISM: Artificial Sequence
<220> FEATURE:
<223> OTHER INFORMATION: Description of Artificial Sequence: Synthetic primer

<400> SEQUENCE: 184
gtggaagaaa accccggtcc catggactcc tggaccttct gctg         44

<210> SEQ ID NO 185
<211> LENGTH: 41
<212> TYPE: DNA
<213> ORGANISM: Artificial Sequence
<220> FEATURE:
<223> OTHER INFORMATION: Description of Artificial Sequence: Synthetic primer

<400> SEQUENCE: 185
gtggaagaaa accccggtcc catggctacc aggctcctct g            41

<210> SEQ ID NO 186
<211> LENGTH: 45
<212> TYPE: DNA
<213> ORGANISM: Artificial Sequence
<220> FEATURE:
<223> OTHER INFORMATION: Description of Artificial Sequence: Synthetic primer

<400> SEQUENCE: 186
gtggaagaaa accccggtcc catgcttagt cctgacctgc ctgac        45

<210> SEQ ID NO 187
<211> LENGTH: 46
<212> TYPE: DNA
<213> ORGANISM: Artificial Sequence
<220> FEATURE:
<223> OTHER INFORMATION: Description of Artificial Sequence: Synthetic primer

<400> SEQUENCE: 187
gtggaagaaa accccggtcc catggtttcc aggcttctca gtttag       46

<210> SEQ ID NO 188
<211> LENGTH: 42
<212> TYPE: DNA
<213> ORGANISM: Artificial Sequence
<220> FEATURE:
<223> OTHER INFORMATION: Description of Artificial Sequence: Synthetic primer

<400> SEQUENCE: 188
gtggaagaaa accccggtcc catgggtcct gggcttctcc ac        42

<210> SEQ ID NO 189
<211> LENGTH: 45
<212> TYPE: DNA
<213> ORGANISM: Artificial Sequence
<220> FEATURE:
<223> OTHER INFORMATION: Description of Artificial Sequence: Synthetic primer

<400> SEQUENCE: 189
gtggaagaaa accccggtcc catgagccca atattcacct gcatc        45

<210> SEQ ID NO 190
<211> LENGTH: 46
<212> TYPE: DNA
<213> ORGANISM: Artificial Sequence
<220> FEATURE:
<223> OTHER INFORMATION: Description of Artificial Sequence: Synthetic primer

<400> SEQUENCE: 190
gtggaagaaa accccggtcc catggacact agagtactct gctgtg        46

<210> SEQ ID NO 191
<211> LENGTH: 44
<212> TYPE: DNA
<213> ORGANISM: Artificial Sequence
<220> FEATURE:
<223> OTHER INFORMATION: Description of Artificial Sequence: Synthetic primer

<400> SEQUENCE: 191
gtggaagaaa accccggtcc catgagtaac caggtgctct gctg        44

<210> SEQ ID NO 192
<211> LENGTH: 43
<212> TYPE: DNA
<213> ORGANISM: Artificial Sequence
<220> FEATURE:
<223> OTHER INFORMATION: Description of Artificial Sequence: Synthetic primer

<400> SEQUENCE: 192
gtggaagaaa accccggtcc catgctgctg cttctgctgc ttc        43

<210> SEQ ID NO 193
<211> LENGTH: 42
<212> TYPE: DNA
<213> ORGANISM: Artificial Sequence
<220> FEATURE:
<223> OTHER INFORMATION: Description of Artificial Sequence: Synthetic primer

<400> SEQUENCE: 193
gtggaagaaa accccggtcc catggcctcc ctgctcttct tc        42

```
<210> SEQ ID NO 194
<211> LENGTH: 45
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 194
gtggaagaaa accccggtcc catgactatc aggctcctct gctac              45

<210> SEQ ID NO 195
<211> LENGTH: 40
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 195
gtggaagaaa accccggtcc catgggcccc cagctccttg                    40

<210> SEQ ID NO 196
<211> LENGTH: 43
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 196
gtggaagaaa accccggtcc catgggaatc aggctcctct gtc                43

<210> SEQ ID NO 197
<211> LENGTH: 45
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 197
gtggaagaaa accccggtcc catgctgagt cttctgctcc ttctc              45

<210> SEQ ID NO 198
<211> LENGTH: 46
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 198
gtggaagaaa accccggtcc catgctctgc tctctccttg cccttc             46

<210> SEQ ID NO 199
<211> LENGTH: 42
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 199
tctctaggcg ccggaattca atgctgcaga tgtggggtt tg                  42

<210> SEQ ID NO 200
```

```
<211> LENGTH: 42
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 200
tctctaggcg ccggaattca atgaagcagg tggcaaaagt ga                    42

<210> SEQ ID NO 201
<211> LENGTH: 42
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 201
tctctaggcg ccggaattca atgaaaracrg tgactggacc tt                   42

<210> SEQ ID NO 202
<211> LENGTH: 38
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 202
tctctaggcg ccggaattca atggagagga gcccggga                         38

<210> SEQ ID NO 203
<211> LENGTH: 42
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 203
tctctaggcg ccggaattca atgsagagga acctgggagc tg                    42

<210> SEQ ID NO 204
<211> LENGTH: 42
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 204
tctctaggcg ccggaattca atgsagagga acctggttgc tg                    42

<210> SEQ ID NO 205
<211> LENGTH: 42
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 205
tctctaggcg ccggaattca atgaagacag ctatccatgc tt                    42

<210> SEQ ID NO 206
<211> LENGTH: 47
```

```
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 206
tctctaggcg ccggaattca atgaaaacay aygctyctac attattc                    47

<210> SEQ ID NO 207
<211> LENGTH: 46
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 207
tctctaggcg ccggaattca atgaacwmtt cyccagcttt agtgac                     46

<210> SEQ ID NO 208
<211> LENGTH: 46
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 208
tctctaggcg ccggaattca atgaatactt ctccagtttt agtrac                     46

<210> SEQ ID NO 209
<211> LENGTH: 42
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 209
tctctaggcg ccggaattca atgaaccttt rtcctgaact gg                         42

<210> SEQ ID NO 210
<211> LENGTH: 42
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 210
tctctaggcg ccggaattca atggactytt caccaggctt cg                         42

<210> SEQ ID NO 211
<211> LENGTH: 42
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 211
tctctaggcg ccggaattca atgaactctt ctccaggctt ca                         42

<210> SEQ ID NO 212
<211> LENGTH: 42
<212> TYPE: DNA
```

```
<213> ORGANISM: Artificial Sequence
<220> FEATURE:
<223> OTHER INFORMATION: Description of Artificial Sequence: Synthetic
      primer

<400> SEQUENCE: 212
tctctaggcg ccggaattca atgaagtcct tgtgtgtttc ac                           42

<210> SEQ ID NO 213
<211> LENGTH: 45
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 213
tctctaggcg ccggaattca atgaagtcct tgagtgttty actag                        45

<210> SEQ ID NO 214
<211> LENGTH: 45
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 214
tctctaggcg ccggaattca atgaagtcct tkagtrtttc cctag                        45

<210> SEQ ID NO 215
<211> LENGTH: 42
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 215
tctctaggcg ccggaattca atgcattcct tacatgtttc ac                           42

<210> SEQ ID NO 216
<211> LENGTH: 42
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 216
tctctaggcg ccggaattca atgcacagcc tcctrgggtt gt                           42

<210> SEQ ID NO 217
<211> LENGTH: 42
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 217
tctctaggcg ccggaattca atgaacagat tcctgggaat at                           42

<210> SEQ ID NO 218
<211> LENGTH: 42
<212> TYPE: DNA
<213> ORGANISM: Artificial Sequence
```

```
<220> FEATURE:
<223> OTHER INFORMATION: Description of Artificial Sequence: Synthetic
      primer

<400> SEQUENCE: 218
tctctaggcg ccggaattca atgctcctgg tyctcatctc gt                          42

<210> SEQ ID NO 219
<211> LENGTH: 38
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 219
tctctaggcg ccggaattca atgctcctgg yrctcctc                               38

<210> SEQ ID NO 220
<211> LENGTH: 42
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 220
tctctaggcg ccggaattca atgaagacat ccctccacac tg                          42

<210> SEQ ID NO 221
<211> LENGTH: 42
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 221
tctctaggcg ccggaattca atgaaaaagt gccttagtgc ct                          42

<210> SEQ ID NO 222
<211> LENGTH: 42
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 222
tctctaggcg ccggaattca atgcrtcctg tcacctgctc ag                          42

<210> SEQ ID NO 223
<211> LENGTH: 42
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 223
tctctaggcg ccggaattca atgcgtcctg wcacctcctc ag                          42

<210> SEQ ID NO 224
<211> LENGTH: 42
<212> TYPE: DNA
<213> ORGANISM: Artificial Sequence
<220> FEATURE:
```

```
<223> OTHER INFORMATION: Description of Artificial Sequence: Synthetic
      primer

<400> SEQUENCE: 224
tctctaggcg ccggaattca atgcgtcctg rcacctgctc ag                            42

<210> SEQ ID NO 225
<211> LENGTH: 42
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 225
tctctaggcg ccggaattca atgargaggc tgmtgtgttc tc                            42

<210> SEQ ID NO 226
<211> LENGTH: 42
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 226
tctctaggcg ccggaattca atgaagaggc tgctgtgctc tc                            42

<210> SEQ ID NO 227
<211> LENGTH: 42
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 227
tctctaggcg ccggaattca atgaacaggc tgctgtgctc tc                            42

<210> SEQ ID NO 228
<211> LENGTH: 42
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 228
tctctaggcg ccggaattca atgaagaggc tgctgagctc tc                            42

<210> SEQ ID NO 229
<211> LENGTH: 42
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 229
tctctaggcg ccggaattca atggacaaga tcctgacagc at                            42

<210> SEQ ID NO 230
<211> LENGTH: 42
<212> TYPE: DNA
<213> ORGANISM: Artificial Sequence
<220> FEATURE:
<223> OTHER INFORMATION: Description of Artificial Sequence: Synthetic
``` primer

<400> SEQUENCE: 230
tctctaggcg ccggaattca atggacaaga tcctgacagc aa                              42

<210> SEQ ID NO 231
<211> LENGTH: 42
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 231
tctctaggcg ccggaattca atggacacga tcctgacagc at                              42

<210> SEQ ID NO 232
<211> LENGTH: 42
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 232
tctctaggcg ccggaattca atggacaaga ttctgacagc at                              42

<210> SEQ ID NO 233
<211> LENGTH: 38
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 233
tctctaggcg ccggaattca atgcctcctc asagcctg                                   38

<210> SEQ ID NO 234
<211> LENGTH: 42
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 234
tctctaggcg ccggaattca atgctgattc taagcctgtt gg                              42

<210> SEQ ID NO 235
<211> LENGTH: 42
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 235
tctctaggcg ccggaattca atgttcccag tgaccattct gc                              42

<210> SEQ ID NO 236
<211> LENGTH: 42
<212> TYPE: DNA
<213> ORGANISM: Artificial Sequence
<220> FEATURE:
<223> OTHER INFORMATION: Description of Artificial Sequence: Synthetic
      primer

```
<400> SEQUENCE: 236
tctctaggcg ccggaattca atgactggtt tcctgaaggc ct                              42

<210> SEQ ID NO 237
<211> LENGTH: 42
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 237
tctctaggcg ccggaattca atgggatgtg tgagtggaat tg                              42

<210> SEQ ID NO 238
<211> LENGTH: 42
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 238
tggaagaaaa ccccggtccc atgtggcagt tttgcattct gt                              42

<210> SEQ ID NO 239
<211> LENGTH: 42
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 239
tggaagaaaa ccccggtccc atgggctcca ttttcctcag tt                              42

<210> SEQ ID NO 240
<211> LENGTH: 42
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 240
tggaagaaaa ccccggtccc atggatatct ggcttctagg tt                              42

<210> SEQ ID NO 241
<211> LENGTH: 42
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 241
tggaagaaaa ccccggtccc atgggctgta ggctcctaag ct                              42

<210> SEQ ID NO 242
<211> LENGTH: 42
<212> TYPE: DNA
<213> ORGANISM: Artificial Sequence
<220> FEATURE:
<223> OTHER INFORMATION: Description of Artificial Sequence: Synthetic
      primer
```

```
<400> SEQUENCE: 242
tggaagaaaa ccccggtccc atgagctgca ggcttctcct ct                              42

<210> SEQ ID NO 243
<211> LENGTH: 42
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 243
tggaagaaaa ccccggtccc atgtctaaca ctgtcctcgc tg                              42

<210> SEQ ID NO 244
<211> LENGTH: 42
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 244
tggaagaaaa ccccggtccc atgtctaaca ctgccttccc tg                              42

<210> SEQ ID NO 245
<211> LENGTH: 42
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 245
tggaagaaaa ccccggtccc atgggctcca ggctctttct gg                              42

<210> SEQ ID NO 246
<211> LENGTH: 42
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 246
tggaagaaaa ccccggtccc atgggctcca ggctcttctt cg                              42

<210> SEQ ID NO 247
<211> LENGTH: 42
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 247
tggaagaaaa ccccggtccc atgggctcca gactcttctt tg                              42

<210> SEQ ID NO 248
<211> LENGTH: 38
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 248
```
tggaagaaaa ccccggtccc atgggcacca ggcttctt         38

<210> SEQ ID NO 249
<211> LENGTH: 42
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 249
tggaagaaaa ccccggtccc atgggcatcc agaccctctg tt         42

<210> SEQ ID NO 250
<211> LENGTH: 41
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 250
tggaagaaaa ccccggtccc atggccccca ggctcctttt c         41

<210> SEQ ID NO 251
<211> LENGTH: 42
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 251
tggaagaaaa ccccggtccc atggatccta gacttctttg ct         42

<210> SEQ ID NO 252
<211> LENGTH: 42
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 252
tggaagaaaa ccccggtccc atgaacaagt gggttttctg ct         42

<210> SEQ ID NO 253
<211> LENGTH: 45
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 253
tggaagaaaa ccccggtccc atgttactgc ttctattact tctgg         45

<210> SEQ ID NO 254
<211> LENGTH: 44
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 254
tggaagaaaa ccccggtccc atgggtgcac ggctcatttg ctat        44

<210> SEQ ID NO 255
<211> LENGTH: 38
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 255
tggaagaaaa ccccggtccc atgggtgcaa gactgctc        38

<210> SEQ ID NO 256
<211> LENGTH: 43
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 256
tggaagaaaa ccccggtccc atggctacaa ggctcctctg tta        43

<210> SEQ ID NO 257
<211> LENGTH: 42
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 257
tggaagaaaa ccccggtccc atgagagtta ggctcatctc tg        42

<210> SEQ ID NO 258
<211> LENGTH: 42
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 258
tggaagaaaa ccccggtccc atgtggacat tcctgctact tc        42

<210> SEQ ID NO 259
<211> LENGTH: 42
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 259
tggaagaaaa ccccggtccc atgctgtact ctctccttgc ct        42

<210> SEQ ID NO 260
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 260
ttcaggtgtc gtgaggatct atttccggtg        30

<210> SEQ ID NO 261
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 261
gtggaagaaa accccggtcc c                                            21

<210> SEQ ID NO 262
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 262
tctctaggcg ccggaattca                                              20

<210> SEQ ID NO 263
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 263
tggaagaaaa ccccggtccc                                              20

<210> SEQ ID NO 264
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 264
cacatcagaa tccttacttt gtgacac                                      27

<210> SEQ ID NO 265
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 265
atcggtgaat aggcagacag acttg                                        25

<210> SEQ ID NO 266
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 266
tcttggaatc catagctttc atg                                          23

<210> SEQ ID NO 267
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 267
cattcaccca ccagctcag                                                  19

<210> SEQ ID NO 268
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 268
gtgtgggaga tctctgcttc tg                                              22

<210> SEQ ID NO 269
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 269
ccacgtggtc agggaagaag                                                 20

<210> SEQ ID NO 270
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 270
gacttgtcac tggatttaga gtctc                                           25

<210> SEQ ID NO 271
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 271
aggttctggg ttctggatgt                                                 20

<210> SEQ ID NO 272
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 272
tgcttctgat ggctcaaaca c                                               21

-continued

```
<210> SEQ ID NO 273
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 273
ggagtcacat ttctcagatc ct                                              22

<210> SEQ ID NO 274
<211> LENGTH: 22
<212> TYPE: PRT
<213> ORGANISM: Porcine teschovirus-1

<400> SEQUENCE: 274

Gly Ser Gly Ala Thr Asn Phe Ser Leu Leu Lys Gln Ala Gly Asp Val
1               5                   10                  15

Glu Glu Asn Pro Gly Pro
            20

<210> SEQ ID NO 275
<211> LENGTH: 21
<212> TYPE: PRT
<213> ORGANISM: Thosea asigna virus

<400> SEQUENCE: 275

Gly Ser Gly Glu Gly Arg Gly Ser Leu Leu Thr Cys Gly Asp Val Glu
1               5                   10                  15

Glu Asn Pro Gly Pro
            20

<210> SEQ ID NO 276
<211> LENGTH: 23
<212> TYPE: PRT
<213> ORGANISM: Equine rhinitis A virus

<400> SEQUENCE: 276

Gly Ser Gly Gln Cys Thr Asn Tyr Ala Leu Leu Lys Leu Ala Gly Asp
1               5                   10                  15

Val Glu Ser Asn Pro Gly Pro
            20

<210> SEQ ID NO 277
<211> LENGTH: 25
<212> TYPE: PRT
<213> ORGANISM: Foot-and-mouth disease virus

<400> SEQUENCE: 277

Gly Ser Gly Val Lys Gln Thr Leu Asn Phe Asp Leu Leu Lys Leu Ala
1               5                   10                  15

Gly Asp Val Glu Ser Asn Pro Gly Pro
            20                  25

<210> SEQ ID NO 278
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 278
```

Leu Thr Phe Asn Tyr Arg Asn Leu
1               5

<210> SEQ ID NO 279
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 279

Ser Ile Asn Phe Glu Lys Leu
1               5

<210> SEQ ID NO 280
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 280
ctcccttgag agtcctgttc                                              20

<210> SEQ ID NO 281
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 281
cttccttgag agtcctgttc                                              20

<210> SEQ ID NO 282
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 282
cccccttgag agtcctgttc                                              20

<210> SEQ ID NO 283
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 283
ggacctgtga gcatggcatg                                              20

<210> SEQ ID NO 284
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 284
gttcagatca gaagaggagg cttc                                          24

<210> SEQ ID NO 285
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 285
ctcaaggttc agatcagaag aggag                                         25

<210> SEQ ID NO 286
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 286
tgagttttca gtgaactgga cag                                           23

<210> SEQ ID NO 287
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 287
ctcctaaatc tgagttttca gtgaact                                       27

<210> SEQ ID NO 288
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 288
caaggctcct aaatctgagt tttcagtg                                      28

<210> SEQ ID NO 289
<211> LENGTH: 17
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 289
cccaggagac cagcaac                                                  17

<210> SEQ ID NO 290
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 290
ggagcaaaag ccctgctttc t                                            21

<210> SEQ ID NO 291
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 291
aaacggtgag gaggagcaaa ag                                           22

<210> SEQ ID NO 292
<211> LENGTH: 29
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 292
cttgtaagct ccttcttcat ctggaaatg                                    29

<210> SEQ ID NO 293
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 293
cagatttgct ttcctttttc tcatac                                       26

<210> SEQ ID NO 294
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 294
ttacagggcc aagagacaga tttg                                         24

<210> SEQ ID NO 295
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 295
aggaaggagg agagaatgaa atc                                          23

<210> SEQ ID NO 296
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 296
aggaaagaag agagaatgaa atc                                          23

```
<210> SEQ ID NO 297
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 297
gtggaagaaa accccggtcc c                                             21

<210> SEQ ID NO 298
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 298
tctctaggcg ccggaattca                                               20

<210> SEQ ID NO 299
<211> LENGTH: 42
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 299
tctctaggcg ccggaattca atgaagacgg tgactggacc tt                      42

<210> SEQ ID NO 300
<211> LENGTH: 42
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 300
tctctaggcg ccggaattca atgaagacag tgactggacc tt                      42

<210> SEQ ID NO 301
<211> LENGTH: 42
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 301
tctctaggcg ccggaattca atgaaaacag tgactggacc tt                      42

<210> SEQ ID NO 302
<211> LENGTH: 47
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 302
tctctaggcg ccggaattca atgaaaacat acgctcctac attattc                 47
```

```
<210> SEQ ID NO 303
<211> LENGTH: 47
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 303
tctctaggcg ccggaattca atgaaaacat atgctcctac attattc                    47

<210> SEQ ID NO 304
<211> LENGTH: 47
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 304
tctctaggcg ccggaattca atgaaaacac atgcttctac attattc                    47

<210> SEQ ID NO 305
<211> LENGTH: 46
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 305
tctctaggcg ccggaattca atgaaccatt ccccagcttt agtgac                     46

<210> SEQ ID NO 306
<211> LENGTH: 46
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 306
tctctaggcg ccggaattca atgaaccttt ctccagcttt agtgac                     46

<210> SEQ ID NO 307
<211> LENGTH: 46
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 307
tctctaggcg ccggaattca atgaaccatt ctccagcttt agtgac                     46

<210> SEQ ID NO 308
<211> LENGTH: 46
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 308
tctctaggcg ccggaattca atgaactatt ctccagcttt agtgac                     46
```

```
<210> SEQ ID NO 309
<211> LENGTH: 45
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 309
tctctaggcg ccggaattca atgaagtcct tgagtgtttc cctag            45

<210> SEQ ID NO 310
<211> LENGTH: 45
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 310
tctctaggcg ccggaattca atgaagtcct ttagtatttc cctag            45

<210> SEQ ID NO 311
<211> LENGTH: 38
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 311
tctctaggcg ccggaattca atgctcctgg cactcctc                    38

<210> SEQ ID NO 312
<211> LENGTH: 38
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 312
tctctaggcg ccggaattca atgctcctgg cgctcctc                    38

<210> SEQ ID NO 313
<211> LENGTH: 38
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 313
tctctaggcg ccggaattca atgctcctgg tgctcctc                    38

<210> SEQ ID NO 314
<211> LENGTH: 42
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 314
tctctaggcg ccggaattca atgaagaggc tgctgtgttc tc               42

<210> SEQ ID NO 315
```

```
<211> LENGTH: 42
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 315
tctctaggcg ccggaattca atgaggaggc tgatgtgttc tc                           42

<210> SEQ ID NO 316
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 316
tggaagaaaa ccccggtccc                                                    20

<210> SEQ ID NO 317
<211> LENGTH: 20
<212> TYPE: PRT
<213> ORGANISM: Mus sp.

<400> SEQUENCE: 317

Met Leu Thr Ala Ser Leu Leu Arg Ala Val Ile Ala Ser Ile Cys Val
1               5                   10                  15

Val Ser Ser Met
            20

<210> SEQ ID NO 318
<211> LENGTH: 18
<212> TYPE: PRT
<213> ORGANISM: Mus sp.

<400> SEQUENCE: 318

Met Ser Thr Arg Leu Leu Cys Trp Met Ala Leu Cys Leu Leu Gly Ala
1               5                   10                  15

Leu Ser

<210> SEQ ID NO 319
<211> LENGTH: 18
<212> TYPE: PRT
<213> ORGANISM: Homo sapiens

<400> SEQUENCE: 319

Met Leu Gln Met Trp Gly Phe Val Leu Tyr Leu Phe Leu Met Val Gly
1               5                   10                  15

Ala Ala

<210> SEQ ID NO 320
<211> LENGTH: 18
<212> TYPE: PRT
<213> ORGANISM: Homo sapiens

<400> SEQUENCE: 320

Met Trp Gln Phe Cys Ile Leu Cys Leu Cys Val Leu Met Ala Ser Val
1               5                   10                  15

Ala Thr

<210> SEQ ID NO 321
```

```
<211> LENGTH: 451
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 321
agactctaaa tccagtgaca agtctgtctg cctattcacc gattttgatt ctcaaacaaa      60
tgtgtcacaa agtaaggatt ctgatgtgta tatcacagac aaaactgtgc tagacatgag    120
gtctatggac ttcaagagca acagtgctgt ggcctggagc aacaaatctg actttgcatg    180
tgcaaacgcc ttcaacaaca gcattattcc agaagacacc ttcttcccca gcccagaaag    240
ttcctgtgat gtcaagctgg tcgagaaaag ctttgaaaca gatacgaacc taaactttca    300
aaacctgtca gtgattgggt tccgaatcct cctcctgaaa gtggccgggt ttaatctgct    360
catgacgctg cggctgtggt ccagcggctc cggagccacg aacttctctc tgttaaagca    420
agcaggagac gtggaagaaa accccggtcc c                                    451

<210> SEQ ID NO 322
<211> LENGTH: 476
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 322
acatccagaa cccagaacct gctgtgtacc agttaaaaga tcctcggtct caggacagca      60
ccctctgcct gttcaccgac tttgactccc aaatcaatgt gccgaaaacc atggaatctg    120
gaacgttcat cactgacaaa actgtgctgg acatgaaagc tatggattcc aagagcaatg    180
gggccattgc ctggagcaac cagacaagct tcacctgcca agatatcttc aaagagacca    240
acgccaccta ccccagttca gacgttccct gtgatgccac gttgaccgag aaaagctttg    300
aaacagatat gaacctaaac tttcaaaacc tgtcagttat gggactccga atcctcctgc    360
tgaaagtagc gggatttaac ctgctcatga cgctgaggct gtggtccagt ggctccggag    420
ccacgaactt ctctctgtta aagcaagcag gagacgtgga agaaaacccc ggtccc        476

<210> SEQ ID NO 323
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 323
tcccactctt ccaccttcga                                                  20

<210> SEQ ID NO 324
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 324
agttgggata gggcctctct t                                                21
```

```
<210> SEQ ID NO 325
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 325
agggatctga aacaacattc                                                   20

<210> SEQ ID NO 326
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 326
gcctgatatg ttttaagtgg g                                                 21

<210> SEQ ID NO 327
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 327
gtctgaagcc tacaagaaag                                                   20

<210> SEQ ID NO 328
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 328
tgtcaatttt cttctccacg                                                   20

<210> SEQ ID NO 329
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 329
tcccactctt ccaccttcga                                                   20

<210> SEQ ID NO 330
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 330
agttggatag ggcctctctt                                                   20

<210> SEQ ID NO 331
```

```
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Val or Ile
<220> FEATURE:
<221> NAME/KEY: MOD_RES
<222> LOCATION: (4)..(4)
<223> OTHER INFORMATION: Any amino acid

<400> SEQUENCE: 331

Asp Xaa Glu Xaa Asn Pro Gly Pro
1               5

<210> SEQ ID NO 332
<211> LENGTH: 22
<212> TYPE: PRT
<213> ORGANISM: Foot-and-mouth disease virus

<400> SEQUENCE: 332

Val Lys Gln Thr Leu Asn Phe Asp Leu Leu Lys Leu Ala Gly Asp Val
1               5                   10                  15

Glu Ser Asn Pro Gly Pro
            20

<210> SEQ ID NO 333
<211> LENGTH: 20
<212> TYPE: PRT
<213> ORGANISM: Equine rhinitis A virus

<400> SEQUENCE: 333

Gln Cys Thr Asn Tyr Ala Leu Leu Lys Leu Ala Gly Asp Val Glu Ser
1               5                   10                  15

Asn Pro Gly Pro
            20

<210> SEQ ID NO 334
<211> LENGTH: 18
<212> TYPE: PRT
<213> ORGANISM: Thosea asigna virus

<400> SEQUENCE: 334

Glu Gly Arg Gly Ser Leu Leu Thr Cys Gly Asp Val Glu Glu Asn Pro
1               5                   10                  15

Gly Pro

<210> SEQ ID NO 335
<211> LENGTH: 19
<212> TYPE: PRT
<213> ORGANISM: Porcine teschovirus-1

<400> SEQUENCE: 335

Ala Thr Asn Phe Ser Leu Leu Lys Gln Ala Gly Asp Val Glu Glu Asn
1               5                   10                  15

Pro Gly Pro

<210> SEQ ID NO 336
<211> LENGTH: 57
<212> TYPE: DNA
<213> ORGANISM: Porcine teschovirus-1
```

<220> FEATURE:
<221> NAME/KEY: CDS
<222> LOCATION: (1)..(57)

<400> SEQUENCE: 336

```
gcc acg aac ttc tct ctg tta aag caa gca gga gac gtg gaa gaa aac      48
Ala Thr Asn Phe Ser Leu Leu Lys Gln Ala Gly Asp Val Glu Glu Asn
1               5                   10                  15 ccc ggt ccc                                                          57
Pro Gly Pro
```

<210> SEQ ID NO 337
<211> LENGTH: 476
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: CDS
<222> LOCATION: (3)..(476)

<400> SEQUENCE: 337

```
ac atc cag aac cca gaa cct gct gtg tac cag tta aaa gat cct cgg       47
   Ile Gln Asn Pro Glu Pro Ala Val Tyr Gln Leu Lys Asp Pro Arg
   1               5                   10                  15 tct cag gac agc acc ctc tgc ctg ttc acc gac ttt gac tcc caa atc      95
Ser Gln Asp Ser Thr Leu Cys Leu Phe Thr Asp Phe Asp Ser Gln Ile
                20                  25                  30 aat gtg ccg aaa acc atg gaa tct gga acg ttc atc act gac aaa act     143
Asn Val Pro Lys Thr Met Glu Ser Gly Thr Phe Ile Thr Asp Lys Thr
            35                  40                  45 gtg ctg gac atg aaa gct atg gat tcc aag agc aat ggg gcc att gcc     191
Val Leu Asp Met Lys Ala Met Asp Ser Lys Ser Asn Gly Ala Ile Ala
        50                  55                  60 tgg agc aac cag aca agc ttc acc tgc caa gat atc ttc aaa gag acc     239
Trp Ser Asn Gln Thr Ser Phe Thr Cys Gln Asp Ile Phe Lys Glu Thr
65                  70                  75 aac gcc acc tac ccc agt tca gac gtt ccc tgt gat gcc acg ttg acc     287
Asn Ala Thr Tyr Pro Ser Ser Asp Val Pro Cys Asp Ala Thr Leu Thr
80                  85                  90                  95 gag aaa agc ttt gaa aca gat atg aac cta aac ttt caa aac ctg tca     335
Glu Lys Ser Phe Glu Thr Asp Met Asn Leu Asn Phe Gln Asn Leu Ser
                100                 105                 110 gtt atg gga ctc cga atc ctc ctg ctg aaa gta gcg gga ttt aac ctg     383
Val Met Gly Leu Arg Ile Leu Leu Leu Lys Val Ala Gly Phe Asn Leu
            115                 120                 125 ctc atg acg ctg agg ctg tgg tcc agt ggc tcc gga gcc acg aac ttc     431
Leu Met Thr Leu Arg Leu Trp Ser Ser Gly Ser Gly Ala Thr Asn Phe
        130                 135                 140 tct ctg tta aag caa gca gga gac gtg gaa gaa aac ccc ggt ccc         476
Ser Leu Leu Lys Gln Ala Gly Asp Val Glu Glu Asn Pro Gly Pro
    145                 150                 155
```

<210> SEQ ID NO 338
<211> LENGTH: 521
<212> TYPE: DNA
<213> ORGANISM: Unknown
<220> FEATURE:
<223> OTHER INFORMATION: Description of Unknown:
      Sequence encoding C-beta

<400> SEQUENCE: 338

```
aggatctgag aaatgtgact ccacccaagg tctccttgtt tgagccatca aaagcagaga    60
```

```
ttgcaaacaa acaaaaggct accctcgtgt gcttggccag gggcttcttc cctgaccacg    120
tggagctgag ctggtgggtg aatggcaagg aggtccacag tggggtcagc acggaccctc    180
aggcctacaa ggagagcaat tatagctact gcctgagcag ccgcctgagg gtctctgcta    240
ccttctggca caatcctcga aaccacttcc gctgccaagt gcagttccat gggctttcag    300
aggaggacaa gtggccagag ggctcaccca aacctgtcac acagaacatc agtgcagagg    360
cctggggccg agcagactgt ggaatcactt cagcatccta tcatcagggg gttctgtctg    420
caaccatcct ctatgagatc ctactgggga aggccaccct atatgctgtg ctggtcagtg    480
gcctggtgct gatggccatg gtcaagaaaa aaaattcctg a                        521

<210> SEQ ID NO 339
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 339
gtcaaagtcg gtgaacaggc                                                 20

<210> SEQ ID NO 340
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 340
ttgggtggag tcacatttct c                                               21

<210> SEQ ID NO 341
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 341
aggttctggg ttctggatgt                                                 20

<210> SEQ ID NO 342
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 342
ggagtcacat ttctcagatc ct                                              22

<210> SEQ ID NO 343
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 343
```

```
tctaggcgcc ggaattca                                                  18

<210> SEQ ID NO 344
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 344
gaagaaaacc ccggtcccc                                                 18

<210> SEQ ID NO 345
<211> LENGTH: 42
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 345
tctctaggcg ccggaattca atgctgcaga tgtgggggtt tg                       42

<210> SEQ ID NO 346
<211> LENGTH: 42
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 346
tctctaggcg ccggaattca atgaagacat cccttcacac tg                       42

<210> SEQ ID NO 347
<211> LENGTH: 42
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 347
tctctaggcg ccggaattca atggataaaa catcccttca ca                       42

<210> SEQ ID NO 348
<211> LENGTH: 42
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 348
tctctaggcg ccggaattca atggattaag acatcccttc ac                       42

<210> SEQ ID NO 349
<211> LENGTH: 42
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 349
```
tctctaggcg ccggaattca atgaaaaagt gccttagtgc ct    42

<210> SEQ ID NO 350
<211> LENGTH: 42
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 350
tctctaggcg ccggaattca atgaaaaagc gcctgagtgc ct    42

<210> SEQ ID NO 351
<211> LENGTH: 42
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 351
tctctaggcg ccggaattca atgaaaaagt gcctgagtgc ct    42

<210> SEQ ID NO 352
<211> LENGTH: 42
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 352
tctctaggcg ccggaattca atgcgtcctg tcacctgctc ag    42

<210> SEQ ID NO 353
<211> LENGTH: 42
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 353
tctctaggcg ccggaattca atgaacatgc atcctgtcac ct    42

<210> SEQ ID NO 354
<211> LENGTH: 38
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 354
tctctaggcg ccggaattca atgcgtcctg gcacctgc    38

<210> SEQ ID NO 355
<211> LENGTH: 42
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 355
tctctaggcg ccggaattca atgcgtcctg acacctgctc ag    42

<210> SEQ ID NO 356
<211> LENGTH: 42
<212> TYPE: DNA
<213> ORGANISM: Artificial Sequence
<220> FEATURE:
<223> OTHER INFORMATION: Description of Artificial Sequence: Synthetic primer

<400> SEQUENCE: 356
tctctaggcg ccggaattca atgaacatgc gtcctgtcac ct                42

<210> SEQ ID NO 357
<211> LENGTH: 42
<212> TYPE: DNA
<213> ORGANISM: Artificial Sequence
<220> FEATURE:
<223> OTHER INFORMATION: Description of Artificial Sequence: Synthetic primer

<400> SEQUENCE: 357
tctctaggcg ccggaattca atgcgtcctg tcacctcctc ag                42

<210> SEQ ID NO 358
<211> LENGTH: 42
<212> TYPE: DNA
<213> ORGANISM: Artificial Sequence
<220> FEATURE:
<223> OTHER INFORMATION: Description of Artificial Sequence: Synthetic primer

<400> SEQUENCE: 358
tctctaggcg ccggaattca atgcgtcctg acacctcctc ag                42

<210> SEQ ID NO 359
<211> LENGTH: 42
<212> TYPE: DNA
<213> ORGANISM: Artificial Sequence
<220> FEATURE:
<223> OTHER INFORMATION: Description of Artificial Sequence: Synthetic primer

<400> SEQUENCE: 359
tctctaggcg ccggaattca atgaacaggc tgctgtgctc tc                42

<210> SEQ ID NO 360
<211> LENGTH: 42
<212> TYPE: DNA
<213> ORGANISM: Artificial Sequence
<220> FEATURE:
<223> OTHER INFORMATION: Description of Artificial Sequence: Synthetic primer

<400> SEQUENCE: 360
tctctaggcg ccggaattca atgaagaggc tgctgtgttc tc                42

<210> SEQ ID NO 361
<211> LENGTH: 42
<212> TYPE: DNA
<213> ORGANISM: Artificial Sequence
<220> FEATURE:
<223> OTHER INFORMATION: Description of Artificial Sequence: Synthetic primer

<400> SEQUENCE: 361
tctctaggcg ccggaattca atgaagaggc tgctgtgctc tc                42

<210> SEQ ID NO 362
<211> LENGTH: 42
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 362
tctctaggcg ccggaattca atgaagaggc tgatgtgctc tc                          42

<210> SEQ ID NO 363
<211> LENGTH: 42
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 363
tctctaggcg ccggaattca atgaggaggc tgatgtgttc tc                          42

<210> SEQ ID NO 364
<211> LENGTH: 42
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 364
tctctaggcg ccggaattca atgaagaggc tgctgagctc tc                          42

<210> SEQ ID NO 365
<211> LENGTH: 42
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 365
tctctaggcg ccggaattca atgaagaggc tagtgtgttc tc                          42

<210> SEQ ID NO 366
<211> LENGTH: 42
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 366
tctctaggcg ccggaattca atgaaaaggc tgctgtgctc tc                          42

<210> SEQ ID NO 367
<211> LENGTH: 42
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 367
tctctaggcg ccggaattca atggacaaga tcctgacagc aa                          42

```
<210> SEQ ID NO 368
<211> LENGTH: 42
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 368
tctctaggcg ccggaattca atggacacga tcctgacagc at                    42

<210> SEQ ID NO 369
<211> LENGTH: 42
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 369
tctctaggcg ccggaattca atggacaaga tcctgacagc at                    42

<210> SEQ ID NO 370
<211> LENGTH: 42
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 370
tctctaggcg ccggaattca atggacaaga ttctgacagc at                    42

<210> SEQ ID NO 371
<211> LENGTH: 42
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 371
tctctaggcg ccggaattca atggacaaga acctgacagc at                    42

<210> SEQ ID NO 372
<211> LENGTH: 38
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 372
tctctaggcg ccggaattca atgcctcctc acagcctg                         38

<210> SEQ ID NO 373
<211> LENGTH: 38
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 373
tctctaggcg ccggaattca atgcctcctc agagcctg                         38

<210> SEQ ID NO 374
```

```
<211> LENGTH: 42
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 374
tctctaggcg ccggaattca atgcctcctc acagcctgtt ct                    42

<210> SEQ ID NO 375
<211> LENGTH: 42
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 375
tctctaggcg ccggaattca atgctgattc taagcctgtt gg                    42

<210> SEQ ID NO 376
<211> LENGTH: 42
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 376
tctctaggcg ccggaattca atgttcctag tgaccattct gc                    42

<210> SEQ ID NO 377
<211> LENGTH: 42
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 377
tctctaggcg ccggaattca atgttcccag tgaccattct gc                    42

<210> SEQ ID NO 378
<211> LENGTH: 42
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 378
tctctaggcg ccggaattca atgactggct tcctgaaggc ct                    42

<210> SEQ ID NO 379
<211> LENGTH: 42
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 379
tctctaggcg ccggaattca atgaagcagg tggcaaaagt ga                    42

<210> SEQ ID NO 380
<211> LENGTH: 42
```

```
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 380
tctctaggcg ccggaattca atgggatgtg tgagtggaat tg                          42

<210> SEQ ID NO 381
<211> LENGTH: 42
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 381
tctctaggcg ccggaattca atgaagacag tgactggacc tt                          42

<210> SEQ ID NO 382
<211> LENGTH: 42
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 382
tctctaggcg ccggaattca atgaagacgg tgactggacc tt                          42

<210> SEQ ID NO 383
<211> LENGTH: 42
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 383
tctctaggcg ccggaattca atgaaaacag tgactggacc tt                          42

<210> SEQ ID NO 384
<211> LENGTH: 38
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 384
tctctaggcg ccggaattca atggagagga gcccggga                               38

<210> SEQ ID NO 385
<211> LENGTH: 42
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 385
tctctaggcg ccggaattca atggagagga acctggttgc tg                          42

<210> SEQ ID NO 386
<211> LENGTH: 42
<212> TYPE: DNA
```

<213> ORGANISM: Artificial Sequence
<220> FEATURE:
<223> OTHER INFORMATION: Description of Artificial Sequence: Synthetic
    primer

<400> SEQUENCE: 386
tctctaggcg ccggaattca atgcagagga acctgggagc tg            42

<210> SEQ ID NO 387
<211> LENGTH: 42
<212> TYPE: DNA
<213> ORGANISM: Artificial Sequence
<220> FEATURE:
<223> OTHER INFORMATION: Description of Artificial Sequence: Synthetic
    primer

<400> SEQUENCE: 387
tctctaggcg ccggaattca atgcagagga acctggttgc tg            42

<210> SEQ ID NO 388
<211> LENGTH: 42
<212> TYPE: DNA
<213> ORGANISM: Artificial Sequence
<220> FEATURE:
<223> OTHER INFORMATION: Description of Artificial Sequence: Synthetic
    primer

<400> SEQUENCE: 388
tctctaggcg ccggaattca atggagagga acctgggagc tg            42

<210> SEQ ID NO 389
<211> LENGTH: 42
<212> TYPE: DNA
<213> ORGANISM: Artificial Sequence
<220> FEATURE:
<223> OTHER INFORMATION: Description of Artificial Sequence: Synthetic
    primer

<400> SEQUENCE: 389
tctctaggcg ccggaattca atgaagacag ctattcatgc tt            42

<210> SEQ ID NO 390
<211> LENGTH: 42
<212> TYPE: DNA
<213> ORGANISM: Artificial Sequence
<220> FEATURE:
<223> OTHER INFORMATION: Description of Artificial Sequence: Synthetic
    primer

<400> SEQUENCE: 390
tctctaggcg ccggaattca atgaaaacat acgctcctac at            42

<210> SEQ ID NO 391
<211> LENGTH: 48
<212> TYPE: DNA
<213> ORGANISM: Artificial Sequence
<220> FEATURE:
<223> OTHER INFORMATION: Description of Artificial Sequence: Synthetic
    primer

<400> SEQUENCE: 391
tctctaggcg ccggaattca atgaaaacat atgctcctac attattca      48

<210> SEQ ID NO 392
<211> LENGTH: 44
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 392
tctctaggcg ccggaattca atgaactatt ctccagcttt agtg                    44

<210> SEQ ID NO 393
<211> LENGTH: 42
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 393
tctctaggcg ccggaattca atgaacactt ctccagcttt ag                      42

<210> SEQ ID NO 394
<211> LENGTH: 42
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 394
tctctaggcg ccggaattca atgaacaatt ccccagcttt ag                      42

<210> SEQ ID NO 395
<211> LENGTH: 47
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 395
tctctaggcg ccggaattca atgaatactt ctccagtttt agtaact                 47

<210> SEQ ID NO 396
<211> LENGTH: 42
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 396
tctctaggcg ccggaattca atgaaccttt atcctgaact gg                      42

<210> SEQ ID NO 397
<211> LENGTH: 42
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 397
tctctaggcg ccggaattca atgaaccttt gtcctgaact gg                      42

<210> SEQ ID NO 398
<211> LENGTH: 42
<212> TYPE: DNA
<213> ORGANISM: Artificial Sequence
<220> FEATURE:

```
<223> OTHER INFORMATION: Description of Artificial Sequence: Synthetic
      primer

<400> SEQUENCE: 398
tctctaggcg ccggaattca atggactctt ctccaggctt cg                       42

<210> SEQ ID NO 399
<211> LENGTH: 42
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 399
tctctaggcg ccggaattca atgaactctt ctccaggctt ca                       42

<210> SEQ ID NO 400
<211> LENGTH: 45
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 400
tctctaggcg ccggaattca atgaatactt ctccagtttt agtga                    45

<210> SEQ ID NO 401
<211> LENGTH: 42
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 401
tctctaggcg ccggaattca atggactttt ctccaggctt cg                       42

<210> SEQ ID NO 402
<211> LENGTH: 42
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 402
tctctaggcg ccggaattca atgaagtcct tgtgtgtttc ac                       42

<210> SEQ ID NO 403
<211> LENGTH: 43
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 403
tctctaggcg ccggaattca atgaaatcct tgagtgtttc act                      43

<210> SEQ ID NO 404
<211> LENGTH: 47
<212> TYPE: DNA
<213> ORGANISM: Artificial Sequence
<220> FEATURE:
<223> OTHER INFORMATION: Description of Artificial Sequence: Synthetic
``` primer

<400> SEQUENCE: 404
tctctaggcg ccggaattca atgaaatcct ttagtatttc cctagtg        47

<210> SEQ ID NO 405
<211> LENGTH: 42
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 405
tctctaggcg ccggaattca atgaaatcct tgagtgtttc cc        42

<210> SEQ ID NO 406
<211> LENGTH: 42
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 406
tctctaggcg ccggaattca atgcattcct tacatgtttc ac        42

<210> SEQ ID NO 407
<211> LENGTH: 42
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 407
tctctaggcg ccggaattca atggtacaaa cacagatgtt ct        42

<210> SEQ ID NO 408
<211> LENGTH: 46
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 408
tctctaggcg ccggaattca atgaaatcct tgagtgtttt actagt        46

<210> SEQ ID NO 409
<211> LENGTH: 38
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 409
tctctaggcg ccggaattca atgcacagcc tcctgggg        38

<210> SEQ ID NO 410
<211> LENGTH: 42
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 410
tctctaggcg ccggaattca atgaacagat tcctgggaat at                               42

<210> SEQ ID NO 411
<211> LENGTH: 42
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 411
tctctaggcg ccggaattca atgcacagcc tcctagggtt gt                               42

<210> SEQ ID NO 412
<211> LENGTH: 42
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 412
tctctaggcg ccggaattca atgctcctgg tcctcatctc gt                               42

<210> SEQ ID NO 413
<211> LENGTH: 42
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 413
tctctaggcg ccggaattca atgctcctgg ttctcatctc gt                               42

<210> SEQ ID NO 414
<211> LENGTH: 38
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 414
tctctaggcg ccggaattca atgctcctgg tgctcctc                                   38

<210> SEQ ID NO 415
<211> LENGTH: 38
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 415
tctctaggcg ccggaattca atgctcctgg cgctcctc                                   38

<210> SEQ ID NO 416
<211> LENGTH: 38
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 416
tctctaggcg ccggaattca atgctcctgg cactcctc                                   38

<210> SEQ ID NO 417
<211> LENGTH: 42
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 417
tggaagaaaa ccccggtccc atgtggcagt tttgcattct gt                              42

<210> SEQ ID NO 418
<211> LENGTH: 38
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 418
tggaagaaaa ccccggtccc atgccacgga caccaggc                                   38

<210> SEQ ID NO 419
<211> LENGTH: 42
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 419
tggaagaaaa ccccggtccc atgtctaaca ctgtcctcgc tg                              42

<210> SEQ ID NO 420
<211> LENGTH: 42
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 420
tggaagaaaa ccccggtccc atgtctaaca ctgccttccc tg                              42

<210> SEQ ID NO 421
<211> LENGTH: 47
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 421
tggaagaaaa ccccggtccc atgtgtaata ctaccctcct taattttt                        47

<210> SEQ ID NO 422
<211> LENGTH: 42
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 422

```
tggaagaaaa ccccggtccc atgggctcca ggctcttttct gg                              42

<210> SEQ ID NO 423
<211> LENGTH: 42
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 423
tggaagaaaa ccccggtccc atgggctcca ggctcttctt cg                              42

<210> SEQ ID NO 424
<211> LENGTH: 42
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 424
tggaagaaaa ccccggtccc atgggctcca gactcttctt tg                              42

<210> SEQ ID NO 425
<211> LENGTH: 38
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 425
tggaagaaaa ccccggtccc atgggcacca ggcttctt                                   38

<210> SEQ ID NO 426
<211> LENGTH: 42
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 426
tggaagaaaa ccccggtccc atgggcatcc agaccctctg tt                              42

<210> SEQ ID NO 427
<211> LENGTH: 41
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 427
tggaagaaaa ccccggtccc atggccccca ggctcctttt c                               41

<210> SEQ ID NO 428
<211> LENGTH: 42
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 428
```
tggaagaaaa ccccggtccc atggatccta gacttctttg ct        42

<210> SEQ ID NO 429
<211> LENGTH: 42
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 429
tggaagaaaa ccccggtccc atgaacaagt gggttttctg ct        42

<210> SEQ ID NO 430
<211> LENGTH: 42
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 430
tggaagaaaa ccccggtccc atgggctcca ttttcctcag tt        42

<210> SEQ ID NO 431
<211> LENGTH: 45
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 431
tggaagaaaa ccccggtccc atgttactgc ttctattact tctgg        45

<210> SEQ ID NO 432
<211> LENGTH: 44
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 432
tggaagaaaa ccccggtccc atgggtgcac ggctcatttg ctat        44

<210> SEQ ID NO 433
<211> LENGTH: 38
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 433
tggaagaaaa ccccggtccc atgggtgcaa gactgctc        38

<210> SEQ ID NO 434
<211> LENGTH: 42
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 434
tggaagaaaa ccccggtccc atgactgcca agttcatgca tt        42

<210> SEQ ID NO 435
<211> LENGTH: 42
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 435
tggaagaaaa ccccggtccc atggtcacca gtctctcaag at                    42

<210> SEQ ID NO 436
<211> LENGTH: 42
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 436
tggaagaaaa ccccggtccc atgagagtta ggctcatctc tg                    42

<210> SEQ ID NO 437
<211> LENGTH: 42
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 437
tggaagaaaa ccccggtccc atggatatct ggcttctagg tt                    42

<210> SEQ ID NO 438
<211> LENGTH: 42
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 438
tggaagaaaa ccccggtccc atgctgtact ctctccttgc ct                    42

<210> SEQ ID NO 439
<211> LENGTH: 42
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 439
tggaagaaaa ccccggtccc atgggctgta ggctcctaag ct                    42

<210> SEQ ID NO 440
<211> LENGTH: 42
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 440
tggaagaaaa ccccggtccc atgagctgca ggcttctcct ct                    42

<210> SEQ ID NO 441
<211> LENGTH: 42
<212> TYPE: DNA
<213> ORGANISM: Artificial Sequence
<220> FEATURE:
<223> OTHER INFORMATION: Description of Artificial Sequence: Synthetic primer

<400> SEQUENCE: 441
tggaagaaaa ccccggtccc atgggctgaa aaatgctctg ct                42

<210> SEQ ID NO 442
<211> LENGTH: 18
<212> TYPE: DNA
<213> ORGANISM: Artificial Sequence
<220> FEATURE:
<223> OTHER INFORMATION: Description of Artificial Sequence: Synthetic primer

<400> SEQUENCE: 442
tttttttttt tttttttt                18

<210> SEQ ID NO 443
<211> LENGTH: 70
<212> TYPE: DNA
<213> ORGANISM: Mus sp.

<400> SEQUENCE: 443
caccacagcc cagggcctgg ttacttgctt ctgtctccag cagccacaca agcaccatga        60
agaggctgct        70

<210> SEQ ID NO 444
<211> LENGTH: 70
<212> TYPE: DNA
<213> ORGANISM: Mus sp.

<400> SEQUENCE: 444
caccacagcc ccggggctgg ttacttgctt ctgtctccag cagccacaca agcaccatga        60
agaggctgct        70

<210> SEQ ID NO 445
<211> LENGTH: 70
<212> TYPE: DNA
<213> ORGANISM: Mus sp.

<400> SEQUENCE: 445
caccacagcc cagggggctgg ttacttgctt ctgtctccag cagccacaca agcaccatga        60
agaggctgct        70

<210> SEQ ID NO 446
<211> LENGTH: 70
<212> TYPE: DNA
<213> ORGANISM: Mus sp.

<400> SEQUENCE: 446
caccacagcc cagggactgg ttacttgctt ctgtctccag cagccacaca agcaccatga        60
agaggctgct        70

<210> SEQ ID NO 447
<211> LENGTH: 70
<212> TYPE: DNA
<213> ORGANISM: Mus sp.

<400> SEQUENCE: 447
caccacagcc cagggactgg ttacttgctt ctgtctccag cagccacaca agcaccatga    60
agaggctgct    70

<210> SEQ ID NO 448
<211> LENGTH: 70
<212> TYPE: DNA
<213> ORGANISM: Mus sp.

<400> SEQUENCE: 448
caccacagcc cagggactgg ttacttgctt ctgtctccag cagccacaca agcaccatga    60
agaggctgct    70

<210> SEQ ID NO 449
<211> LENGTH: 70
<212> TYPE: DNA
<213> ORGANISM: Mus sp.

<400> SEQUENCE: 449
caccacagcc caggggctgg ttacttgctt ctgtctccag cagccacaca agcaccatga    60
agaggctgct    70

<210> SEQ ID NO 450
<211> LENGTH: 70
<212> TYPE: DNA
<213> ORGANISM: Mus sp.

<400> SEQUENCE: 450
caccacagcc caggggctgg ttacttgctt ctgtctccag cagccacaca agcaccatga    60
agaggctgct    70

<210> SEQ ID NO 451
<211> LENGTH: 70
<212> TYPE: DNA
<213> ORGANISM: Mus sp.

<400> SEQUENCE: 451
caccacagcc caggagctgg ttacttgctt ctgtctccag cagctacaca agcaccatga    60
agaggctgct    70

<210> SEQ ID NO 452
<211> LENGTH: 70
<212> TYPE: DNA
<213> ORGANISM: Mus sp.

<400> SEQUENCE: 452
caccacagcc caggagctgg ttacttgctt ctgtctccag cagctacaca agcaccatga    60
agaggctgct    70

<210> SEQ ID NO 453
<211> LENGTH: 70
<212> TYPE: DNA
<213> ORGANISM: Mus sp.

<400> SEQUENCE: 453
caccacagcc caggggctgg ttacttgctt ctgtctccag cagccacaca agcaccatga    60
acaggctgct    70

<210> SEQ ID NO 454
<211> LENGTH: 70
<212> TYPE: DNA
<213> ORGANISM: Mus sp.

<400> SEQUENCE: 454
caccacagcc cagggactgg ttacttgctt ctgtctccag caaccacaca agcaccatga    60
agaggctgct                                                          70

<210> SEQ ID NO 455
<211> LENGTH: 70
<212> TYPE: DNA
<213> ORGANISM: Mus sp.

<400> SEQUENCE: 455
caccacagcc cagggcctgg ttacttgctt ctgtctccag cagccacaca agcaccatga    60
ggaggctgat                                                          70

<210> SEQ ID NO 456
<211> LENGTH: 158
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 456

Ile Gln Asn Pro Glu Pro Ala Val Tyr Gln Leu Lys Asp Pro Arg Ser
1               5                   10                  15

Gln Asp Ser Thr Leu Cys Leu Phe Thr Asp Phe Asp Ser Gln Ile Asn
                20                  25                  30

Val Pro Lys Thr Met Glu Ser Gly Thr Phe Ile Thr Asp Lys Thr Val
            35                  40                  45

Leu Asp Met Lys Ala Met Asp Ser Lys Ser Asn Gly Ala Ile Ala Trp
        50                  55                  60

Ser Asn Gln Thr Ser Phe Thr Cys Gln Asp Ile Phe Lys Glu Thr Asn
65                  70                  75                  80

Ala Thr Tyr Pro Ser Ser Asp Val Pro Cys Asp Ala Thr Leu Thr Glu
                85                  90                  95

Lys Ser Phe Glu Thr Asp Met Asn Leu Asn Phe Gln Asn Leu Ser Val
                100                 105                 110

Met Gly Leu Arg Ile Leu Leu Leu Lys Val Ala Gly Phe Asn Leu Leu
            115                 120                 125

Met Thr Leu Arg Leu Trp Ser Ser Gly Ser Gly Ala Thr Asn Phe Ser
        130                 135                 140

Leu Leu Lys Gln Ala Gly Asp Val Glu Glu Asn Pro Gly Pro
145                 150                 155

<210> SEQ ID NO 457
<211> LENGTH: 606
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 457
ccttctctag gcgccggaat tcatatcgat gcatgcggcg gtgtttaaac ggcggtcgga    60
ccgaggatct gagaaatgtg actccaccca aggtctcctt gtttgagcca tcaaaagcag   120

-continued

```
agattgcaaa caaacaaaag gctaccctcg tgtgcttggc caggggcttc ttccctgacc      180
acgtggagct gagctggtgg gtgaatggca aggaggtcca cagtggggtc agcacggacc      240
ctcaggccta caaggagagc aattatagct actgcctgag cagccgcctg agggtctctg      300
ctaccttctg gcacaatcct cgaaaccact tccgctgcca agtgcagttc catgggcttt      360
cagaggagga caagtggcca gagggctcac ccaaacctgt cacacagaac atcagtgcag      420
aggcctgggg ccgagcagac tgtggaatca cttcagcatc ctatcatcag ggggttctgt      480
ctgcaaccat cctctatgag atcctactgg ggaaggccac cctatatgct gtgctggtca      540
gtggcctggt gctgatggcc atggtcaaga aaaaaattc ctgaactagt atcgatgatc      600
ccaatt                                                                  606
```